US009304137B2

(12) United States Patent
Kearney et al.

(10) Patent No.: US 9,304,137 B2
(45) Date of Patent: *Apr. 5, 2016

(54) COMPOSITIONS, METHODS AND KITS FOR DIAGNOSIS OF LUNG CANCER

(71) Applicant: Integrated Diagnostics, Inc., Seattle, WA (US)

(72) Inventors: Paul Edward Kearney, Seattle, WA (US); Kenneth Charles Fang, San Francisco, CA (US); Xiao-Jun Li, Bellevue, WA (US); Clive Hayward, Seattle, WA (US)

(73) Assignee: Integrated Diagnostics, Inc., Seattle, WA (US)

(*) Notice: Subject to any disclaimer, the term of this patent is extended or adjusted under 35 U.S.C. 154(b) by 229 days.

This patent is subject to a terminal disclaimer.

(21) Appl. No.: 13/775,494

(22) Filed: Feb. 25, 2013

(65) Prior Publication Data

US 2013/0230877 A1 Sep. 5, 2013

Related U.S. Application Data

(63) Continuation-in-part of application No. 13/724,823, filed on Dec. 21, 2012.

(60) Provisional application No. 61/578,712, filed on Dec. 21, 2011, provisional application No. 61/589,920, filed on Jan. 24, 2012, provisional application No. 61/676,859, filed on Jul. 27, 2012, provisional application No. 61/725,153, filed on Nov. 12, 2012.

(51) Int. Cl.
*G01N 33/68* (2006.01)
*G01N 30/72* (2006.01)
*G01N 33/574* (2006.01)
G06F 19/18 (2011.01)
G06F 19/24 (2011.01)

(52) U.S. Cl.
CPC ...... *G01N 33/6893* (2013.01); *G01N 33/57423* (2013.01); *G01N 33/6848* (2013.01); *G06F 19/18* (2013.01); *G06F 19/24* (2013.01)

(58) Field of Classification Search
None
See application file for complete search history.

(56) References Cited

U.S. PATENT DOCUMENTS

| 7,183,188 | B2 | 2/2007 | Kronke et al. | |
| 2006/0257857 | A1* | 11/2006 | Keene et al. | 435/5 |
| 2007/0099251 | A1 | 5/2007 | Zhang et al. | |
| 2007/0111322 | A1* | 5/2007 | Yang | 436/180 |
| 2007/0128598 | A1* | 6/2007 | Boender | 435/6 |
| 2007/0202539 | A1 | 8/2007 | Aebersold et al. | |
| 2007/0269895 | A1 | 11/2007 | Aebersold et al. | |
| 2009/0317392 | A1 | 12/2009 | Nakamura et al. | |
| 2010/0093108 | A1 | 4/2010 | Khattar et al. | |
| 2010/0184034 | A1 | 7/2010 | Bankaitis-Davis et al. | |
| 2010/0279382 | A1 | 11/2010 | Aebersold et al. | |
| 2012/0142558 | A1 | 6/2012 | Li et al. | |
| 2013/0230877 | A1 | 9/2013 | Kearney | |

FOREIGN PATENT DOCUMENTS

| WO | WO-2011085163 A2 | 7/2011 |
| WO | WO 2011085163 A2 * | 7/2011 |
| WO | 2012075042 A1 | 6/2012 |
| WO | 2013096845 A2 | 6/2013 |

OTHER PUBLICATIONS

Tockman., Cancer Res. 1992, 52: 2711s-2718s.*
Ozaki et al., Cancer, 2002, 95:1954-1962.*
Ueda et al., PloS One, 2011, Apr. 12, 6(4): e18567, pp. 1-12.*
Rho et al., Protein J., 2009,28:148-160.*
Milman et al., Oncol Rep. 2002, 9(1): 193-8.*
Lange et al., Mol. Sys. Biol. 2008, vol. 4, Article No. 222, pp. 1-14.*
"Evolution of Translational Omics: Lessons Learned and the Path Forward." *Committee on the Review of Omics-Based Tests for Predicting Patient Outcomes in Clinical Trials.* Micheel et al., eds. (2012):xv-338.
Addona et al. "A Pipeline that Integrates the Discovery and Verification of Plasma Protein Biomarkers Reveals Candidate Markers for Cardiovascular Disease." *Nat. Biotechnol.* 29.7(2011):635-643.
Addona et al. "Multi-Site Assessment of the Precision and Reproducibility of Multiple Reaction Monitoring-Based Measurements of Proteins in Plasma." *Nat. Biotechnol.* 27.7(2009):633-641.
Albert et al. "Evaluation of the Solitary Pulmonary Nodule." *Am. Fam. Physician.* 80.8(2009):827-831.
Bigbee et al. "A Multiplexed Serum Biomarker Immunoassay Panel Discriminates Clinical Lung Cancer Patients from High-Risk Individuals Found to be Cancer-Free by CT Scanning." *J. Thorac Oncol.* 7.4(2012):698-708.
Brusniak et al. "Corra: Computational Framework and Tools for LC-MS Discovery and Targeted Mass Spectrometry-Based Proteomics." *BMC Bioinformatics.* 9(2008):542.
Carozzi et al. "Molecular Profile in Body Fluids in Subjects Enrolled in a Randomised Trial for Lung Cancer Screening: Perspectives of Integrated Strategies for Early Diagnosis." *Lung Cancer.* 68.2(2010):216-221.

(Continued)

*Primary Examiner* — Hong Sang
(74) *Attorney, Agent, or Firm* — Cooley LLP; Ivor R. Elrifi; Matthew Pavao

(57) ABSTRACT

Methods are provided for identifying biomarker proteins that exhibit differential expression in subjects with a first lung condition versus healthy subjects or subjects with a second lung condition. Also provided are compositions comprising these biomarker proteins and methods of using these biomarker proteins or panels thereof to diagnose, classify, and monitor various lung conditions. The methods and compositions provided herein may be used to diagnose or classify a subject as having lung cancer or a non-cancerous condition, and to distinguish between different types of cancer (e.g., malignant versus benign, SCLC versus NSCLC).

16 Claims, 15 Drawing Sheets

(56) References Cited

OTHER PUBLICATIONS

Chapman et al. "EarlyCDT®-Lung Test: Improved Clinical Utility Through Additional Autoantibody Assays." *Tumor Biol.* 33.5(2012):1319-1326.
Cima et al. "Cancer Genetics-Guided Discovery of Serum Biomarker Signatures for Diagnosis and Prognosis of Prostate Cancer." *PNAS.* 108.8(2011):3342-3347.
Desiere et al. "The PeptideAtlas Project." *Nucleic Acids Res.* 34(2006):D655-D658.
Farrah et al. "A High-Confidence Human Plasma Proteome Reference Set with Estimated Concentrations in PeptideAtlas." *Mol. Cell. Proteomics.* 10.9(2011):M110.006353.
Gould et al. "Evaluation of Patients with Pulmonary Nodules: When is it Lung Cancer?" *Chest.* 132.S3(2007):108S-130S.
Halliwell et al. "Oxidative Stress and Cancer: Have We Moved Forward?" *Biochem. J.* 401.1(2007):1-11.
Hanash et al. "Emerging Molecular Biomarkers—Blood-Based Strategies to Detect and Monitor Cancer." *Nat. Rev. Clin. Oncol.* 8.3(2011):142-150.
Hassanein et al. "Advances in Proteomic Strategies Toward the Early Detection of Lung Cancer." *Proc. Am. Thorac. Soc.* 8.2(2011):183-188.
Hennessey et al. "Serum MicroRNA Biomarkers for Detection of Non-Small Cell Lung Cancer." *PLoS One.* 7.2(2012):e32307.
Henschke et al. "CT Screening for Lung Cancer: Suspiciousness of Nodules According to Size on Baseline Scans." *Radiology.* 231.1(2004):164-168.
Henschke et al. "Early Lung Cancer Action Project: Overall Design and Findings from Baseline Screenings." *Lancet.* 354.9173(1999):99-105.
Hüttenhain et al. "Reproducible Quantification of Cancer-Associated Proteins in Body Fluids using Targeted Proteomics." *Sci. Transl. Med.* 4.142(2012):149ra194.
Kearney et al. "Protein Identification and Peptide Expression Resolver: Harmonizing Protein Identification with Protein Expression Data." *J. Proteome Res.* 7.1(2008):234-244.
Kitteringham et al. "Multiple Reaction Monitoring for Quantitative Biomarker Analysis in Proteomics and Metabolomics." *J. Chromatogr. B.* 877.13(2009):1229-1239.
Lam et al. "EarlyCDT-Lung: An Immunobiomarker Test as an Aid to Early Detection of Lung Cancer." *Cancer Prev. Res.* 4.7(2011):1126-1134.
Lange et al. "Selected Reaction Monitoring for Quantitative Proteomics: A Tutorial." *Mol. Sys. Biol.* 4(2008):222.
Lehtiö et al. "Lung Cancer Proteomics, Clinical and Technological Considerations." *J. Proteomics.* 73.10(2010):1851-1863.
Lombardi et al. Clinical Significance of a Multiple Biomarker Assay in Patients with Lung Cancer. *Chest.* 97.3(1990):639-644.
MacMahon et al. "Guidelines for Management of Small Pulmonary Nodules Detected on CT Scans: A Statement from the Fleischner Society." *Radiology.* 237.2(2005):395-400.
Makawita et al. "The Bottleneck in the Cancer Biomarker Pipeline and Protein Quantification through Mass Spectrometry-Based Approaches: Current Strategies for Candidate Verification." *Clin. Chem.* 56.2(2010):212-222.
McClish. "Analyzing a Portion of the ROC Curve." *Med. Decis. Making.* 9.3(1989):190-195.
Miller et al. "Minimizing Unintended Consequences of Detecting Lung Nodules by Computed Tomography." *Am. J. Resp. Crit. Care Med.* 178.9(2008):891-892.
Ocak et al. "Mass Spectrometry-Based Proteomic Profiling of Lung Cancer." *Proc. Am. Thorac. Soc.* 6.2(2009):159-170.
Omenn et al. "Overview of the HUPO Plasma Proteome Project: Results from the Pilot Phase with 35 Collaborating Laboratories and Multiple Analytical Groups, Generating a Core Dataset of 3020 Proteins and a Publicly-Available Database." *Proteomics.* 5.13(2005):3226-3245.
Ost et al. "Decision Making in Patients with Pulmonary Nodules." *Am. J. Respir. Crit. Care Med.* 185.4(2012):363-372.
Ostroff et al. "Unlocking Biomarker Discovery: Large Scale Application of Aptamer Proteomic Technology for Early Detection of Lung Cancer." *PLoS One.* 5.12(2010):e15003.
Pecot et al. "Added Value of a Serum Proteomic Signature in the Diagnostic Evaluation of Lung Nodules." *Cancer Epidemiol. Biomarkers Prev.* 21.5(2012):786-792.
Perkins et al. "Probability-Based Protein Identification by Searching Sequence Databases Using Mass Spectrometry Data." *Electrophoresis.* 20.18(1999):3551-3567.
Picotti et al. "High-Throughput Generation of Selected Reaction-Monitoring Assays for Proteins and Proteomes." *Nat. Meth.* 7.1(2010):43-46.
Polanski et al. "A List of Candidiate Cancer Biomarkers for Targeted Proteomics." *Biomarker Insights.* 1(2007):1-48.
Price et al. "Highly Accurate Two-Gene Classifier for Differentiating Gastrointestinal Stromal Tumors and Leiomyosarcomas." *PNAS.* 104.9(2007):3414-3419.
Qin et al. "SRM Targeted Proteomics in Seach for Biomarkers of HCV-Induced Progression of Fibrosis to Cirrhosis in HALT-C Patients." *Proteomics.* 12.8(2012):1244-1252.
Radulovic et al. "Informatics Platform for Global Proteomic Profiling and Biomarker Discovery Using Liquid Chromatography-Tandem Mass Spectrometry." *Mol. Cell. Proteins.* 3.10(2004):984-997.
Reiter et al. "mProphet: Automated Data Processing and Statistical Validation for Large-Scale SRM Experiments." *Nat. Meth.* 8.5(2011):430-435.
Rho et al. "Glycoproteomic Analysis of Human Lung Adenocarcinomas Using Glycoarrays and Tandem Mass Spectrometry: Differential Expression and Glycosylation Patterns of Vimentin and Fetuin A Isoforms." *Protein J.* 28.3-4(2009):148-160.
Rom et al. "Identification of an Autoantibody Panel to Separate Lung Cancer from Smokers and Nonsmokers." *BMC Cancer.* 10(2010):234.
Schauer et al. "National Council on Radiation Protection and Measurements Report Shows Substantial Medical Exposure Increase." *Radiol.* 253.2(2009):293-296.
States et al. "Challenges in Deriving High-Confidence Protein Identifications from Data Gathered by a HUPO Plasma Proteome Collaborative Study." *Nat. Biotechnol.* 24.3(2006):333-338.
Stern et al. "Nationwide Evaluation of X-Ray Trends (*NEXT*) 2000-01 Survey of Patient Radiation Exposure from Computed Tomographic (CT) Examinations in the United States." *87th Scientific Assembly and Annual Meeting of the Radiological Society of North America, Chicago*, Nov. 25-30, 2001.
Taguchi et al. "Unleashing the Power of Proteomics to Develop Blood-Based Cancer Markers." *Clin. Chem.* 59(2013):1.
Teutsch et al. "The Evaluation of Genomic Applications in Practice and Prevention (EGAPP) Initiative: Methods of the EGAPP Working Group." *Genet. Med.* 11.1(2009):3-14.
Walser et al. "Smoking and Lung Cancer: The Role of Inflammation." *Proc. Am. Thorac. Soc.* 5.8(2008):811-815.
Whiteaker et al. "A Targeted Proteomics-Based Pipeline for Verification of Biomarkers in Plasma." *Nat. Biotechnol.* 29.7(2011):625-634.
Wiener et al. "Population-Based Risk for Complications after Transthoracic Needle Lung Biopsy of a Pulmonary Nodule: An Analysis of Discharge Records." *Ann. Int. Med.* 155.3(2011):137-144.
Yildiz et al. "Diagnostic Accuracy of MALDI Mass Spectrometic Analysis of Unfractionated Serum in Lung Cancer." *J. Thorac. Oncol.* 2.10(2007):893-901.
Zeng et al. "Lung Cancer Serum Biomarker Discovery Using Glycoprotein Capture and Liquid Chromatography Mass Spectrometry." *J. Proteome Res.* 9.12(2010):6440-6449.
Jung-Hyun Rho et al., "Glycoproteomic Analysis of Human Lung Adenocarcinomas Using Glycoarrays and Tandem Mass Spectrometry: Differential Expression and Glycosylation Patterns of Vimentin and Fetuin A Isoforms", Journal of Protein Chemistry, Kluwer Academic Publishers—Plenum Publishers, NE, vol. 28, No. 3-4, May 2, 2009, pp. 148-160.
Bouchal et al. "Biomarker Discovery in Low-Grade Breast Cancer Using Isobaric Stable Isotope Tags and Two-Dimensional Liquid Chromatography-Tandem Mass Spectrometry (iTRAQ-2DLC-MS/

(56) References Cited

OTHER PUBLICATIONS

MS) Based Quantitative Proteomic Analysis", *Journal of Proteome Research*, (2009), vol. 8, p. 362-373.

Kitada et al. "Role of treatment for solitary pulmonary nodule in breast cancer patients", *World Journal of Surgical Oncology*, (2011), vol. 9, p. 124 (internet pp. 1-5).

Bouchal et al. "Biomarker Discovery in Low-Grade Breast Cancer Using Isobaric Stable Isotope Tags and Two-Dimensional Liquid Chromatography-Tandem Mass Spectrometry (iTRAQ-2DLC-MS/MS) Based Quantitative Proteomic Analysis", *Journal of Proteome Research*, (2009), vol. 8, p. 362-373, Supplementary Table 2.

Wang et al. "The evolving role of mass spectrometry in cancer biomarker discovery", *Cancer Biology and Therapy*, (2009), vol. 8, p. 1083-1094.

Swensen et al., "Lung Cancer Screening with CT: Mayo Clinic Experience", *Radiology*, (2003), vol. 226, p. 756-761.

Wei et al. "Primary Tumor Xenografts of Human Lung Adeno and Squamous Cell Carcinoma Express Distinct Proteomic Signatures", *Journal of Proteome Research*, (2011), vol. 10, p. 161-174, published online Sep. 3, 2010.

\* cited by examiner

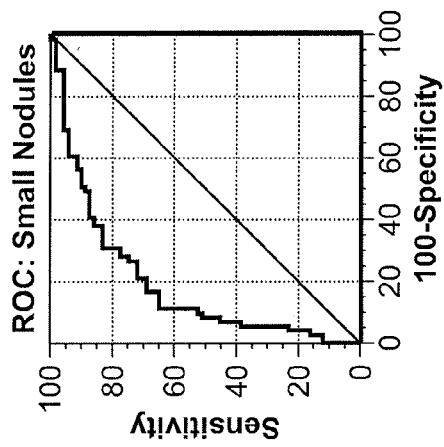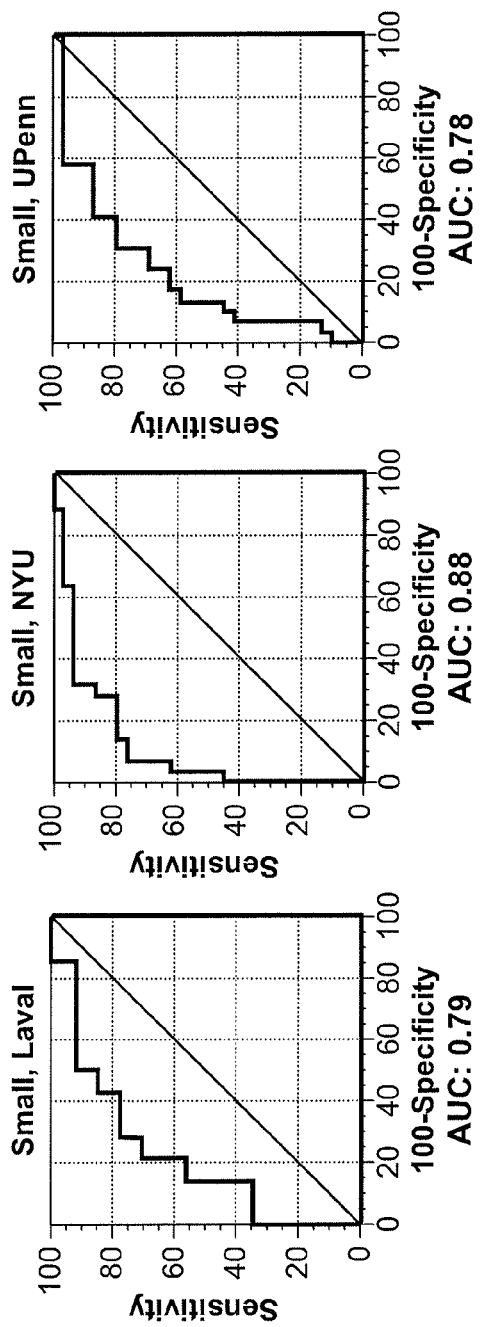
FIG. 4
FIG. 5

```
                        SEQUENCE LISTING

<160> NUMBER OF SEQ ID NOS: 75

<210> SEQ ID NO 1
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1

Tyr Gly Phe Ile Glu Gly His Val Val Ile Pro Arg
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 2

Tyr Glu Val Thr Val Val Ser Val Arg
1               5

<210> SEQ ID NO 3
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 3

Ala Ser Ser Ile Ile Asp Glu Leu Phe Gln Asp Arg
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 4

Phe Leu Asn Val Leu Ser Pro Arg
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 5

Thr Ala Ser Asp Phe Ile Thr Lys
1               5

<210> SEQ ID NO 6
<211> LENGTH: 15
<212> TYPE: PRT
<213> ORGANISM: Artificial Sequence
```

```
<220> FEATURE:
<223> OTHER INFORMATION: Synthetic Polypeptide

<400> SEQUENCE: 6

Thr Gly Val Ile Thr Ser Pro Asp Phe Pro Asn Pro Tyr Pro Lys
1               5                   10                  15

<210> SEQ ID NO 7
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 7

Ala Leu Gln Ala Ser Ala Leu Lys
1               5

<210> SEQ ID NO 8
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 8

Leu Thr Leu Leu Ala Pro Leu Asn Ser Val Phe Lys
1               5                   10

<210> SEQ ID NO 9
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 9

Leu Ala Ala Leu Asn Pro Glu Ser Asn Thr Ala Gly Leu Asp Ile Phe
1               5                   10                  15

Ala Lys

<210> SEQ ID NO 10
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 10

Val Ala Val Val Gln Tyr Ser Asp Arg
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 11

Ala Val Gly Leu Ala Gly Thr Phe Arg
1               5

<210> SEQ ID NO 12
<211> LENGTH: 15
<212> TYPE: PRT
```

```
<213> ORGANISM: Artificial Sequence
<220> FEATURE:
<223> OTHER INFORMATION: Synthetic Polypeptide

<400> SEQUENCE: 12

Val Pro Gly Thr Ser Thr Ser Ala Thr Leu Thr Gly Leu Thr Arg
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 13

Gly Ala Leu Gln Asn Ile Ile Pro Ala Ser Thr Gly Ala Ala Lys
1               5                   10                  15

<210> SEQ ID NO 14
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 14

Ala Leu Pro Gly Thr Pro Val Ala Ser Ser Gln Pro Arg
1               5                   10

<210> SEQ ID NO 15
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 15

Thr Val Leu Trp Pro Asn Gly Leu Ser Leu Asp Ile Pro Ala Gly Arg
1               5                   10                  15

<210> SEQ ID NO 16
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 16

Gln Ile Thr Val Asn Asp Leu Pro Val Gly Arg
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 17

Ser Thr Gly Gly Ala Pro Thr Phe Asn Val Thr Val Thr Lys
1               5                   10

<210> SEQ ID NO 18
<211> LENGTH: 7
<212> TYPE: PRT
<213> ORGANISM: Artificial Sequence
```

```
<220> FEATURE:
<223> OTHER INFORMATION: Synthetic Polypeptide

<400> SEQUENCE: 18

Ser Val Asp Ile Trp Leu Arg
1               5

<210> SEQ ID NO 19
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 19

Ile Ser Val Tyr Tyr Asn Glu Ala Ser Ser His Lys
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 20

Leu Asp Thr Leu Ala Gln Glu Val Ala Leu Leu Lys
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 21

Val Val Phe Glu Gln Thr Lys
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 22

Gly Phe Leu Leu Leu Ala Ser Leu Arg
1               5

<210> SEQ ID NO 23
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 23

Thr Trp Asn Asp Pro Ser Val Gln Gln Asp Ile Lys
1               5                   10

<210> SEQ ID NO 24
<211> LENGTH: 15
<212> TYPE: PRT
<213> ORGANISM: Artificial Sequence
<220> FEATURE:
```

```
<223> OTHER INFORMATION: Synthetic Polypeptide

<400> SEQUENCE: 24

Leu Gly Gly Pro Glu Ala Gly Leu Gly Glu Tyr Leu Phe Glu Arg
1               5                   10                  15

<210> SEQ ID NO 25
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 25

Val Glu Ile Phe Tyr Arg
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 26

Asn Ser Leu Phe Glu Tyr Gln Lys
1               5

<210> SEQ ID NO 27
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 27

Ile Ile Ile Gln Glu Ser Ala Leu Asp Tyr Arg
  1               5                   10

<210> SEQ ID NO 28
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 28

Leu Gln Ser Leu Phe Asp Ser Pro Asp Phe Ser Lys
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 29

Ser Leu Glu Asp Leu Gln Leu Thr His Asn Lys
1               5                   10

<210> SEQ ID NO 30
<211> LENGTH: 8
<212> TYPE: PRT
<213> ORGANISM: Artificial Sequence
<220> FEATURE:
<223> OTHER INFORMATION: Synthetic Polypeptide
```

<400> SEQUENCE: 30

Ile Asn Pro Ala Ser Leu Asp Lys
1               5

<210> SEQ ID NO 31
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 31

Val Ile Thr Glu Pro Ile Pro Val Ser Asp Leu Arg
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 32

Tyr Val Ser Glu Leu His Leu Thr Arg
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 33

Ala Thr Val Asn Pro Ser Ala Pro Arg
1               5

<210> SEQ ID NO 34
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 34

Ile Gly Gly Ile Gly Thr Val Pro Val Gly Arg
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 35

Glu Leu Trp Phe Ser Asp Asp Pro Asn Val Thr Lys
1               5                   10

<210> SEQ ID NO 36
<211> LENGTH: 9
<212> TYPE: PRT
<213> ORGANISM: Artificial Sequence
<220> FEATURE:
<223> OTHER INFORMATION: Synthetic Polypeptide

```
<400> SEQUENCE: 36

Tyr Tyr Ile Ala Ala Ser Tyr Val Lys
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 37

Ser Gly Tyr Leu Leu Pro Asp Thr Lys
1               5

<210> SEQ ID NO 38
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 38

Val Leu Pro Phe Phe Glu Arg Pro Asp Phe Gln Leu Phe Thr Gly Asn
1               5                   10                  15

Lys

<210> SEQ ID NO 39
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 39

Leu Val Pro Leu Leu Asp Thr Gly Asp Ile Ile Ile Asp Gly Gly Asn
1               5                   10                  15

Ser Glu Tyr Arg
            20

<210> SEQ ID NO 40
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 40

Val Glu Leu Ala Pro Leu Pro Ser Trp Gln Pro Val Gly Lys
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 41

Phe Gly Ser Leu Leu Pro Ile His Pro Val Thr Ser Gly
1               5                   10

<210> SEQ ID NO 42
<211> LENGTH: 12
<212> TYPE: PRT
```

```
<213> ORGANISM: Artificial Sequence
<220> FEATURE:
<223> OTHER INFORMATION: Synthetic Polypeptide

<400> SEQUENCE: 42

Gly Ala Thr Gly Ile Phe Pro Leu Ser Phe Val Lys
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 43

Leu Phe Leu Gly Gly Leu Asp Ala Leu Tyr Ser Leu Arg
1               5                   10

<210> SEQ ID NO 44
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 44

Thr Ala Phe Asp Glu Ala Ile Ala Glu Leu Asp Thr Leu Asn Glu Asp
1               5                   10                  15

Ser Tyr Lys

<210> SEQ ID NO 45
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 45

Val Asp Leu Glu Gly Glu Arg
1               5

<210> SEQ ID NO 46
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 46

Ala Phe Ala Leu Trp Ser Ala Val Thr Pro Leu Thr Phe Thr Arg
1               5                   10                  15

<210> SEQ ID NO 47
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 47

Leu Gly Ser Gly Asn Asp Phe Glu Val Phe Phe Gln Arg
1               5                   10

<210> SEQ ID NO 48
<211> LENGTH: 20
```

```
<212> TYPE: PRT
<213> ORGANISM: Artificial Sequence
<220> FEATURE:
<223> OTHER INFORMATION: Synthetic Polypeptide

<400> SEQUENCE: 48

Ala Leu Pro Gly Gln Leu Lys Pro Phe Glu Thr Leu Leu Ser Gln Asn
1               5                   10                  15

Gln Gly Gly Lys
            20

<210> SEQ ID NO 49
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 49

Phe Ser Val Ser Pro Val Val Arg
1               5

<210> SEQ ID NO 50
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 50

Leu Val Leu Val Gly Asp Gly Gly Thr Gly Lys
1               5                   10

<210> SEQ ID NO 51
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 51

Asn Val Arg Pro Asp Tyr Leu Lys
1               5

<210> SEQ ID NO 52
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 52

Gly Gln Ile Ile Gly Asn Phe Gln Ala Phe Asp Glu Asp Thr Gly Leu
1               5                   10                  15

Pro Ala His Ala Arg
            20

<210> SEQ ID NO 53
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 53

Tyr Val Gly Gly Gln Glu His Phe Ala His Leu Leu Ile Leu Arg
```

```
1               5                  10                 15
```

<210> SEQ ID NO 54
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 54

```
Asp His Ser Ala Ile Pro Val Ile Asn Arg
1               5                  10
```

<210> SEQ ID NO 55
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 55

```
Glu Ser Asp Thr Ser Tyr Val Ser Leu Lys
1               5                  10
```

<210> SEQ ID NO 56
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 56

```
Ser Phe Glu Gly Asn Asn Asn Tyr Asp Thr Pro Glu Leu Arg
1               5                  10
```

<210> SEQ ID NO 57
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 57

```
Val Leu Leu Pro Glu Tyr Gly Gly Thr Lys
1               5                  10
```

<210> SEQ ID NO 58
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 58

```
Tyr Ala Leu Tyr Asp Ala Thr Tyr Glu Thr Lys
1               5                  10
```

<210> SEQ ID NO 59
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 59

```
Ile Ser Ser Leu Arg Pro Gln Gly Leu Ser Asn Pro Ser Thr Leu Ser
1               5                  10                 15
```

Ala Gln Pro Gln Leu Ser Arg
            20

<210> SEQ ID NO 60
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 60

Ser Gln Val Val Ala Gly Thr Asn Tyr Phe Ile Lys
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 61

Val Ser Glu Ala Leu Gly Gln Gly Thr Arg
1               5                   10

<210> SEQ ID NO 62
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 62

Val Ala Gln Val Ser Ile Thr Lys
1               5

<210> SEQ ID NO 63
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 63

Thr Tyr Asn Phe Leu Pro Glu Phe Leu Val Ser Thr Gln Lys
1               5                   10

<210> SEQ ID NO 64
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 64

Phe Gly Ala Gln Leu Ala His Ile Gln Ala Leu Ile Ser Gly Ile Glu
1               5                   10                  15

Ala Gln Leu Gly Asp Val Arg
            20

<210> SEQ ID NO 65
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 65

Thr Pro Ile Leu Leu Ile Arg
1               5

<210> SEQ ID NO 66
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 66

Leu Ser Gln Asp Asp Ile Lys
1               5

<210> SEQ ID NO 67
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 67

Glu Leu Ser Asp Phe Ile Ser Tyr Leu Gln Arg
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 68

Leu Leu Leu Phe Pro Phe Leu Ser Pro Gln Arg
1               5                   10

<210> SEQ ID NO 69
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 69

Leu Phe Thr Pro Glu Glu Phe Phe Arg
1               5

<210> SEQ ID NO 70
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 70

Ala Val Phe Val Asp Leu Glu Pro Thr Val Ile Asp Glu Val Arg
1               5                   10                  15

<210> SEQ ID NO 71
<211> LENGTH: 11
<212> TYPE: PRT
<213> ORGANISM: Artificial Sequence
<220> FEATURE:
<223> OTHER INFORMATION: Synthetic Polypeptide

```
<400> SEQUENCE: 71

Ile His Pro Thr Ser Val Ile Ser Gly Tyr Arg
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 72

Gly Ile Leu Leu Tyr Gly Pro Pro Gly Thr Gly Lys
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 73

Gly Phe Gln Ala Leu Gly Asp Ala Ala Asp Ile Arg
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 74

Ala Ala Pro Phe Leu Thr Tyr Phe Gly Leu Phe Gln Val His
1               5                   10

<210> SEQ ID NO 75
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 75

Leu Val Glu Ile Ala Gln Val Pro Lys
1               5
```

COMPOSITIONS, METHODS AND KITS FOR DIAGNOSIS OF LUNG CANCER

RELATED APPLICATIONS

This application is a continuation-in-part of U.S. application Ser. No. 13/724,823, filed Dec. 21, 2012, which claims priority to, and the benefit of, U.S. Application No. 61/578,712, filed Dec. 21, 2011, U.S. Application No. 61/589,920, filed Jan. 24, 2012, U.S. Application No. 61/676,859, filed Jul. 27, 2012 and U.S. Application No. 61/725,153, filed Nov. 12, 2012, the contents of each of which are incorporated herein by reference in their entireties.

INCORPORATION-BY-REFERENCE OF SEQUENCE LISTING

The contents of the text file named "IDIA-005_X02US_Sequence Listing_ST25.txt", which was created on Feb. 27, 2015 and is 14 KB in size, are hereby incorporated by reference in their entireties.

BACKGROUND

Lung conditions and particularly lung cancer present significant diagnostic challenges. In many asymptomatic patients, radiological screens such as computed tomography (CT) scanning are a first step in the diagnostic paradigm. Pulmonary nodules (PNs) or indeterminate nodules are located in the lung and are often discovered during screening of both high risk patients or incidentally. The number of PNs identified is expected to rise due to increased numbers of patients with access to health care, the rapid adoption of screening techniques and an aging population. It is estimated that over 3 million PNs are identified annually in the US. Although the majority of PNs are benign, some are malignant leading to additional interventions. For patients considered low risk for malignant nodules, current medical practice dictates scans every three to six months for at least two years to monitor for lung cancer. The time period between identification of a PN and diagnosis is a time of medical surveillance or "watchful waiting" and may induce stress on the patient and lead to significant risk and expense due to repeated imaging studies. If a biopsy is performed on a patient who is found to have a benign nodule, the costs and potential for harm to the patient increase unnecessarily. Major surgery is indicated in order to excise a specimen for tissue biopsy and diagnosis. All of these procedures are associated with risk to the patient including: illness, injury and death as well as high economic costs.

Frequently, PNs cannot be biopsied to determine if they are benign or malignant due to their size and/or location in the lung. However, PNs are connected to the circulatory system, and so if malignant, protein markers of cancer can enter the blood and provide a signal for determining if a PN is malignant or not.

Diagnostic methods that can replace or complement current diagnostic methods for patients presenting with PNs are needed to improve diagnostics, reduce costs and minimize invasive procedures and complications to patients. The present invention provides novel compositions, methods and kits for identifying protein markers to identify, diagnose, classify and monitor lung conditions, and particularly lung cancer. The present invention uses a blood-based multiplexed assay to distinguish benign pulmonary nodules from malignant pulmonary nodules to classify patients with or without lung cancer. The present invention may be used in patients who present with symptoms of lung cancer, but do not have pulmonary nodules.

SUMMARY

The present invention provides a method of determining the likelihood that a lung condition in a subject is cancer by measuring an abundance of a panel of proteins in a sample obtained from the subject; calculating a probability of cancer score based on the protein measurements and ruling out cancer for the subject if the score is lower than a pre-determined score. When cancer is ruled out, the subject does not receive a treatment protocol. Treatment protocols include for example pulmonary function test (PFT), pulmonary imaging, a biopsy, a surgery, a chemotherapy, a radiotherapy, or any combination thereof. In some embodiments, the imaging is an x-ray, a chest computed tomography (CT) scan, or a positron emission tomography (PET) scan.

The present invention further provides a method of ruling in the likelihood of cancer for a subject by measuring an abundance of panel of proteins in a sample obtained from the subject, calculating a probability of cancer score based on the protein measurements and ruling in the likelihood of cancer for the subject if the score is higher than a pre-determined score.

In another aspect, the invention further provides a method of determining the likelihood of the presence of a lung condition in a subject by measuring an abundance of panel of proteins in a sample obtained from the subject, calculating a probability of cancer score based on the protein measurements and concluding the presence of said lung condition if the score is equal or greater than a pre-determined score. The lung condition is lung cancer such as for example, non-small cell lung cancer (NSCLC). The subject is at risk of developing lung cancer.

In some embodiments, the panel includes at least 3 proteins selected from ALDOA, FRIL, LG3BP, IBP3, LRP1, ISLR, TSP1, COIA1, GRP78, TETN, PRDX1 and CD14. Optionally, the panel further includes at least one protein selected from BGH3, COIA1, TETN, GRP78, PRDX, FIBA and GSLG1.

In some embodiments, the panel includes at least 4 proteins selected from ALDOA, FRIL, LG3BP, IBP3, LRP1, ISLR, TSP1, COIA1, GRP78, TETN, PRDX1 and CD14.

In a preferred embodiment, the panel comprises LRP1, COIA1, ALDOA, and LG3BP.

In another preferred embodiment, the panel comprises LRP1, COIA1, ALDOA, LG3BP, BGH3, PRDX1, TETN, and ISLR.

In yet another preferred embodiment, the panel comprises LRP1, COIA1, ALDOA, LG3BP, BGH3, PRDX1, TETN, ISLR, TSP1, GRP78, FRIL, FIBA and GSLG1.

The subject has or is suspected of having a pulmonary nodule. The pulmonary nodule has a diameter of less than or equal to 3 cm. In one embodiment, the pulmonary nodule has a diameter of about 0.8 cm to 2.0 cm.

The score is calculated from a logistic regression model applied to the protein measurements. For example, the score is determined as $P_s = 1/[1+\exp(-\alpha - \Sigma_{i=1}^{N} \beta_i * \tilde{I}_{i,s})]$, where $\tilde{I}_{i,s}$ is logarithmically transformed and normalized intensity of transition i in said sample (s), $\beta_i$ is the corresponding logistic regression coefficient, $\alpha$ was a panel-specific constant, and N was the total number of transitions in said panel.

In various embodiments, the method of the present invention further comprises normalizing the protein measurements. For example, the protein measurements are normalized by one or more proteins selected from PEDF, MASP1, GELS, LUM, C163A and PTPRJ.

The biological sample includes, such as for example tissue, blood, plasma, serum, whole blood, urine, saliva, genital secretion, cerebrospinal fluid, sweat and excreta.

In one aspect, the determining the likelihood of cancer is determined by the sensitivity, specificity, negative predictive value or positive predictive value associated with the score. The score determined has a negative predictive value (NPV) at least about 80%.

The measuring step is performed by selected reaction monitoring mass spectrometry, using a compound that specifically binds the protein being detected or a peptide transition. In one embodiment, the compound that specifically binds to the protein being measured is an antibody or an aptamer.

BRIEF DESCRIPTION OF THE DRAWINGS

FIG. 4 is a line graph showing area under the curve for a receiving operating curve for a 15 protein LC-SRM-MS panel.

FIG. 5 shows three line graphs each showing area under the curve for a receiving operating curve for a 15 protein LC-SRM-MS panel for a different patient population.

DETAILED DESCRIPTION

Figure 1:
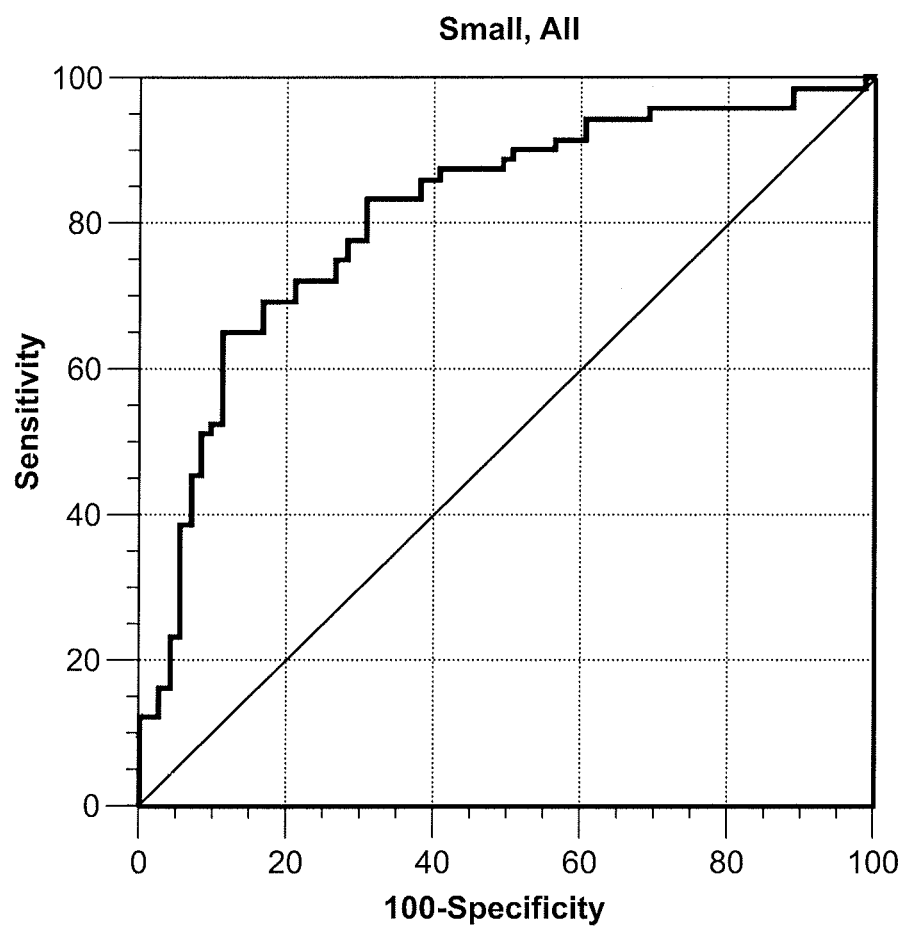
FIG. 1 is a line graph showing area under the curve for a receiving operating curve for 15 protein LC-SRM-MS panels.

The disclosed invention derives from the surprising discovery, that in patients presenting with pulmonary nodule(s), protein markers in the blood exist that specifically identify and classify lung cancer. Accordingly the invention provides unique advantages to the patient associated with early detection of lung cancer in a patient, including increased life span, decreased morbidity and mortality, decreased exposure to radiation during screening and repeat screenings and a minimally invasive diagnostic model. Importantly, the methods of the invention allow for a patient to avoid invasive procedures.

The routine clinical use of chest computed tomography (CT) scans identifies millions of pulmonary nodules annually, of which only a small minority are malignant but contribute to the dismal 15% five-year survival rate for patients diagnosed with non-small cell lung cancer (NSCLC). The early diagnosis of lung cancer in patients with pulmonary nodules is a top priority, as decision-making based on clinical presentation, in conjunction with current non-invasive diagnostic options such as chest CT and positron emission tomography (PET) scans, and other invasive alternatives, has not altered the clinical outcomes of patients with Stage I NSCLC. The subgroup of pulmonary nodules between 8 mm and 20 mm in size is increasingly recognized as being "intermediate" relative to the lower rate of malignancies below 8 mm and the higher rate of malignancies above 20 mm [9]. Invasive sampling of the lung nodule by biopsy using transthoracic needle aspiration or bronchoscopy may provide a cytopathologic diagnosis of NSCLC, but are also associated with both false-negative and non-diagnostic results. In summary, a key unmet clinical need for the management of pulmonary nodules is a non-invasive diagnostic test that discriminates between malignant and benign processes in patients with indeterminate pulmonary nodules (IPNs), especially between 8 mm and 20 mm in size.

The clinical decision to be more or less aggressive in treatment is based on risk factors, primarily nodule size, smoking history and age [9] in addition to imaging. As these are not conclusive, there is a great need for a molecular-based blood test that would be both non-invasive and provide complementary information to risk factors and imaging.

Accordingly, these and related embodiments will find uses in screening methods for lung conditions, and particularly lung cancer diagnostics. More importantly, the invention finds use in determining the clinical management of a patient. That is, the method of invention is useful in ruling in or ruling out a particular treatment protocol for an individual subject.

Cancer biology requires a molecular strategy to address the unmet medical need for an assessment of lung cancer risk. The field of diagnostic medicine has evolved with technology and assays that provide sensitive mechanisms for detection of changes in proteins. The methods described herein use a LC-SRM-MS technology for measuring the concentration of blood plasma proteins that are collectively changed in patients with a malignant PN. This protein signature is indicative of lung cancer. LC-SRM-MS is one method that provides for both quantification and identification of circulating proteins in plasma. Changes in protein expression levels, such as but not limited to signaling factors, growth factors, cleaved surface proteins and secreted proteins, can be detected using such a sensitive technology to assay cancer. Presented herein is a blood-based classification test to determine the likelihood that a patient presenting with a pulmonary nodule has a nodule that is benign or malignant. The present invention presents a classification algorithm that predicts the relative likelihood of the PN being benign or malignant.

More broadly, it is demonstrated that there are many variations on this invention that are also diagnostic tests for the likelihood that a PN is benign or malignant. These are variations on the panel of proteins, protein standards, measurement methodology and/or classification algorithm.

As disclosed herein, archival plasma samples from subjects presenting with PNs were analyzed for differential protein expression by mass spectrometry and the results were used to identify biomarker proteins and panels of biomarker proteins that are differentially expressed in conjunction with various lung conditions (cancer vs. non-cancer).

In one aspect of the invention, one hundred and sixty three panels were discovered that allow for the classification of PN as being benign or malignant. These panels include those listed on Table 1. In some embodiments the panel according to the invention includes measuring 1, 2, 3, 4, 5 or more proteins selected from ISLR, ALDOA, KIT, GRP78, AIFM1, CD14, COIA1, IBP3, TSP1, BGH3, TETN, FRI, LG3BP, GGH, PRDX1 or LRP1. In other embodiments the panel includes any panel or protein exemplified on Table 1. For, example the panel includes ALDOA, GRP78, CD14, COIA1, IBP3, FRIL, LG3BP, and LRP1

TABLE 1

| Identifier | Number Proteins | pAUC Factor | ISLR | ALDOA | KIT | GRP78 | AIFM1 | CD14 | COIA1 |
|---|---|---|---|---|---|---|---|---|---|
| 1 | 9 | 4.562 | 0 | 1 | 0 | 1 | 0 | 1 | 1 |
| 2 | 8 | 4.488 | 0 | 1 | 0 | 1 | 0 | 1 | 1 |
| 3 | 11 | 4.451 | 1 | 1 | 0 | 1 | 0 | 0 | 1 |
| 4 | 11 | 4.357 | 1 | 1 | 0 | 1 | 0 | 0 | 1 |
| 5 | 11 | 4.331 | 1 | 1 | 0 | 0 | 0 | 1 | 1 |
| 6 | 13 | 4.324 | 1 | 1 | 0 | 0 | 0 | 1 | 1 |
| 7 | 10 | 4.205 | 1 | 1 | 0 | 1 | 0 | 0 | 1 |
| 8 | 11 | 4.193 | 1 | 1 | 0 | 0 | 0 | 0 | 1 |
| 9 | 12 | 4.189 | 1 | 1 | 0 | 1 | 0 | 0 | 1 |
| 10 | 12 | 4.182 | 1 | 0 | 0 | 0 | 0 | 1 | 1 |
| 11 | 12 | 4.169 | 1 | 1 | 0 | 1 | 0 | 0 | 1 |
| 12 | 8 | 4.107 | 1 | 1 | 0 | 1 | 0 | 1 | 1 |
| 13 | 13 | 4.027 | 0 | 1 | 1 | 1 | 0 | 1 | 1 |
| 14 | 10 | 3.994 | 0 | 1 | 1 | 1 | 0 | 1 | 1 |
| 15 | 11 | 3.979 | 1 | 1 | 1 | 1 | 0 | 1 | 1 |
| 16 | 10 | 3.932 | 1 | 1 | 0 | 1 | 0 | 1 | 1 |
| 17 | 11 | 3.926 | 1 | 1 | 0 | 0 | 0 | 1 | 1 |
| 18 | 12 | 3.913 | 1 | 0 | 1 | 1 | 0 | 0 | 1 |
| 19 | 12 | 3.872 | 0 | 1 | 1 | 1 | 0 | 1 | 1 |
| 20 | 12 | 3.864 | 1 | 1 | 1 | 0 | 0 | 1 | 1 |
| 21 | 14 | 3.853 | 1 | 1 | 0 | 1 | 0 | 1 | 1 |
| 22 | 9 | 3.849 | 1 | 1 | 0 | 1 | 0 | 0 | 1 |
| 23 | 12 | 3.846 | 1 | 1 | 1 | 1 | 0 | 0 | 1 |
| 24 | 10 | 3.829 | 0 | 1 | 1 | 1 | 0 | 1 | 0 |
| 25 | 10 | 3.829 | 0 | 1 | 1 | 1 | 0 | 1 | 1 |
| 26 | 12 | 3.826 | 1 | 0 | 0 | 0 | 1 | 0 | 1 |
| 27 | 7 | 3.804 | 1 | 1 | 0 | 1 | 0 | 1 | 1 |
| 28 | 10 | 3.802 | 0 | 1 | 0 | 1 | 0 | 1 | 1 |
| 29 | 10 | 3.787 | 0 | 1 | 0 | 1 | 0 | 1 | 0 |
| 30 | 9 | 3.779 | 1 | 1 | 0 | 1 | 0 | 1 | 1 |
| 31 | 11 | 3.774 | 0 | 1 | 0 | 1 | 0 | 1 | 1 |
| 32 | 8 | 3.759 | 1 | 1 | 0 | 0 | 0 | 0 | 1 |
| 33 | 13 | 3.758 | 1 | 1 | 0 | 0 | 0 | 1 | 1 |
| 34 | 11 | 3.757 | 1 | 1 | 0 | 1 | 0 | 0 | 0 |
| 35 | 12 | 3.754 | 0 | 1 | 1 | 1 | 0 | 1 | 1 |
| 36 | 10 | 3.750 | 1 | 1 | 0 | 1 | 0 | 1 | 1 |
| 37 | 11 | 3.747 | 0 | 1 | 1 | 1 | 0 | 1 | 1 |
| 38 | 12 | 3.744 | 1 | 0 | 1 | 1 | 0 | 0 | 1 |
| 39 | 11 | 3.742 | 1 | 1 | 0 | 1 | 0 | 1 | 1 |
| 40 | 9 | 3.740 | 1 | 1 | 0 | 1 | 0 | 1 | 1 |
| 41 | 12 | 3.740 | 1 | 1 | 1 | 1 | 0 | 1 | 1 |
| 42 | 12 | 3.739 | 1 | 1 | 0 | 1 | 0 | 1 | 1 |
| 43 | 9 | 3.734 | 1 | 1 | 0 | 0 | 0 | 0 | 1 |
| 44 | 12 | 3.730 | 1 | 1 | 0 | 1 | 0 | 0 | 1 |
| 45 | 11 | 3.725 | 0 | 1 | 1 | 1 | 0 | 1 | 1 |
| 46 | 12 | 3.717 | 0 | 1 | 0 | 0 | 1 | 1 | 1 |
| 47 | 9 | 3.713 | 0 | 1 | 0 | 1 | 0 | 1 | 1 |
| 48 | 9 | 3.713 | 1 | 1 | 1 | 1 | 0 | 1 | 1 |
| 49 | 10 | 3.709 | 0 | 1 | 0 | 1 | 0 | 1 | 1 |
| 50 | 11 | 3.709 | 1 | 1 | 0 | 1 | 0 | 1 | 1 |
| 51 | 11 | 3.701 | 0 | 1 | 1 | 1 | 1 | 1 | 1 |
| 52 | 12 | 3.685 | 1 | 1 | 0 | 1 | 0 | 1 | 1 |
| 53 | 10 | 3.680 | 0 | 0 | 0 | 1 | 0 | 1 | 0 |
| 54 | 11 | 3.676 | 1 | 1 | 1 | 1 | 0 | 0 | 1 |
| 55 | 9 | 3.668 | 0 | 1 | 0 | 1 | 0 | 1 | 1 |

TABLE 1-continued

| | | | | | | | | | |
|---|---|---|---|---|---|---|---|---|---|
| 56 | 9 | 3.659 | 0 | 0 | 0 | 1 | 0 | 1 | 0 |
| 57 | 14 | 3.657 | 1 | 1 | 0 | 1 | 1 | 1 | 1 |
| 58 | 10 | 3.655 | 1 | 1 | 0 | 1 | 0 | 0 | 1 |
| 59 | 11 | 3.643 | 0 | 1 | 1 | 1 | 0 | 1 | 1 |
| 60 | 9 | 3.643 | 0 | 1 | 0 | 1 | 0 | 1 | 0 |
| 61 | 8 | 3.640 | 1 | 1 | 0 | 1 | 0 | 1 | 0 |
| 62 | 12 | 3.640 | 1 | 1 | 1 | 1 | 0 | 1 | 1 |
| 63 | 10 | 3.638 | 1 | 1 | 0 | 1 | 0 | 0 | 1 |
| 64 | 12 | 3.633 | 1 | 0 | 0 | 1 | 1 | 0 | 1 |
| 65 | 10 | 3.632 | 1 | 1 | 0 | 1 | 0 | 1 | 1 |
| 66 | 11 | 3.627 | 1 | 1 | 0 | 1 | 0 | 1 | 0 |
| 67 | 10 | 3.627 | 1 | 1 | 0 | 0 | 0 | 1 | 0 |
| 68 | 10 | 3.623 | 1 | 1 | 1 | 0 | 0 | 0 | 1 |
| 69 | 11 | 3.619 | 1 | 0 | 0 | 1 | 0 | 1 | 1 |
| 70 | 6 | 3.617 | 1 | 1 | 0 | 1 | 0 | 0 | 1 |
| 71 | 12 | 3.617 | 1 | 0 | 0 | 1 | 0 | 1 | 1 |
| 72 | 11 | 3.613 | 1 | 1 | 0 | 1 | 0 | 1 | 0 |
| 73 | 11 | 3.608 | 1 | 1 | 0 | 1 | 0 | 1 | 0 |
| 74 | 13 | 3.608 | 1 | 1 | 1 | 1 | 0 | 1 | 1 |
| 75 | 11 | 3.605 | 0 | 1 | 1 | 1 | 0 | 1 | 1 |
| 76 | 11 | 3.602 | 0 | 1 | 1 | 1 | 0 | 1 | 1 |
| 77 | 10 | 3.600 | 1 | 1 | 0 | 1 | 0 | 0 | 0 |
| 78 | 11 | 3.596 | 1 | 1 | 0 | 1 | 0 | 0 | 1 |
| 79 | 10 | 3.592 | 1 | 1 | 0 | 1 | 0 | 1 | 0 |
| 80 | 11 | 3.587 | 1 | 0 | 1 | 0 | 0 | 0 | 1 |
| 81 | 13 | 3.584 | 1 | 1 | 0 | 1 | 1 | 1 | 1 |
| 82 | 8 | 3.584 | 0 | 1 | 0 | 1 | 0 | 1 | 0 |
| 83 | 11 | 3.581 | 1 | 1 | 1 | 1 | 0 | 1 | 0 |
| 84 | 13 | 3.578 | 1 | 1 | 0 | 1 | 0 | 1 | 0 |
| 85 | 9 | 3.573 | 1 | 1 | 1 | 0 | 0 | 1 | 1 |
| 86 | 9 | 3.572 | 1 | 1 | 0 | 1 | 0 | 0 | 1 |
| 87 | 13 | 3.571 | 1 | 1 | 1 | 1 | 0 | 1 | 0 |
| 88 | 10 | 3.569 | 1 | 1 | 0 | 1 | 0 | 0 | 1 |
| 89 | 9 | 3.569 | 0 | 1 | 0 | 1 | 0 | 1 | 0 |
| 90 | 8 | 3.559 | 0 | 1 | 0 | 1 | 0 | 1 | 0 |
| 91 | 10 | 3.558 | 0 | 1 | 0 | 1 | 0 | 1 | 0 |
| 92 | 12 | 3.554 | 1 | 1 | 0 | 1 | 0 | 1 | 1 |
| 93 | 11 | 3.552 | 0 | 1 | 0 | 1 | 0 | 1 | 0 |
| 94 | 12 | 3.549 | 0 | 1 | 0 | 1 | 0 | 1 | 0 |
| 95 | 8 | 3.547 | 1 | 1 | 1 | 0 | 0 | 1 | 1 |
| 96 | 12 | 3.545 | 1 | 1 | 1 | 1 | 0 | 1 | 1 |
| 97 | 8 | 3.542 | 1 | 1 | 1 | 0 | 0 | 0 | 0 |
| 98 | 11 | 3.536 | 1 | 1 | 1 | 1 | 0 | 0 | 1 |
| 99 | 14 | 3.530 | 1 | 1 | 1 | 1 | 0 | 1 | 1 |
| 100 | 9 | 3.527 | 1 | 1 | 0 | 1 | 0 | 1 | 1 |
| 101 | 10 | 3.522 | 0 | 1 | 1 | 0 | 1 | 1 | 1 |
| 102 | 12 | 3.509 | 1 | 1 | 0 | 1 | 0 | 1 | 1 |
| 103 | 5 | 3.505 | 0 | 1 | 0 | 0 | 0 | 1 | 0 |
| 104 | 11 | 3.500 | 1 | 1 | 0 | 0 | 1 | 0 | 1 |
| 105 | 11 | 3.497 | 1 | 1 | 1 | 1 | 0 | 0 | 1 |
| 106 | 9 | 3.491 | 1 | 1 | 0 | 0 | 0 | 1 | 0 |
| 107 | 7 | 3.489 | 0 | 1 | 1 | 0 | 0 | 1 | 0 |
| 108 | 13 | 3.486 | 1 | 1 | 1 | 1 | 0 | 1 | 1 |
| 109 | 11 | 3.483 | 1 | 1 | 1 | 1 | 0 | 0 | 1 |
| 110 | 10 | 3.477 | 1 | 1 | 1 | 1 | 0 | 1 | 1 |
| 111 | 10 | 3.473 | 1 | 1 | 0 | 0 | 0 | 1 | 1 |
| 112 | 15 | 3.468 | 1 | 1 | 0 | 1 | 1 | 1 | 1 |
| 113 | 10 | 3.467 | 0 | 1 | 0 | 0 | 1 | 1 | 0 |
| 114 | 12 | 3.467 | 1 | 1 | 0 | 0 | 1 | 1 | 1 |
| 115 | 13 | 3.467 | 1 | 1 | 0 | 1 | 1 | 0 | 1 |
| 116 | 10 | 3.467 | 0 | 1 | 0 | 1 | 0 | 1 | 0 |
| 117 | 8 | 3.465 | 1 | 1 | 0 | 1 | 0 | 0 | 1 |
| 118 | 10 | 3.464 | 0 | 1 | 0 | 1 | 1 | 1 | 1 |
| 119 | 15 | 3.464 | 1 | 1 | 0 | 1 | 1 | 1 | 1 |
| 120 | 11 | 3.462 | 1 | 1 | 0 | 1 | 0 | 1 | 1 |
| 121 | 9 | 3.460 | 1 | 1 | 0 | 0 | 0 | 1 | 0 |
| 122 | 13 | 3.453 | 1 | 1 | 0 | 1 | 0 | 1 | 1 |
| 123 | 12 | 3.449 | 1 | 1 | 1 | 0 | 0 | 1 | 0 |
| 124 | 10 | 3.448 | 1 | 1 | 0 | 1 | 0 | 1 | 0 |
| 125 | 10 | 3.445 | 0 | 1 | 1 | 1 | 0 | 1 | 0 |
| 126 | 6 | 3.441 | 0 | 1 | 0 | 0 | 0 | 1 | 0 |
| 127 | 11 | 3.440 | 1 | 1 | 0 | 1 | 0 | 1 | 0 |
| 128 | 12 | 3.440 | 1 | 1 | 0 | 1 | 1 | 0 | 0 |
| 129 | 11 | 3.439 | 1 | 1 | 0 | 1 | 0 | 1 | 0 |
| 130 | 10 | 3.426 | 0 | 1 | 0 | 0 | 1 | 0 | 0 |
| 131 | 11 | 3.423 | 1 | 1 | 0 | 0 | 0 | 0 | 1 |
| 132 | 10 | 3.420 | 1 | 1 | 0 | 0 | 0 | 1 | 0 |
| 133 | 10 | 3.419 | 1 | 1 | 1 | 1 | 0 | 1 | 0 |
| 134 | 11 | 3.417 | 1 | 1 | 0 | 1 | 1 | 0 | 1 |
| 135 | 12 | 3.414 | 0 | 1 | 0 | 1 | 1 | 1 | 1 |

TABLE 1-continued

| | | | | | | | | | |
|---|---|---|---|---|---|---|---|---|---|
| 136 | 10 | 3.413 | 0 | 1 | 1 | 1 | 0 | 1 | 0 |
| 137 | 11 | 3.400 | 0 | 1 | 0 | 0 | 1 | 1 | 0 |
| 138 | 12 | 3.398 | 1 | 1 | 0 | 1 | 0 | 1 | 0 |
| 139 | 13 | 3.396 | 1 | 1 | 0 | 1 | 0 | 1 | 0 |
| 140 | 9 | 3.386 | 1 | 1 | 0 | 0 | 0 | 1 | 0 |
| 141 | 9 | 3.373 | 1 | 1 | 0 | 1 | 0 | 1 | 0 |
| 142 | 12 | 3.363 | 1 | 1 | 0 | 0 | 1 | 0 | 1 |
| 143 | 8 | 3.362 | 0 | 1 | 0 | 1 | 0 | 1 | 0 |
| 144 | 10 | 3.360 | 1 | 1 | 0 | 1 | 0 | 1 | 1 |
| 145 | 9 | 3.359 | 1 | 1 | 1 | 0 | 0 | 1 | 0 |
| 146 | 7 | 3.349 | 0 | 1 | 0 | 0 | 0 | 0 | 0 |
| 147 | 7 | 3.348 | 1 | 1 | 0 | 0 | 0 | 1 | 1 |
| 148 | 9 | 3.340 | 1 | 0 | 0 | 0 | 0 | 1 | 0 |
| 149 | 9 | 3.335 | 1 | 1 | 0 | 1 | 0 | 1 | 0 |
| 150 | 11 | 3.333 | 0 | 1 | 1 | 1 | 0 | 1 | 0 |
| 151 | 9 | 3.333 | 0 | 0 | 0 | 1 | 0 | 1 | 0 |
| 152 | 10 | 3.328 | 1 | 1 | 0 | 1 | 0 | 1 | 0 |
| 153 | 7 | 3.315 | 0 | 1 | 0 | 1 | 0 | 1 | 0 |
| 154 | 11 | 3.311 | 1 | 1 | 0 | 1 | 1 | 1 | 1 |
| 155 | 11 | 3.293 | 1 | 1 | 0 | 1 | 0 | 1 | 0 |
| 156 | 8 | 3.292 | 1 | 1 | 0 | 1 | 0 | 0 | 0 |
| 157 | 9 | 3.289 | 0 | 1 | 0 | 1 | 0 | 1 | 0 |
| 158 | 7 | 3.229 | 0 | 1 | 0 | 0 | 0 | 1 | 0 |
| 159 | 7 | 3.229 | 1 | 1 | 0 | 0 | 0 | 1 | 0 |
| 160 | 7 | 3.203 | 1 | 1 | 0 | 1 | 0 | 0 | 0 |
| 161 | 12 | 3.161 | 1 | 1 | 1 | 0 | 1 | 1 | 0 |
| 162 | 9 | 3.138 | 1 | 1 | 0 | 0 | 1 | 0 | 1 |
| 163 | 13 | 3.078 | 1 | 1 | 0 | 0 | 1 | 0 | 1 |

| | Proteins | | | | | | | | |
|---|---|---|---|---|---|---|---|---|---|
| Identifier | IBP3 | TSP1 | BGH3 | TETN | FRIL | LG3BP | GGH | PRDX1 | LRP1 |
| 1 | 1 | 0 | 0 | 0 | 1 | 1 | 0 | 0 | 1 |
| 2 | 1 | 0 | 0 | 0 | 1 | 1 | 0 | 0 | 1 |
| 3 | 1 | 1 | 1 | 1 | 1 | 0 | 0 | 1 | 1 |
| 4 | 1 | 1 | 0 | 0 | 1 | 1 | 1 | 1 | 1 |
| 5 | 0 | 1 | 1 | 1 | 1 | 0 | 1 | 1 | 1 |
| 6 | 1 | 1 | 1 | 1 | 1 | 1 | 1 | 1 | 1 |
| 7 | 0 | 1 | 1 | 1 | 1 | 0 | 0 | 1 | 1 |
| 8 | 0 | 1 | 1 | 1 | 1 | 0 | 1 | 1 | 1 |
| 9 | 1 | 1 | 1 | 1 | 1 | 0 | 0 | 1 | 1 |
| 10 | 1 | 1 | 1 | 1 | 1 | 1 | 0 | 1 | 1 |
| 11 | 1 | 1 | 0 | 0 | 1 | 1 | 1 | 1 | 1 |
| 12 | 0 | 0 | 0 | 0 | 1 | 1 | 0 | 0 | 1 |
| 13 | 1 | 1 | 0 | 0 | 1 | 1 | 1 | 1 | 1 |
| 14 | 1 | 0 | 0 | 0 | 1 | 1 | 0 | 0 | 1 |
| 15 | 0 | 0 | 0 | 0 | 1 | 1 | 1 | 0 | 1 |
| 16 | 0 | 0 | 0 | 1 | 1 | 1 | 0 | 0 | 1 |
| 17 | 1 | 1 | 1 | 1 | 1 | 0 | 0 | 1 | 1 |
| 18 | 1 | 1 | 0 | 0 | 1 | 1 | 1 | 1 | 1 |
| 19 | 1 | 0 | 0 | 0 | 1 | 1 | 1 | 1 | 1 |
| 20 | 0 | 1 | 1 | 1 | 1 | 1 | 0 | 1 | 1 |
| 21 | 1 | 1 | 1 | 1 | 1 | 1 | 0 | 1 | 1 |
| 22 | 0 | 1 | 1 | 1 | 1 | 0 | 0 | 0 | 1 |
| 23 | 1 | 1 | 0 | 0 | 1 | 1 | 1 | 1 | 1 |
| 24 | 1 | 0 | 0 | 0 | 1 | 1 | 1 | 1 | 1 |
| 25 | 1 | 0 | 0 | 0 | 1 | 1 | 1 | 0 | 1 |
| 26 | 1 | 1 | 1 | 1 | 1 | 0 | 1 | 1 | 1 |
| 27 | 0 | 0 | 0 | 0 | 0 | 1 | 0 | 0 | 1 |
| 28 | 1 | 0 | 0 | 0 | 1 | 1 | 1 | 1 | 1 |
| 29 | 1 | 1 | 0 | 0 | 1 | 1 | 1 | 1 | 1 |
| 30 | 0 | 0 | 0 | 0 | 1 | 1 | 0 | 0 | 1 |
| 31 | 1 | 0 | 0 | 0 | 1 | 1 | 1 | 1 | 1 |
| 32 | 0 | 0 | 1 | 1 | 1 | 0 | 0 | 1 | 1 |
| 33 | 1 | 1 | 1 | 1 | 1 | 1 | 0 | 1 | 1 |
| 34 | 1 | 1 | 1 | 1 | 1 | 1 | 0 | 1 | 1 |
| 35 | 1 | 1 | 0 | 0 | 1 | 1 | 1 | 1 | 1 |
| 36 | 1 | 0 | 0 | 0 | 1 | 1 | 0 | 1 | 1 |
| 37 | 1 | 1 | 0 | 0 | 1 | 1 | 1 | 1 | 0 |
| 38 | 1 | 1 | 1 | 1 | 1 | 0 | 0 | 0 | 1 |
| 39 | 1 | 1 | 0 | 1 | 1 | 1 | 0 | 0 | 1 |
| 40 | 1 | 0 | 0 | 0 | 1 | 1 | 0 | 0 | 1 |
| 41 | 1 | 0 | 0 | 1 | 1 | 1 | 0 | 0 | 1 |
| 42 | 1 | 1 | 0 | 0 | 1 | 1 | 1 | 1 | 1 |
| 43 | 0 | 1 | 1 | 1 | 1 | 0 | 0 | 1 | 1 |
| 44 | 1 | 1 | 1 | 1 | 1 | 1 | 0 | 1 | 1 |
| 45 | 1 | 0 | 0 | 1 | 1 | 1 | 0 | 0 | 1 |
| 46 | 1 | 1 | 1 | 1 | 1 | 1 | 1 | 1 | 0 |
| 47 | 1 | 0 | 0 | 0 | 1 | 1 | 0 | 1 | 1 |

TABLE 1-continued

| | | | | | | | | | |
|---|---|---|---|---|---|---|---|---|---|
| 48 | 0 | 0 | 0 | 0 | 1 | 1 | 0 | 0 | 1 |
| 49 | 1 | 0 | 0 | 0 | 1 | 1 | 1 | 0 | 1 |
| 50 | 0 | 1 | 1 | 1 | 1 | 1 | 0 | 0 | 1 |
| 51 | 1 | 0 | 0 | 0 | 1 | 1 | 0 | 0 | 1 |
| 52 | 1 | 1 | 1 | 1 | 1 | 1 | 0 | 0 | 1 |
| 53 | 1 | 1 | 1 | 1 | 1 | 1 | 0 | 1 | 1 |
| 54 | 0 | 1 | 1 | 1 | 1 | 0 | 0 | 1 | 1 |
| 55 | 1 | 0 | 0 | 0 | 1 | 1 | 1 | 0 | 1 |
| 56 | 1 | 1 | 0 | 0 | 1 | 1 | 1 | 1 | 0 |
| 57 | 1 | 1 | 1 | 1 | 1 | 0 | 0 | 1 | 1 |
| 58 | 0 | 1 | 0 | 0 | 1 | 1 | 1 | 0 | 1 |
| 59 | 1 | 0 | 0 | 0 | 1 | 1 | 1 | 1 | 1 |
| 60 | 1 | 0 | 1 | 0 | 1 | 1 | 0 | 0 | 1 |
| 61 | 1 | 0 | 0 | 0 | 1 | 1 | 0 | 0 | 1 |
| 62 | 0 | 0 | 0 | 1 | 1 | 1 | 0 | 1 | 1 |
| 63 | 0 | 1 | 1 | 1 | 1 | 1 | 0 | 0 | 1 |
| 64 | 1 | 1 | 1 | 1 | 1 | 0 | 0 | 1 | 1 |
| 65 | 1 | 0 | 0 | 0 | 1 | 1 | 0 | 0 | 1 |
| 66 | 1 | 1 | 1 | 1 | 1 | 1 | 0 | 0 | 1 |
| 67 | 1 | 1 | 1 | 1 | 1 | 1 | 0 | 0 | 1 |
| 68 | 0 | 1 | 1 | 1 | 1 | 1 | 0 | 0 | 1 |
| 69 | 1 | 1 | 1 | 0 | 1 | 1 | 0 | 0 | 1 |
| 70 | 0 | 0 | 0 | 0 | 0 | 1 | 0 | 0 | 1 |
| 71 | 1 | 1 | 1 | 1 | 1 | 0 | 0 | 1 | 1 |
| 72 | 1 | 1 | 0 | 0 | 1 | 1 | 1 | 1 | 1 |
| 73 | 1 | 1 | 1 | 0 | 1 | 1 | 0 | 1 | 1 |
| 74 | 1 | 1 | 0 | 0 | 1 | 1 | 0 | 1 | 1 |
| 75 | 1 | 0 | 0 | 0 | 1 | 1 | 0 | 1 | 1 |
| 76 | 1 | 0 | 0 | 0 | 1 | 1 | 1 | 0 | 1 |
| 77 | 1 | 1 | 1 | 1 | 1 | 1 | 0 | 1 | 0 |
| 78 | 1 | 1 | 1 | 1 | 1 | 0 | 1 | 0 | 1 |
| 79 | 1 | 1 | 0 | 0 | 1 | 1 | 0 | 1 | 1 |
| 80 | 1 | 1 | 1 | 1 | 0 | 1 | 0 | 1 | 1 |
| 81 | 1 | 1 | 1 | 1 | 1 | 1 | 0 | 0 | 1 |
| 82 | 1 | 1 | 0 | 0 | 1 | 1 | 0 | 1 | 0 |
| 83 | 1 | 1 | 0 | 0 | 1 | 1 | 1 | 1 | 0 |
| 84 | 1 | 1 | 1 | 1 | 1 | 1 | 0 | 1 | 1 |
| 85 | 1 | 0 | 0 | 0 | 1 | 1 | 0 | 0 | 0 |
| 86 | 0 | 1 | 0 | 0 | 1 | 1 | 0 | 0 | 1 |
| 87 | 1 | 1 | 0 | 0 | 1 | 1 | 1 | 1 | 1 |
| 88 | 1 | 1 | 0 | 1 | 1 | 0 | 0 | 1 | 1 |
| 89 | 1 | 1 | 0 | 0 | 1 | 1 | 0 | 1 | 1 |
| 90 | 1 | 0 | 0 | 0 | 1 | 1 | 0 | 0 | 1 |
| 91 | 1 | 0 | 0 | 1 | 1 | 1 | 1 | 1 | 1 |
| 92 | 0 | 1 | 1 | 1 | 1 | 0 | 1 | 1 | 1 |
| 93 | 1 | 1 | 0 | 0 | 1 | 1 | 1 | 1 | 1 |
| 94 | 1 | 1 | 1 | 1 | 1 | 1 | 1 | 1 | 1 |
| 95 | 1 | 1 | 0 | 0 | 0 | 1 | 0 | 0 | 0 |
| 96 | 1 | 0 | 0 | 0 | 1 | 1 | 1 | 0 | 1 |
| 97 | 1 | 1 | 0 | 1 | 0 | 1 | 0 | 0 | 0 |
| 98 | 1 | 0 | 0 | 0 | 1 | 1 | 1 | 1 | 1 |
| 99 | 1 | 1 | 0 | 1 | 1 | 1 | 1 | 1 | 0 |
| 100 | 0 | 1 | 0 | 0 | 1 | 1 | 0 | 0 | 1 |
| 101 | 1 | 1 | 0 | 0 | 1 | 1 | 0 | 1 | 0 |
| 102 | 0 | 0 | 1 | 1 | 1 | 1 | 0 | 1 | 1 |
| 103 | 1 | 1 | 0 | 0 | 0 | 1 | 0 | 0 | 0 |
| 104 | 1 | 1 | 1 | 1 | 1 | 0 | 1 | 1 | 0 |
| 105 | 1 | 1 | 0 | 0 | 1 | 1 | 0 | 0 | 1 |
| 106 | 1 | 1 | 0 | 0 | 0 | 1 | 1 | 1 | 0 |
| 107 | 1 | 1 | 0 | 0 | 0 | 1 | 0 | 1 | 0 |
| 108 | 1 | 0 | 0 | 1 | 1 | 1 | 0 | 1 | 1 |
| 109 | 1 | 0 | 0 | 0 | 1 | 1 | 1 | 0 | 1 |
| 110 | 1 | 0 | 0 | 0 | 1 | 1 | 0 | 0 | 1 |
| 111 | 0 | 0 | 1 | 1 | 1 | 1 | 0 | 0 | 1 |
| 112 | 1 | 1 | 1 | 1 | 1 | 0 | 1 | 1 | 1 |
| 113 | 1 | 1 | 1 | 1 | 1 | 1 | 0 | 1 | 0 |
| 114 | 1 | 1 | 1 | 1 | 0 | 1 | 0 | 0 | 1 |
| 115 | 1 | 1 | 1 | 1 | 1 | 0 | 0 | 1 | 1 |
| 116 | 1 | 1 | 0 | 0 | 1 | 1 | 1 | 0 | 1 |
| 117 | 0 | 1 | 0 | 0 | 1 | 1 | 0 | 0 | 1 |
| 118 | 1 | 0 | 0 | 0 | 1 | 1 | 0 | 0 | 1 |
| 119 | 1 | 1 | 1 | 1 | 1 | 1 | 1 | 1 | 0 |
| 120 | 0 | 0 | 0 | 1 | 1 | 1 | 0 | 1 | 1 |
| 121 | 1 | 1 | 1 | 1 | 0 | 1 | 0 | 1 | 0 |
| 122 | 1 | 1 | 1 | 1 | 1 | 1 | 1 | 1 | 0 |
| 123 | 1 | 1 | 0 | 1 | 1 | 1 | 1 | 1 | 0 |
| 124 | 1 | 1 | 0 | 0 | 1 | 1 | 1 | 1 | 0 |
| 125 | 1 | 1 | 0 | 0 | 1 | 1 | 0 | 1 | 1 |
| 126 | 1 | 1 | 0 | 0 | 0 | 1 | 0 | 0 | 0 |
| 127 | 1 | 1 | 0 | 0 | 1 | 1 | 1 | 0 | 1 |

TABLE 1-continued

|     | | | | | | | | | |
| --- | --- | --- | --- | --- | --- | --- | --- | --- | --- |
| 128 | 1 | 1 | 1 | 1 | 1 | 0 | 0 | 1 | 1 |
| 129 | 1 | 0 | 0 | 0 | 1 | 1 | 1 | 1 | 1 |
| 130 | 1 | 1 | 1 | 1 | 0 | 1 | 0 | 1 | 0 |
| 131 | 1 | 1 | 1 | 1 | 1 | 1 | 1 | 1 | 0 |
| 132 | 1 | 1 | 0 | 1 | 1 | 1 | 1 | 1 | 0 |
| 133 | 1 | 0 | 0 | 0 | 1 | 1 | 0 | 0 | 1 |
| 134 | 0 | 0 | 1 | 1 | 1 | 0 | 0 | 1 | 1 |
| 135 | 1 | 1 | 0 | 1 | 1 | 1 | 0 | 0 | 1 |
| 136 | 1 | 1 | 0 | 0 | 1 | 1 | 0 | 1 | 0 |
| 137 | 1 | 1 | 1 | 1 | 1 | 1 | 0 | 1 | 0 |
| 138 | 1 | 0 | 1 | 1 | 1 | 1 | 1 | 1 | 1 |
| 139 | 1 | 1 | 1 | 1 | 1 | 1 | 1 | 1 | 1 |
| 140 | 1 | 1 | 0 | 0 | 1 | 1 | 1 | 1 | 0 |
| 141 | 1 | 0 | 0 | 0 | 1 | 1 | 0 | 0 | 1 |
| 142 | 1 | 1 | 1 | 1 | 1 | 1 | 1 | 1 | 0 |
| 143 | 1 | 0 | 0 | 0 | 1 | 1 | 0 | 1 | 1 |
| 144 | 0 | 0 | 0 | 1 | 1 | 1 | 0 | 1 | 0 |
| 145 | 1 | 1 | 0 | 0 | 1 | 1 | 0 | 0 | 0 |
| 146 | 1 | 1 | 1 | 1 | 0 | 1 | 0 | 0 | 0 |
| 147 | 1 | 1 | 0 | 0 | 0 | 1 | 0 | 0 | 0 |
| 148 | 1 | 1 | 1 | 1 | 0 | 1 | 0 | 1 | 0 |
| 149 | 1 | 1 | 0 | 0 | 1 | 1 | 0 | 0 | 1 |
| 150 | 1 | 1 | 0 | 0 | 1 | 1 | 0 | 1 | 1 |
| 151 | 1 | 1 | 1 | 0 | 1 | 1 | 0 | 0 | 1 |
| 152 | 1 | 0 | 0 | 0 | 1 | 1 | 1 | 0 | 1 |
| 153 | 1 | 0 | 0 | 0 | 1 | 1 | 0 | 0 | 1 |
| 154 | 0 | 0 | 0 | 1 | 1 | 1 | 1 | 0 | 0 |
| 155 | 1 | 0 | 1 | 0 | 1 | 1 | 0 | 1 | 1 |
| 156 | 1 | 1 | 0 | 0 | 1 | 1 | 0 | 0 | 1 |
| 157 | 1 | 1 | 0 | 0 | 1 | 1 | 0 | 1 | 0 |
| 158 | 1 | 1 | 0 | 0 | 1 | 1 | 0 | 0 | 0 |
| 159 | 1 | 1 | 0 | 0 | 0 | 1 | 0 | 1 | 0 |
| 160 | 1 | 0 | 0 | 0 | 1 | 1 | 0 | 0 | 1 |
| 161 | 1 | 1 | 1 | 1 | 1 | 1 | 0 | 1 | 0 |
| 162 | 0 | 0 | 1 | 1 | 1 | 1 | 0 | 0 | 0 |
| 163 | 1 | 1 | 1 | 1 | 1 | 1 | 1 | 1 | 0 |

1 = in the panel;
0 = not in the panel.

The one hundred best random panels of proteins out of the 35 million generated are shown in Table 2.

TABLE 2

|   | Protein 1 | Protein 2 | Protein 3 | Protein 4 | Protein 5 | Protein 6 | Protein 7 | Protein 8 | Protein 9 | Protein 10 |
| --- | --- | --- | --- | --- | --- | --- | --- | --- | --- | --- |
| 1 | IBP3 | TSP1 | CO6A3 | PDIA3 | SEM3G | SAA | 6PGD | EF1A1 | PRDX1 | TERA |
| 2 | EPHB6 | CNTN1 | CLUS | IBP3 | BGH3 | 6PGD | FRIL | LRP1 | TBB3 | ERO1A |
| 3 | PPIB | LG3BP | MDHC | DSG2 | BST1 | CD14 | DESP | PRDX1 | CDCP1 | MMP9 |
| 4 | TPIS | COIA1 | IBP3 | GGH | ISLR | MMP2 | AIFM1 | DSG2 | 1433T | CBPB2 |
| 5 | TPIS | IBP3 | CH10 | SEM3G | 6PGD | FRIL | ICAM3 | TERA | FINC | ERO1A |
| 6 | BGH3 | ICAM1 | MMP12 | 6PGD | CD14 | EF1A1 | HYOU1 | PLXC1 | PROF1 | ERO1A |
| 7 | KIT | LG3BP | TPIS | IBP3 | LDHB | GGH | TCPA | ISLR | CBPB2 | EF1A1 |
| 8 | LG3BP | IBP3 | LDHB | TSP1 | CRP | ZA2G | CD14 | LRP1 | PLIN2 | ERO1A |
| 9 | COIA1 | TSP1 | ISLR | TFR1 | CBPB2 | FRIL | LRP1 | UGPA | PTPA | ERO1A |
| 10 | CO6A3 | SEM3G | APOE | FRIL | ICAM3 | PRDX1 | EF2 | HS90B | NCF4 | PTPA |
| 11 | PPIB | LG3BP | COIA1 | APOA1 | DSG2 | APOE | CD14 | PLXC1 | NCF4 | GSLG1 |
| 12 | SODM | EPHB6 | C163A | COIA1 | LDHB | TETN | 1433T | CD14 | PTPA | ERO1A |
| 13 | SODM | KPYM | IBP3 | TSP1 | BGH3 | SEM3G | 6PGD | CD14 | RAP2B | EREG |
| 14 | EPHB6 | ALDOA | MMP7 | COIA1 | TIMP1 | GRP78 | MMP12 | CBPB2 | G3P | PTPA |
| 15 | KIT | TSP1 | SCF | TIMP1 | OSTP | PDIA3 | GRP78 | TNF12 | PRDX1 | PTPA |
| 16 | IBP2 | LG3BP | GELS | HPT | FIBA | GGH | ICAM1 | BST1 | HYOU1 | GSLG1 |
| 17 | KIT | CD44 | CH10 | PEDF | ICAM1 | 6PGD | S10A1 | ERO1A | GSTP1 | MMP9 |
| 18 | LG3BP | C163A | GGH | ERBB3 | TETN | BGH3 | ENOA | GDIR2 | LRP1 | ERO1A |
| 19 | SODM | KPYM | BGH3 | FOLH1 | 6PGD | DESP | LRP1 | TBA1B | ERO1A | GSTP1 |
| 20 | CNTN1 | TETN | ICAM1 | K1C19 | ZA2G | 6PGD | EF2 | RAN | ERO1A | GSTP1 |
| 21 | GELS | ENPL | OSTP | PEDF | ICAM1 | BST1 | TNF12 | GDIR2 | LRP1 | ERO1A |
| 22 | KIT | LDHA | IBP3 | PEDF | DSG2 | FOLH1 | CD14 | LRP1 | UGPA | ERO1A |
| 23 | KIT | TSP1 | ISLR | BGH3 | COF1 | PTPRJ | 6PGD | LRP1 | S10A6 | MPRI |
| 24 | LG3BP | C163A | GGH | DSG2 | ICAM1 | 6PGD | GDIR2 | HYOU1 | EREG | ERO1A |
| 25 | IBP2 | C163A | ENPL | FIBA | BGH3 | CERU | 6PGD | LRP1 | PRDX1 | MMP9 |
| 26 | LG3BP | C163A | TENX | PDIA3 | SEM3G | BST1 | VTNC | FRIL | PRDX1 | ERO1A |
| 27 | ALDOA | COIA1 | TETN | 1433T | CBPB2 | CD14 | G3P | CD59 | ERO1A | MMP9 |
| 28 | IBP3 | TENX | CRP | TETN | MMP2 | SEM3G | VTNC | CD14 | PROF1 | ERO1A |

TABLE 2-continued

|    | Protein 1 | Protein 2 | Protein 3 | Protein 4 | Protein 5 | Protein 6 | Protein 7 | Protein 8 | Protein 9 | Protein 10 |
|----|-----------|-----------|-----------|-----------|-----------|-----------|-----------|-----------|-----------|------------|
| 29 | SODM | EPHB6 | TPIS | TENX | ERBB3 | SCF | TETN | FRIL | LRP1 | ERO1A |
| 30 | LG3BP | IBP3 | POSTN | DSG2 | MDHM | 1433Z | CD14 | EF1A1 | PLXC1 | ERO1A |
| 31 | IBP2 | LG3BP | COIA1 | CNTN1 | IBP3 | POSTN | TETN | BGH3 | 6PGD | ERO1A |
| 32 | PVR | TSP1 | GGH | CYTB | AIFM1 | ICAM1 | MDHM | 1433Z | 6PGD | FRIL |
| 33 | LYOX | GELS | COIA1 | IBP3 | AIFM1 | ICAM1 | FRIL | PRDX1 | RAP2B | NCF4 |
| 34 | KIT | AMPN | TETN | TNF12 | 6PGD | FRIL | LRP1 | EF2 | ERO1A | MMP9 |
| 35 | LG3BP | GELS | COIA1 | CLUS | CALU | AIFM1 | 1433T | CD14 | UGPA | S10A1 |
| 36 | ALDOA | IBP3 | TSP1 | TETN | SEM3G | ICAM1 | EF1A1 | G3P | RAP2B | NCF4 |
| 37 | ALDOA | COIA1 | CH10 | TETN | PTPRJ | SEM3G | 1433T | 6PGD | FRIL | ERO1A |
| 38 | LG3BP | COIA1 | PLSL | FIBA | TENX | POSTN | CD14 | LRP1 | NCF4 | ERO1A |
| 39 | LUM | IBP3 | CH10 | AIFM1 | MDHM | 6PGD | PLXC1 | EF2 | CD59 | GSTP1 |
| 40 | SODM | LG3BP | LUM | LDHA | MDHC | GGH | ICAM1 | LRP1 | TBA1B | ERO1A |
| 41 | LG3BP | CD44 | IBP3 | CALU | CERU | 1433T | CD14 | EF1A1 | NCF4 | ERO1A |
| 42 | LG3BP | TPIS | COIA1 | HPT | FIBA | AIFM1 | 1433Z | 6PGD | CD14 | EF2 |
| 43 | ALDOA | CD44 | MMP2 | CD14 | FRIL | PRDX1 | RAN | NCF4 | MPRI | PTPA |
| 44 | COIA1 | CLUS | OSTP | ICAM1 | 1433T | PLXC1 | PTGIS | RAP2B | PTPA | GSTP1 |
| 45 | KIT | LYOX | IBP3 | GRP78 | FOLH1 | MASP1 | CD14 | LRP1 | ERO1A | GSTP1 |
| 46 | LG3BP | GGH | CRP | SCF | ICAM1 | ZA2G | 1433T | RAN | NCF4 | ERO1A |
| 47 | LG3BP | C163A | BGH3 | MMP2 | GRP78 | LRP1 | RAN | ITA5 | HS90B | PTPA |
| 48 | ALDOA | CLUS | TENX | ICAM1 | K1C19 | MASP1 | 6PGD | CBPB2 | PRDX1 | PTPA |
| 49 | IBP3 | PDIA3 | PEDF | FOLH1 | ICAM1 | NRP1 | 6PGD | UGPA | RAN | ERO1A |
| 50 | ENPL | FIBA | ISLR | SAA | 6PGD | PRDX1 | EF2 | PLIN2 | HS90B | GSLG1 |
| 51 | LG3BP | COIA1 | CO6A3 | GGH | ERBB3 | FOLH1 | ICAM1 | RAN | CDCP1 | ERO1A |
| 52 | GELS | ENPL | A1AG1 | SCF | COF1 | ICAM1 | 6PGD | RAP2B | EF2 | HS90B |
| 53 | SODM | IBP2 | COIA1 | CLUS | IBP3 | ENPL | PLSL | TNF12 | 6PGD | ERO1A |
| 54 | KIT | MMP7 | COIA1 | TSP1 | CO6A3 | GGH | PDIA3 | ICAM1 | LRP1 | GSLG1 |
| 55 | ALDOA | COIA1 | TSP1 | CH10 | NRP1 | CD14 | DESP | LRP1 | CLIC1 | ERO1A |
| 56 | C163A | GELS | CALU | A1AG1 | AIFM1 | DSG2 | ICAM1 | 6PGD | RAP2B | NCF4 |
| 57 | PPIB | LG3BP | IBP3 | TSP1 | PLSL | GRP78 | FOLH1 | 6PGD | HYOU1 | RAP2B |
| 58 | KIT | LG3BP | LUM | GELS | OSTP | ICAM1 | CD14 | EF1A1 | NCF4 | MMP9 |
| 59 | KIT | PPIB | LG3BP | GELS | FOLH1 | ICAM1 | MASP1 | GDIR2 | ITA5 | NCF4 |
| 60 | IBP3 | ENPL | ERBB3 | BGH3 | VTNC | 6PGD | EF1A1 | TBA1B | S10A6 | HS90B |
| 61 | LG3BP | CLUS | IBP3 | SCF | TCPA | ISLR | GRP78 | 6PGD | ERO1A | GSTP1 |
| 62 | LG3BP | LEG1 | GELS | GGH | TETN | ENOA | ICAM1 | MASP1 | FRIL | NCF4 |
| 63 | LG3BP | CD44 | TETN | BGH3 | G3P | LRP1 | PRDX1 | CDCP1 | PTPA | MMP9 |
| 64 | CALU | ENPL | ICAM1 | VTNC | FRIL | LRP1 | PROF1 | TBB3 | GSLG1 | ERO1A |
| 65 | PPIB | PLSL | TENX | A1AG1 | COF1 | 6PGD | FRIL | LRP1 | CLIC1 | ERO1A |
| 66 | IBP2 | IBP3 | CERU | ENOA | 6PGD | CD14 | LRP1 | PDGFB | ERO1A | GSTP1 |
| 67 | COIA1 | 1433T | CD14 | DESP | GDIR2 | PLXC1 | PROF1 | RAP2B | RAN | ERO1A |
| 68 | LYOX | OSTP | TETN | SEM3G | ICAM1 | ZA2G | FRIL | EREG | RAN | ERO1A |
| 69 | LG3BP | IBP3 | TSP1 | PEDF | FOLH1 | MDHM | TNF12 | NRP1 | S10A6 | RAP2B |
| 70 | KIT | ALDOA | LG3BP | COIA1 | TSP1 | A1AG1 | BGH3 | SEM3G | FOLH1 | RAN |
| 71 | ALDOA | OSTP | BST1 | CD14 | G3P | PRDX1 | PTGIS | FINC | PTPA | MMP9 |
| 72 | EPHB6 | TETN | PEDF | ICAM1 | APOE | PROF1 | UGPA | NCF4 | GSLG1 | PTPA |
| 73 | LG3BP | COIA1 | ENPL | MMP2 | 1433T | EF1A1 | LRP1 | HS90B | GSLG1 | ERO1A |
| 74 | KIT | IBP3 | CYTB | MMP2 | 1433Z | 6PGD | CLIC1 | EF2 | NCF4 | PTPA |
| 75 | SODM | LYOX | IBP3 | TETN | SEM3G | CD14 | PRDX1 | PTPA | ERO1A | GSTP1 |
| 76 | SODM | KPYM | COIA1 | MDHC | TCPA | CD14 | FRIL | LRP1 | EF2 | ERO1A |
| 77 | PPIB | FIBA | LG3BP | GRP78 | AIFM1 | ICAM1 | 6PGD | NCF4 | GSLG1 | PTPA |
| 78 | LG3BP | C163A | PVR | MDHC | TETN | SEM3G | AIFM1 | 6PGD | EREG | ERO1A |
| 79 | GELS | ISLR | BGH3 | DSG2 | ICAM1 | SAA | HYOU1 | ICAM3 | PTGIS | RAP2B |
| 80 | KPYM | TPIS | IBP3 | TIMP1 | GRP78 | ICAM1 | LRP1 | TERA | ERO1A | MMP9 |
| 81 | IBP3 | HPT | TSP1 | GRP78 | SAA | MMP12 | 1433Z | 6PGD | CD14 | S10A6 |
| 82 | TENX | A1AG1 | ENOA | AIFM1 | ICAM1 | CD14 | FRIL | LRP1 | RAP2B | CD59 |
| 83 | ALDOA | KPYM | ISLR | TETN | BGH3 | VTNC | LRP1 | ITA5 | PTPA | MMP9 |
| 84 | SODM | TENX | ISLR | TETN | VTNC | 6PGD | LRP1 | EF2 | ERO1A | MMP9 |
| 85 | LG3BP | C163A | COIA1 | FOLH1 | CD14 | LRP1 | TBA1B | GSLG1 | ERO1A | GSTP1 |
| 86 | SODM | PVR | COIA1 | ISLR | PDIA3 | APOE | CD14 | FRIL | LRP1 | CDCP1 |
| 87 | ALDOA | PEDF | ICAM1 | 6PGD | CD14 | FINC | RAN | NCF4 | GSLG1 | PTPA |
| 88 | LG3BP | KPYM | GELS | COIA1 | IBP3 | CD14 | EF1A1 | PLIN2 | HS90B | ERO1A |
| 89 | LG3BP | PVR | CLUS | TETN | COF1 | SEM3G | DESP | EF2 | HS90B | ERO1A |
| 90 | LG3BP | COIA1 | FIBA | TETN | TFR1 | ICAM1 | MDHM | CD14 | PLXC1 | ERO1A |
| 91 | PPIB | LG3BP | GELS | CLUS | TENX | ICAM1 | SAA | NCF4 | PTPA | ERO1A |
| 92 | COIA1 | TSP1 | ISLR | BGH3 | SAA | 6PGD | LRP1 | PROF1 | EREG | ERO1A |
| 93 | CALU | FIBA | OSTP | ISLR | PDIA3 | SEM3G | K1C19 | 6PGD | HYOU1 | RAP2B |
| 94 | FIBA | CH10 | GRP78 | SEM3G | AIFM1 | ICAM1 | MDHM | FRIL | UGPA | GSTP1 |
| 95 | COIA1 | IBP3 | PDIA3 | ICAM1 | K1C19 | CD14 | EF1A1 | FRIL | PTGIS | PDGFB |
| 96 | LG3BP | C163A | COIA1 | LDHA | 1433T | 1433Z | FRIL | LRP1 | ERO1A | MMP9 |
| 97 | LG3BP | GELS | COIA1 | GRP78 | SEM3G | FRIL | PLXC1 | PROF1 | S10A1 | ERO1A |
| 98 | LG3BP | COIA1 | ENPL | GRP78 | AIFM1 | ICAM1 | 1433Z | CD14 | LRP1 | ERO1A |
| 99 | COIA1 | PLSL | NRP1 | 1433T | CD14 | FRIL | LRP1 | RAP2B | PDGFB | ERO1A |
| 100 | IBP2 | COIA1 | TETN | DSG2 | FOLH1 | 1433T | CD14 | FRIL | LRP1 | ERO1A |

Preferred panels for ruling in treatment for a subject include the panels listed on Table 3 and 4. In various other embodiments, the panels according to the invention include measuring at least 2, 3, 4, 5, 6, 7, or more of the proteins listed on Tables 2 and 3.

TABLE 3

| Average (19) | Rule-out (20) | Rule-in (16) |
|---|---|---|
| ERO1A | ERO1A | ERO1A |
| 6PGD | 6PGD | 6PGD |
| FRIL | FRIL | FRIL |
| GSTP1 | GSTP1 | GSTP1 |
| COIA1 | COIA1 | COIA1 |
| GGH | GGH | GGH |
| PRDX1 | PRDX1 | PRDX1 |
| LRP1 | CD14 | SEM3G |
| ICAM1 | LRP1 | GRP78 |
| CD14 | LG3BP | TETN |
| LG3BP | PTPA | AIFM1 |
| PTPA | ICAM1 | TSP1 |
| TETN | TSP1 | MPRI |
| GRP78 | IBP3 | TNF12 |
| AIFM1 | FOLH1 | MMP9 |
| SEM3G | SODM | OSTP |
| BGH3 | FIBA | |
| PDIA3 | GSLG1 | |
| FINC | RAP2B | |
| | C163A | |

TABLE 4

| Average (13) | Rule-out (13) | Rule-in (9) |
|---|---|---|
| LRP1 | LRP1 ( | LRP1 |
| BGH3 | COIA1 | COIA1 |
| COIA1 | TETN | TETN |
| TETN | TSP1 | TSP1 |
| TSP1 | ALDOA | ALDOA |
| PRDX1 | GRP78 | GRP78 |
| PROF1 | FRIL | FRIL |
| GRP78 | LG3BP | APOE |
| FRIL | BGH3 | TBB3 |
| LG3BP | ISLR | |
| CD14 | PRDX1 | |
| GGH | FIBA | |
| AIFM1 | GSLG1 | |

A preferred normalizer panel is listed in Table 5.

TABLE 5

| Normalizer (6) |
|---|
| PEDF |
| MASP1 |
| GELS |
| LUM |
| C163A |
| PTPRJ |

The term "pulmonary nodules" (PNs) refers to lung lesions that can be visualized by radiographic techniques. A pulmonary nodule is any nodules less than or equal to three centimeters in diameter. In one example a pulmonary nodule has a diameter of about 0.8 cm to 2 cm.

The term "masses" or "pulmonary masses" refers to lung nodules that are greater than three centimeters maximal diameter.

The term "blood biopsy" refers to a diagnostic study of the blood to determine whether a patient presenting with a nodule has a condition that may be classified as either benign or malignant.

The term "acceptance criteria" refers to the set of criteria to which an assay, test, diagnostic or product should conform to be considered acceptable for its intended use. As used herein, acceptance criteria are a list of tests, references to analytical procedures, and appropriate measures, which are defined for an assay or product that will be used in a diagnostic. For example, the acceptance criteria for the classifier refers to a set of predetermined ranges of coefficients.

The term "average maximal AUC" refers to the methodology of calculating performance. For the present invention, in the process of defining the set of proteins that should be in a panel by forward or backwards selection proteins are removed or added one at a time. A plot can be generated with performance (AUC or partial AUC score on the Y axis and proteins on the X axis) the point which maximizes performance indicates the number and set of proteins the gives the best result.

The term "partial AUC factor or pAUC factor" is greater than expected by random prediction. At sensitivity=0.90 the pAUC factor is the trapezoidal area under the ROC curve from 0.9 to 1.0 Specificity/(0.1*0.1/2).

The term "incremental information" refers to information that may be used with other diagnostic information to enhance diagnostic accuracy. Incremental information is independent of clinical factors such as including nodule size, age, or gender.

The term "score" or "scoring" refers to the refers to calculating a probability likelihood for a sample. For the present invention, values closer to 1.0 are used to represent the likelihood that a sample is cancer, values closer to 0.0 represent the likelihood that a sample is benign.

The term "robust" refers to a test or procedure that is not seriously disturbed by violations of the assumptions on which it is based. For the present invention, a robust test is a test wherein the proteins or transitions of the mass spectrometry chromatograms have been manually reviewed and are "generally" free of interfering signals The term "coefficients" refers to the weight assigned to each protein used to in the logistic regression equation to score a sample.

In certain embodiments of the invention, it is contemplated that in terms of the logistic regression model of MC CV, the model coefficient and the coefficient of variation (CV) of each protein's model coefficient may increase or decrease, dependent upon the method (or model) of measurement of the protein classifier. For each of the listed proteins in the panels, there is about, at least, at least about, or at most about a 2-, 3-, 4-, 5-, 6-, 7-, 8-, 9-, or 10-, -fold or any range derivable therein for each of the coefficient and CV. Alternatively, it is contemplated that quantitative embodiments of the invention may be discussed in terms of as about, at least, at least about, or at most about 10, 20, 30, 40, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% or more, or any range derivable therein.

The term "best team players" refers to the proteins that rank the best in the random panel selection algorithm, i.e., perform well on panels. When combined into a classifier these proteins can segregate cancer from benign samples. "Best team player" proteins is synonymous with "cooperative proteins". The term "cooperative proteins" refers proteins that appear more frequently on high performing panels of proteins than expected by chance. This gives rise to a protein's cooperative score which measures how (in)frequently it appears on high performing panels. For example, a protein with a cooperative score of 1.5 appears on high performing panels 1.5× more than would be expected by chance alone.

The term "classifying" as used herein with regard to a lung condition refers to the act of compiling and analyzing expression data for using statistical techniques to provide a classification to aid in diagnosis of a lung condition, particularly lung cancer.

The term "classifier" as used herein refers to an algorithm that discriminates between disease states with a predetermined level of statistical significance. A two-class classifier is an algorithm that uses data points from measurements from a sample and classifies the data into one of two groups. In certain embodiments, the data used in the classifier is the relative expression of proteins in a biological sample. Protein expression levels in a subject can be compared to levels in patients previously diagnosed as disease free or with a specified condition.

The "classifier" maximizes the probability of distinguishing a randomly selected cancer sample from a randomly selected benign sample, i.e., the AUC of ROC curve.

In addition to the classifier's constituent proteins with differential expression, it may also include proteins with minimal or no biologic variation to enable assessment of variability, or the lack thereof, within or between clinical specimens; these proteins may be termed endogenous proteins and serve as internal controls for the other classifier proteins.

The term "normalization" or "normalizer" as used herein refers to the expression of a differential value in terms of a standard value to adjust for effects which arise from technical variation due to sample handling, sample preparation and mass spectrometry measurement rather than biological variation of protein concentration in a sample. For example, when measuring the expression of a differentially expressed protein, the absolute value for the expression of the protein can be expressed in terms of an absolute value for the expression of a standard protein that is substantially constant in expression. This prevents the technical variation of sample preparation and mass spectrometry measurement from impeding the measurement of protein concentration levels in the sample.

The term "condition" as used herein refers generally to a disease, event, or change in health status.

The term "treatment protocol" as used herein including further diagnostic testing typically performed to determine whether a pulmonary nodule is benign or malignant. Treatment protocols include diagnostic tests typically used to diagnose pulmonary nodules or masses such as for example, CT scan, positron emission tomography (PET) scan, bronchoscopy or tissue biopsy. Treatment protocol as used herein is also meant to include therapeutic treatments typically used to treat malignant pulmonary nodules and/or lung cancer such as for example, chemotherapy, radiation or surgery.

The terms "diagnosis" and "diagnostics" also encompass the terms "prognosis" and "prognostics", respectively, as well as the applications of such procedures over two or more time points to monitor the diagnosis and/or prognosis over time, and statistical modeling based thereupon. Furthermore the term diagnosis includes: a. prediction (determining if a patient will likely develop a hyperproliferative disease) b. prognosis (predicting whether a patient will likely have a better or worse outcome at a pre-selected time in the future) c. therapy selection d. therapeutic drug monitoring e. relapse monitoring.

In some embodiments, for example, classification of a biological sample as being derived from a subject with a lung condition may refer to the results and related reports generated by a laboratory, while diagnosis may refer to the act of a medical professional in using the classification to identify or verify the lung condition.

The term "providing" as used herein with regard to a biological sample refers to directly or indirectly obtaining the biological sample from a subject. For example, "providing" may refer to the act of directly obtaining the biological sample from a subject (e.g., by a blood draw, tissue biopsy, lavage and the like). Likewise, "providing" may refer to the act of indirectly obtaining the biological sample. For example, providing may refer to the act of a laboratory receiving the sample from the party that directly obtained the sample, or to the act of obtaining the sample from an archive.

As used herein, "lung cancer" preferably refers to cancers of the lung, but may include any disease or other disorder of the respiratory system of a human or other mammal. Respiratory neoplastic disorders include, for example small cell carcinoma or small cell lung cancer (SCLC), non-small cell carcinoma or non-small cell lung cancer (NSCLC), squamous cell carcinoma, adenocarcinoma, broncho-alveolar carcinoma, mixed pulmonary carcinoma, malignant pleural mesothelioma, undifferentiated large cell carcinoma, giant cell carcinoma, synchronous tumors, large cell neuroendocrine carcinoma, adenosquamous carcinoma, undifferentiated carcinoma; and small cell carcinoma, including oat cell cancer, mixed small cell/large cell carcinoma, and combined small cell carcinoma; as well as adenoid cystic carcinoma, hamartomas, mucoepidermoid tumors, typical carcinoid lung tumors, atypical carcinoid lung tumors, peripheral carcinoid lung tumors, central carcinoid lung tumors, pleural mesotheliomas, and undifferentiated pulmonary carcinoma and cancers that originate outside the lungs such as secondary cancers that have metastasized to the lungs from other parts of the body. Lung cancers may be of any stage or grade. Preferably the term may be used to refer collectively to any dysplasia, hyperplasia, neoplasia, or metastasis in which the protein biomarkers expressed above normal levels as may be determined, for example, by comparison to adjacent healthy tissue.

Examples of non-cancerous lung condition include chronic obstructive pulmonary disease (COPD), benign tumors or masses of cells (e.g., hamartoma, fibroma, neurofibroma), granuloma, sarcoidosis, and infections caused by bacterial (e.g., tuberculosis) or fungal (e.g. histoplasmosis) pathogens. In certain embodiments, a lung condition may be associated with the appearance of radiographic PNs.

As used herein, "lung tissue", and "lung cancer" refer to tissue or cancer, respectively, of the lungs themselves, as well as the tissue adjacent to and/or within the strata underlying the lungs and supporting structures such as the pleura, intercostal muscles, ribs, and other elements of the respiratory system. The respiratory system itself is taken in this context as representing nasal cavity, sinuses, pharynx, larynx, trachea, bronchi, lungs, lung lobes, aveoli, aveolar ducts, aveolar sacs, aveolar capillaries, bronchioles, respiratory bronchioles, visceral pleura, parietal pleura, pleural cavity, diaphragm, epiglottis, adenoids, tonsils, mouth and tongue, and the like. The tissue or cancer may be from a mammal and is preferably from a human, although monkeys, apes, cats, dogs, cows, horses and rabbits are within the scope of the present invention. The term "lung condition" as used herein refers to a disease, event, or change in health status relating to the lung, including for example lung cancer and various non-cancerous conditions.

"Accuracy" refers to the degree of conformity of a measured or calculated quantity (a test reported value) to its actual (or true) value. Clinical accuracy relates to the proportion of true outcomes (true positives (TP) or true negatives (TN)

versus misclassified outcomes (false positives (FP) or false negatives (FN)), and may be stated as a sensitivity, specificity, positive predictive values (PPV) or negative predictive values (NPV), or as a likelihood, odds ratio, among other measures.

The term "biological sample" as used herein refers to any sample of biological origin potentially containing one or more biomarker proteins. Examples of biological samples include tissue, organs, or bodily fluids such as whole blood, plasma, serum, tissue, lavage or any other specimen used for detection of disease.

The term "subject" as used herein refers to a mammal, preferably a human.

The term "biomarker protein" as used herein refers to a polypeptide in a biological sample from a subject with a lung condition versus a biological sample from a control subject. A biomarker protein includes not only the polypeptide itself, but also minor variations thereof, including for example one or more amino acid substitutions or modifications such as glycosylation or phosphorylation.

The term "biomarker protein panel" as used herein refers to a plurality of biomarker proteins. In certain embodiments, the expression levels of the proteins in the panels can be correlated with the existence of a lung condition in a subject. In certain embodiments, biomarker protein panels comprise 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90 or 100 proteins. In certain embodiments, the biomarker proteins panels comprise from 100-125 proteins, 125-150 proteins, 150-200 proteins or more.

"Treating" or "treatment" as used herein with regard to a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

The term "ruling out" as used herein is meant that the subject is selected not to receive a treatment protocol.

The term "ruling-in" as used herein is meant that the subject is selected to receive a treatment protocol.

Biomarker levels may change due to treatment of the disease. The changes in biomarker levels may be measured by the present invention. Changes in biomarker levels may be used to monitor the progression of disease or therapy.

"Altered", "changed" or "significantly different" refer to a detectable change or difference from a reasonably comparable state, profile, measurement, or the like. One skilled in the art should be able to determine a reasonable measurable change. Such changes may be all or none. They may be incremental and need not be linear. They may be by orders of magnitude. A change may be an increase or decrease by 1%, 5%, 10%, 20%, 30%, 40%, 50%, 60%, 70%, 80%, 90%, 95%, 99%, 100%, or more, or any value in between 0% and 100%. Alternatively the change may be 1-fold, 1.5-fold 2-fold, 3-fold, 4-fold, 5-fold or more, or any values in between 1-fold and five-fold. The change may be statistically significant with a p value of 0.1, 0.05, 0.001, or 0.0001.

Using the methods of the current invention, a clinical assessment of a patient is first performed. If there exists is a higher likelihood for cancer, the clinician may rule in the disease which will require the pursuit of diagnostic testing options yielding data which increase and/or substantiate the likelihood of the diagnosis. "Rule in" of a disease requires a test with a high specificity.

"FN" is false negative, which for a disease state test means classifying a disease subject incorrectly as non-disease or normal.

"FP" is false positive, which for a disease state test means classifying a normal subject incorrectly as having disease.

The term "rule in" refers to a diagnostic test with high specificity that coupled with a clinical assessment indicates a higher likelihood for cancer. If the clinical assessment is a lower likelihood for cancer, the clinician may adopt a stance to rule out the disease, which will require diagnostic tests which yield data that decrease the likelihood of the diagnosis. "Rule out" requires a test with a high sensitivity.

The term "rule out" refers to a diagnostic test with high sensitivity that coupled with a clinical assessment indicates a lower likelihood for cancer.

The term "sensitivity of a test" refers to the probability that a patient with the disease will have a positive test result. This is derived from the number of patients with the disease who have a positive test result (true positive) divided by the total number of patients with the disease, including those with true positive results and those patients with the disease who have a negative result, i.e. false negative.

The term "specificity of a test" refers to the probability that a patient without the disease will have a negative test result. This is derived from the number of patients without the disease who have a negative test result (true negative) divided by all patients without the disease, including those with a true negative result and those patients without the disease who have a positive test result, e.g. false positive. While the sensitivity, specificity, true or false positive rate, and true or false negative rate of a test provide an indication of a test's performance, e.g. relative to other tests, to make a clinical decision for an individual patient based on the test's result, the clinician requires performance parameters of the test with respect to a given population.

The term "positive predictive value" (PPV) refers to the probability that a positive result correctly identifies a patient who has the disease, which is the number of true positives divided by the sum of true positives and false positives.

The term "negative predictive value" or "NPV" is calculated by TN/(TN+FN) or the true negative fraction of all negative test results. It also is inherently impacted by the prevalence of the disease and pre-test probability of the population intended to be tested.

The term "disease prevalence" refers to the number of all new and old cases of a disease or occurrences of an event during a particular period. Prevalence is expressed as a ratio in which the number of events is the numerator and the population at risk is the denominator.

The term disease incidence refers to a measure of the risk of developing some new condition within a specified period of time; the number of new cases during some time period, it is better expressed as a proportion or a rate with a denominator.

Lung cancer risk according to the "National Lung Screening Trial" is classified by age and smoking history. High risk—age ≥55 and ≥30 pack-years smoking history; Moderate risk—age ≥50 and ≥20 pack-years smoking history; Low risk—<age 50 or <20 pack-years smoking history.

The term "negative predictive value" (NPV) refers to the probability that a negative test correctly identifies a patient without the disease, which is the number of true negatives divided by the sum of true negatives and false negatives. A positive result from a test with a sufficient PPV can be used to rule in the disease for a patient, while a negative result from a test with a sufficient NPV can be used to rule out the disease, if the disease prevalence for the given population, of which the patient can be considered a part, is known.

The clinician must decide on using a diagnostic test based on its intrinsic performance parameters, including sensitivity and specificity, and on its extrinsic performance parameters, such as positive predictive value and negative predictive value, which depend upon the disease's prevalence in a given population.

Additional parameters which may influence clinical assessment of disease likelihood include the prior frequency and closeness of a patient to a known agent, e.g. exposure risk, that directly or indirectly is associated with disease causation, e.g. second hand smoke, radiation, etc., and also the radiographic appearance or characterization of the pulmonary nodule exclusive of size. A nodule's description may include solid, semi-solid or ground glass which characterizes it based on the spectrum of relative gray scale density employed by the CT scan technology.

"Mass spectrometry" refers to a method comprising employing an ionization source to generate gas phase ions from an analyte presented on a sample presenting surface of a probe and detecting the gas phase ions with a mass spectrometer.

The technology liquid chromatography selected reaction monitoring mass spectrometry (LC-SRM-MS) was used to assay the expression levels of a cohort of 388 proteins in the blood to identify differences for individual proteins which may correlate with the absence or presence of the disease. The individual proteins have not only been implicated in lung cancer biology, but are also likely to be present in plasma based on their expression as membrane-anchored or secreted proteins. An analysis of epithelial and endothelial membranes of resected lung cancer tissues (including the subtypes of adenocarcinoma, squamous, and large cell) identified 217 tissue proteins. A review of the scientific literature with search terms relevant to lung cancer biology identified 319 proteins. There was an overlap of 148 proteins between proteins identified by cancer tissue analysis or literature review, yielding a total of 388 unique proteins as candidates. The majority of candidate proteins included in the multiplex LC-SRM-MS assay were discovered following proteomics analysis of secretory vesicle contents from fresh NSCLC resections and from adjacent non-malignant tissue. The secretory proteins reproducibly upregulated in the tumor tissue were identified and prioritized for inclusion in the LC-SRM-MS assay using extensive bioinformatic and literature annotation. An additional set of proteins that were present in relevant literature was also added to the assay. In total, 388 proteins associated with lung cancer were prioritized for SRM assay development. Of these, 371 candidate protein biomarkers were ultimately included in the assay. These are listed in Table 6, below.

TABLE 6

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| 1433B_HUMAN | 14-3-3 protein beta/alpha | YWHAB | Secreted, EPI | LungCancers | Cytoplasm. Melanosome. Note = Identified by mass spectrometry in melanosome fractions from stage I to stage IV. | Literature, Detection |
| 1433E_HUMAN | 14-3-3 protein epsilon | YWHAE | ENDO | LungCancers, Benign-Nodules | Cytoplasm (By similarity). Melanosome. Note = Identified by mass spectrometry in melanosome fractions from stage I to stage IV. | Literature, Detection |
| 1433S_HUMAN | 14-3-3 protein sigma | SFN | Secreted, EPI | LungCancers | Cytoplasm. Nucleus (By similarity). Secreted. Note = May be secreted by a non-classical secretory pathway. | UniProt, Literature, Detection |
| 1433T_HUMAN | 14-3-3 protein theta | YWHAQ | EPI | LungCancers, Benign-Nodules | Cytoplasm. Note = In neurons, axonally transported to the nerve terminals. | Detection |
| 1433Z_HUMAN | 14-3-3 protein zeta/delta | YWHAZ | EPI | LungCancers, Benign-Nodules | Cytoplasm. Melanosome. Note = Located to stage I to stage IV melanosomes. | Detection |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| 6PGD_HUMAN | 6-phosphogluconate dehydrogenase, decarboxylating | PGD | EPI, ENDO | | Cytoplasm (By similarity). | Detection |
| A1AG1_HUMAN | Alpha-1-acid glycoprotein 1 | ORM1 | EPI | Symptoms | Secreted. | UniProt, Literature, Detection, Prediction |
| ABCD1_HUMAN | ATP-binding cassette sub-family D member 1 | ABCD1 | ENDO | | Peroxisome membrane; Multi-pass membrane protein. | Detection, Prediction |
| ADA12_HUMAN | Disintegrin and metalloproteinase domain-containing protein 12 | ADAM12 | | LungCancers, Benign-Nodules, Symptoms | Isoform 1: Cell membrane; Single-pass type I membrane protein. \|Isoform 2: Secreted. \|Isoform 3: Secreted (Potential). \|Isoform 4: Secreted (Potential). | UniProt, Detection, Prediction |
| ADML_HUMAN | ADM | ADM | | LungCancers, Benign-Nodules, Symptoms | Secreted. | UniProt, Literature, Detection, Prediction |
| AGR2_HUMAN | Anterior gradient protein 2 homolog | AGR2 | EPI | LungCancers | Secreted. Endoplasmic reticulum (By similarity). | UniProt, Prediction |
| AIFM1_HUMAN | Apoptosis-inducing factor 1, mitochondrial | AIFM1 | EPI, ENDO | LungCancers | Mitochondrion inter-membrane space. Nucleus. Note = Translocated to the nucleus upon induction of apoptosis. | Detection, Prediction |
| ALDOA_HUMAN | Fructose-bisphosphate aldolase A | ALDOA | Secreted, EPI | LungCancers, Symptoms | | Literature, Detection |
| AMPN_HUMAN | Aminopeptidase N | ANPEP | EPI, ENDO | LungCancers, Benign-Nodules, Symptoms | Cell membrane; Single-pass type II membrane protein. Cytoplasm, cytosol (Potential). Note = A soluble form has also been detected. | UniProt, Detection |
| ANGP1_HUMAN | Angiopoietin-1 | ANGPT1 | | LungCancers, Benign-Nodules | Secreted. | UniProt, Literature, Prediction |
| ANGP2_HUMAN | Angiopoietin-2 | ANGPT2 | | LungCancers, Benign-Nodules | Secreted. | UniProt, Literature, Prediction |
| APOA1_HUMAN | Apolipoprotein A-I | APOA1 | | LungCancers, Benign-Nodules, Symptoms | Secreted. | UniProt, Literature, Detection, Prediction |
| APOE_HUMAN | Apolipoprotein E | APOE | EPI, ENDO | LungCancers, Benign-Nodules, Symptoms | Secreted. | UniProt, Literature, Detection, Prediction |
| ASM3B_HUMAN | Acid sphingomyelinase- | SMPDL3B | EPI, ENDO | | Secreted (By similarity). | UniProt, Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | like phosphodiesterase 3b | | | | | |
| AT2A2_HUMAN | Sarcoplasmic/ endoplasmic reticulum calcium ATPase 2 | ATP2A2 | EPI, ENDO | LungCancers, Benign-Nodules | Endoplasmic reticulum membrane; Multi-pass membrane protein. Sarcoplasmic reticulum membrane; Multi-pass membrane protein. | Detection |
| ATS1_HUMAN | A disintegrin and metallo-proteinase with thrombospondin motifs 1 | ADAMTS1 | | LungCancers, Benign-Nodules, Symptoms | Secreted, extracellular space, extra-cellular matrix (By similarity). | UniProt, Literature, Prediction |
| ATS12_HUMAN | A disintegrin and metallo-proteinase with thrombospondin motifs 12 | ADAMTS12 | | LungCancers | Secreted, extracellular space, extra-cellular matrix (By similarity). | UniProt, Detection, Prediction |
| ATS19_HUMAN | A disintegrin and metallo-proteinase with thrombospondin motifs 19 | ADAMTS19 | | LungCancers | Secreted, extracellular space, extra-cellular matrix (By similarity). | UniProt, Prediction |
| BAGE1_HUMAN | B melanoma antigen 1 | BAGE | | LungCancers | Secreted (Potential). | UniProt, Prediction |
| BAGE2_HUMAN | B melanoma antigen 2 | BAGE2 | | LungCancers | Secreted (Potential). | UniProt, Prediction |
| BAGE3_HUMAN | B melanoma antigen 3 | BAGE3 | | LungCancers | Secreted (Potential). | UniProt, Prediction |
| BAGE4_HUMAN | B melanoma antigen 4 | BAGE4 | | LungCancers | Secreted (Potential). | UniProt, Prediction |
| BAGE5_HUMAN | B melanoma antigen 5 | BAGE5 | | LungCancers | Secreted (Potential). | UniProt, Prediction |
| BASP1_HUMAN | Brain acid soluble protein 1 | BASP1 | Secreted, EPI | | Cell membrane; Lipid-anchor. Cell projection, growth cone. Note = Associated with the membranes of growth cones that form the tips of elongating axons. | Detection |
| BAX_HUMAN | Apoptosis regulator BAX | BAX | EPI | LungCancers, Benign-Nodules | Isoform Alpha: Mitochondrion membrane; Single-pass membrane protein. Cytoplasm. Note = Colocalizes with 14-3-3 proteins in the cytoplasm. Under stress conditions, redistributes to the mitochondrion | UniProt, Literature, Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | membrane through the release from JNK-phosphorylated 14-3-3 proteins. \|Isoform Beta: Cytoplasm. \|Isoform Gamma: Cytoplasm. \|Isoform Delta: Cytoplasm (Potential). | |
| BDNF_HUMAN | Brain-derived neurotrophic factor | BDNF | | Benign-Nodules, Symptoms | Secreted. | UniProt, Literature, Prediction |
| BGH3_HUMAN | Transforming growth factor-beta-induced protein igh3 | TGFBI | | LungCancers, Benign-Nodules | Secreted, extracellular space, extra-cellular matrix. Note = May be associated both with microfibrils and with the cell surface. | UniProt, Detection |
| BMP2_HUMAN | Bone morphogenetic protein 2 | BMP2 | | LungCancers, Benign-Nodules, Symptoms | Secreted. | UniProt, Literature |
| BST1_HUMAN | ADP-ribosyl cyclase 2 | BST1 | EPI | Symptoms | Cell membrane; Lipid-anchor, GPI-anchor. | Detection, Prediction |
| C163A_HUMAN | Scavenger receptor cysteine-rich type 1 protein M130 | CD163 | EPI | Symptoms | Soluble CD163: Secreted. \|Cell membrane; Single-pass type I membrane protein. Note = Isoform 1 and isoform 2 show a lower surface expression when expressed in cells. | UniProt, Detection |
| C4BPA_HUMAN | C4b-binding protein alpha chain | C4BPA | | LungCancers, Symptoms | Secreted. | UniProt, Detection, Prediction |
| CAH9_HUMAN | Carbonic anhydrase 9 | CA9 | | LungCancers, Benign-Nodules, Symptoms | Nucleus. Nucleus, nucleolus. Cell membrane; Single-pass type I membrane protein. Cell projection, microvillus membrane; Single-pass type I membrane protein. Note = Found on the surface | UniProt |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| CALR_HUMAN | Calreticulin | CALR | EPI | Symptoms | microvilli and in the nucleus, particularly in nucleolus. Endoplasmic reticulum lumen. Cytoplasm, cytosol. Secreted, extracellular space, extracellular matrix. Cell surface. Note = Also found in cell surface (T cells), cytosol and extracellular matrix. Associated with the lytic granules in the cytolytic T-lymphocytes. | UniProt, Literature, Detection, Prediction |
| CALU_HUMAN | Calumenin | CALU | EPI | Symptoms | Endoplasmic reticulum lumen. Secreted. Melanosome. Sarcoplasmic reticulum lumen (By similarity). Note = Identified by mass spectrometry in melanosome fractions from stage I to stage IV. | UniProt, Detection, Prediction |
| CALX_HUMAN | Calnexin | CANX | Secreted, EPI, ENDO | Benign-Nodules | Endoplasmic reticulum membrane; Single-pass type I membrane protein. Melanosome. Note = Identified by mass spectrometry in melanosome fractions from stage I to stage IV. | UniProt, Literature, Detection |
| CAP7_HUMAN | Azurocidin | AZU1 | EPI | Symptoms | Cytoplasmic granule. Note = Cytoplasmic granules of neutrophils. | Prediction |
| CATB_HUMAN | Cathepsin B | CTSB | Secreted | LungCancers | Lysosome. Melanosome. Note = Identified by mass spectrometry in melanosome fractions from stage I to stage IV. | Literature, Detection, Prediction |
| CATG_HUMAN | Cathepsin G | CTSG | Secreted, ENDO | Benign-Nodules | Cell surface. | Detection, Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| CBPB2_HUMAN | Carboxy-peptidase B2 | CPB2 | | LungCancers, Benign-Nodules, Symptoms | Secreted. | UniProt, Detection, Prediction |
| CCL22_HUMAN | C-C motif chemokine 22 | CCL22 | | LungCancers, Benign-Nodules | Secreted. | UniProt, Prediction |
| CD14_HUMAN | Monocyte differentiation antigen CD14 | CD14 | EPI | LungCancers, Benign-Nodules, Symptoms | Cell membrane; Lipid-anchor, GPI-anchor. | Literature, Detection, Prediction |
| CD24_HUMAN | Signal transducer CD24 | CD24 | | LungCancers, Benign-Nodules | Cell membrane; Lipid-anchor, GPI-anchor. | Literature |
| CD2A2_HUMAN | Cyclin-dependent kinase inhibitor 2A, isoform 4 | CDKN2A | | LungCancers, Benign-Nodules | Cytoplasm. Nucleus. \|Nucleus, nucleolus (By similarity). | Literature, Prediction |
| CD38_HUMAN | ADP-ribosyl cyclase 1 | CD38 | EPI, ENDO | Symptoms | Membrane; Single-pass type II membrane protein. | UniProt, Literature |
| CD40L_HUMAN | CD40 ligand | CD40LG | | LungCancers, Benign-Nodules, Symptoms | Cell membrane; Single-pass type II membrane protein. \|CD40 ligand, soluble form: Secreted. | UniProt, Literature |
| CD44_HUMAN | CD44 antigen | CD44 | EPI | LungCancers, Benign-Nodules, Symptoms | Membrane; Single-pass type I membrane protein. | UniProt, Literature, Detection, Prediction |
| CD59_HUMAN | CD59 glycoprotein | CD59 | | LungCancers, Benign-Nodules, Symptoms | Cell membrane; Lipid-anchor, GPI-anchor. Secreted. Note = Soluble form found in a number of tissues. | UniProt, Literature, Detection, Prediction |
| CD97_HUMAN | CD97 antigen | CD97 | EPI, ENDO | Symptoms | Cell membrane; Multi-pass membrane protein. \|CD97 antigen sub-unit alpha: Secreted, extracellular space. | UniProt |
| CDCP1_HUMAN | CUB domain-containing protein 1 | CDCP1 | | LungCancers | Isoform 1: Cell membrane; Single-pass membrane protein (Potential). Note = Shedding may also lead to a soluble peptide. \|Isoform 3: Secreted. | UniProt, Prediction |
| CDK4_HUMAN | Cell division protein kinase 4 | CDK4 | | LungCancers, Symptoms | | Literature |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| CEAM5_HUMAN | Carcinoembryonic antigen related cell adhesion molecule 5 | CEACAM5 | EPI | LungCancers, Benign-Nodules, Symptoms | Cell membrane; Lipid-anchor, GPI-anchor. | Literature, Prediction |
| CEAM8_HUMAN | Carcinoembryonic antigen-related cell adhesion molecule 8 | CEACAM8 | EPI | LungCancers | Cell membrane; Lipid-anchor, GPI-anchor. | Detection, Prediction |
| CERU_HUMAN | Ceruloplasmin | CP | EPI | LungCancers, Symptoms | Secreted. | UniProt, Literature, Detection, Prediction |
| CH10_HUMAN | 10 kDa heat shock protein, mitochondrial | HSPE1 | ENDO | LungCancers | Mitochondrion matrix. | Literature, Detection, Prediction |
| CH60_HUMAN | 60 kDa heat shock protein, mitochondrial | HSPD1 | Secreted, EPI, ENDO | LungCancers, Symptoms | Mitochondrion matrix. | Literature, Detection |
| CKAP4_HUMAN | Cytoskeleton-associated protein 4 | CKAP4 | EPI, ENDO | LungCancers | Endoplasmic reticulum-Golgi intermediate compartment membrane; Single-pass membrane protein (Potential). | UniProt |
| CL041_HUMAN | Uncharacterized protein C12orf41 | C12orf41 | ENDO | | | Prediction |
| CLCA1_HUMAN | Calcium-activated chloride channel regulator 1 | CLCA1 | | LungCancers, Benign-Nodules | Secreted, extracellular space. Cell membrane; Peripheral membrane protein; Extracellular side. Note = Protein that remains attached to the plasma membrane appeared to be predominantly localized to microvilli. | UniProt, Prediction |
| CLIC1_HUMAN | Chloride intracellular channel protein 1 | CLIC1 | EPI | | Nucleus. Nucleus membrane; Single-pass membrane protein (Probable). Cytoplasm. Cell membrane; Single-pass membrane protein (Probable). Note = Mostly in the nucleus including in the nuclear membrane. Small amount in the cytoplasm and | UniProt, Literature, Detection |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | the plasma membrane. Exists both as soluble cytoplasmic protein and as membrane protein with probably a single transmembrane domain. | |
| CLUS_HUMAN | Clusterin | CLU | EPI, ENDO | LungCancers, Benign-Nodules, Symptoms | Secreted. | UniProt, Literature, Detection, Prediction |
| CMGA_HUMAN | Chromogranin-A | CHGA | | LungCancers, Benign-Nodules | Secreted. Note = Neuro endocrine and endocrine secretory granules. | UniProt, Literature, Detection, Prediction |
| CNTN1_HUMAN | Contactin-1 | CNTN1 | | LungCancers | Isoform 1: Cell membrane; Lipid-anchor, GPI-anchor; Extracellular side.\|Isoform 2: Cell membrane; Lipid-anchor, GPI-anchor; Extracellular side. | Detection, Prediction |
| CO4A1_HUMAN | Collagen alpha-1(IV) chain | COL4A1 | | LungCancers | Secreted, extracellular space, extra-cellular matrix, basement membrane. | UniProt, Detection, Prediction |
| CO5A2_HUMAN | Collagen alpha-2(V) chain | COL5A2 | | LungCancers | Secreted, extracellular space, extra-cellular matrix (By similarity). | UniProt, Detection, Prediction |
| CO6A3_HUMAN | Collagen alpha-3(VI) chain | COL6A3 | Secreted | Symptoms | Secreted, extracellular space, extra-cellular matrix (By similarity). | UniProt, Detection, Prediction |
| COCA1_HUMAN | Collagen alpha-1(XII) chain | COL12A1 | ENDO | LungCancers, Symptoms | Secreted, extracellular space, extra-cellular matrix (By similarity). | UniProt, Prediction |
| COF1_HUMAN | Cofilin-1 | CFL1 | Secreted, EPI | LungCancers, Benign-Nodules | Nucleus matrix. Cytoplasm, cytoskeleton. Note = Almost completely in nucleus in cells exposed to heat shock or 10% di-methyl sulfoxide. | Detection, Prediction |
| COIA1_HUMAN | Collagen alpha-1(XVIII) chain | COL18A1 | | LungCancers, Benign-Nodules | Secreted, extracellular space, extra-cellular matrix (By similarity). | UniProt, Literature, Detection, Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| COX5A_HUMAN | Cytochrome c oxidase subunit 5A, mitochondrial | COX5A | Secreted, ENDO | | Mitochondrion inner membrane. | Prediction |
| CRP_HUMAN | C-reactive protein | CRP | | LungCancers, Benign-Nodules, Symptoms | Secreted. | UniProt, Literature, Detection, Prediction |
| CS051_HUMAN | UPF0470 protein C19orf51 | C19orf51 | ENDO | | | Prediction |
| CSF1_HUMAN | Macrophage colony-stimulating factor 1 | CSF1 | | LungCancers, Benign-Nodules | Cell membrane; Single-pass membrane protein (By similarity). |Processed macrophage colony-stimulating factor 1: Secreted, extracellular space (By similarity). | UniProt, Literature, Detection |
| CSF2_HUMAN | Granulocyte-macrophage colony-stimulating factor | CSF2 | | LungCancers, Benign-Nodules | Secreted. | UniProt, Literature, Prediction |
| CT085_HUMAN | Uncharacterized protein C20orf85 | C20orf85 | | LungCancers, Benign-Nodules | | Prediction |
| CTGF_HUMAN | Connective tissue growth factor | CTGF | | LungCancers, Benign-Nodules | Secreted, extracellular space, extra-cellular matrix (By similarity). Secreted (By similarity). | UniProt, Literature, Detection, Prediction |
| CYR61_HUMAN | Protein CYR61 | CYR61 | | LungCancers, Benign-Nodules | Secreted. | UniProt, Prediction |
| CYTA_HUMAN | Cystatin-A | CSTA | | LungCancers | Cytoplasm. | Literature, Detection |
| CYTB_HUMAN | Cystatin-B | CSTB | Secreted | | Cytoplasm. Nucleus. | Literature, Detection |
| DDX17_HUMAN | Probable ATP-dependent RNA helicase DDX17 | DDX17 | ENDO | LungCancers, Benign-Nodules | Nucleus. | Detection, Prediction |
| DEFB1_HUMAN | Beta-defensin 1 | DEFB1 | | LungCancers, Benign-Nodules | Secreted. | UniProt, Prediction |
| DESP_HUMAN | Desmoplakin | DSP | EPI, ENDO | LungCancers | Cell junction, desmosome. Cytoplasm, cytoskeleton. Note = Inner most portion of the desmosomal plaque. | Detection |
| DFB4A_HUMAN | Beta-defensin 4A | DEFB4A | | LungCancers, Benign-Nodules | Secreted. | UniProt |
| DHI1L_HUMAN | Hydroxysteroid 11-beta-dehydro-genase 1-like protein | HSD11B1L | | LungCancers | Secreted (Potential). | UniProt, Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| DMBT1_HUMAN | Deleted in malignant brain tumors 1 protein | DMBT1 | | LungCancers, Benign-Nodules | Secreted (By similarity). Note = Some isoforms may be membrane-bound. Localized to the lumenal aspect of crypt cells in the small intestine. In the colon, seen in the lumenal aspect of surface epithelial cells. Formed in the ducts of von Ebner gland, and released into the fluid bathing the taste buds contained in the taste papillae (By similarity). | UniProt, Detection, Prediction |
| DMKN_HUMAN | Dermokine | DMKN | | LungCancers | Secreted. | UniProt, Detection, Prediction |
| DPP4_HUMAN | Dipeptidyl peptidase 4 | DPP4 | EPI | LungCancers, Benign-Nodules, Symptoms | Dipeptidyl peptidase 4 soluble form: Secreted. \|Cell membrane; Single-pass type II membrane protein. | UniProt, Detection |
| DSG2_HUMAN | Desmoglein-2 | DSG2 | ENDO | Symptoms | Cell membrane; Single-pass type I membrane protein. Cell junction, desmosome. | UniProt, Detection |
| DX39A_HUMAN | ATP-dependent RNA helicase DDX39A | DDX39A | EPI | | Nucleus (By similarity). | Prediction |
| DX39B_HUMAN | Spliceosome RNA helicase DDX39B | DDX39B | EPI | | Nucleus. Nucleus speckle. | Prediction |
| DYRK2_HUMAN | Dual specificity tyrosine-phosphorylation-regulated kinase 2 | DYRK2 | ENDO | LungCancers | Cytoplasm. Nucleus. Note = Translocates into the nucleus following DNA damage. | Literature |
| EDN2_HUMAN | Endothelin-2 | EDN2 | | LungCancers | Secreted. | UniProt, Prediction |
| EF1A1_HUMAN | Elongation factor 1-alpha 1 | EEF1A1 | Secreted, EPI | LungCancers, Benign-Nodules | Cytoplasm. | Detection |
| EF1D_HUMAN | Elongation factor 1-delta | EEF1D | Secreted, EPI | LungCancers | | Prediction |
| EF2_HUMAN | Elongation factor 2 | EEF2 | Secreted, EPI | | Cytoplasm. | Literature, Detection |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| EGF_HUMAN | Pro-epidermal growth factor | EGF | | LungCancers, Benign-Nodules, Symptoms | Membrane; Single-pass type I membrane protein. | UniProt, Literature |
| EGFL6_HUMAN | Epidermal growth factor-like protein 6 | EGFL6 | | LungCancers | Secreted, extracellular space, extra-cellular matrix, basement membrane (By similarity). | UniProt, Detection, Prediction |
| ENOA_HUMAN | Alpha-enolase | ENO1 | Secreted, EPI, ENDO | LungCancers, Benign-Nodules, Symptoms | Cytoplasm. Cell membrane. Cytoplasm, myofibril, sarcomere, M-band. Note = Can translocate to the plasma membrane in either the homodimeric (alpha/alpha) or heterodimeric (alpha/gamma) form. ENO1 is localized to the M-band.\|Isoform MBP-1: Nucleus. | Literature, Detection, Prediction |
| ENOG_HUMAN | Gamma-enolase | ENO2 | EPI | LungCancers, Symptoms | Cytoplasm (By similarity). Cell membrane (By similarity). Note = Can translocate to the plasma membrane in either the homodimeric (alpha/alpha) or heterodimeric (alpha/gamma) form (By similarity). | Literature, Detection, Prediction |
| ENOX2_HUMAN | Ecto-NOX di-sulfide-thiol exchanger 2 | ENOX2 | | LungCancers | Cell membrane. Secreted, extracellular space. Note = Extracellular and plasma membrane-associated. | UniProt, Detection |
| ENPL_HUMAN | Endo-plasmin | HSP90B1 | Secreted, EPI, ENDO | LungCancers, Benign-Nodules, Symptoms | Endoplasmic reticulum lumen. Melanosome. Note = Identified by mass spectrometry in melanosome fractions from stage I to stage IV. | Literature, Detection, Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| EPHB6_HUMAN | Ephrin type-B receptor 6 | EPHB6 | | LungCancers | Membrane; Single-pass type I membrane protein. \|Isoform 3: Secreted (Probable). | UniProt, Literature |
| EPOR_HUMAN | Erythropoietin receptor | EPOR | | LungCancers, Benign-Nodules, Symptoms | Cell membrane; Single-pass type I membrane protein. \|Isoform EPOR-S: Secreted. Note = Secreted and located to the cell surface. | UniProt, Literature, Detection |
| ERBB3_HUMAN | Receptor tyrosine-protein kinase erbB-3 | ERBB3 | | LungCancers, Benign-Nodules | Isoform 1: Cell membrane; Single-pass type I membrane protein. \|Isoform 2: Secreted. | UniProt, Literature, Prediction |
| EREG_HUMAN | Proepiregulin | EREG | | LungCancers | Epiregulin: Secreted, extracellular space.\|Proepiregulin: Cell membrane; Single-pass type I membrane protein. | UniProt |
| ERO1A_HUMAN | ERO1-like protein alpha | ERO1L | Secreted, EPI, ENDO | Symptoms | Endoplasmic reticulum membrane; Peripheral membrane protein; Lumenal side. Note = The association with ERP44 is essential for its retention in the endoplasmic reticulum. | Prediction |
| ESM1_HUMAN | Endothelial cell-specific molecule 1 | ESM1 | | LungCancers, Benign-Nodules | Secreted. | UniProt, Prediction |
| EZRI_HUMAN | Ezrin | EZR | Secreted | LungCancers, Benign-Nodules | Apical cell membrane; Peripheral membrane protein; Cytoplasmic side. Cell projection. Cell projection, micro-villus membrane; Peripheral membrane protein; Cytoplasmic side. Cell projection, ruffle membrane; Peripheral membrane protein; Cytoplasmic side. Cytoplasm, | Literature, Detection, Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | cell cortex. Cytoplasm, cytoskeleton. Note = Localization to the apical membrane of parietal cells depends on the interaction with MPP5. Localizes to cell extensions and peripheral processes of astrocytes (By similarity). Microvillar peripheral membrane protein (cytoplasmic side). | |
| F10A1_HUMAN | Hsc70-interacting protein | ST13 | EPI | | Cytoplasm (By similarity). \|Cytoplasm (Probable). | Detection, Prediction |
| FAM3C_HUMAN | Protein FAM3C | FAM3C | EPI, ENDO | | Secreted (Potential). | UniProt, Detection |
| FAS_HUMAN | Fatty acid synthase | FASN | EPI | LungCancers, Benign-Nodules, Symptoms | Cytoplasm. Melanosome. Note = Identified by mass spectrometry in melanosome fractions from stage I to stage IV. | Literature, Detection |
| FCGR1_HUMAN | High affinity immunoglobulin gamma Fc receptor I | FCGR1A | EPI | LungCancers, Benign-Nodules, Symptoms | Cell membrane; Single-pass type I membrane protein. Note = Stabilized at the cell membrane through interaction with FCER1G. | UniProt |
| FGF10_HUMAN | Fibroblast growth factor 10 | FGF10 | | LungCancers | Secreted (Potential). | UniProt, Prediction |
| FGF2_HUMAN | Heparin-binding growth factor 2 | FGF2 | | LungCancers, Benign-Nodules, Symptoms | | Literature |
| FGF7_HUMAN | Keratinocyte growth factor | FGF7 | | LungCancers, Benign-Nodules | Secreted. | UniProt, Literature, Prediction |
| FGF9_HUMAN | Glia-activating factor | FGF9 | | LungCancers | Secreted. | UniProt, Literature, Prediction |
| FGFR2_HUMAN | Fibroblast growth factor receptor 2 | FGFR2 | | LungCancers, Benign-Nodules | Cell membrane; Single-pass type I membrane protein. \|Isoform 14: Secreted. \|Isoform 19: Secreted. | UniProt, Literature, Prediction |
| FGFR3_HUMAN | Fibroblast growth factor receptor 3 | FGFR3 | | LungCancers | Membrane; Single-pass type I membrane protein. | UniProt, Literature, Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| FGL2_HUMAN | Fibroleukin | FGL2 | | Benign-Nodules, Symptoms | Secreted. | UniProt, Detection, Prediction |
| FHIT_HUMAN | Bis(5'-adenosyl)-triphosphatase | FHIT | | LungCancers, Benign-Nodules, Symptoms | Cytoplasm. | Literature |
| FIBA_HUMAN | Fibrinogen alpha chain | FGA | | LungCancers, Benign-Nodules, Symptoms | Secreted. | UniProt, Literature, Detection, Prediction |
| FINC_HUMAN | Fibronectin | FN1 | Secreted, EPI, ENDO | LungCancers, Benign-Nodules, Symptoms | Secreted, extracellular space, extra-cellular matrix. | UniProt, Literature, Detection, Prediction |
| FKB11_HUMAN | Peptidyl-prolyl cis-trans isomerase FKBP11 | FKBP11 | EPI, ENDO | | Membrane; Single-pass membrane protein (Potential). | UniProt, Prediction |
| FOLH1_HUMAN | Glutamate carboxy-peptidase 2 | FOLH1 | ENDO | LungCancers, Symptoms | Cell membrane; Single-pass type II membrane protein. |Isoform PSMA': Cytoplasm. | UniProt, Literature |
| FOLR1_HUMAN | Folate receptor alpha | FOLR1 | | LungCancers | Cell membrane; Lipid-anchor, GPI-anchor. Secreted (Probable). | UniProt |
| FOXA2_HUMAN | Hepatocyte nuclear factor 3-beta | FOXA2 | | LungCancers | Nucleus. | Detection, Prediction |
| FP100_HUMAN | Fanconi anemia-associated protein of 100 kDa | C17orf70 | ENDO | Symptoms | Nucleus. | Prediction |
| FRIH_HUMAN | Ferritin heavy chain | FTH1 | EPI | LungCancers, Benign-Nodules | | Literature, Detection, Prediction |
| FRIL_HUMAN | Ferritin light chain | FTL | Secreted, EPI, ENDO | Benign-Nodules, Symptoms | | Literature, Detection |
| G3P_HUMAN | Glyceraldehyde-3-phosphate dehydrogenase | GAPDH | Secreted, EPI, ENDO | LungCancers, Benign-Nodules, Symptoms | Cytoplasm. Cytoplasm, perinuclear region. Membrane. Note = Postnuclear and Perinuclear regions. | Detection |
| G6PD_HUMAN | Glucose-6-phosphate 1-dehydrogenase | G6PD | Secreted, EPI | LungCancers, Symptoms | | Literature, Detection |
| G6PI_HUMAN | Glucose-6-phosphate isomerase | GPI | Secreted, EPI | Symptoms | Cytoplasm. Secreted. | UniProt, Literature, Detection |
| GA2L1_HUMAN | GAS2-like protein 1 | GAS2L1 | ENDO | | Cytoplasm, cytoskeleton (Probable). | Prediction |
| GALT2_HUMAN | Polypeptide N-acetylgalactosaminyl-transferase 2 | GALNT2 | EPI, ENDO | | Golgi apparatus, Golgi stack membrane; Single-pass type II | UniProt, Detection |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | membrane protein. Secreted. Note = Resides preferentially in the trans and medial parts of the Golgi stack. A secreted form also exists. | |
| GAS6_HUMAN | Growth arrest-specific protein 6 | GAS6 | | LungCancers | Secreted. | UniProt, Detection, Prediction |
| GDIR2_HUMAN | Rho GDP-dissociation inhibitor 2 | ARHGDIB | EPI | | Cytoplasm. | Detection |
| GELS_HUMAN | Gelsolin | GSN | | LungCancers, Benign-Nodules | Isoform 2: Cytoplasm, cytoskeleton. \|Isoform 1: Secreted. | UniProt, Literature, Detection, Prediction |
| GGH_HUMAN | Gamma-glutamyl hydrolase | GGH | | LungCancers | Secreted, extracellular space. Lysosome. Melanosome. Note = While its intracellular location is primarily the lysosome, most of the enzyme activity is secreted. Identified by mass spectrometry in melanosome fractions from stage I to stage IV. | UniProt, Detection, Prediction |
| GPC3_HUMAN | Glypican-3 | GPC3 | | LungCancers, Symptoms | Cell membrane; Lipid-anchor, GPI-anchor; Extracellular side (By similarity). \|Secreted glypican-3: Secreted, extracellular space (By similarity). | UniProt, Literature, Prediction |
| GRAN_HUMAN | Grancalcin | GCA | EPI | | Cytoplasm. Cytoplasmic granule membrane; Peripheral membrane protein; Cytoplasmic side. Note = Primarily cytosolic in the absence of calcium or magnesium ions. Relocates to granules and other membranes | Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | in response to elevated calcium and magnesium levels. | |
| GREB1_HUMAN | Protein GREB1 | GREB1 | ENDO | | Membrane; Single-pass membrane protein (Potential). | UniProt, Prediction |
| GREM1_HUMAN | Gremlin-1 | GREM1 | | LungCancers, Benign-Nodules | Secreted (Probable). | UniProt, Prediction |
| GRP_HUMAN | Gastrin-releasing peptide | GRP | | LungCancers, Symptoms | Secreted. | UniProt, Prediction |
| GRP78_HUMAN | 78 kDa glucose-regulated protein | HSPA5 | Secreted, EPI, ENDO | LungCancers, Benign-Nodules | Endoplasmic reticulum lumen. Melanosome. Note = Identified by mass spectrometry in melanosome fractions from stage I to stage IV. | Detection, Prediction |
| GSLG1_HUMAN | Golgi apparatus protein 1 | GLG1 | EPI, ENDO | Benign-Nodules | Golgi apparatus membrane; Single-pass type I membrane protein. | UniProt |
| GSTP1_HUMAN | Glutathione S-transferase P | GSTP1 | Secreted | LungCancers, Benign-Nodules, Symptoms | | Literature, Detection, Prediction |
| GTR1_HUMAN | Solute carrier family 2, facilitated glucose transporter member 1 | SLC2A1 | EPI, ENDO | LungCancers, Benign-Nodules, Symptoms | Cell membrane; Multi-pass membrane protein (By similarity). Melanosome. Note = Localizes primarily at the cell surface (By similarity). Identified by mass spectrometry in melanosome fractions from stage I to stage IV. | Literature |
| GTR3_HUMAN | Solute carrier family 2, facilitated glucose transporter member 3 | SLC2A3 | EPI | | Membrane; Multi-pass membrane protein. | Detection |
| H2A1_HUMAN | Histone H2A type 1 | HIST1H2AG | Secreted | | Nucleus. | Detection, Prediction |
| H2A1B_HUMAN | Histone H2A type 1-B/E | HIST1H2AB | Secreted | | Nucleus. | Detection, Prediction |
| H2A1C_HUMAN | Histone H2A type 1-C | HIST1H2AC | Secreted | | Nucleus. | Literature, Detection, Prediction |
| H2A1D_HUMAN | Histone H2A type 1-D | HIST1H2AD | Secreted | | Nucleus. | Detection, Prediction |
| HG2A_HUMAN | HLA class II histo- | CD74 | | LungCancers, Benign- | Membrane; Single-pass | UniProt, Literature |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | compatibility antigen gamma chain | | | Nodules, Symptoms | type II membrane protein (Potential). | |
| HGF_HUMAN | Hepatocyte growth factor | HGF | | LungCancers, Benign-Nodules, Symptoms | | Literature, Prediction |
| HMGA1_HUMAN | High mobility group protein HMG-I/HMG-Y | HMGA1 | | LungCancers, Benign-Nodules, Symptoms | Nucleus. | Literature |
| HPRT_HUMAN | Hypoxanthine-guanine phosphoribosyltransferase | HPRT1 | EPI | | Cytoplasm. | Detection, Prediction |
| HPSE_HUMAN | Heparanase | HPSE | | LungCancers, Benign-Nodules, Symptoms | Lysosome membrane; Peripheral membrane protein. Secreted. Note = Secreted, internalised and transferred to late endosomes/ lysosomes as a proheparanase. In lysosomes, it is processed into the active form, the heparanase. The uptake or internalisation of proheparanase is mediated by HSPGs. Heparin appears to be a competitor and retain proheparanase in the extracellular medium. | UniProt, Prediction |
| HPT_HUMAN | Haptoglobin | HP | | LungCancers, Benign-Nodules, Symptoms | Secreted. | UniProt, Literature, Detection, Prediction |
| HS90A_HUMAN | Heat shock protein HSP 90-alpha | HSP90AA1 | Secreted, EPI | LungCancers, Symptoms | Cytoplasm. Melanosome. Note = Identified by mass spectrometry in melanosome fractions from stage I to stage IV. | Literature, Detection |
| HS90B_HUMAN | Heat shock protein HSP 90-beta | HSP90AB1 | Secreted, EPI | LungCancers | Cytoplasm. Melanosome. Note = Identified by mass spectrometry in melanosome fractions from stage I to stage IV. | Literature, Detection |
| HSPB1_HUMAN | Heat shock protein beta-1 | HSPB1 | Secreted, EPI | LungCancers, Benign-Nodules | Cytoplasm. Nucleus. Cytoplasm, cytoskeleton, spindle. | Literature, Detection, Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | Note = Cytoplasmic in interphase cells. Colocalizes with mitotic spindles in mitotic cells. Translocates to the nucleus during heat shock. | |
| HTRA1_HUMAN | Serine protease HTRA1 | HTRA1 | | LungCancers | Secreted. | UniProt, Prediction |
| HXK1_HUMAN | Hexokinase-1 | HK1 | ENDO | Symptoms | Mitochondrion outer membrane. Note = Its hydrophobic N-terminal sequence may be involved in membrane binding. | Literature, Detection |
| HYAL2_HUMAN | Hyaluronidase-2 | HYAL2 | | LungCancers | Cell membrane; Lipid-anchor, GPI-anchor. | Prediction |
| HYOU1_HUMAN | Hypoxia up-regulated protein 1 | HYOU1 | EPI, ENDO | Symptoms | Endoplasmic reticulum lumen. | Detection |
| IBP2_HUMAN | Insulin-like growth factor-binding protein 2 | IGFBP2 | | LungCancers | Secreted. | UniProt, Literature, Detection, Prediction |
| IBP3_HUMAN | Insulin-like growth factor-binding protein 3 | IGFBP3 | | LungCancers, Benign-Nodules, Symptoms | Secreted. | UniProt, Literature, Detection, Prediction |
| ICAM1_HUMAN | Intercellular adhesion molecule 1 | ICAM1 | | LungCancers, Benign-Nodules, Symptoms | Membrane; Single-pass type I membrane protein. | UniProt, Literature, Detection |
| ICAM3_HUMAN | Intercellular adhesion molecule 3 | ICAM3 | EPI, ENDO | LungCancers, Benign-Nodules, Symptoms | Membrane; Single-pass type I membrane protein. | UniProt, Detection |
| IDHP_HUMAN | Isocitrate dehydrogenase [NADP], mitochondrial | IDH2 | Secreted, ENDO | | Mitochondrion. | Prediction |
| IF4A1_HUMAN | Eukaryotic initiation factor 4A-I | EIF4A1 | Secreted, EPI, ENDO | | | Detection, Prediction |
| IGF1_HUMAN | Insulin-like growth factor I | IGF1 | | LungCancers, Benign-Nodules, Symptoms | Secreted. |Secreted. | UniProt, Literature, Detection, Prediction |
| IKIP_HUMAN | Inhibitor of nuclear factor kappa-B kinase-interacting protein | IKIP | ENDO | Symptoms | Endoplasmic reticulum membrane; Single-pass membrane protein. Note = Isoform 4 deletion | UniProt, Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | of the hydrophobic, or transmembrane region between AA 45-63 results in uniform distribution troughout the cell, suggesting that this region is responsible for endoplasmic reticulum localization. | |
| IL18_HUMAN | Interleukin-18 | IL18 | | LungCancers, Benign-Nodules, Symptoms | Secreted. | UniProt, Literature, Prediction |
| IL19_HUMAN | Interleukin-19 | IL19 | | LungCancers | Secreted. | UniProt, Detection, Prediction |
| IL22_HUMAN | Interleukin-22 | IL22 | | LungCancers, Benign-Nodules | Secreted. | UniProt, Prediction |
| IL32_HUMAN | Interleukin-32 | IL32 | | LungCancers, Benign-Nodules | Secreted. | UniProt, Prediction |
| IL7_HUMAN | Interleukin-7 | IL7 | | LungCancers, Benign-Nodules | Secreted. | UniProt, Literature, Prediction |
| IL8_HUMAN | Interleukin-8 | IL8 | | LungCancers, Benign-Nodules, Symptoms | Secreted. | UniProt, Literature |
| ILEU_HUMAN | Leukocyte elastase inhibitor | SERPINB1 | Secreted, EPI | | Cytoplasm (By similarity). | Detection, Prediction |
| ILK_HUMAN | Integrin-linked protein kinase | ILK | Secreted | LungCancers, Benign-Nodules, Symptoms | Cell junction, focal adhesion. Cell membrane; Peripheral membrane protein; Cytoplasmic side. | Literature, Detection |
| INHBA_HUMAN | Inhibin beta A chain | INHBA | | LungCancers, Benign-Nodules | Secreted. | UniProt, Literature, Prediction |
| ISLR_HUMAN | Immuno-globulin super-family containing leucine-rich repeat protein | ISLR | | LungCancers | Secreted (Potential). | UniProt, Detection, Prediction |
| ITA5_HUMAN | Integrin alpha-5 | ITGA5 | EPI | LungCancers, Benign-Nodules, Symptoms | Membrane; Single-pass type I membrane protein. | UniProt, Literature, Detection |
| ITAM_HUMAN | Integrin alpha-M | ITGAM | EPI, ENDO | LungCancers, Benign-Nodules, Symptoms | Membrane; Single-pass type I membrane protein. | UniProt, Literature |
| K0090_HUMAN | Uncharacterized protein KIAA0090 | KIAA0090 | EPI | Symptoms | Membrane; Single-pass type I membrane protein (Potential). | UniProt, Prediction |
| K1C18_HUMAN | Keratin, type I cytoskeletal 18 | KRT18 | Secreted | LungCancers, Benign-Nodules | Cytoplasm, perinuclear region. | Literature, Detection, Prediction |
| K1C19_HUMAN | Keratin, type I | KRT19 | | LungCancers, Benign- | | Literature, Detection, |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | cytoskeletal 19 | | | Nodules | | Prediction |
| K2C8_HUMAN | Keratin, type II cytoskeletal 8 | KRT8 | EPI | LungCancers | Cytoplasm. | Literature, Detection |
| KIT_HUMAN | Mast/stem cell growth factor receptor | KIT | | LungCancers | Membrane; Single-pass type I membrane protein. | UniProt, Literature, Detection |
| KITH_HUMAN | Thymidine kinase, cytosolic | TK1 | | LungCancers | Cytoplasm. | Literature, Prediction |
| KLK11_HUMAN | Kallikrein-11 | KLK11 | | LungCancers | Secreted. | UniProt, Literature, Prediction |
| KLK13_HUMAN | Kallikrein-13 | KLK13 | | LungCancers | Secreted (Probable). | UniProt, Literature, Detection, Prediction |
| KLK14_HUMAN | Kallikrein-14 | KLK14 | | LungCancers, Symptoms | Secreted, extracellular space. | UniProt, Literature, Prediction |
| KLK6_HUMAN | Kallikrein-6 | KLK6 | | LungCancers, Benign-Nodules, Symptoms | Secreted. Nucleus, nucleolus. Cytoplasm. Mitochondrion. Microsome. Note = In brain, detected in the nucleus of glial cells and in the nucleus and cytoplasm of neurons. Detected in the mitochondrial and microsomal fractions of HEK-293 cells and released into the cytoplasm following cell stress. | UniProt, Literature, Detection, Prediction |
| KNG1_HUMAN | Kininogen-1 | KNG1 | | LungCancers, Benign-Nodules, Symptoms | Secreted, extracellular space. | UniProt, Detection, Prediction |
| KPYM_HUMAN | Pyruvate kinase isozymes M1/M2 | PKM2 | Secreted, EPI | LungCancers, Symptoms | Cytoplasm. Nucleus. Note = Translocates to the nucleus in response to different apoptotic stimuli. Nuclear translocation is sufficient to induce cell death that is caspase independent, isoform-specific and independent of its enzymatic activity. | Literature, Detection |
| KRT35_HUMAN | Keratin, type I cuticular Ha5 | KRT35 | ENDO | | | Detection, Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| LAMB2_HUMAN | Laminin subunit beta-2 | LAMB2 | ENDO | LungCancers, Symptoms | Secreted, extracellular space, extracellular matrix, basement membrane. Note = S-laminin is concentrated in the synaptic cleft of the neuromuscular junction. | UniProt, Detection, Prediction |
| LDHA_HUMAN | L-lactate dehydrogenase A chain | LDHA | Secreted, EPI, ENDO | LungCancers | Cytoplasm. | Literature, Detection, Prediction |
| LDHB_HUMAN | L-lactate dehydrogenase B chain | LDHB | EPI | LungCancers | Cytoplasm. | Detection, Prediction |
| LEG1_HUMAN | Galectin-1 | LGALS1 | Secreted | LungCancers | Secreted, extracellular space, extracellular matrix. | UniProt, Detection |
| LEG3_HUMAN | Galectin-3 | LGALS3 | | LungCancers, Benign-Nodules | Nucleus. Note = Cytoplasmic in adenomas and carcinomas. May be secreted by a non-classical secretory pathway and associate with the cell surface. | Literature, Detection, Prediction |
| LEG9_HUMAN | Galectin-9 | LGALS9 | ENDO | Symptoms | Cytoplasm (By similarity). Secreted (By similarity). Note = May also be secreted by a non-classical secretory pathway (By similarity). | UniProt |
| LG3BP_HUMAN | Galectin-3-binding protein | LGALS3BP | Secreted | LungCancers, Benign-Nodules, Symptoms | Secreted. Secreted, extracellular space, extracellular matrix. | UniProt, Literature, Detection, Prediction |
| LPLC3_HUMAN | Long palate, lung and nasal epithelium carcinoma-associated protein 3 | C20orf185 | | LungCancers | Secreted (By similarity). Cytoplasm. Note = According to PubPubMed: 12837268 it is cytoplasmic. | UniProt, Prediction |
| LPLC4_HUMAN | Long palate, lung and nasal epithelium carcinoma-associated protein 4 | C20orf186 | | LungCancers | Secreted (By similarity). Cytoplasm. | UniProt, Prediction |
| LPPRC_HUMAN | Leucine-rich PPR motif-containing | LRPPRC | Secreted, ENDO | LungCancers, Symptoms | Mitochondrion. Nucleus, nucleoplasm. Nucleus | Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | protein, mitochondrial | | | | inner membrane. Nucleus outer membrane. Note = Seems to be predominantly mitochondrial. | |
| LRP1_HUMAN | Prolow-density lipoprotein receptor-related protein 1 | LRP1 | EPI | LungCancers, Symptoms | Low-density lipoprotein receptor-related protein 1 85 kDa subunit: Cell membrane; Single-pass type I membrane protein. Membrane, coated pit.\|Low-density lipo-protein receptor-related protein 1 515 kDa subunit: Cell membrane; Peripheral membrane protein; Extracellular side. Membrane, coated pit.\|Low-density lipo-protein receptor-related protein 1 intra-cellular domain: Cytoplasm. Nucleus. Note = After cleavage, the intracellular domain (LRPICD) is detected both in the cytoplasm and in the nucleus. | UniProt, Detection |
| LUM_HUMAN | Lumican | LUM | Secreted, EPI | LungCancers, Benign-Nodules, Symptoms | Secreted, extracellular space, extra-cellular matrix (By similarity). | UniProt, Detection, Prediction |
| LY6K_HUMAN | Lymphocyte antigen 6K | LY6K | | LungCancers, Symptoms | Secreted. Cytoplasm. Cell membrane; Lipid-anchor, GPI-anchor (Potential). | UniProt, Prediction |
| LYAM2_HUMAN | E-selectin | SELE | | LungCancers, Benign-Nodules, Symptoms | Membrane; Single-pass type I membrane protein. | UniProt, Literature, Detection |
| LYAM3_HUMAN | P-selectin | SELP | | LungCancers, Benign-Nodules, Symptoms | Membrane; Single-pass type I membrane protein. | UniProt, Literature, Detection |
| LYOX_HUMAN | Protein-lysine 6-oxidase | LOX | | LungCancers, Benign-Nodules | Secreted, extracellular space. | UniProt, Detection, Prediction |
| LYPD3_HUMAN | Ly6/PLAUR domain- | LYPD3 | | LungCancers | Cell membrane; Lipid- | Detection, Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| MAGA4_HUMAN | containing protein 3 Melanoma-associated antigen 4 | MAGEA4 | | LungCancers | anchor, GPI-anchor. | Literature, Prediction |
| MASP1_HUMAN | Mannan-binding lectin serine protease 1 | MASP1 | | LungCancers, Symptoms | Secreted. | UniProt, Detection, Prediction |
| MDHC_HUMAN | Malate dehydrogenase, cytoplasmic | MDH1 | Secreted | | Cytoplasm. | Literature, Detection, Prediction |
| MDHM_HUMAN | Malate dehydrogenase, mitochondrial | MDH2 | ENDO | LungCancers | Mitochondrion matrix. | Detection, Prediction |
| MIF_HUMAN | Macrophage migration inhibitory factor | MIF | Secreted | LungCancers, Benign-Nodules, Symptoms | Secreted. Cytoplasm. Note = Does not have a cleavable signal sequence and is secreted via a specialized, non-classical pathway. Secreted by macrophages upon stimulation by bacterial lipopolysaccharide (LPS), or by M. tuberculosis antigens. | UniProt, Literature, Prediction |
| MLH1_HUMAN | DNA mismatch repair protein Mlh1 | MLH1 | ENDO | LungCancers, Benign-Nodules, Symptoms | Nucleus. | Literature |
| MMP1_HUMAN | Interstitial collagenase | MMP1 | | LungCancers, Benign-Nodules, Symptoms | Secreted, extracellular space, extra-cellular matrix (Probable). | UniProt, Literature, Prediction |
| MMP11_HUMAN | Stromelysin-3 | MMP11 | | LungCancers, Symptoms | Secreted, extracellular space, extra-cellular matrix (Probable). | UniProt, Literature, Prediction |
| MMP12_HUMAN | Macrophage metalloelastase | MMP12 | | LungCancers, Benign-Nodules, Symptoms | Secreted, extracellular space, extra-cellular matrix (Probable). | UniProt, Literature, Prediction |
| MMP14_HUMAN | Matrix metallo-proteinase-14 | MMP14 | ENDO | LungCancers, Benign-Nodules, Symptoms | Membrane; Single-pass type I membrane protein (Potential). Melanosome. Note = Identified by mass spectrometry in melanosome fractions from stage I to stage IV. | UniProt, Literature, Detection |
| MMP2_HUMAN | 72 kDa type IV collagenase | MMP2 | | LungCancers, Benign-Nodules, Symptoms | Secreted, extracellular space, extra-cellular matrix (Probable). | UniProt, Literature, Detection, Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| MMP26_HUMAN | Matrix metallo-proteinase-26 | MMP26 | | LungCancers | Secreted, extracellular space, extra-cellular matrix. | UniProt, Prediction |
| MMP7_HUMAN | Matrilysin | MMP7 | | LungCancers, Benign-Nodules, Symptoms | Secreted, extracellular space, extra-cellular matrix (Probable). | UniProt, Literature, Prediction |
| MMP9_HUMAN | Matrix metallo-proteinase-9 | MMP9 | | LungCancers, Benign-Nodules, Symptoms | Secreted, extracellular space, extra-cellular matrix (Probable). | UniProt, Literature, Detection, Prediction |
| MOGS_HUMAN | Mannosyl-oligosaccharide glucosidase | MOGS | ENDO | | Endoplasmic reticulum membrane; Single-pass type II membrane protein. | UniProt, Prediction |
| MPRI_HUMAN | Cation-independent mannose-6-phosphate receptor | IGF2R | EPI, ENDO | LungCancers, Symptoms | Lysosome membrane; Single-pass type I membrane protein. | UniProt, Literature, Detection |
| MRP3_HUMAN | Canalicular multi-specific organic anion transporter 2 | ABCC3 | EPI | LungCancers | Membrane; Multi-pass membrane protein. | Literature, Detection |
| MUC1_HUMAN | Mucin-1 | MUC1 | EPI | LungCancers, Benign-Nodules, Symptoms | Apical cell membrane; Single-pass type I membrane protein. Note = Exclusively located in the apical domain of the plasma membrane of highly polarized epithelial cells. After endocytosis, internalized and recycled to the cell membrane. Located to microvilli and to the tips of long filopodial protusitusisions. |Isoform 5: Secreted. |Isoform 7: Secreted. |Isoform 9: Secreted. |Mucin-1 subunit beta: Cell membrane. Cytoplasm. Nucleus. Note = On EGF and PDGFRB stimulation, | UniProt, Literature, Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | transported to the nucleus through interaction with CTNNB1, a process which is stimulated by phosphorylation. On HRG stimulation, colocalizes with JUP/gamma-catenin at the nucleus. | |
| MUC16_HUMAN | Mucin-16 | MUC16 | | LungCancers | Cell membrane; Single-pass type I membrane protein. Secreted, extracellular space. Note = May be liberated into the extracellular space following the phosphorylation of the intracellular C-terminus which induces the proteolytic cleavage and liberation of the extracellular domain. | UniProt, Detection |
| MUC4_HUMAN | Mucin-4 | MUC4 | | LungCancers, Benign-Nodules | Membrane; Single-pass membrane protein (Potential). Secreted. Note = Isoforms lacking the Cys-rich region, EGF-like domains and transmembrane region are secreted. Secretion occurs by splicing or proteolytic processcessing. \|Mucin-4 beta chain: Cell membrane; Single-pass membrane protein. \|Mucin-4 alpha chain: creted. \|Isoform 3: Cell membrane; Single-pass membrane | UniProt |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | protein. \|Isoform 15: Secreted. | |
| MUC5B_HUMAN | Mucin-5B | MUC5B | | LungCancers, Benign-Nodules | Secreted. | UniProt, Detection, Prediction |
| MUCL1_HUMAN | Mucin-like protein 1 | MUCL1 | | LungCancers | Secreted (Probable). Membrane (Probable). | UniProt, Prediction |
| NAMPT_HUMAN | Nicotinamide phosphoribosyltransferase | NAMPT | EPI | LungCancers, Benign-Nodules, Symptoms | Cytoplasm (By similarity). | Literature, Detection |
| NAPSA_HUMAN | Napsin-A | NAPSA | Secreted | LungCancers | | Prediction |
| NCF4_HUMAN | Neutrophil cytosol factor 4 | NCF4 | ENDO | | Cytoplasm. | Prediction |
| NDKA_HUMAN | Nucleoside di-phosphate kinase A | NME1 | Secreted | LungCancers, Benign-Nodules, Symptoms | Cytoplasm. Nucleus. Note = Cell-cycle dependent nuclear localization which can be induced by interaction with Epstein-barr viral proteins or by degradation of the SET complex by GzmA. | Literature, Detection |
| NDKB_HUMAN | Nucleoside di-phosphate kinase B | NME2 | Secreted, EPI | Benign-Nodules | Cytoplasm. Nucleus. Note = Isoform 2 is mainly cytoplasmic and isoform 1 and isoform 2 are excluded from the nucleolus. | Literature, Detection |
| NDUS1_HUMAN | NADH-ubiquinone oxidoreductase 75 kDa subunit, mitochondrial | NDUFS1 | Secreted, ENDO | Symptoms | Mitochondrion inner membrane. | Prediction |
| NEBL_HUMAN | Nebulette | NEBL | ENDO | | | Prediction |
| NEK4_HUMAN | Serine/threonine protein kinase Nek4 | NEK4 | ENDO | LungCancers | Nucleus (Probable). | Prediction |
| NET1_HUMAN | Netrin-1 | NTN1 | | LungCancers, Benign-Nodules | Secreted, extracellular space, extra-cellular matrix (By similarity). | UniProt, Literature, Prediction |
| NEU2_HUMAN | Vasopressin neurophysin 2-copeptin | AVP | | LungCancers, Symptoms | Secreted. | UniProt, Prediction |
| NGAL_HUMAN | Neutrophil gelatinase-associated lipocalin | LCN2 | EPI | LungCancers, Benign-Nodules, Symptoms | Secreted. | UniProt, Detection, Prediction |
| NGLY1_HUMAN | Peptide-N(4)-(N-acetyl-beta- | NGLY1 | ENDO | | Cytoplasm. | Detection, Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | glucosaminiyl)asparagine amidase | | | | | |
| NHRF1_HUMAN | Na(+)/H(+) exchange regulatory cofactor NHE-RF1 | SLC9A3R1 | EPI | Benign-Nodules | Endomembrane system; Peripheral membrane protein. Cell projection, filopodium. Cell projection, ruffle. Cell projection, microvillus. Note = Colocalizes with actin in microvilli-rich apical regions of the syncytio-trophoblast. Found in microvilli, ruffling membrane and filopodia of HeLa cells. Present in lipid rafts of T-cells. | Detection |
| NIBAN_HUMAN | Protein Niban | FAM129A | EPI | | Cytoplasm. | Literature, Detection |
| NMU_HUMAN | Neuromedin-U | NMU | | LungCancers | Secreted. | UniProt, Prediction |
| NRP1_HUMAN | Neuropilin-1 | NRP1 | | LungCancers, Benign-Nodules, Symptoms | Cell membrane; Single-pass type I membrane protein. IIsoform 2: Secreted. | UniProt, Literature, Detection, Prediction |
| ODAM_HUMAN | Odontogenic ameloblast-associated protein | ODAM | | LungCancers | Secreted (By similarity). | UniProt, Prediction |
| OSTP_HUMAN | Osteopontin | SPP1 | | LungCancers, Benign-Nodules, Symptoms | Secreted. | UniProt, Literature, Detection, Prediction |
| OVOS2_HUMAN | Ovostatin homolog 2 | OVOS2 | ENDO | | Secreted (By similarity). | UniProt, Prediction |
| P5CS_HUMAN | Delta-1-pyrroline-5-carboxylate synthase | ALDH18A1 | ENDO | | Mitochondrion inner membrane. | Prediction |
| PA2GX_HUMAN | Group 10 secretory phospholipase A2 | PLA2G10 | | Symptoms | Secreted. | UniProt |
| PAPP1_HUMAN | Pappalysin-1 | PAPPA | | LungCancers, Benign-Nodules, Symptoms | Secreted. | UniProt, Literature, Prediction |
| PBIP1_HUMAN | Pre-B-cell leukemia transcription factor-interacting protein 1 | PBXIP1 | EPI | | Cytoplasm, cytoskeleton. Nucleus. Note = Shuttles between the nucleus and the cytosol. Mainly localized in the cytoplasm, associated | Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | with microtubules. Detected in small amounts in the nucleus. | |
| PCBP1_HUMAN | Poly(rC)-binding protein 1 | PCBP1 | EPI, ENDO | | Nucleus. Cytoplasm. Note = Loosely bound in the nucleus. May shuttle between the nucleus and the cytoplasm. | Detection, Prediction |
| PCBP2_HUMAN | Poly(rC)-binding protein 2 | PCBP2 | EPI | | Nucleus. Cytoplasm. Note = Loosely bound in the nucleus. May shuttle between the nucleus and the cytoplasm. | Detection, Prediction |
| PCD15_HUMAN | Protocadherin-15 | PCDH15 | ENDO | | Cell membrane; Single-pass type I membrane protein (By similarity). \|Isoform 3: Secreted. | UniProt, Detection |
| PCNA_HUMAN | Proliferating cell nuclear antigen | PCNA | EPI | LungCancers, Benign-Nodules, Symptoms | Nucleus. | Literature, Prediction |
| PCYOX_HUMAN | Prenylcysteine oxidase 1 | PCYOX1 | Secreted | LungCancers, Symptoms | Lysosome. | Detection, Prediction |
| PDGFA_HUMAN | Platelet-derived growth factor subunit A | PDGFA | | LungCancers | Secreted. | UniProt, Literature, Prediction |
| PDGFB_HUMAN | Platelet-derived growth factor subunit B | PDGFB | | LungCancers, Benign-Nodules, Symptoms | Secreted. | UniProt, Literature, Detection, Prediction |
| PDGFD_HUMAN | Platelet-derived growth factor D | PDGFD | | LungCancers | Secreted. | UniProt, Prediction |
| PDIA3_HUMAN | Protein disulfide-isomerase A3 | PDIA3 | ENDO | LungCancers | Endoplasmic reticulum lumen (By similarity). Melanosome. Note = Identified by mass spectrometry in melanosome fractions from stage I to stage IV. | Detection, Prediction |
| PDIA4_HUMAN | Protein disulfide-isomerase A4 | PDIA4 | Secreted, EPI, ENDO | | Endoplasmic reticulum lumen. Melanosome. Note = Identified by mass spectrometry | Detection, Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| PDIA6_HUMAN | Protein disulfide-isomerase A6 | PDIA6 | Secreted, EPI, ENDO | | in melanosome fractions from stage I to stage IV. Endoplasmic reticulum lumen (By similarity). Melanosome. Note = Identified by mass spectrometry in melanosome fractions from stage I to stage IV. | Detection, Prediction |
| PECA1_HUMAN | Platelet endothelial cell adhesion molecule | PECAM1 | | LungCancers, Benign-Nodules, Symptoms | Membrane; Single-pass type I membrane protein. | UniProt, Literature, Detection |
| PEDF_HUMAN | Pigment epithelium-derived factor | SERPINF1 | | LungCancers, Symptoms | Secreted. Melanosome. Note = Enriched in stage I melanosomes. | UniProt, Literature, Detection, Prediction |
| PERM_HUMAN | Myeloperoxidase | MPO | Secreted, EPI, ENDO | LungCancers, Benign-Nodules, Symptoms | Lysosome. | Literature, Detection, Prediction |
| PERP1_HUMAN | Plasma cell-induced resident endoplasmic reticulum protein | PACAP | EPI, ENDO | | Secreted (Potential). Cytoplasm. Note = In (PubMed: 11350957) diffuse granular localization in the cytoplasm surrounding the nucleus. | UniProt, Detection, Prediction |
| PGAM1_HUMAN | Phosphoglycerate mutase 1 | PGAM1 | Secreted, EPI | LungCancers, Symptoms | | Detection |
| PLAC1_HUMAN | Placenta-specific protein 1 | PLAC1 | | LungCancers | Secreted (Probable). | UniProt, Prediction |
| PLACL_HUMAN | Placenta-specific 1-like protein | PLAC1L | | LungCancers | Secreted (Potential). | UniProt, Prediction |
| PLIN2_HUMAN | Perilipin-2 | ADFP | ENDO | LungCancers | Membrane; Peripheral membrane protein. | Prediction |
| PLIN3_HUMAN | Perilipin-3 | M6PRBP1 | EPI | | Cytoplasm. Endosome membrane; Peripheral membrane protein; Cytoplasmic side (Potential). Lipid droplet (Potential). Note = Membrane associated on endosomes. Detected in the envelope and the core of lipid bodies and in lipid sails. | Detection, Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| PLOD1_HUMAN | Procollagen-lysine,2-oxoglutarate 5-dioxygenase 1 | PLOD1 | EPI, ENDO | | Rough endoplasmic reticulum membrane; Peripheral membrane protein; Lumenal side. | Prediction |
| PLOD2_HUMAN | Procollagen-lysine,2-oxoglutarate 5-dioxygenase 2 | PLOD2 | ENDO | Benign-Nodules, Symptoms | Rough endoplasmic reticulum membrane; Peripheral membrane protein; Lumenal side. | Prediction |
| PLSL_HUMAN | Plastin-2 | LCP1 | Secreted, EPI | LungCancers | Cytoplasm, cytoskeleton. Cell junction. Cell projection. Cell projection, ruffle membrane; Peripheral membrane protein; Cytoplasmic side (By similarity). Note = Relocalizes to the immunological synapse between peripheral blood T lymphocytes and anti-body-presenting cells in response to costimulation through TCR/CD3 and CD2 or CD28. Associated with the actin cytoskeleton at membrane ruffles (By similarity). Relocalizes to actin-rich cell projections upon serine phosphorylation. | Detection, Prediction |
| PLUNC_HUMAN | Protein Plunc | PLUNC | | LungCancers, Benign-Nodules | Secreted (By similarity). Note = Found in the nasal mucus (By similarity). Apical side of airway epithelial cells. Detected in nasal mucus (By similarity). | UniProt, Prediction |
| PLXB3_HUMAN | Plexin-B3 | PLXNB3 | ENDO | | Membrane; Single-pass type I membrane protein. | UniProt, Detection, Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| PLXC1_HUMAN | Plexin-C1 | PLXNC1 | EPI | | Membrane; Single-pass type I membrane protein (Potential). | UniProt, Detection |
| POSTN_HUMAN | Periostin | POSTN | Secreted, ENDO | LungCancers, Benign-Nodules, Symptoms | Secreted, extracellular space, extra-cellular matrix. | UniProt, Literature, Detection, Prediction |
| PPAL_HUMAN | Lysosomal acid phosphatase | ACP2 | EPI | Symptoms | Lysosome membrane; Single-pass membrane protein; Lumenal side. Lysosome lumen. Note = The soluble form arises by proteolytic processing of the membrane-bound form. | UniProt, Prediction |
| PPBT_HUMAN | Alkaline phosphatase, tissue-nonspecific isozyme | ALPL | EPI | LungCancers, Benign-Nodules, Symptoms | Cell membrane; Lipid-anchor, GPI-anchor. | Literature, Detection, Prediction |
| PPIB_HUMAN | Peptidyl-prolyl cis-trans isomerase B | PPIB | Secreted, EPI, ENDO | | Endoplasmic reticulum lumen. Melanosome. Note = Identified by mass spectrometry in melanosome fractions from stage I to stage IV. | Detection, Prediction |
| PRDX1_HUMAN | Peroxiredoxin-1 | PRDX1 | EPI | LungCancers | Cytoplasm. Melanosome. Note = Identified by mass spectrometry in melanosome fractions from stage I to stage IV. | Detection, Prediction |
| PRDX4_HUMAN | Peroxiredoxin-4 | PRDX4 | Secreted, EPI, ENDO | | Cytoplasm. | Literature, Detection, Prediction |
| PROF1_HUMAN | Profilin-1 | PFN1 | Secreted, EPI | LungCancers | Cytoplasm, cytoskeleton. | Detection |
| PRP31_HUMAN | U4/U6 small nuclear ribo-nucleo-protein Prp31 | PRPF31 | ENDO | | Nucleus speckle. Nucleus, Cajal body. Note = Predominantly found in speckles and in Cajal bodies. | Prediction |
| PRS6A_HUMAN | 26S protease regulatory subunit 6A | PSMC3 | EPI | Benign-Nodules | Cytoplasm (Potential). Nucleus (Potential). | Detection |
| PSCA_HUMAN | Prostate stem cell antigen | PSCA | | LungCancers | Cell membrane; Lipid-anchor, GPI-anchor. | Literature, Prediction |
| PTGIS_HUMAN | Prostacyclin synthase | PTGIS | EPI | LungCancers, Benign-Nodules | Endoplasmic reticulum membrane; Single- | UniProt, Detection, Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | pass membrane protein. | |
| PTPA_HUMAN | Serine/threonine-protein phosphatase 2A activator | PPP2R4 | ENDO | Symptoms | | Detection, Prediction |
| PTPRC_HUMAN | Receptor-type tyrosine-protein phosphatase C | PTPRC | Secreted, EPI, ENDO | LungCancers | Membrane; Single-pass type I membrane protein. | UniProt, Detection, Prediction |
| PTPRJ_HUMAN | Receptor-type tyrosine-protein phosphatase eta | PTPRJ | EPI | LungCancers, Symptoms | Membrane; Single-pass type I membrane protein. | UniProt, Detection, Prediction |
| PVR_HUMAN | Poliovirus receptor | PVR | | Symptoms | Isoform Alpha: Cell membrane; Single-pass type I membrane protein. \|Isoform Delta: Cell membrane; Single-pass type I membrane protein. \|Isoform Beta: Secretcreted. \|Isoform Gamma: Secreted. | UniProt, Detection, Prediction |
| RAB32_HUMAN | Ras-related protein Rab-32 | RAB32 | EPI | | Mitochondrion. | Prediction |
| RAGE_HUMAN | Advanced glycosylation end product-specific receptor | AGER | Secreted | LungCancers, Benign-Nodules | Isoform 1: Cell membrane; Single-pass type I membrane protein. \|Isoform 2: Secreted. | UniProt, Literature |
| RAN_HUMAN | GTP-binding nuclear protein Ran | RAN | Secreted, EPI | LungCancers, Benign-Nodules | Nucleus. Cytoplasm. Melanosome. Note = Becomes dispersed throughout the cytoplasm during mitosis. Identified by mass spectrometry in melanosome fractions from stage I to stage IV. | Detection, Prediction |
| RAP2B_HUMAN | Ras-related protein Rap-2b | RAP2B | EPI | | Cell membrane; Lipid-anchor; Cytoplasmicside (Potential). | Prediction |
| RAP2C_HUMAN | Ras-related protein Rap-2c | RAP2C | EPI | | Cell membrane; Lipid-anchor; Cytoplasmic side (Potential). | Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| RCN3_HUMAN | Reticulocalbin-3 | RCN3 | EPI | Symptoms | Endoplasmic reticulum lumen (Potential). | Prediction |
| RL24_HUMAN | 60S ribosomal protein L24 | RPL24 | EPI | | | Prediction |
| S10A1_HUMAN | Protein S100-A1 | S100A1 | | Symptoms | Cytoplasm. | Literature, Prediction |
| S10A6_HUMAN | Protein S100-A6 | S100A6 | Secreted | LungCancers | Nucleus envelope. Cytoplasm. | Literature, Detection, Prediction |
| S10A7_HUMAN | Protein S100-A7 | S100A7 | | LungCancers | Cytoplasm. Secreted. Note = Secreted by a non-classical secretory pathway. | UniProt, Literature, Detection, Prediction |
| SAA_HUMAN | Serum amyloid A protein | SAA1 | | Symptoms | Secreted. | UniProt, Literature, Detection, Prediction |
| SCF_HUMAN | Kit ligand | KITLG | | LungCancers, Symptoms | Isoform 1: Cell membrane; Single-pass type I membrane protein (By similarity). Secreted (By similarity). Note = Also exists as a secreted soluble form (isoform 1 only) (By similarity). \|Isoform 2: Cell membrane; Single-pass type I membrane protein (By similarity). Cytoplasm, cytoskeleton (By similarity). | UniProt, Literature |
| SDC1_HUMAN | Syndecan-1 | SDC1 | | LungCancers, BenignNodules, Symptoms | Membrane; Single-pass type I membrane protein. | UniProt, Literature, Detection |
| SEM3G_HUMAN | Semaphorin-3G | SEMA3G | | LungCancers | Secreted (By similarity). | UniProt, Prediction |
| SEPR_HUMAN | Seprase | FAP | ENDO | Symptoms | Cell membrane; Single-pass type II membrane protein. Cell projection, lamellipodium membrane; Single-pass type II membrane protein. Cell projection, invadopodium membrane; Single-pass type II | UniProt, Literature, Detection |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | membrane protein. Note = Found in cell surface lamellipodia, invadopodia and on shed vesicles. | |
| SERPH_HUMAN | Serpin H1 | SERPINH1 | Secreted, EPI, ENDO | LungCancers, Benign-Nodules | Endoplasmic reticulum lumen. | Detection, Prediction |
| SFPA2_HUMAN | Pulmonary surfactant-associated protein A2 | SFTPA2 | Secreted | LungCancers, Benign-Nodules | Secreted, extracellular space, extracellular matrix. Secreted, extracellular space, surface film. | UniProt, Prediction |
| SFTA1_HUMAN | Pulmonary surfactant-associated protein A1 | SFTPA1 | Secreted | LungCancers, Benign-Nodules, Symptoms | Secreted, extracellular space, extracellular matrix. Secreted, extracellular space, surface film. | UniProt, Prediction |
| SG3A2_HUMAN | Secretoglobin family 3A member 2 | SCGB3A2 | | LungCancers, Benign-Nodules | Secreted. | UniProt, Prediction |
| SGPL1_HUMAN | Sphingosine-1-phosphate lyase 1 | SGPL1 | ENDO | | Endoplasmic reticulum membrane; Single-pass type III membrane protein. | UniProt, Prediction |
| SIAL_HUMAN | Bone sialoprotein 2 | IBSP | | LungCancers | Secreted. | UniProt, Literature, Prediction |
| SLPI_HUMAN | Antileukoproteinase | SLPI | | LungCancers, Benign-Nodules | Secreted. | UniProt, Literature, Detection, Prediction |
| SMD3_HUMAN | Small nuclear ribonucleoprotein Sm D3 | SNRPD3 | Secreted | Benign-Nodules | Nucleus. | Prediction |
| SMS_HUMAN | Somatostatin | SST | | LungCancers | Secreted. | UniProt, Literature, Prediction |
| SODM_HUMAN | Superoxide dismutase [Mn], mitochondrial | SOD2 | Secreted | LungCancers, Benign-Nodules, Symptoms | Mitochondrion matrix. | Literature, Detection, Prediction |
| SORL_HUMAN | Sortilin-related receptor | SORL1 | EPI | LungCancers, Symptoms | Membrane; Single-pass type I membrane protein (Potential). | UniProt, Detection |
| SPB3_HUMAN | Serpin B3 | SERPINB3 | | LungCancers, Benign-Nodules | Cytoplasm. Note = Seems to also be secreted in plasma by cancerous cells but at a low level. | Literature, Detection |
| SPB5_HUMAN | Serpin B5 | SERPINB5 | | LungCancers | Secreted, extracellular space. | UniProt, Detection |
| SPON2_HUMAN | Spondin-2 | SPON2 | | LungCancers, Benign-Nodules | Secreted, extracellular space, extracellular matrix (By similarity). | UniProt, Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| SPRC_HUMAN | SPARC | SPARC | | LungCancers, BenignNodules, Symptoms | Secreted, extracellular space, extra-cellular matrix, basement membrane. Note = In or around the basement membrane. | UniProt, Literature, Detection, Prediction |
| SRC_HUMAN | Proto-oncogene tyrosine-protein kinase Src | SRC | ENDO | LungCancers, BenignNodules, Symptoms | | Literature |
| SSRD_HUMAN | Trans-locon-associated protein subunit delta | SSR4 | Secreted, ENDO | | Endoplasmic reticulum membrane; Single-pass type I membrane protein. | UniProt, Prediction |
| STAT1_HUMAN | Signal transducer and activator of transcription 1-alpha/beta | STAT1 | EPI | LungCancers, BenignNodules | Cytoplasm. Nucleus. Note = Translocated into the nucleus in response to IFN-gamma-induced tyrosine phosphorylation and dimerization. | Detection |
| STAT3_HUMAN | Signal transducer and activator of transcription 3 | STAT3 | ENDO | LungCancers, BenignNodules, Symptoms | Cytoplasm. Nucleus. Note = Shuttles between the nucleus and the cytoplasm. Constitutive nuclear presence is independent of tyrosine phosphorylation. | Prediction |
| STC1_HUMAN | Stannio-calcin-1 | STC1 | | LungCancers, Symptoms | Secreted. | UniProt, Prediction |
| STT3A_HUMAN | Dolichyl-diphosphooligo-saccharide--protein glycosyl-transferase subunit STT3A | STT3A | EPI | Symptoms | Endoplasmic reticulum membrane; Multi-pass membrane protein. | Literature |
| TAGL_HUMAN | Transgelin | TAGLN | EPI | LungCancers | Cytoplasm (Probable). | Literature, Prediction |
| TARA_HUMAN | TRIO and F-actin-binding protein | TRIOBP | ENDO | | Nucleus. Cytoplasm, cytoskeleton. Note = Localized to F-actin in a periodic pattern. | Detection, Prediction |
| TBA1B_HUMAN | Tubulin alpha-1B chain | TUBA1B | EPI | LungCancers | | Detection |
| TBB2A_HUMAN | Tubulin beta-2A chain | TUBB2A | EPI | LungCancers, BenignNodules | | Detection, Prediction |
| TBB3_HUMAN | Tubulin beta-3 chain | TUBB3 | EPI | LungCancers, BenignNodules | | Detection |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| TBB5_HUMAN | Tubulin beta chain | TUBB | EPI | LungCancers, Benign-Nodules | | Detection |
| TCPA_HUMAN | T-complex protein 1 subunit alpha | TCP1 | EPI | | Cytoplasm. | Prediction |
| TCPD_HUMAN | T-complex protein 1 subunit delta | CCT4 | EPI | | Cytoplasm. Melanosome. Note = Identified by mass spectrometry in melanosome fractions from stage I to stage IV. | Detection, Prediction |
| TCPQ_HUMAN | T-complex protein 1 subunit theta | CCT8 | Secreted, EPI | | Cytoplasm. | Prediction |
| TCPZ_HUMAN | T-complex protein 1 subunit zeta | CCT6A | Secreted, EPI | | Cytoplasm. | Detection |
| TDRD3_HUMAN | Tudor domain-containing protein 3 | TDRD3 | ENDO | | Cytoplasm. Nucleus. Note = Predominantly cytoplasmic. Associated with actively translating polyribosomes and with mRNA stress granules. | Prediction |
| TENA_HUMAN | Tenascin | TNC | ENDO | LungCancers, Benign-Nodules, Symptoms | Secreted, extracellular space, extra-cellular matrix. | UniProt, Literature, Detection |
| TENX_HUMAN | Tenascin-X | TNXB | ENDO | LungCancers, Symptoms | Secreted, extracellular space, extra-cellular matrix. | UniProt, Detection, Prediction |
| TERA_HUMAN | Transitional endo-plasmic reticulum ATPase | VCP | EPI | LungCancers, Benign-Nodules | Cytoplasm, cytosol. Nucleus. Note = Present in the neuronal hyaline inclusion bodies specifically found in motor neurons from amyotrophic lateral sclerosis patients. Present in the Lewy bodies specifically found in neurons from Parkinson disease patients. | Detection |
| TETN_HUMAN | Tetranectin | CLEC3B | | LungCancers | Secreted. | UniProt, Literature, Detection, Prediction |
| TF_HUMAN | Tissue factor | F3 | | LungCancers, Benign-Nodules, Symptoms | Membrane; Single-pass type I membrane protein. | UniProt, Literature |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| TFR1_HUMAN | Transferrin receptor protein 1 | TFRC | Secreted, EPI, ENDO | LungCancers, Benign-Nodules, Symptoms | Cell membrane; Single-pass type II membrane protein. Melanosome. Note = Identified by mass spectrometry in melanosome fractions from stage I to stage IV.|Transferrin receptor protein 1, serum form: Secreted. | UniProt, Literature, Detection |
| TGFA_HUMAN | Protransforming growth factor alpha | TGFA | | LungCancers, Benign-Nodules | Transforming growth factor alpha: Secreted, extracellular space.|Protransforming growth factor alpha: Cell membrane; Single-pass type I membrane protein. | UniProt, Literature |
| THAS_HUMAN | Thromboxane-A synthase | TBXAS1 | EPI, ENDO | LungCancers, Benign-Nodules, Symptoms | Membrane; Multi-pass membrane protein. | Prediction |
| THY1_HUMAN | Thy-1 membrane glycoprotein | THY1 | EPI | Symptoms | Cell membrane; Lipid-anchor, GPI-anchor (By similarity). | Detection, Prediction |
| TIMP1_HUMAN | Metalloproteinase inhibitor 1 | TIMP1 | | LungCancers, Benign-Nodules, Symptoms | Secreted. | UniProt, Literature, Detection, Prediction |
| TIMP3_HUMAN | Metalloproteinase inhibitor 3 | TIMP3 | | LungCancers, Benign-Nodules | Secreted, extracellular space, extracellular matrix. | UniProt, Literature, Prediction |
| TLL1_HUMAN | Tolloid-like protein 1 | TLL1 | ENDO | | Secreted (Probable). | UniProt, Prediction |
| TNF12_HUMAN | Tumor necrosis factor ligand superfamily member 12 | TNFSF12 | | LungCancers, Benign-Nodules | Cell membrane; Single-pass type II membrane protein. |Tumor necrosis factor ligand superfamily member 12, secreted form: Secreted. | UniProt |
| TNR6_HUMAN | Tumor necrosis factor receptor superfamily member 6 | FAS | | LungCancers, Benign-Nodules, Symptoms | Isoform 1: Cell membrane; Single-pass type I membrane protein. |Isoform 2: Secreted. |Isoform 3: Secreted. |Isoform 4: Secreted. | UniProt, Literature, Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | \|Isoform 5: Secreted. \|Isoform 6: Secreted. | |
| TPIS_HUMAN | Triosephosphate isomerase | TPI1 | Secreted, EPI | Symptoms | | Literature, Detection, Prediction |
| TRFL_HUMAN | Lactotransferrin | LTF | Secreted, EPI, ENDO | LungCancers, Benign-Nodules, Symptoms | Secreted. | UniProt, Literature, Detection, Prediction |
| TSP1_HUMAN | Thrombospondin-1 | THBS1 | | LungCancers, Benign-Nodules, Symptoms | | Literature, Detection, Prediction |
| TTHY_HUMAN | Transthyretin | TTR | | LungCancers, Benign-Nodules | Secreted. Cytoplasm. | UniProt, Literature, Detection, Prediction |
| TYPH_HUMAN | Thymidine phosphorylase | TYMP | EPI | LungCancers, Benign-Nodules, Symptoms | | Literature, Detection, Prediction |
| UGGG1_HUMAN | UDP-glucose:glycoprotein glucosyl-transferase 1 | UGGT1 | Secreted, ENDO | | Endoplasmic reticulum lumen. Endoplasmic reticulum-Golgi intermediate compartment. | Detection, Prediction |
| UGGG2_HUMAN | UDP-glucose:glycoprotein glucosyl-transferase 2 | UGGT2 | ENDO | | Endoplasmic reticulum lumen. Endoplasmic reticulum-Golgi intermediate compartment. | Prediction |
| UGPA_HUMAN | UTP--glucose-1-phosphate uridyl-dyl-yltransferase | UGP2 | EPI | Symptoms | Cytoplasm. | Detection |
| UPAR_HUMAN | Urokinase plasminogen activator surface receptor | PLAUR | | LungCancers, Benign-Nodules, Symptoms | Isoform 1: Cell membrane; Lipid-anchor, GPI-anchor. \|Isoform 2: Secreted (Probable). | UniProt, Literature, Prediction |
| UTER_HUMAN | Uteroglobin | SCGB1A1 | | LungCancers, Benign-Nodules, Symptoms | Secreted. | UniProt, Literature, Detection, Prediction |
| VA0D1_HUMAN | V-type proton ATPase subunit d1 | ATP6V0D1 | EPI | | | Prediction |
| VAV3_HUMAN | Guanine nucleotide exchange factor VAV3 | VAV3 | ENDO | | | Prediction |
| VEGFA_HUMAN | Vascular endothelial growth factor A | VEGFA | | LungCancers, Benign-Nodules, Symptoms | Secreted. Note = VEGF 121 is acidic and freely secreted. VEGF165 is more basic, has heparin-binding properties and, although a | UniProt, Literature, Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | signicant proportion remains cell-associated, most is freely secreted. VEGF189 is very basic, it is cell-associated after secretion and is bound avidly by heparin and the extracellular matrix, although it may be released as a soluble form by heparin, heparinase or plasmin. | |
| VEGFC_HUMAN | Vascular endothelial growth factor C | VEGFC | | LungCancers, Benign-Nodules | Secreted. | UniProt, Literature, Prediction |
| VEGFD_HUMAN | Vascular endothelial growth factor D | FIGF | | LungCancers | Secreted. | UniProt, Literature, Prediction |
| VGFR1_HUMAN | Vascular endothelial growth factor receptor 1 | FLT1 | | LungCancers, Benign-Nodules, Symptoms | Isoform Flt1: Cell membrane; Single-pass type I membrane protein. \|Isoform sFlt1: Secreted. | UniProt, Literature, Detection, Prediction |
| VTNC_HUMAN | Vitronectin | VTN | ENDO | Symptoms | Secreted, extracellular space. | UniProt, Literature, Detection, Prediction |
| VWC2_HUMAN | Brorin | VWC2 | | LungCancers | Secreted, extracellular space, extra-cellular matrix, basement membrane (By similarity). | UniProt, Prediction |
| WNT3A_HUMAN | Protein Wnt-3a | WNT3A | | LungCancers, Symptoms | Secreted, extracellular space, extra-cellular matrix. | UniProt, Prediction |
| WT1_HUMAN | Wilms tumor protein | WT1 | | LungCancers, Benign-Nodules, Symptoms | Nucleus. Cytoplasm (By similarity). Note = Shuttles between nucleus and cytoplasm (By similarity). \|Isoform 1: Nucleus speckle. \|Isoform 4: Nucleus, nucleoplasm. | Literature, Prediction |
| ZA2G_HUMAN | Zinc-alpha-2-glycoprotein | AZGP1 | | LungCancers, Symptoms | Secreted. | UniProt, Literature, Detection, Prediction |

TABLE 6-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| ZG16B_HUMAN | Zymogen granule protein 16 homolog B | ZG16B | | LungCancers | Secreted (Potential). | UniProt, Prediction |

190 of these candidate protein biomarkers were shown to be measured reproducibly in blood. A moderately powered multisite and unbiased study of 242 blood samples from patients with PN was designed to determine whether a statistically significant subpanel of proteins could be identified to distinguish benign and malignant nodules of sizes under 2 cm. The three sites contributing samples and clinical data to this study were the University of Laval, University of Pennsylvania and New York University.

In an embodiment of the invention, a panel of 15 proteins effectively distinguished between samples derived from patients with benign and malignant nodules less than 2 cm diameter.

Bioinformatic and biostatistical analyses were used first to identify individual proteins with statistically significant differential expression, and then using these proteins to derive one or more combinations of proteins or panels of proteins, which collectively demonstrated superior discriminatory performance compared to any individual protein. Bioinformatic and biostatistical methods are used to derive coefficients (C) for each individual protein in the panel that reflects its relative expression level, i.e. increased or decreased, and its weight or importance with respect to the panel's net discriminatory ability, relative to the other proteins. The quantitative discriminatory ability of the panel can be expressed as a mathematical algorithm with a term for each of its constituent proteins being the product of its coefficient and the protein's plasma expression level (P) (as measured by LC-SRM-MS), e.g. C×P, with an algorithm consisting of n proteins described as: C1×P1+C2×P2+C3×P3+ . . . +Cn×Pn. An algorithm that discriminates between disease states with a predetermined level of statistical significance may be refers to a "disease classifier". In addition to the classifier's constituent proteins with differential expression, it may also include proteins with minimal or no biologic variation to enable assessment of variability, or the lack thereof, within or between clinical specimens; these proteins may be termed typical native proteins and serve as internal controls for the other classifier proteins.

In certain embodiments, expression levels are measured by MS. MS analyzes the mass spectrum produced by an ion after its production by the vaporization of its parent protein and its separation from other ions based on its mass-to-charge ratio. The most common modes of acquiring MS data are 1) full scan acquisition resulting in the typical total ion current plot (TIC), 2) selected ion monitoring (SIM), and 3) selected reaction monitoring (SRM).

In certain embodiments of the methods provided herein, biomarker protein expression levels are measured by LC-SRM-MS. LC-SRM-MS is a highly selective method of tandem mass spectrometry which has the potential to effectively filter out all molecules and contaminants except the desired analyte(s). This is particularly beneficial if the analysis sample is a complex mixture which may comprise several isobaric species within a defined analytical window. LC-SRM-MS methods may utilize a triple quadrupole mass spectrometer which, as is known in the art, includes three quadrupole rod sets. A first stage of mass selection is performed in the first quadrupole rod set, and the selectively transmitted ions are fragmented in the second quadrupole rod set. The resultant transition (product) ions are conveyed to the third quadrupole rod set, which performs a second stage of mass selection. The product ions transmitted through the third quadrupole rod set are measured by a detector, which generates a signal representative of the numbers of selectively transmitted product ions. The RF and DC potentials applied to the first and third quadruples are tuned to select (respectively) precursor and product ions that have m/z values lying within narrow specified ranges. By specifying the appropriate transitions (m/z values of precursor and product ions), a peptide corresponding to a targeted protein may be measured with high degrees of sensitivity and selectivity. Signal-to-noise ratio is superior to conventional tandem mass spectrometry (MS/MS) experiments, which select one mass window in the first quadrupole and then measure all generated transitions in the ion detector. LC-SRM-MS.

In certain embodiments, an SRM-MS assay for use in diagnosing or monitoring lung cancer as disclosed herein may utilize one or more peptides and/or peptide transitions derived from the proteins set forth in Table 6. In certain embodiments, the assay may utilize peptides and/or peptide transitions from 100 or more, 150 or more, 200 or more, 250 or more, 300 or more, 345 or more, or 371 or more biomarker proteins. In certain embodiments, two or more peptides may be utilized per biomarker proteins, and in certain of these embodiments three or more of four or more peptides may be utilized. Similarly, in certain embodiments two or more transitions may be utilized per peptide, and in certain of these embodiments three or more; four or more; or five or more transitions may be utilized per peptide. In one embodiment, an LC-SRM-MS assay for use in diagnosing lung cancer may measure the intensity of five transitions that correspond to selected peptides associated with each biomarker protein. The achievable limit of quantification (LOQ) may be estimated for each peptide according to the observed signal intensities during this analysis. For examples, for sets of target proteins associated with lung cancer see Table 12.

The expression level of a biomarker protein can be measured using any suitable method known in the art, including but not limited to mass spectrometry (MS), reverse transcriptase-polymerase chain reaction (RT-PCR), microarray, serial analysis of gene expression (SAGE), gene expression analysis by massively parallel signature sequencing (MPSS), immunoassays (e.g., ELISA), immunohistochemistry (IHC), transcriptomics, and proteomics.

To evaluate the diagnostic performance of a particular set of peptide transitions, a ROC curve is generated for each significant transition.

Figure 7:
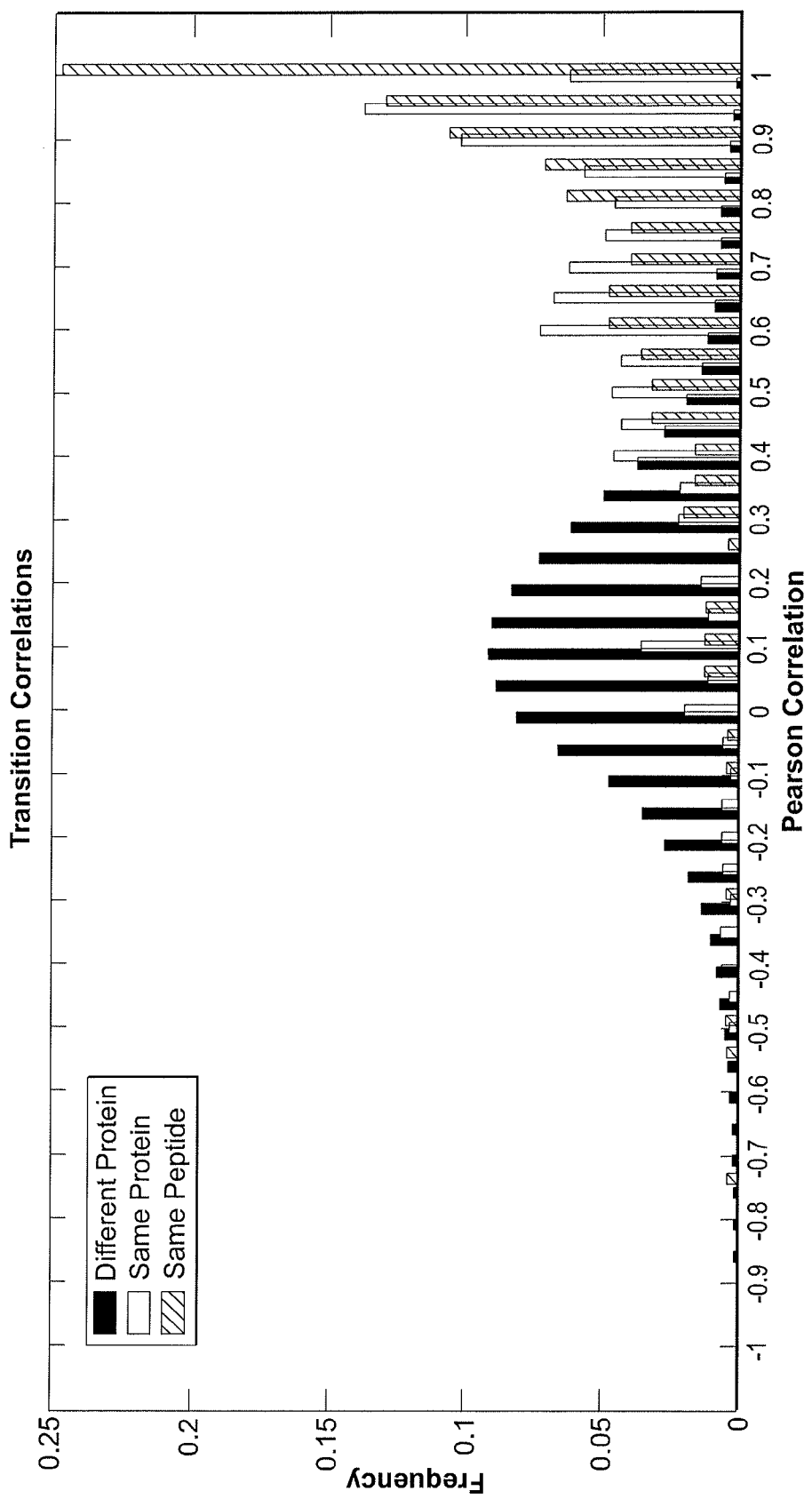
FIG. 7 is a bar diagram showing Pearson correlations for peptides from the same peptide, from the same protein and from different proteins.
Figure 9:
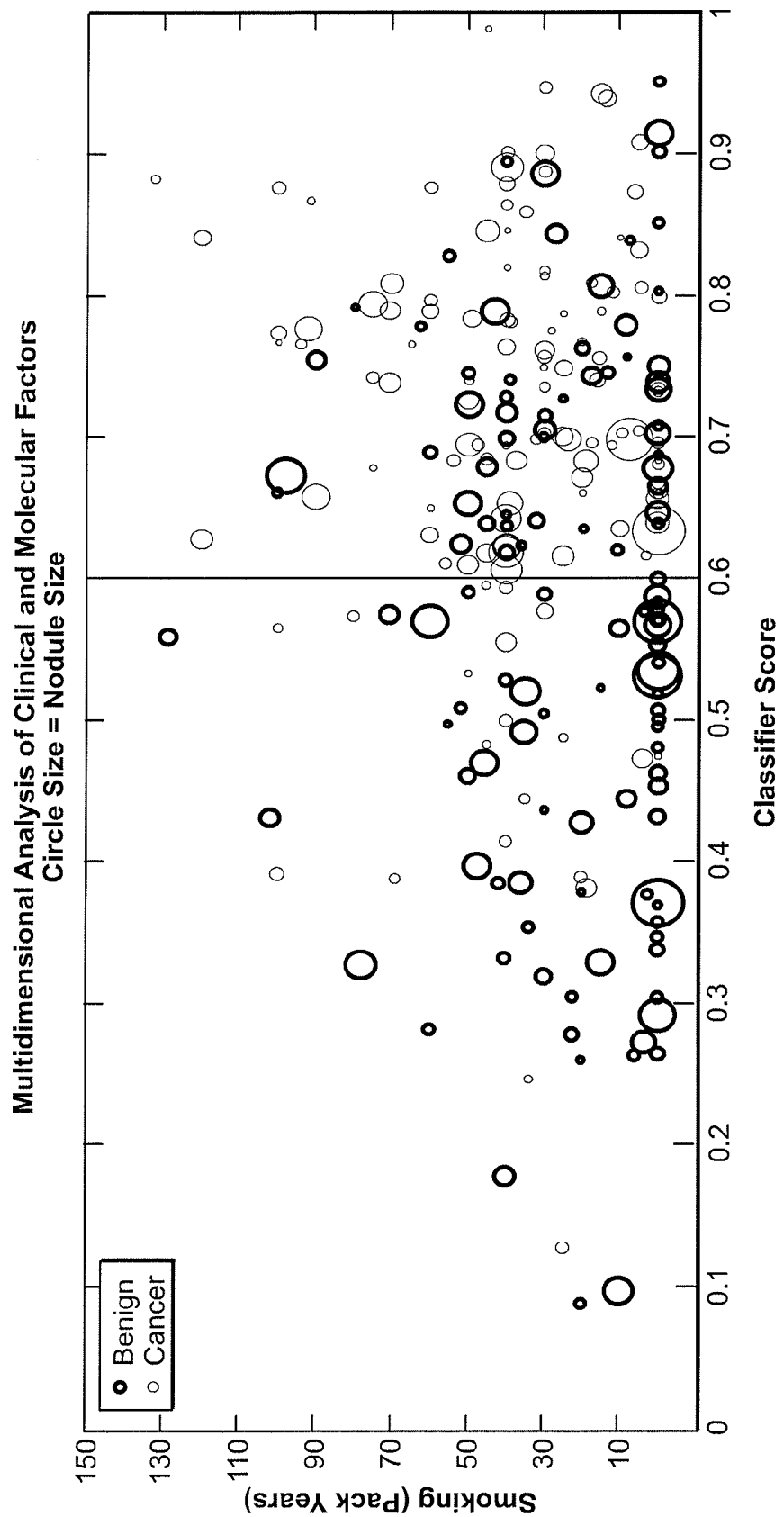
FIG. 9 is a graph showing clinical and molecular factors.

An "ROC curve" as used herein refers to a plot of the true positive rate (sensitivity) against the false positive rate (specificity) for a binary classifier system as its discrimination threshold is varied. A ROC curve can be represented equivalently by plotting the fraction of true positives out of the positives (TPR=true positive rate) versus the fraction of false positives out of the negatives (FPR=false positive rate). Each point on the ROC curve represents a sensitivity/specificity pair corresponding to a particular decision threshold. FIGS. 7 and 9 provide a graphical representation of the functional relationship between the distribution of biomarker or biomarker panel sensitivity and specificity values in a cohort of diseased subjects and in a cohort of non-diseased subjects.

AUC represents the area under the ROC curve. The AUC is an overall indication of the diagnostic accuracy of 1) a biomarker or a panel of biomarkers and 2) a ROC curve. AUC is determined by the "trapezoidal rule." For a given curve, the data points are connected by straight line segments, perpendiculars are erected from the abscissa to each data point, and the sum of the areas of the triangles and trapezoids so constructed is computed. In certain embodiments of the methods provided herein, a biomarker protein has an AUC in the range of about 0.75 to 1.0. In certain of these embodiments, the AUC is in the range of about 0.8 to 0.8, 0.9 to 0.95, or 0.95 to 1.0.

The methods provided herein are minimally invasive and pose little or no risk of adverse effects. As such, they may be used to diagnose, monitor and provide clinical management of subjects who do not exhibit any symptoms of a lung condition and subjects classified as low risk for developing a lung condition. For example, the methods disclosed herein may be used to diagnose lung cancer in a subject who does not present with a PN and/or has not presented with a PN in the past, but who nonetheless deemed at risk of developing a PN and/or a lung condition. Similarly, the methods disclosed herein may be used as a strictly precautionary measure to diagnose healthy subjects who are classified as low risk for developing a lung condition.

The present invention provides a method of determining the likelihood that a lung condition in a subject is cancer by measuring an abundance of a panel of proteins in a sample obtained from the subject; calculating a probability of cancer score based on the protein measurements and ruling out cancer for the subject if the score) is lower than a pre-determined score, wherein when cancer is ruled out the subject does not receive a treatment protocol. Treatment protocols include for example pulmonary function test (PFT), pulmonary imaging, a biopsy, a surgery, a chemotherapy, a radiotherapy, or any combination thereof. In some embodiments, the imaging is an x-ray, a chest computed tomography (CT) scan, or a positron emission tomography (PET) scan.

The present invention further provides a method of ruling in the likelihood of cancer for a subject by measuring an abundance of panel of proteins in a sample obtained from the subject, calculating a probability of cancer score based on the protein measurements and ruling in the likelihood of cancer for the subject if the score in step is higher than a pre-determined score In another aspect the invention further provides a method of determining the likelihood of the presence of a lung condition in a subject by measuring an abundance of panel of proteins in a sample obtained from the subject, calculating a probability of cancer score based on the protein measurements and concluding the presence of said lung condition if the score is equal or greater than a pre-determined score. The lung condition is lung cancer such as for example, non-small cell lung cancer (NSCLC). The subject at risk of developing lung cancer The panel includes at least 4 proteins selected from ALDOA, FRIL, LG3BP, IBP3, LRP1, ISLR, TSP1, COIA1, GRP78, TETN, PRDX1 and CD14. Optionally, the panel further includes at least one protein selected from BGH3, COIA1, TETN, GRP78, PRDX, FIBA and GSLG1.

Alternatively, the panel includes at least 3 proteins selected from ALDOA, FRIL, LG3BP, IBP3, LRP1, ISLR, TSP1, COIA1, GRP78, TETN, PRDX1 and CD14. In some embodiments, the panel comprises at least 1, 2, 3, or 4 proteins selected from LRP1, COIA1, ALDOA, and LG3BP. In some embodiments, the panel comprises at least 1, 2, 3, 4, 5, 6, 7, or 8 proteins selected from LRP1, COIA1, ALDOA, LG3BP, BGH3, PRDX1, TETN, and ISLR. In some embodiments, the panel comprises at least 1, 2, 3, 4, 5, 6, 7, 8, 9, 10, 11, 12, or 13 proteins selected from LRP1, COIA1, ALDOA, LG3BP, BGH3, PRDX1, TETN, ISLR, TSP1, GRP78, FRIL, FIBA, GSLG1.

Optionally, the panel includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 proteins selected from TSP1, COIA1, ISLR, TETN, FRIL, GRP78, ALDOA, BGH3, LG3BP, LRP1, FIBA, PRDX1, GSLG1, KIT, CD14, EF1A1, TENX, AIFM1, GGH, IBP3, ENPL, ERO1A, 6PGD, ICAM1, PTPA, NCF4, SEM3G, 1433T, RAP2B, MMP9, FOLH1, GSTP1, EF2, RAN, SODM, and DSG2.

Optionally, the panel includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 proteins selected from FRIL, TSP1, LRP1, PRDX1, TETN, TBB3, COIA1, GGH, A1AG1, AIFM1, AMPN, CRP, GSLG1, IBP3, KIT, NRP1, 6PGD, CH10, CLIC1, COF1, CSF1, CYTB, DMKN, DSG2, EREG, ERO1A, FOLH1, ILEU, K1C19, LYOX, MMPI, NCF4, PDIA3, PTGIS, PTPA, RAN, SCF, SEM3G, TBA1B, TCPA, TERA, TIMP1, TNF12, and UGPA.

The subject has or is suspected of having a pulmonary nodule. The pulmonary nodule has a diameter of less than or equal to 3 cm. In one embodiment, the pulmonary nodule has a diameter of about 0.8 cm to 2.0 cm. The subject may have stage IA lung cancer (i.e., the tumor is smaller than 3 cm).

The score is calculated from a logistic regression model applied to the protein measurements. For example, the score is determined as $P_s=1/[1+\exp(-\alpha-\Sigma_{i=1}^{N}\beta_i \check{I}_{i,s})]$, where $\check{I}_{i,s}$ is logarithmically transformed and normalized intensity of transition i in said sample (s), $\beta_i$ is the corresponding logistic regression coefficient, $\alpha$ was a panel-specific constant, and N was the total number of transitions in said panel.

In various embodiments, the method of the present invention further comprises normalizing the protein measurements. For example, the protein measurements are normalized by one or more proteins selected from PEDF, MASP1, GELS, LUM, C163A and PTPRJ.

The biological sample such as for example tissue, blood, plasma, serum, whole blood, urine, saliva, genital secretion, cerebrospinal fluid, sweat and excreta.

In one aspect, the determining the likelihood of cancer is determined by the sensitivity, specificity, negative predictive value or positive predictive value associated with the score. The score determined has a negative predictive value (NPV) is at least about 60%, at least 70% or at least 80%.

The measuring step is performed by selected reaction monitoring mass spectrometry, using a compound that specifically binds the protein being detected or a peptide transition. In one embodiment, the compound that specifically binds to the protein being measured is an antibody or an aptamer.

In specific embodiments, the diagnostic methods disclosed herein are used to rule out a treatment protocol for a subject, measuring the abundance of a panel of proteins in a sample obtained from the subject, calculating a probability of cancer score based on the protein measurements and ruling out the treatment protocol for the subject if the score determined in the sample is lower than a pre-determined score. In some embodiments the panel contains at least 3 proteins selected ALDOA, FRIL, LG3BP, IBP3, LRP1, ISLR, TSP1, COIA1, GRP78, TETN, PRDX1 and CD14.

Optionally, the panel further comprises one or more proteins selected from ERO1A, 6PGD, GSTP1, GGH, PRDX1, CD14, PTPA, ICAM1, FOLH1, SODM, FIBA, GSLG1, RAP2B, or C163A or one or more proteins selected from LRP1, COIA1, TSP1, ALDOA, GRP78, FRIL, LG3BP, BGH3, ISLR, PRDX1, FIBA, or GSLG. In preferred embodiments, the panel contains at least TSP1, LG3BP, LRP1, ALDOA, and COIA1. In more a preferred embodiment, the panel contains at least TSP1, LRP1, ALDOA and COIA1.

In specific embodiments, the diagnostic methods disclosed herein are used to rule in a treatment protocol for a subject by measuring the abundance of a panel of proteins in a sample obtained from the subject, calculating a probability of cancer score based on the protein measurements and ruling in the treatment protocol for the subject if the score determined in the sample is greater than a pre-determined score. In some embodiments the panel contains at least 3 proteins selected ALDOA, FRIL, LG3BP, IBP3, LRP1, ISLR or TSP1 or ALDOA, FRIL, LG3BP, IBP3, LRP1, ISLR, TSP1, COIA1, GRP78, TETN, PRDX1 and CD14. Optionally, the panel further comprises one or more proteins selected from ERO1A, 6PGD, GSTP1, COIA1, GGH, PRDX1, SEM3G, GRP78, TETN, AIFM1, MPRI, TNF12, MMP9 or OSTP or COIA1, TETN, GRP78, APOE or TBB3.

In certain embodiments, the diagnostic methods disclosed herein can be used in combination with other clinical assessment methods, including for example various radiographic and/or invasive methods. Similarly, in certain embodiments, the diagnostic methods disclosed herein can be used to identify candidates for other clinical assessment methods, or to assess the likelihood that a subject will benefit from other clinical assessment methods.

The high abundance of certain proteins in a biological sample such as plasma or serum can hinder the ability to assay a protein of interest, particularly where the protein of interest is expressed at relatively low concentrations. Several methods are available to circumvent this issue, including enrichment, separation, and depletion. Enrichment uses an affinity agent to extract proteins from the sample by class, e.g., removal of glycosylated proteins by glycocapture. Separation uses methods such as gel electrophoresis or isoelectric focusing to divide the sample into multiple fractions that largely do not overlap in protein content. Depletion typically uses affinity columns to remove the most abundant proteins in blood, such as albumin, by utilizing advanced technologies such as IgY14/Supermix (SigmaSt. Louis, Mo.) that enable the removal of the majority of the most abundant proteins.

In certain embodiments of the methods provided herein, a biological sample may be subjected to enrichment, separation, and/or depletion prior to assaying biomarker or putative biomarker protein expression levels. In certain of these embodiments, blood proteins may be initially processed by a glycocapture method, which enriches for glycosylated proteins, allowing quantification assays to detect proteins in the high pg/ml to low ng/ml concentration range. Exemplary methods of glycocapture are well known in the art (see, e.g., U.S. Pat. No. 7,183,188; U.S. Patent Appl. Publ. No. 2007/0099251; U.S. Patent Appl. Publ. No. 2007/0202539; U.S. Patent Appl. Publ. No. 2007/0269895; and U.S. Patent Appl. Publ. No. 2010/0279382). In other embodiments, blood proteins may be initially processed by a protein depletion method, which allows for detection of commonly obscured biomarkers in samples by removing abundant proteins. In one such embodiment, the protein depletion method is a Supermix (Sigma) depletion method.

In certain embodiments, a biomarker protein panel comprises two to 100 biomarker proteins. In certain of these embodiments, the panel comprises 2 to 5, 6 to 10, 11 to 15, 16 to 20, 21-25, 5 to 25, 26 to 30, 31 to 40, 41 to 50, 25 to 50, 51 to 75, 76 to 100, biomarker proteins. In certain embodiments, a biomarker protein panel comprises one or more subpanels of biomarker proteins that each comprise at least two biomarker proteins. For example, biomarker protein panel may comprise a first subpanel made up of biomarker proteins that are overexpressed in a particular lung condition and a second subpanel made up of biomarker proteins that are underexpressed in a particular lung condition.

In certain embodiments of the methods, compositions, and kits provided herein, a biomarker protein may be a protein that exhibits differential expression in conjunction with lung cancer. For example, in certain embodiments a biomarker protein may be one of the proteins associated with lung cancer set forth in Table 6.

In other embodiments, the diagnosis methods disclosed herein may be used to distinguish between two different lung conditions. For example, the methods may be used to classify a lung condition as malignant lung cancer versus benign lung cancer, NSCLC versus SCLC, or lung cancer versus non-cancer condition (e.g., inflammatory condition).

In certain embodiments, kits are provided for diagnosing a lung condition in a subject. These kits are used to detect expression levels of one or more biomarker proteins. Optionally, a kit may comprise instructions for use in the form of a label or a separate insert. The kits can contain reagents that specifically bind to proteins in the panels described, herein. These reagents can include antibodies. The kits can also contain reagents that specifically bind to mRNA expressing proteins in the panels described, herein. These reagents can include nucleotide probes. The kits can also include reagents for the detection of reagents that specifically bind to the proteins in the panels described herein. These reagents can include fluorophores.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention

EXAMPLES

Example 1

Identification of Lung Cancer Biomarker Proteins

A retrospective, case-control study design was used to identify biomarker proteins and panels thereof for diagnosing various lung diseases in pre-defined control and experimental groups. The first goal of these studies was to demonstrate statistically significant differential expression for individual proteins between control and experimental groups. The second goal is to identify a panel of proteins which all individually demonstrate statistically significant differential expression between control and experimental groups. This panel of proteins can then be used collectively to distinguish between dichotomous disease states.

Specific study comparisons may include 1) cancer vs. non-cancer, 2) small cell lung cancer versus non-small cell lung cancer (NSCLC), 3) cancer vs. inflammatory disease state (e.g., infectious granuloma), or 4) different nodule size, e.g., <10 mm versus ≥10 mm (alternatively using 10, 15 or 20 mm cut-offs depending upon sample distributions).

Data for each subject consisted of the following:

Archived plasma samples from subjects previously enrolled in Institute Review Board (IRB)-approved studies was used to identify biomarker proteins and biomarker panels for distinguishing lung malignancies from non-malignancies. Plasma samples were originally obtained by routine phlebotomy, aliquotted, and stored at −80° C. or lower. Sample preparation, assignment of subject identification codes, initial subject record entry, and specimen storage were performed as per IRB study protocols. Sample eligibility is based on clinical parameters, including the subject, PN, and clinical staging parameters. Parameters for inclusion and exclusion are set forth in Table 7.

TABLE 7

| | Inclusion Criteria |
|---|---|
| Sample Inclusion Criteria | Sample eligibility will be based on clinical parameters, including the following subject, nodule and clinical staging parameters:<br>Subject<br>    age ≥40<br>    any smoking status, e.g. current, former, or never<br>    co-morbid conditions, e.g. COPD<br>    prior malignancy - only skin carcinomas - squamous or basal cell<br>Nodule<br>    radiology<br>        size ≥4 mm and ≤30 mm<br>        solid, semi-solid or non-solid<br>        any spiculation or ground glass opacity<br>    pathology<br>        malignant - e.g. adenocarcinoma, squamous, or large cell<br>        benign - inflammatory (e.g. granulomatous, infectious) or non-inflammatory (e.g. hamartoma)<br>        confirmed by biopsy, surgery or stability of lung nodule for 2 years or more.<br>Clinical stage<br>    Primary tumor: ≤T1 (e.g. 1A, 1B)<br>    Regional lymph nodes: N0 or N1 only<br>    Distant metastasis: M0 only |
| Sample Exclusion Criteria | Subject<br>    prior malignancy within 5 years of lung nodule diagnosis<br>Nodule<br>    size data unavailable<br>    for cancer or benign nodule, no pathology or follow-up CT data available<br>Clinical stage<br>    Primary tumor: ≥T2<br>    Regional lymph nodes: ≥N2<br>    Distant metastasis: ≥M1 |

The assignment of a sample to a control or experimental group, and its further stratification or matching to other samples within and between these groups, is dependent on various clinical data about the subject. This data includes, for example, demographic information such as age, gender, and clinical history (e.g., smoking status), co-morbid conditions, PN characterization, and pathologic interpretation of resected lesions and tissues (Table 8).

TABLE 8

| | |
|---|---|
| | 1. Enrollment Data<br>  a. Demographics - age, birth date, gender, ethnicity<br>  b. Measurements - Height (cm) and weight (kg)<br>  c. Smoking history - never, former, or current with pack-year estimation<br>  d. Medical history - details of co-morbid conditions, e.g. chronic obstructive pulmonary disease (COPD), inflammatory or autoimmune diseases, endocrine (diabetes), and cardiovascular<br>  e. Medication history - current medications, dosages and indications<br>  f. Radiographic data and nodule characteristics<br>    1) nodule size in millimeters (width × height × length)<br>    2) location, e.g. right or left and upper, lower or middle<br>    3) quality, e.g. solid, semi-solid, ground glass, calcified, etc.<br>2. Diagnostic Evaluation Data<br>  a. Primary diagnosis and associated reports (clinical history, physical exam, and laboratory tests report)<br>  b. Pulmonary Function Tests (PFTs), if available<br>  c. Follow-up CT scans - subsequent nodule evaluations by chest CT<br>  d. PET scan<br>  e. Clinical Staging<br>  f. Biopsy procedures<br>    1) FNA or TTNA<br>    2) bronchoscopy with transbronchial or needle biopsy<br>    3) surgical diagnostic procedures, e.g. VATS and/or thoracotomy<br>3. Radiology Report(s)<br>4. Pathology Report(s)<br>5. Blood Sample Collection Information<br>6. Reporting of Adverse Events<br>  a. AEs resulting from center's SOC, e.g. procedural morbidity. |
| Subject | demographics - e.g. age, gender, ethnicity<br>smoking status - e.g. never-, former- ("ex-") or current- smoker; pack-years<br>clinical history - e.g. co-morbid conditions, e.g. COPD, infection |
| Nodule | size - e.g. planar (width × height × length) and volume dimensions<br>appearance - e.g. calcifications, ground glass appearance, eccentricity |
| Pathology | primary lung vs. systemic disorder<br>malignancy status - malignant vs. benign (vs. indeterminate)<br>histopathology - e.g. small cell lung cancer (SCLC) vs. non-small cell lung cancer (NSCLC - adenocarcinoma, squamous carcinoma, large cell |

TABLE 8-continued carcinoma); other types, e.g. hematologic, carcinoid, etc.
immunologically quiescent, e.g. hamartoma, vs. inflammatory, e.g.
granulomatous and/or infectious, e.g. fungal The study design and analytical plan prioritizes the control: experimental group pairings set forth in Table 9. Additional clinical and molecular insights may be gained by selective inclusion of phenotypes, e.g. effect of smoking, in the assignment of experimental and control groups. Demographic information available in the clinical database will enable further refinements in sample selection via the stratification or matching of samples in the case-control analyses with respect to clinical parameters, e.g., age and nodule size.

TABLE 9

Assignment of Experimental and Control Groups
to Achieve Proteomic Analysis Objectives

| Analysis | Objective | Experimental Group | Control Group |
|---|---|---|---|
| 1 | Differentiate cancer from benign lung nodule | A. Cancer nodule | Any non-malignant (benign) phenotype with nodule ≥4 mm in diameter |
| 2 | Differentiate cancer from non-malignant (inflammatory, infectious) lung nodule | A. Cancer nodule | Non-malignant (non-benign) lung disorder, e.g. granulomatous (fungal) disease, with nodule |

LC-SRM-MS is performed to identify and quantify various plasma proteins in the plasma samples. Prior to LC-SRM-MS analysis, each sample is depleted using IgY14/Supermix (Sigma) and then trypsin-digested. Samples from each control or experimental group are batched randomly and processed together on a QTrap 5500 instrument (AB SCIEX, Foster City, Calif.) for unbiased comparisons. Each sample analysis takes approximately 30 minutes. Peak areas for two transitions (native and heavy label) are collected and reported for all peptides and proteins. The data output for each protein analyzed by LC-SRM-MS typically yields four measurements consisting of two transition measurements from each of two peptides from the same protein. These measurements enable an inference of the relative abundance of the target protein, which will be used as its expression level in the bioinformatics and statistical analyses.

Identification of biomarker proteins having differential expression levels between the control and experimental groups yields one or more novel proteomic profiles. For example, biomarker proteins are identified with expression levels that differ in subjects with PNs who are diagnosed with NSCLC versus those without an NSCLC diagnosis, or in subjects with PNs who are diagnosed with NSCLC versus an inflammatory disorder. Panels of biomarker proteins are also identified which can collectively discriminate between dichotomous disease states.

Analyses may be (a priori) powered appropriately to control type 1 and type 2 errors at 0.05 and to detect inter-cohort differences of 25% per analyte. The diagnostic power of individual proteins is generally assessed to distinguish between two cohorts, assuming a one-sided paired non-parametric test is used. This provides a lower bound on the sample size required to demonstrate differential expression between experimental and control groups. Multiple testing effects apply for the identification of panels of proteins for assessing diagnostic efficacy, which requires larger sample sizes.

The sequence of steps for determining statistical significance for differential expression of an individual protein includes the following: 1) assessing and correlating the calibrated values of transitions of a single protein (a quality control measure); 2) comparing paired analysis of groups to control for other influences using the Mann-Whitney U-test (rank sum) to determine statistical significance; and 3) determining its significance based on a pre-defined significance threshold. Transitions within a protein that are not correlated across samples (e.g., Pearson correlation <0.5) will be deemed unreliable and excluded from the analysis.

Comparison of calibrated samples between two cohorts, e.g., cancer and non-cancer, requires pairing or matching using a variety of clinical parameters such as nodule size, age and gender. Such pairing controls for the potential influence of these other parameters on the actual comparison goal, e.g. cancer and non-cancer. A non-parametric test such as the Mann-Whitney U-test (rank sum) will then be applied to measure the statistical difference between the groups. The resulting p value can be adjusted using multiple testing corrections such as the false discovery rate. Permutation tests can be used for further significance assessments.

Significance will be determined by the satisfaction of a pre-defined threshold, such as 0.05, to filter out assays, with the potential use of higher threshold values for additional filtering. An additional significance criterion is that two of three replicate assays must individually be significant in order for the assay, e.g., single protein, to be significant.

Panels of proteins that individually demonstrate statistically significant differential expression as defined above and which can collectively be used to distinguish dichotomous disease states are identified using statistical methods described herein. This requires developing multivariate classifiers and assessing sensitivity, specificity, and ROC AUC for panels. In addition, protein panels with optimal discriminatory performance, e.g., ROC AUC, are identified and may be sufficient for clinical use in discriminating disease states.

The sequence of steps for determining the statistical significance of the discriminatory ability of a panel of proteins includes 1) developing multivariate classifiers for protein panels, and 2) identifying a protein panel with optimal discriminatory performance, e.g. ROC AUC, for a set of disease states.

A multivariate classifier (e.g., majority rule) will be developed for protein panels, including single protein assays deemed to be significant. The sensitivity and specificity of each classifier will be determined and used to generate a receiver operating characteristics (ROC) curve and its AUC to assess a given panel's discriminatory performance for a specific comparison, e.g. cancer versus non-cancer.

Protocol

1. Review clinical data from a set of subjects presenting with lung disease.

2. Provide plasma samples from the subjects wherein the samples are either benign, cancerous, COPD or another lung disease.

3. Group the plasma samples that are benign or cancerous by PNs that are separated by size of the nodule.

4. Target a pool of 371 putative lung cancer biomarker proteins consisting of at least two peptides per protein and at least two LC-SRM-MS transitions per peptide. Measuring the LC-SRM-MS transitions in each specimen along with 5 synthetic internal standards consisting of 10 transitions to compare peptide transitions from the plasma to the synthetic internal standards by LC-SRM-MS mass spectroscopy.

5. Quantitate the intensity of each transition.
6. Normalize the quantitated transitions to internal standards to obtain a normalized intensity.
7. Review the measured peptide transitions for correlations from the same peptide, rejecting discordant transitions.
8. Generate an ROC for each transition by comparing cancerous with benign samples. (ROC compare specificity (true positive) to (1-sensitivity) false positive).
9. Define the AUC for each transition. (An AUC of 0.5 is a random classifier; 1.0 is a perfect classifier).
10. Determine an AUC cut-off point to determine transitions that are statistically significant.
11. Define the transitions that exceed the AUC cutoff point.
12. Combine all pairings of significant transitions.
13. Define a new AUC for each transition pair by means of logistical regression.
14. Repeat pairing combinations into triples, quad, etc.; defining a new AUC based upon the logistical regression of combined transitions until a panel of biomarker transitions with combined desired performance (sensitivity & specificity) have been achieved.
15. The panel of biomarker transitions is verified against previously unused set of plasma panels.

Example 2

Diagnosis/Classification of Lung Disease Using Biomarker Proteins

Plasma samples will be obtained from one or more subjects presenting with PNs to evaluate whether the subjects have a lung condition. The plasma samples will be depleted using IgY14/Supermix (Sigma) and optionally subjected to one or more rounds of enrichment and/or separation, and then trypsinized. The expression level of one or more biomarker proteins previously identified as differentially expressed in subjects with the lung condition will be measured using an LC-SRM-MS assay. The LC-SRM-MS assay will utilize two to five peptide transitions for each biomarker protein. For example, the assay may utilize one or more of the peptide transitions generated from any of the proteins listed in Table 6. Subjects will be classified as having the lung condition if one or more of the biomarker proteins exhibit expression levels that differ significantly from the pre-determined control expression level for that protein.

Example 3

Blood-Based Diagnostic Test to Determine the Likelihood that a Pulmonary Nodule (PN) is Benign or Malignant A panel of 15 proteins was created where the concentration of these 15 proteins relative to the concentration of 6 protein standards is indicative of likelihood of cancer. The relative concentration of these 15 proteins to the 6 protein standards was measured using a mass spectrometry methodology. A classification algorithm is used to combine these relative concentrations into a relative likelihood of the PN being benign or malignant. Further it has been demonstrated that there are many variations on these panels that are also diagnostic tests for the likelihood that a PN is benign or malignant. Variations on the panel of proteins, protein standards, measurement methodology and/or classification algorithm are described herein.

Study Design

A Single Reaction Monitoring (SRM) mass spectrometry (MS) assay was developed consisting of 1550 transitions from 345 lung cancer associated proteins. The SRM-MS assay and methodology is described above. The goal of this study was to develop a blood-based diagnostic for classifying PNs under 2 cm in size as benign or malignant. The study design appears in Table 10.

TABLE 10

| Study Design | | | | | | |
|---|---|---|---|---|---|---|
| | Small (<2 cm) | | | Large (>2 cm) | | |
| | Laval | UPenn | NYU | Laval | UPenn | NYU |
| Benign | 14 | 29 | 29 | 13 | 21 | 15 |
| Malignant | 14 | 29 | 29 | 13 | 21 | 15 |
| Batches | 1 | 2 | 2 | 1 | 2 | 1 |
| | 72 vs. 72 (94% power) | | | 49 vs. 49 (74% power) | | |

The study consisted of 242 plasma samples from three sites (Laval, UPenn and NYU). The number of benign and malignant samples from each site are indicated in Table 10. The study consisted of 144 plasma samples from patients with PNs of size 2 cm or less and of 98 samples from patients with PNs of size larger than 2 cm. This resulted in an estimated power of 94% for discovering proteins with blood concentrations of 1.5 fold or more between benign and malignant cancer samples of size 2 cm or less. Power is 74% for PNs of size larger than 2 cm.

This study was a retrospective multisite study that was intended to derive protein biomarkers of lung cancer that are robust to site-to-site variation. The study included samples larger than 2 cm to ensure that proteins not detectable due to the limit of detection of the measurement technology (LC-SRM-MS) for tumors of size 2 cm or less could still be detected in tumors of size 2 cm or larger.

Samples from each site and in each size class (above and below 2 cm) were matched on nodule size, age and gender.
Sample Analysis Each sample was analyzed using the LC-SRM-MS measurement methodology as follows:

1. Samples were depleted of high abundance proteins using the IGy14 and Supermix depletion columns from Sigma-Aldrich.
2. Samples were digested using trypsin into tryptic peptides.
3. Samples were analyzed by LC-SRM-MS using a 30 minute gradient on a Waters nanoacuity LC system followed by SRM-MS analysis of the 1550 transitions on a AB-Sciex 5500 triple quad device.
4. Raw transition ion counts were obtained and recorded for each of the 1550 transitions.

It is important to note that matched samples were processed at each step either in parallel (steps 2 and 4) or back-to-back serially (steps 1 and 3). This minimizes analytical variation. Finally, steps 1 and 2 of the sample analysis are performed in batches of samples according to day of processing. There were five batches of 'small' samples and four batches of 'large' samples as denoted in Table 10.
Protein Shortlist A shortlist of 68 proteins reproducibly diagnostic across sites was derived as follows. Note that each protein can be measured by multiple transitions.

Step 1: Normalization

Six proteins were identified that had a transition detected in all samples of the study and with low coefficient of variation. For each protein the transition with highest median intensity across samples was selected as the representative transition for the protein. These proteins and transitions are found in Table 11.

TABLE 11

Normalizing Factors

| Protein (Uniprot ID) | Peptide (Amino Acid Sequence) | Transition (m/z) |
|---|---|---|
| CD44_HUMAN | YGFIEGHVVIPR (SEQ ID NO: 1) | 272.2 |
| TENX_HUMAN | YEVTVVSVR (SEQ ID NO: 2) | 759.5 |
| CLUS_HUMAN | ASSIIDELFQDR (SEQ ID NO: 3) | 565.3 |
| IBP3_HUMAN | FLNVLSPR (SEQ ID NO: 4) | 685.4 |
| GELS_HUMAN | TASDFITK (SEQ ID NO: 5) | 710.4 |
| MASP1_HUMAN | TGVITSPDFPNPYPK (SEQ ID NO: 6) | 258.10 |

We refer to the transitions in Table 11 as normalizing factors (NFs). Each of the 1550 transitions were normalized by each of the six normalizing factors where the new intensity of a transition t in a sample s by NF f, denoted New(s,t,f), is calculated as follows:

$$New(s,t,f) = Raw(s,t) * Median(f)/Raw(s,f)$$

where Raw(s,t) is the original intensity of transition t in sample s; Median(f) is the median intensity of the NF f across all samples; and Raw(s,f) is the original intensity of the NF f in sample s.

For each protein and normalized transition, the AUC of each batch was calculated. The NF that minimized the coefficient of variation across the 9 batches was selected as the NF for that protein and for all transitions of that protein. Consequently, every protein (and all of its transitions) are now normalized by a single NF.

Step 2: Reproducible Diagnostic Proteins

For each normalized transition its AUC for each of the nine batches in the study is calculated as follows. If the transition is detected in fewer than half of the cancer samples and in fewer than half of the benign samples then the batch AUC is 'ND'. Otherwise, the batch AUC is calculated comparing the benign and cancer samples in the batch.

The batch AUC values are transformed into percentile AUC scores for each transition. That is, if a normalized transition is in the 82nd percentile of AUC scores for all transitions then it is assigned percentile AUC 0.82 for that batch.

Reproducible transitions are those satisfying at least one of the following criteria:

1. In at least four of the five small batches the percentile AUC is 75% or more (or 25% and less).
2. In at least three of the five small batches the percentile AUC is 80% or more (or 20% and less) AND the remaining percentile AUCs in the small batches are above 50% (below 50%).
3. In all five small batches the percentile AUC is above 50% (below 50%).
4. In at least three of the four large batches the percentile AUC is 85% or more (or 15% and less).
5. In at least three of the four large batches the percentile AUC is 80% or more (or 20% and less) AND the remaining percentile AUCs in the large batches are above 50% (below 50%).
6. In all four large batches the percentile AUC is above 50% (below 50%).

These criteria result in a list of 67 proteins with at least one transition satisfying one or more of the criteria. These proteins appear in Table 12.

TABLE 12

| Protein (Uniprot) | Occurrence Across 131 Panels | Percentage Occurrence Across 131 Panels | Protein Names | Uniprot Accession No. |
|---|---|---|---|---|
| G3P_HUMAN | 113 | 86% | Glyceraldehyde-3-phosphate dehydrogenase; Short name = GAPDH; Alternative name(s): Peptidyl-cysteine S-nitrosylase GAPDH | P04406 |
| FRIL_HUMAN | 107 | 82% | Recommended name: Ferritin light chain Short name = Ferritin L subunit | P02792 |
| HYOU1_HUMAN | 69 | 53% | Recommended name: Hypoxia up-regulated protein 1 Alternative name(s): 150 kDa oxygen-regulated protein Short name = ORP-150 170 kDa glucose-regulated protein Short name = GRP-170 | Q9Y4L1 |
| ALDOA_HUMAN | 66 | 50% | Recommended name: Fructose-bisphosphate aldolase A EC = 4.1.2.13 Alternative name(s): Lung cancer antigen NY-LU-1 Muscle-type aldolase | P04075 |
| HXK1_HUMAN | 65 | 50% | Recommended name: Hexokinase-1 EC = 2.7.1.1 | P19367 |

TABLE 12-continued

| Protein (Uniprot) | Occurrence Across 131 Panels | Percentage Occurrence Across 131 Panels | Protein Names | Uniprot Accession No. |
|---|---|---|---|---|
| | | | Alternative name(s):<br>Brain form hexokinase<br>Hexokinase type I<br>Short name = HK I | |
| APOE_HUMAN | 63 | 48% | Recommended name:<br>Apolipoprotein E<br>Short name = Apo-E | P02649 |
| TSP1_HUMAN | 63 | 48% | Recommended name:<br>Thrombospondin-1 | P07996 |
| FINC_HUMAN | 62 | 47% | Recommended name:<br>Fibronectin<br>Short name = FN<br>Alternative name(s):<br>Cold-insoluble globulin<br>Short name = CIG<br>Cleaved into the following 4 chains:<br>1. Anastellin<br>2. Ugl-Y1<br>3. Ugl-Y2<br>4. Ugl-Y3 | P02751 |
| LRP1_HUMAN | 58 | 44% | Recommended name:<br>Prolow-density lipoprotein receptor-related protein 1<br>Short name = LRP-1<br>Alternative name(s):<br>Alpha-2-macroglobulin receptor<br>Short name = A2MR<br>Apolipoprotein E receptor<br>Short name = APOER<br>CD_antigen = CD91<br>Cleaved into the following 3 chains:<br>1. Low-density lipoprotein receptor-related protein 1 85 kDa subunit<br>Short name = LRP-85<br>2. Low-density lipoprotein receptor-related protein 1 515 kDa subunit<br>Short name = LRP-515<br>3. Low-density lipoprotein receptor-related protein 1 intracellular domain<br>Short name = LRPICD | |
| 6PGD_HUMAN | 50 | 38% | Recommended name:<br>6-phosphogluconate dehydrogenase, decarboxylating | P52209 |
| S10A6_HUMAN | 47 | 36% | Recommended name:<br>Protein S100-A6<br>Alternative name(s):<br>Calcyclin<br>Growth factor-inducible protein 2A9<br>MLN 4<br>Prolactin receptor-associated protein<br>Short name = PRA<br>S100 calcium-binding protein A6 | P06703 |
| CALU_HUMAN | 45 | 34% | Recommended name:<br>Calumenin<br>Alternative name(s):<br>Crocalbin<br>IEF SSP 9302 | O43852 |
| PRDX1_HUMAN | 45 | 34% | Recommended name:<br>Peroxiredoxin-1<br>EC = 1.11.1.15<br>Alternative name(s):<br>Natural killer cell-enhancing factor A<br>Short name = NKEF-A<br>Proliferation-associated gene protein<br>Short name = PAG<br>Thioredoxin peroxidase 2<br>Thioredoxin-dependent peroxidereductase 2 | Q06830 |
| RAN_HUMAN | 45 | 34% | Recommended name:<br>GTP-binding nuclear protein Ran<br>Alternative name(s):<br>Androgen receptor-associated protein 24<br>GTPase Ran<br>Ras-like protein TC4<br>Ras-related nuclear protein | P62826 |

TABLE 12-continued

| Protein (Uniprot) | Occurrence Across 131 Panels | Percentage Occurrence Across 131 Panels | Protein Names | Uniprot Accession No. |
|---|---|---|---|---|
| CD14_HUMAN | 43 | 33% | Recommended name:<br>Monocyte differentiation antigen CD14<br>Alternative name(s):<br>Myeloid cell-specific leucine-rich glycoprotein<br>CD_antigen = CD14<br>Cleaved into the following 2 chains:<br>1. Monocyte differentiation antigen CD14, urinary form<br>2. Monocyte differentiation antigen CD14, membrane-bound form | P08571 |
| AMPN_HUMAN | 41 | 31% | Recommended name:<br>Aminopeptidase N<br>Short name = AP-N<br>Short name = hAPN<br>EC = 3.4.11.2<br>Alternative name(s):<br>Alanyl aminopeptidase<br>Aminopeptidase M<br>Short name = AP-M<br>Microsomal aminopeptidase<br>Myeloid plasma membrane glycoprotein CD13<br>gp150<br>CD_antigen = CD13 | P15144 |
| GSLG1_HUMAN | 36 | 27% | Recommended name:<br>Golgi apparatus protein 1<br>Alternative name(s):<br>CFR-1<br>Cysteine-rich fibroblast growth factor receptor<br>E-selectin ligand 1<br>Short name = ESL-1<br>Golgi sialoglycoprotein MG-160 | Q92896 |
| 1433Z_HUMAN | 32 | 24% | Recommended name:<br>14-3-3 protein zeta/delta<br>Alternative name(s):<br>Protein kinase C inhibitor protein 1<br>Short name = KCIP-1 | P63104 |
| IBP3_HUMAN | 31 | 24% | Recommended name:<br>Insulin-like growth factor-binding protein 3<br>Short name = IBP-3<br>Short name = IGF-binding protein 3<br>Short name = IGFBP-3 | P17936 |
| ILK_HUMAN | 31 | 24% | Recommended name:<br>Integrin-linked protein kinase<br>EC = 2.7.11.1<br>Alternative name(s):<br>59 kDa serine/threonine-protein kinase<br>ILK-1<br>ILK-2<br>p59ILK | Q13418 |
| LDHB_HUMAN | 30 | 23% | Recommended name:<br>L-lactate dehydrogenase B chain<br>Short name = LDH-B<br>EC = 1.1.1.27<br>Alternative name(s):<br>LDH heart subunit<br>Short name = LDH-H<br>Renal carcinoma antigen NY-REN-46 | P07195 |
| MPRI_HUMAN | 29 | 22% | Recommended name:<br>Cation-independent mannose-6-phosphate receptor<br>Short name = CI Man-6-P receptor<br>Short name = CI-MPR<br>Short name = M6PR<br>Alternative name(s):<br>300 kDa mannose 6-phosphate receptor<br>Short name = MPR 300<br>Insulin-like growth factor 2 receptor<br>Insulin-like growth factor II receptor<br>Short name = IGF-II receptor<br>M6P/IGF2 receptor<br>Short name = M6P/IGF2R<br>CD_antigen = CD222 | P11717 |

TABLE 12-continued

| Protein (Uniprot) | Occurrence Across 131 Panels | Percentage Occurrence Across 131 Panels | Protein Names | Uniprot Accession No. |
|---|---|---|---|---|
| PROF1_HUMAN | 29 | 22% | Recommended name:<br>Profilin-1<br>Alternative name(s):<br>Profilin I | P07737 |
| PEDF_HUMAN | 28 | 21% | Recommended name:<br>Pigment epithelium-derived factor<br>Short name = PEDF<br>Alternative name(s):<br>Cell proliferation-inducing gene 35 protein<br>EPC-1<br>Serpin F1 | P36955 |
| CLIC1_HUMAN | 26 | 20% | Recommended name:<br>Chloride intracellular channel protein 1<br>Alternative name(s):<br>Chloride channel ABP<br>Nuclear chloride ion channel 27<br>Short name = NCC27<br>Regulatory nuclear chloride ion channel protein<br>Short name = hRNCC | O00299 |
| GRP78_HUMAN | 25 | 19% | Recommended name:<br>78 kDa glucose-regulated protein<br>Short name = GRP-78<br>Alternative name(s):<br>Endoplasmic reticulum lumenal Ca(2+)-binding protein grp78<br>Heat shock 70 kDa protein 5<br>Immunoglobulin heavy chain-binding protein<br>Short name = BiP | P11021 |
| CEAM8_HUMAN | 24 | 18% | Recommended name:<br>Carcinoembryonic antigen-related cell adhesion molecule 8<br>Alternative name(s):<br>CD67 antigen<br>Carcinoembryonic antigen CGM6<br>Non-specific cross-reacting antigen<br>NCA-95<br>CD_antigen = CD66b | P31997 |
| VTNC_HUMAN | 24 | 18% | Recommended name:<br>Vitronectin<br>Alternative name(s):<br>S-protein<br>Serum-spreading factor<br>V75<br>Cleaved into the following 3 chains:<br>1. Vitronectin V65 subunit<br>2. Vitronectin V10 subunit<br>3. Somatomedin-B | P04004 |
| CERU_HUMAN | 22 | 17% | Recommended name:<br>Ceruloplasmin<br>EC = 1.16.3.1<br>Alternative name(s):<br>Ferroxidase | P00450 |
| DSG2_HUMAN | 22 | 17% | Recommended name:<br>Desmoglein-2<br>Alternative name(s):<br>Cadherin family member 5<br>HDGC | Q14126 |
| KIT HUMAN | 22 | 17% | Recommended name:<br>Mast/stem cell growth factor receptor Kit<br>Short name = SCFR<br>EC = 2.7.10.1<br>Alternative name(s):<br>Piebald trait protein<br>Short name = PBT<br>Proto-oncogene c-Kit<br>Tyrosine-protein kinase Kit<br>p145 c-kit<br>v-kit Hardy-Zuckerman 4 feline sarcoma viral oncogene homolog<br>CD_antigen = CD117 | P10721 |
| TBB3_HUMAN | 22 | 17% | Recommended name:<br>Tubulin beta-3 chain<br>Alternative name(s): | Q13509 |

TABLE 12-continued

| Protein (Uniprot) | Occurrence Across 131 Panels | Percentage Occurrence Across 131 Panels | Protein Names | Uniprot Accession No. |
|---|---|---|---|---|
| | | | Tubulin beta-4 chain<br>Tubulin beta-III | |
| CH10_HUMAN | 21 | 16% | Recommended name:<br>10 kDa heat shock protein, mitochondrial<br>Short name = Hsp10<br>Alternative name(s):<br>10 kDa chaperonin<br>Chaperonin 10<br>Short name = CPN10<br>Early-pregnancy factor<br>Short name = EPF | P61604 |
| ISLR_HUMAN | 21 | 16% | Immunoglobulin superfamily containing leucine-rich repeat protein | O14498 |
| MASP1_HUMAN | 21 | 16% | Recommended name:<br>Mannan-binding lectin serine protease 1<br>EC = 3.4.21.—<br>Alternative name(s):<br>Complement factor MASP-3<br>Complement-activating component of Ra-reactive factor<br>Mannose-binding lectin-associated serine protease 1<br>Short name = MASP-1<br>Mannose-binding protein-associated serine protease<br>Ra-reactive factor serine protease p100<br>Short name = RaRF<br>Serine protease 5<br>Cleaved into the following 2 chains:<br>1. Mannan-binding lectin serine protease 1 heavy chain<br>2. Mannan-binding lectin serine protease 1 light chain | P48740 |
| ICAM3_HUMAN | 20 | 15% | Recommended name:<br>Intercellular adhesion molecule 3<br>Short name = ICAM-3<br>Alternative name(s):<br>CDw50<br>ICAM-R<br>CD_antigen = CD50 | P32942 |
| PTPRJ_HUMAN | 20 | 15% | Recommended name:<br>Receptor-type tyrosine-protein phosphatase eta<br>Short name = Protein-tyrosine phosphatase eta<br>Short name = R-PTP-eta<br>EC = 3.1.3.48<br>Alternative name(s):<br>Density-enhanced phosphatase 1<br>Short name = DEP-1<br>HPTP eta<br>Protein-tyrosine phosphatase receptor type J<br>Short name = R-PTP-J<br>CD_antigen = CD148 | Q12913 |
| A1AG1_HUMAN | 19 | 15% | Recommended name:<br>Alpha-1-acid glycoprotein 1<br>Short name = AGP 1<br>Alternative name(s):<br>Orosomucoid-1<br>Short name = OMD 1 | P02763 |
| CD59_HUMAN | 18 | 14% | Recommended name:<br>CD59 glycoprotein<br>Alternative name(s):<br>1F5 antigen<br>20 kDa homologous restriction factor<br>Short name = HRF-20<br>Short name = HRF20<br>MAC-inhibitory protein<br>Short name = MAC-IP<br>MEM43 antigen<br>Membrane attack complex inhibition factor<br>Short name = MACIF<br>Membrane inhibitor of reactive lysis | P13987 |

TABLE 12-continued

| Protein (Uniprot) | Occurrence Across 131 Panels | Percentage Occurrence Across 131 Panels | Protein Names | Uniprot Accession No. |
|---|---|---|---|---|
| | | | Short name = MIRL<br>Protectin<br>CD_antigen = CD59 | |
| MDHM_HUMAN | 18 | 14% | commended name:<br>Malate dehydrogenase, mitochondrial | P40926 |
| PVR_HUMAN | 18 | 14% | Recommended name:<br>Poliovirus receptor<br>Alternative name(s):<br>Nectin-like protein 5<br>Short name = NECL-5<br>CD_antigen = CD155 | P15151 |
| SEM3G_HUMAN | 18 | 14% | Recommended name:<br>Semaphorin-3G<br>Alternative name(s):<br>Semaphorin sem2 | Q9NS98 |
| CO6A3_HUMAN | 17 | 13% | Collagen alpha-3(VI) chain | P12111 |
| MMP9_HUMAN | 17 | 13% | Recommended name:<br>Matrix metalloproteinase-9<br>Short name = MMP-9<br>EC = 3.4.24.35<br>Alternative name(s):<br>92 kDa gelatinase<br>92 kDa type IV collagenase<br>Gelatinase B<br>Short name = GELB<br>Cleaved into the following 2 chains:<br>1. 67 kDa matrix metalloproteinase-9<br>2. 82 kDa matrix metalloproteinase-9 | P14780 |
| TETN_HUMAN | 17 | 13% | Recommended name:<br>Tetranectin<br>Short name = TN<br>Alternative name(s):<br>C-type lectin domain family 3 member B<br>Plasminogen kringle 4-binding protein | P05452 |
| TNF12_HUMAN | 17 | 13% | Recommended name:<br>Tumor necrosis factor ligand superfamily member 12<br>Alternative name(s):<br>APO3 ligand<br>TNF-related weak inducer of apoptosis<br>Short name = TWEAK<br>Cleaved into the following 2 chains:<br>1. Tumor necrosis factor ligand superfamily member 12, membrane form<br>2. Tumor necrosis factor ligand superfamily member 12, secreted form | O43508 |
| BST1_HUMAN | 16 | 12% | Recommended name:<br>ADP-ribosyl cyclase 2<br>EC = 3.2.2.5<br>Alternative name(s):<br>Bone marrow stromal antigen 1<br>Short name = BST-1<br>Cyclic ADP-ribose hydrolase 2<br>Short name = cADPr hydrolase 2<br>CD_antigen = CD157 | Q10588 |
| COIA1_HUMAN | 16 | 12% | Recommended name:<br>Collagen alpha-1(XVIII) chain<br>Cleaved into the following chain:<br>1. Endostatin | P39060 |
| CRP_HUMAN | 16 | 12% | Recommended name:<br>C-reactive protein<br>Cleaved into the following chain:<br>1. C-reactive protein(1-205) | P02741 |
| PLSL_HUMAN | 16 | 12% | Recommended name:<br>Plastin-2<br>Alternative name(s):<br>L-plastin<br>LC64P<br>Lymphocyte cytosolic protein 1<br>Short name = LCP-1 | P13796 |
| BGH3_HUMAN | 15 | 11% | Recommended name:<br>Transforming growth factor-beta-induced protein ig-h3<br>Short name = Beta ig-h3<br>Alternative name(s): | Q15582 |

TABLE 12-continued

| Protein (Uniprot) | Occurrence Across 131 Panels | Percentage Occurrence Across 131 Panels | Protein Names | Uniprot Accession No. |
|---|---|---|---|---|
| CD44_HUMAN | 15 | 11% | Kerato-epithelin<br>RGD-containing collagen-associated protein<br>Short name = RGD-CAP<br>Recommended name:<br>CD44 antigen<br>Alternative name(s):<br>CDw44<br>Epican<br>Extracellular matrix receptor III<br>Short name = ECMR-III<br>GP90 lymphocyte homing/adhesion receptor<br>HUTCH-I<br>Heparan sulfate proteoglycan<br>Hermes antigen<br>Hyaluronate receptor<br>Phagocytic glycoprotein 1<br>Short name = PGP-1<br>Phagocytic glycoprotein I<br>Short name = PGP-I<br>CD_antigen = CD44 | P16070 |
| ENOA_HUMAN | 15 | 11% | Recommended name:<br>Alpha-enolase<br>EC = 4.2.1.11<br>Alternative name(s):<br>2-phospho-D-glycerate hydrolyase<br>C-myc promoter-binding protein<br>Enolase 1<br>MBP-1<br>MPB-1<br>Non-neural enolase<br>Short name = NNE<br>Phosphopyruvate hydratase<br>Plasminogen-binding protein | P06733 |
| LUM_HUMAN | 15 | 11% | | |
| SCF_HUMAN | 15 | 11% | Recommended name:<br>Kit ligand<br>Alternative name(s):<br>Mast cell growth factor<br>Short name = MGF<br>Stem cell factor<br>Short name = SCF<br>c-Kit ligand<br>Cleaved into the following chain:<br>1. Soluble KIT ligand<br>Short name = sKITLG | P21583 |
| UGPA_HUMAN | 15 | 11% | Recommended name:<br>UTP--glucose-1-phosphate uridylyltransferase<br>EC = 2.7.7.9<br>Alternative name(s):<br>UDP-glucose pyrophosphorylase<br>Short name = UDPGP<br>Short name = UGPase | Q16851 |
| ENPL_HUMAN | 14 | 11% | Recommended name:<br>Endoplasmin<br>Alternative name(s):<br>94 kDa glucose-regulated protein<br>Short name = GRP-94<br>Heat shock protein 90 kDa beta member 1<br>Tumor rejection antigen 1<br>gp96 homolog | P14625 |
| GDIR2_HUMAN | 14 | 11% | Recommended name:<br>Rho GDP-dissociation inhibitor 2<br>Short name = Rho GDI 2<br>Alternative name(s):<br>Ly-GDI<br>Rho-GDI beta | P52566 |
| GELS_HUMAN | 14 | 11% | Recommended name:<br>Gelsolin<br>Alternative name(s):<br>AGEL | P06396 |

TABLE 12-continued

| Protein (Uniprot) | Occurrence Across 131 Panels | Percentage Occurrence Across 131 Panels | Protein Names | Uniprot Accession No. |
|---|---|---|---|---|
| | | | Actin-depolymerizing factor<br>Short name = ADF<br>Brevin | |
| SODM_HUMAN | 14 | 11% | Recommended name:<br>Superoxide dismutase [Mn], mitochondrial | P04179 |
| TPIS_HUMAN | 14 | 11% | Recommended name:<br>Triosephosphate isomerase<br>Short name = TIM<br>EC = 5.3.1.1<br>Alternative name(s):<br>Triose-phosphate isomerase | P60174 |
| TENA_HUMAN | 13 | 10% | Recommended name:<br>Tenascin<br>Short name = TN<br>Alternative name(s):<br>Cytotactin<br>GMEM<br>GP 150-225<br>Glioma-associated-extracellular matrix antigen<br>Hexabrachion<br>JI<br>Myotendinous antigen<br>Neuronectin<br>Tenascin-C<br>Short name = TN-C | P24821 |
| ZA2G_HUMAN | 13 | 10% | Recommended name:<br>Zinc-alpha-2-glycoprotein<br>Short name = Zn-alpha-2-GP<br>Short name = Zn-alpha-2-glycoprotein | P25311 |
| LEG1_HUMAN | 11 | 8% | Recommended name:<br>Galectin-1<br>Short name = Gal-1<br>Alternative name(s):<br>14 kDa laminin-binding protein<br>Short name = HLBP14<br>14 kDa lectin<br>Beta-galactoside-binding lectin L-14-I<br>Galaptin<br>HBL<br>HPL<br>Lactose-binding lectin 1<br>Lectin galactoside-binding soluble 1<br>Putative MAPK-activating protein PM12<br>S-Lac lectin 1 | P09382 |
| FOLH1_HUMAN | 9 | 7% | Recommended name:<br>Glutamate carboxypeptidase 2<br>EC = 3.4.17.21<br>Alternative name(s):<br>Cell growth-inhibiting gene 27 protein<br>Folate hydrolase 1<br>Folylpoly-gamma-glutamate carboxypeptidase<br>Short name = FGCP<br>Glutamate carboxypeptidase II<br>Short name = GCPII<br>Membrane glutamate carboxypeptidase<br>Short name = mGCP<br>N-acetylated-alpha-linked acidic dipeptidase I<br>Short name = NAALADase I<br>Prostate-specific membrane antigen<br>Short name = PSM<br>Short name = PSMA<br>Pteroylpoly-gamma-glutamate carboxypeptidase | Q04609 |
| PLXC1_HUMAN | 9 | 7% | | |
| PTGIS_HUMAN | 9 | 7% | Recommended name:<br>Prostacyclin synthase<br>EC = 5.3.99.4<br>Alternative name(s):<br>Prostaglandin I2 synthase | Q16647 |

Step 3: Significance and Occurrence

Figure 2:
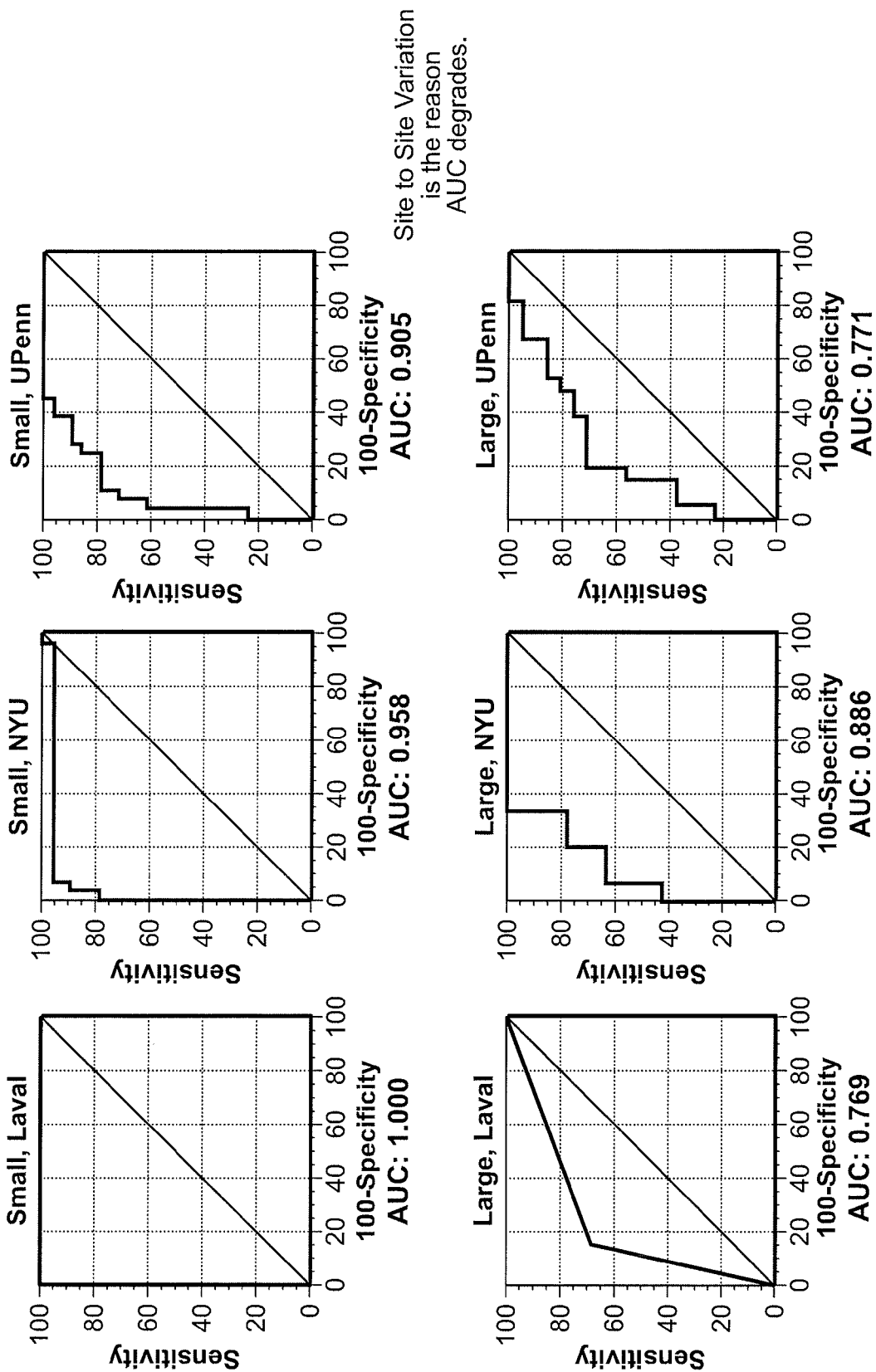
FIG. 2 shows six line graphs each showing area under the curve for a receiving operating curve for 15 protein LC-SRM-MS panels for different patient populations and for subjects with large and small PN
Figure 3:
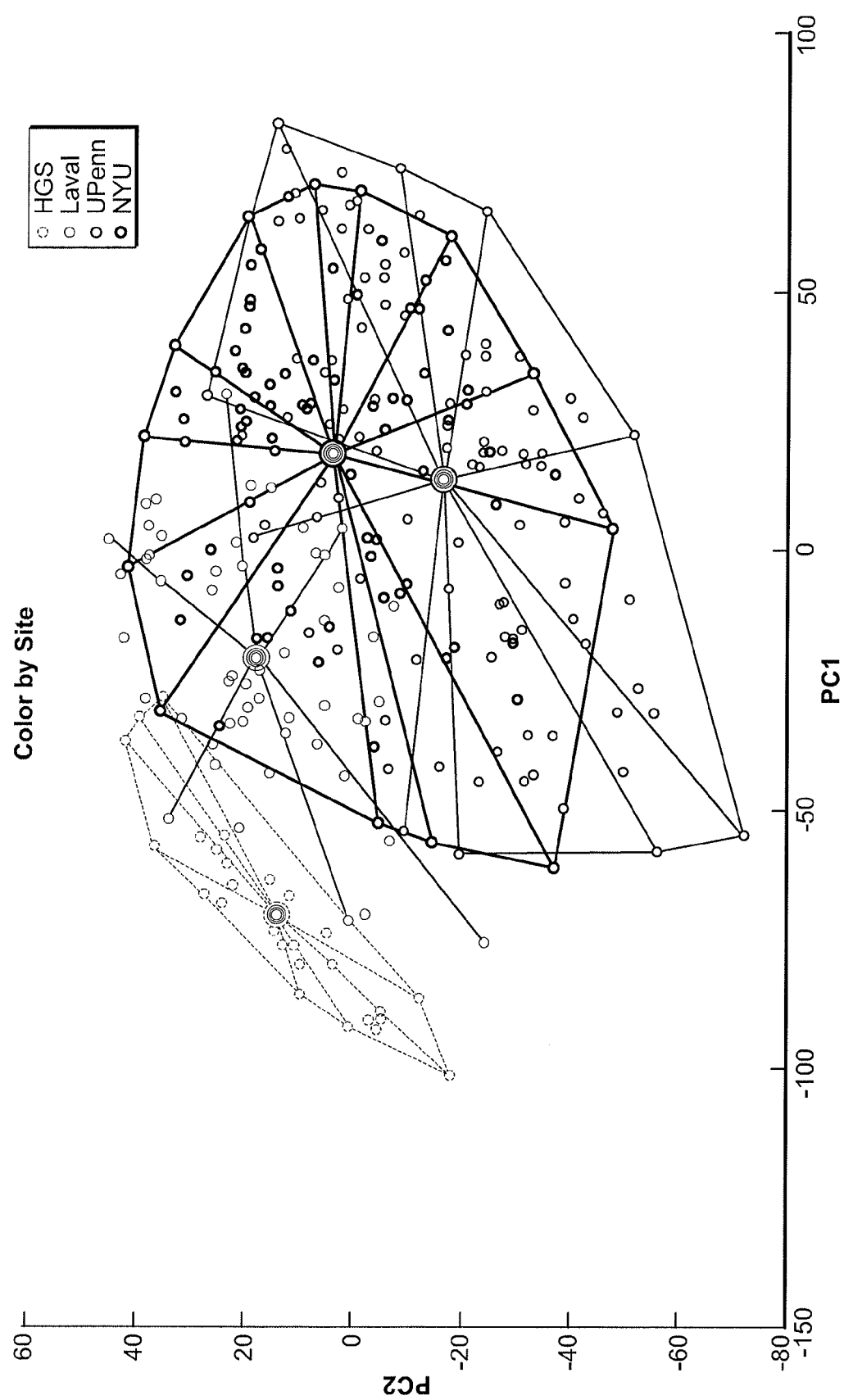
FIG. 3 is a graph showing variability among three studies used to evaluate 15 protein panels.

To find high performing panels, 10,000 trials were performed where on each trial the combined AUC of a random panel of 15 proteins selected from Table 12 was estimated. To calculate the combined AUC of each panel of 15 proteins, the highest intensity normalized transition was utilized. Logistic regression was used to calculate the AUC of the panel of 15 across all small samples. 131 panels of 15 proteins had combined AUC above 0.80, as shown in FIG. 1. (The significance by study separated into small (<2.0 cm) and large (>2.0 cm) PN are shown in FIG. 2). The resilience of the panels persisted despite site based variation in the samples as shown in FIG. 3. The panels are listed in Table 13.

TABLE 13

| AUC | P1 | P2 | P3 | P4 | P5 | P6 | P7 |
| --- | --- | --- | --- | --- | --- | --- | --- |
| 0.8282 | CD59 | CALU | LDHB | ALDOA | DSG2 | MDHM | TENA |
| 0.8255 | CD59 | TSP1 | KIT | ISLR | ALDOA | DSG2 | 1433Z |
| 0.8194 | S10A6 | ALDOA | PVR | TSP1 | CD44 | CH10 | PEDF |
| 0.8189 | ALDOA | LEG1 | CALU | LDHB | TETN | FOLH1 | MASP1 |
| 0.8187 | PVR | CD59 | CRP | ALDOA | GRP78 | DSG2 | 6PGD |
| 0.8171 | AMPN | IBP3 | CALU | CD44 | BGH3 | GRP78 | 1433Z |
| 0.8171 | CALU | CH10 | ALDOA | BST1 | MDHM | VTNC | APOE |
| 0.8165 | LDHB | CO6A3 | CD44 | A1AG1 | GRP78 | DSG2 | MDHM |
| 0.8163 | TPIS | CD59 | S10A6 | CALU | ENPL | CH10 | ALDOA |
| 0.8163 | LEG1 | AMPN | S10A6 | CALU | ISLR | ENOA | VTNC |
| 0.8161 | AMPN | S10A6 | TSP1 | MPRI | VTNC | LUM | 6PGD |
| 0.8159 | ALDOA | AMPN | TSP1 | BGH3 | GRP78 | PTPRJ | MASP1 |
| 0.8159 | ALDOA | CO6A3 | MPRI | SEM3G | CERU | LUM | APOE |
| 0.8159 | AMPN | CALU | ISLR | SODM | CERU | LUM | 6PGD |
| 0.8159 | CALU | PEDF | CRP | GRP78 | VTNC | 1433Z | CD14 |
| 0.8157 | TPIS | LEG1 | S10A6 | LDHB | TSP1 | ENPL | MDHM |
| 0.8155 | CALU | CRP | ALDOA | SODM | SEM3G | 1433Z | FRIL |
| 0.8153 | CALU | MPRI | ALDOA | PEDF | DSG2 | CERU | APOE |
| 0.814 | LEG1 | COIA1 | AMPN | S10A6 | TSP1 | MPRI | PEDF |
| 0.8138 | TSP1 | KIT | CERU | 6PGD | APOE | CD14 | FRIL |
| 0.8132 | S10A6 | COIA1 | AMPN | TSP1 | PEDF | ISLR | PTPRJ |
| 0.8128 | TPIS | LEG1 | AMPN | S10A6 | IBP3 | CALU | DSG2 |
| 0.8128 | TPIS | AMPN | TSP1 | PEDF | A1AG1 | MPRI | ALDOA |
| 0.8124 | ALDOA | CALU | LDHB | PLSL | PEDF | MASP1 | 6PGD |
| 0.8124 | AMPN | S10A6 | TSP1 | ENOA | GRP78 | 6PGD | APOE |
| 0.812 | IBP3 | TSP1 | CRP | A1AG1 | SCF | ALDOA | PEDF |
| 0.8106 | COIA1 | CALU | CD44 | BGH3 | ALDOA | TETN | BST1 |
| 0.8106 | TSP1 | PLSL | CRP | ALDOA | GRP78 | MDHM | APOE |
| 0.8099 | CD59 | CALU | ENPL | CD44 | ALDOA | TENA | 6PGD |
| 0.8097 | AMPN | S10A6 | IBP3 | A1AG1 | MPRI | ALDOA | GRP78 |
| 0.8093 | ALDOA | S10A6 | TSP1 | ENPL | PEDF | A1AG1 | GRP78 |
| 0.8093 | PVR | IBP3 | LDHB | SCF | TNF12 | LUM | 1433Z |
| 0.8093 | CALU | LDHB | CO6A3 | PEDF | CH10 | BGH3 | PTPRJ |
| 0.8087 | ALDOA | AMPN | ENPL | KIT | MPRI | GRP78 | LUM |
| 0.8087 | CD59 | S10A6 | IBP3 | TSP1 | ENPL | SODM | MDHM |
| 0.8083 | ALDOA | AMPN | S10A6 | IBP3 | PLSL | CRP | SCF |
| 0.8081 | PVR | IBP3 | TSP1 | CRP | ALDOA | SODM | MDHM |
| 0.8081 | S10A6 | LDHB | ENPL | PLSL | CH10 | CERU | FRIL |
| 0.8081 | IBP3 | LDHB | PEDF | MPRI | SEM3G | VTNC | APOE |
| 0.8079 | ALDOA | AMPN | CALU | PLSL | PEDF | CH10 | MASP1 |
| 0.8077 | S10A6 | IBP3 | LDHB | MDHM | ZA2G | FRIL | G3P |
| 0.8077 | CD59 | S10A6 | LDHB | TSP1 | CD44 | ISLR | CERU |
| 0.8077 | AMPN | CALU | LDHB | TSP1 | PLSL | CD44 | ALDOA |
| 0.8075 | TPIS | AMPN | S10A6 | TSP1 | CH10 | COIA1 | CERU |
| 0.8073 | CALU | PEDF | MPRI | ISLR | BGH3 | ENOA | CERU |
| 0.8071 | TPIS | CALU | CO6A3 | KIT | DSG2 | MASP1 | 6PGD |
| 0.8071 | LEG1 | COIA1 | TSP1 | CD44 | MPRI | ALDOA | FOLH1 |
| 0.8065 | AMPN | S10A6 | CALU | CO6A3 | TSP1 | PLSL | KIT |
| 0.8063 | S10A6 | TSP1 | A1AG1 | BGH3 | ZA2G | 1433Z | FRIL |
| 0.8063 | CALU | KIT | ENOA | 6PGD | APOE | CD14 | G3P |
| 0.8061 | AMPN | MPRI | GRP78 | DSG2 | TENA | APOE | CD14 |
| 0.8059 | TPIS | IBP3 | TSP1 | PEDF | TNF12 | 1433Z | 6PGD |
| 0.8059 | CALU | LDHB | PLSL | CRP | PEDF | SEM3G | MDHM |
| 0.8058 | ALDOA | TSP1 | PLSL | CD44 | KIT | CRP | ISLR |
| 0.8058 | TPIS | TSP1 | MPRI | ISLR | ALDOA | PEDF | GRP78 |
| 0.8054 | ALDOA | S10A6 | CALU | CRP | A1AG1 | VTNC | TENA |
| 0.8054 | TPIS | CO6A3 | TSP1 | MPRI | DSG2 | TNF12 | FRIL |
| 0.8054 | CALU | LDHB | DSG2 | 1433Z | CD14 | FRIL | G3P |
| 0.805 | CALU | MPRI | ENOA | FOLH1 | LUM | ZA2G | APOE |
| 0.8048 | PVR | S10A6 | IBP3 | PEDF | ALDOA | BST1 | MDHM |
| 0.8048 | AMPN | CALU | CH10 | DSG2 | TNF12 | CERU | 6PGD |
| 0.8046 | ALDOA | LDHB | TSP1 | KIT | ISLR | DSG2 | MASP1 |
| 0.8046 | ALDOA | COIA1 | CD59 | IBP3 | PTPRJ | SEM3G | CERU |
| 0.8046 | PVR | CD59 | S10A6 | PLSL | PEDF | CH10 | SCF |
| 0.8046 | COIA1 | IBP3 | MASP1 | DSG2 | TENA | ZA2G | 1433Z |
| 0.8042 | BGH3 | CD59 | CALU | LDHB | CO6A3 | SODM | TENA |
| 0.8042 | IBP3 | TSP1 | ENPL | CH10 | CD14 | FRIL | G3P |
| 0.8042 | IBP3 | TSP1 | KIT | ZA2G | 6PGD | APOE | CD14 |
| 0.804 | TPIS | BGH3 | S10A6 | LDHB | CO6A3 | CH10 | PEDF |

TABLE 13-continued

| | | | | | | | |
|---|---|---|---|---|---|---|---|
| 0.804 | CALU | LDHB | BGH3 | TETN | FOLH1 | TNF12 | VTNC |
| 0.8038 | TPIS | PVR | COIA1 | CALU | SCF | MPRI | ALDOA |
| 0.8036 | S10A6 | TPIS | COIA1 | CD59 | CO6A3 | TSP1 | MPRI |
| 0.8036 | LEG1 | CD59 | AMPN | CALU | CH10 | GRP78 | SEM3G |
| 0.8036 | AMPN | S10A6 | TSP1 | ENPL | PEDF | SODM | FOLH1 |
| 0.8036 | S10A6 | CALU | MASP1 | A1AG1 | MPRI | ALDOA | VTNC |
| 0.8036 | IBP3 | CALU | PLSL | CD44 | KIT | CERU | 6PGD |
| 0.8036 | TSP1 | PLSL | FOLH1 | COIA1 | TNF12 | VTNC | 6PGD |
| 0.8034 | ALDOA | BGH3 | CD59 | TSP1 | KIT | CH10 | SODM |
| 0.8034 | S10A6 | CALU | LDHB | TSP1 | GRP78 | 1433Z | 6PGD |
| 0.8032 | S10A6 | CALU | TSP1 | KIT | CH10 | PEDF | GRP78 |
| 0.8032 | TSP1 | MASP1 | CRP | ALDOA | GRP78 | TETN | TNF12 |
| 0.803 | AMPN | TSP1 | KIT | MPRI | SEM3G | TETN | DSG2 |
| 0.803 | CALU | CO6A3 | PLSL | A1AG1 | ALDOA | GRP78 | 6PGD |
| 0.8028 | COIA1 | CD59 | AMPN | TSP1 | KIT | ISLR | ALDOA |
| 0.8024 | S10A6 | CD44 | SCF | MPRI | ISLR | ALDOA | APOE |
| 0.8024 | S10A6 | TSP1 | ALDOA | SODM | ENOA | BST1 | FRIL |
| 0.8024 | IBP3 | TSP1 | SCF | ALDOA | SODM | DSG2 | VTNC |
| 0.802 | ALDOA | TSP1 | PLSL | CD44 | CH10 | A1AG1 | ENOA |
| 0.802 | LEG1 | CALU | LDHB | TSP1 | CH10 | ALDOA | MDHM |
| 0.802 | CD59 | IBP3 | TSP1 | A1AG1 | MPRI | PTPRJ | 6PGD |
| 0.802 | IBP3 | TSP1 | CRP | BST1 | TNF12 | VTNC | 1433Z |
| 0.8018 | LEG1 | S10A6 | IBP3 | CALU | TSP1 | MASP1 | A1AG1 |
| 0.8018 | COIA1 | CD59 | AMPN | CALU | MASP1 | BST1 | VTNC |
| 0.8018 | AMPN | ALDOA | SODM | GRP78 | MDHM | VTNC | 6PGD |
| 0.8018 | LDHB | CO6A3 | ALDOA | SEM3G | DSG2 | 6PGD | APOE |
| 0.8016 | S10A6 | LDHB | SCF | MPRI | ALDOA | PEDF | ENOA |
| 0.8016 | LDHB | CO6A3 | TSP1 | 1433Z | APOE | CD14 | FRIL |
| 0.8014 | ALDOA | PEDF | MPRI | ISLR | FOLH1 | TNF12 | MASP1 |
| 0.8014 | COIA1 | PEDF | CRP | A1AG1 | ENOA | CERU | FRIL |
| 0.8014 | CD59 | IBP3 | TSP1 | KIT | MASP1 | ENOA | TNF12 |
| 0.8014 | LDHB | KIT | SCF | BGH3 | SEM3G | VTNC | 1433Z |
| 0.8013 | PVR | AMPN | CD44 | DSG2 | TETN | MDHM | |
| 0.8013 | S10A6 | LDHB | TSP1 | ISLR | LUM | G3P | HYOU1 |
| 0.8013 | CALU | A1AG1 | MPRI | ALDOA | PEDF | DSG2 | VTNC |
| 0.8013 | TSP1 | ENPL | KIT | SODM | SEM3G | DSG2 | TETN |
| 0.8013 | TSP1 | PLSL | ISLR | ALDOA | ENOA | MDHM | APOE |
| 0.8011 | ALDOA | AMPN | CO6A3 | SEM3G | APOE | CD14 | FRIL |
| 0.8011 | TPIS | BGH3 | AMPN | S10A6 | CALU | LDHB | KIT |
| 0.8011 | COIA1 | IBP3 | TSP1 | A1AG1 | TETN | DSG2 | 6PGD |
| 0.8011 | AMPN | S10A6 | IBP3 | CALU | KIT | SCF | ALDOA |
| 0.8011 | IBP3 | A1AG1 | PEDF | SEM3G | MDHM | TNF12 | VTNC |
| 0.8009 | ALDOA | BGH3 | AMPN | LDHB | TSP1 | PLSL | MPRI |
| 0.8009 | LEG1 | COIA1 | IBP3 | CH10 | MASP1 | SCF | ALDOA |
| 0.8009 | AMPN | ENPL | ALDOA | TETN | FOLH1 | BST1 | ZA2G |
| 0.8009 | CALU | CO6A3 | ENPL | ALDOA | GRP78 | PTPRJ | VTNC |
| 0.8009 | TSP1 | CH10 | PTPRJ | TETN | TNF12 | VTNC | TENA |
| 0.8007 | CD59 | S10A6 | IBP3 | CO6A3 | TSP1 | KIT | ISLR |
| 0.8007 | AMPN | TSP1 | KIT | SCF | TETN | ZA2G | 1433Z |
| 0.8007 | S10A6 | IBP3 | TSP1 | CD44 | PEDF | A1AG1 | PTPRJ |
| 0.8007 | CALU | CO6A3 | TSP1 | CH10 | SCF | BGH3 | ALDOA |
| 0.8007 | ENPL | CD44 | MASP1 | GRP78 | 1433Z | CD14 | FRIL |
| 0.8005 | TPIS | LEG1 | LDHB | TSP1 | MASP1 | A1AG1 | MPRI |
| 0.8005 | PEDF | CRP | ISLR | ALDOA | GRP78 | PTPRJ | ZA2G |
| 0.8003 | ALDOA | S10A6 | CALU | CRP | BGH3 | TETN | 6PGD |
| 0.8003 | AMPN | TSP1 | A1AG1 | MPRI | ISLR | ALDOA | MASP1 |
| 0.8003 | CO6A3 | TSP1 | SCF | MPRI | ISLR | FOLH1 | 1433Z |
| 0.8001 | S10A6 | IBP3 | TSP1 | KIT | TETN | COIA1 | CERU |
| 0.8001 | S10A6 | CALU | CH10 | ISLR | ALDOA | SODM | PTPRJ |
| 0.8001 | IBP3 | TSP1 | ENPL | CH10 | CRP | ISLR | ALDOA |
| 0.8001 | IBP3 | TSP1 | PTPRJ | ALDOA | BST1 | LUM | 1433Z |
| 0.8001 | LDHB | TSP1 | MPRI | GRP78 | SEM3G | LUM | ZA2G |

| AUC | P8 | P9 | P10 | P11 | P12 | P13 | P14 | P15 |
|---|---|---|---|---|---|---|---|---|
| 0.8282 | 6PGD | APOE | FRIL | G3P | HYOU1 | LRP1 | RAN | HXK1 |
| 0.8255 | CD14 | FRIL | HYOU1 | LRP1 | PROF1 | TBB3 | FINC | CEAM8 |
| 0.8194 | APOE | FRIL | G3P | HYOU1 | LRP1 | TBB3 | CLIC1 | RAN |
| 0.8189 | 1433Z | APOE | G3P | HYOU1 | PRDX1 | PROF1 | ILK | HXK1 |
| 0.8187 | CD14 | FRIL | G3P | PRDX1 | ILK | FINC | GSLG1 | HXK1 |
| 0.8171 | 6PGD | CD14 | FRIL | G3P | LRP1 | TBB3 | FINC | RAN |
| 0.8171 | CD14 | FRIL | G3P | ICAM3 | PRDX1 | PROF1 | PVR | HXK1 |
| 0.8165 | VTNC | 1433Z | FRIL | G3P | S10A6 | FINC | GSLG1 | HXK1 |
| 0.8163 | DSG2 | 6PGD | FRIL | G3P | HYOU1 | ICAM3 | PRDX1 | FINC |
| 0.8163 | 6PGD | APOE | G3P | LRP1 | UGPA | RAN | CEAM8 | HXK1 |
| 0.8161 | APOE | CD14 | FRIL | G3P | LRP1 | PROF1 | RAN | CEAM8 |
| 0.8159 | CERU | 6PGD | FRIL | G3P | HYOU1 | LRP1 | PRDX1 | CEAM8 |
| 0.8159 | CD14 | FRIL | G3P | LRP1 | TBB3 | FINC | GSLG1 | HXK1 |
| 0.8159 | APOE | CD14 | FRIL | G3P | PRDX1 | CLIC1 | ILK | HXK1 |
| 0.8159 | FRIL | G3P | TBB3 | ILK | GELS | FINC | RAN | GSLG1 |

TABLE 13-continued

| | | | | | | | |
|---|---|---|---|---|---|---|---|
| 0.8157 | 6PGD | APOE | FRIL | G3P | HYOU1 | CLIC1 | ILK | HXK1 |
| 0.8155 | G3P | HYOU1 | LRP1 | PRDX1 | PROF1 | FINC | RAN | GSLG1 |
| 0.8153 | G3P | HYOU1 | PLXC1 | PRDX1 | ILK | CEAM8 | HXK1 | BST1 |
| 0.814 | GRP78 | CERU | FRIL | G3P | PLXC1 | PRDX1 | ILK | HXK1 |
| 0.8138 | G3P | HYOU1 | PLXC1 | RAN | CEAM8 | HXK1 | BST1 | MMP9 |
| 0.8132 | CERU | 6PGD | CD14 | FRIL | HYOU1 | FINC | GSLG1 | BST1 |
| 0.8128 | PTPRJ | BST1 | 6PGD | G3P | HYOU1 | ILK | FINC | HXK1 |
| 0.8128 | VTNC | 1433Z | APOE | FRIL | LRP1 | PTGIS | RAN |
| 0.8124 | APOE | CD14 | FRIL | G3P | GDIR2 | FINC | GSLG1 | HXK1 |
| 0.8124 | FRIL | GDIR2 | LRP1 | CLIC1 | FINC | GSLG1 | HXK1 | BST1 |
| 0.812 | DSG2 | 1433Z | APOE | FRIL | LRP1 | PRDX1 | PROF1 | FINC |
| 0.8106 | LUM | 1433Z | 6PGD | FRIL | G3P | HYOU1 | PRDX1 | CLIC1 |
| 0.8106 | FRIL | G3P | PRDX1 | UGPA | ILK | CEAM8 | GSLG1 | HXK1 |
| 0.8099 | FRIL | G3P | HYOU1 | PRDX1 | PROF1 | FINC | GSLG1 | HXK1 |
| 0.8097 | FRIL | G3P | HYOU1 | LRP1 | PTGIS | ILK | FINC | MMP9 |
| 0.8093 | APOE | CD14 | FRIL | G3P | LRP1 | PLXC1 | CLIC1 | GSLG1 |
| 0.8093 | FRIL | G3P | GDIR2 | PRDX1 | UGPA | CLIC1 | FINC | HXK1 |
| 0.8093 | ALDOA | SEM3G | MASP1 | G3P | HYOU1 | FINC | CEAM8 | HXK1 |
| 0.8087 | 1433Z | 6PGD | CD14 | FRIL | HYOU1 | TBB3 | CLIC1 | FINC |
| 0.8087 | 6PGD | FRIL | G3P | HYOU1 | LRP1 | FINC | CEAM8 | HXK1 |
| 0.8083 | MPRI | GRP78 | CERU | CD14 | FRIL | LRP1 | FINC | CEAM8 |
| 0.8081 | TNF12 | TENA | FRIL | G3P | HYOU1 | PROF1 | RAN | HXK1 |
| 0.8081 | G3P | HYOU1 | ICAM3 | PLXC1 | CLIC1 | ILK | FINC | GSLG1 |
| 0.8081 | CD14 | FRIL | G3P | HYOU1 | S10A6 | CEAM8 | GSLG1 | HXK1 |
| 0.8079 | TNF12 | LUM | 6PGD | APOE | FRIL | HYOU1 | RAN | HXK1 |
| 0.8077 | HYOU1 | LRP1 | PTGIS | CLIC1 | FINC | RAN | GSLG1 | MMP9 |
| 0.8077 | 1433Z | FRIL | G3P | HYOU1 | LRP1 | ILK | GSLG1 | HXK1 |
| 0.8077 | TETN | APOE | CD14 | FRIL | G3P | LRP1 | PRDX1 | GSLG1 |
| 0.8075 | ZA2G | 6PGD | FRIL | G3P | LRP1 | UGPA | ILK | HXK1 |
| 0.8073 | 1433Z | 6PGD | FRIL | G3P | HYOU1 | LRP1 | PRDX1 | FINC |
| 0.8071 | APOE | CD14 | FRIL | G3P | LRP1 | AMPN | RAN | HXK1 |
| 0.8071 | TNF12 | APOE | FRIL | HYOU1 | LRP1 | PTGIS | CLIC1 | AMPN |
| 0.8065 | MASP1 | ALDOA | APOE | FRIL | G3P | TBB3 | RAN | HXK1 |
| 0.8063 | G3P | LRP1 | PROF1 | TBB3 | UGPA | CLIC1 | AMPN | RAN |
| 0.8063 | ICAM3 | LRP1 | PLXC1 | PROF1 | FINC | RAN | HXK1 | MMP9 |
| 0.8061 | FRIL | G3P | LRP1 | PLXC1 | PROF1 | PVR | FINC | CEAM8 |
| 0.8059 | APOE | CD14 | FRIL | G3P | LRP1 | TBB3 | RAN | GSLG1 |
| 0.8059 | APOE | G3P | HYOU1 | PRDX1 | TBB3 | ILK | RAN | HXK1 |
| 0.8058 | TNF12 | APOE | CD14 | FRIL | G3P | HYOU1 | RAN | HXK1 |
| 0.8058 | SEM3G | FRIL | G3P | HYOU1 | PROF1 | GELS | PVR | RAN |
| 0.8054 | ZA2G | 6PGD | FRIL | G3P | HYOU1 | ILK | GSLG1 | HXK1 |
| 0.8054 | G3P | HYOU1 | ICAM3 | PLXC1 | TBB3 | GELS | RAN | BST1 |
| 0.8054 | HYOU1 | PLXC1 | PRDX1 | PROF1 | FINC | CEAM8 | GSLG1 | MMP9 |
| 0.805 | CD14 | G3P | HYOU1 | ICAM3 | PRDX1 | UGPA | ILK | HXK1 |
| 0.8048 | VTNC | CD14 | FRIL | G3P | HYOU1 | PTGIS | FINC | RAN |
| 0.8048 | APOE | G3P | FRIL | G3P | LRP1 | PRDX1 | UGPA | RAN | CEAM8 |
| 0.8046 | 1433Z | FRIL | G3P | GDIR2 | HYOU1 | RAN | GSLG1 | HXK1 |
| 0.8046 | CD14 | FRIL | G3P | LRP1 | PRDX1 | FINC | GSLG1 | MMP9 |
| 0.8046 | BST1 | FRIL | G3P | CLIC1 | ILK | AMPN | FINC | HXK1 |
| 0.8046 | APOE | CD14 | FRIL | G3P | ICAM3 | AMPN | FINC | HXK1 |
| 0.8042 | APOE | G3P | HYOU1 | S10A6 | ILK | FINC | RAN | HXK1 |
| 0.8042 | HYOU1 | ICAM3 | LRP1 | PRDX1 | PROF1 | GELS | FINC | GSLG1 |
| 0.8042 | FRIL | GDIR2 | HYOU1 | LRP1 | PRDX1 | PROF1 | CLIC1 | HXK1 |
| 0.804 | TENA | FRIL | G3P | HYOU1 | LRP1 | PRDX1 | ILK | GSLG1 |
| 0.804 | FRIL | G3P | GDIR2 | PRDX1 | CLIC1 | GELS | FINC | HXK1 |
| 0.8038 | ENOA | MASP1 | APOE | FRIL | G3P | PRDX1 | FINC | HXK1 |
| 0.8036 | ALDOA | ENOA | 6PGD | FRIL | G3P | GDIR2 | LRP1 | PRDX1 |
| 0.8036 | TETN | APOE | G3P | HYOU1 | ICAM3 | RAN | CEAM8 | HXK1 |
| 0.8036 | 6PGD | APOE | FRIL | G3P | HYOU1 | LRP1 | HXK1 | MMP9 |
| 0.8036 | TENA | FRIL | G3P | PROF1 | PTGIS | FINC | CEAM8 | HXK1 |
| 0.8036 | CD14 | FRIL | G3P | HYOU1 | PRDX1 | FINC | CEAM8 | HXK1 |
| 0.8036 | FRIL | G3P | LRP1 | PRDX1 | PROF1 | GELS | FINC | RAN |
| 0.8034 | VTNC | TENA | 6PGD | G3P | HYOU1 | LRP1 | TBB3 | ILK |
| 0.8034 | G3P | HYOU1 | ICAM3 | PROF1 | ILK | GELS | AMPN | FINC |
| 0.8032 | SEM3G | MASP1 | 6PGD | CD14 | FRIL | G3P | HYOU1 | ILK |
| 0.8032 | 1433Z | APOE | CD14 | G3P | HYOU1 | PVR | RAN | HXK1 |
| 0.803 | 1433Z | APOE | FRIL | G3P | TBB3 | UGPA | PVR | RAN |
| 0.803 | APOE | CD14 | FRIL | G3P | HYOU1 | ICAM3 | PRDX1 | RAN |
| 0.8028 | MDHM | CERU | LUM | ZA2G | APOE | FRIL | LRP1 | MMP9 |
| 0.8024 | FRIL | G3P | HYOU1 | PRDX1 | GELS | FINC | CEAM8 | HXK1 |
| 0.8024 | HYOU1 | LRP1 | PROF1 | CLIC1 | GELS | FINC | CEAM8 | GSLG1 |
| 0.8024 | 1433Z | APOE | FRIL | G3P | LRP1 | PRDX1 | UGPA | PTPRJ |
| 0.802 | TETN | TENA | APOE | FRIL | G3P | TBB3 | AMPN | GSLG1 |
| 0.802 | APOE | FRIL | G3P | HYOU1 | ILK | PVR | GSLG1 | PTPRJ |
| 0.802 | APOE | FRIL | G3P | LRP1 | ILK | RAN | CEAM8 | MMP9 |
| 0.802 | FRIL | G3P | GDIR2 | HYOU1 | LRP1 | PRDX1 | TBB3 | FINC |
| 0.8018 | SCF | ALDOA | SEM3G | VTNC | FRIL | G3P | LRP1 | CLIC1 |
| 0.8018 | CERU | 6PGD | APOE | CD14 | FRIL | HYOU1 | PROF1 | GSLG1 |
| 0.8018 | FRIL | G3P | HYOU1 | LRP1 | PTGIS | GELS | FINC | RAN |
| 0.8018 | FRIL | G3P | HYOU1 | ICAM3 | PROF1 | FINC | PTPRJ | HXK1 |

TABLE 13-continued

| | | | | | | | | |
|---|---|---|---|---|---|---|---|---|
| 0.8016 | SEM3G | APOE | FRIL | G3P | HYOU1 | PRDX1 | CLIC1 | GSLG1 |
| 0.8016 | G3P | HYOU1 | PROF1 | UGPA | CLIC1 | RAN | CEAM8 | PTPRJ |
| 0.8014 | CERU | 6PGD | FRIL | G3P | HYOU1 | PRDX1 | FINC | HXK1 |
| 0.8014 | G3P | GDIR2 | LRP1 | S10A6 | GELS | FINC | GSLG1 | HXK1 |
| 0.8014 | CD14 | FRIL | G3P | PRDX1 | UGPA | FINC | PTPRJ | HXK1 |
| 0.8014 | FRIL | G3P | HYOU1 | LRP1 | PRDX1 | PROF1 | FINC | HXK1 |
| 0.8013 | FRIL | G3P | LRP1 | PRDX1 | ILK | FINC | HXK1 | MMP9 |
| 0.8013 | ICAM3 | LRP1 | PROF1 | UGPA | ILK | FINC | PTPRJ | HXK1 |
| 0.8013 | ZA2G | 6PGD | FRIL | G3P | CLIC1 | S10A6 | ILK | PVR |
| 0.8013 | LUM | APOE | FRIL | G3P | HYOU1 | CLIC1 | RAN | HXK1 |
| 0.8013 | G3P | GDIR2 | LRP1 | PTGIS | FINC | RAN | HXK1 | MMP9 |
| 0.8011 | G3P | GDIR2 | HYOU1 | ICAM3 | PRDX1 | FINC | HXK1 | MMP9 |
| 0.8011 | TENA | 6PGD | APOE | G3P | LRP1 | PROF1 | GELS | MMP9 |
| 0.8011 | FRIL | GDIR2 | HYOU1 | LRP1 | CLIC1 | S10A6 | PVR | GSLG1 |
| 0.8011 | APOE | G3P | ICAM3 | LRP1 | GELS | FINC | RAN | CEAM8 |
| 0.8011 | 1433Z | G3P | HYOU1 | PRDX1 | FINC | GSLG1 | PTPRJ | HXK1 |
| 0.8009 | ISLR | APOE | FRIL | LRP1 | PVR | FINC | RAN | PTPRJ |
| 0.8009 | TNF12 | CERU | APOE | CD14 | FRIL | TBB3 | ILK | FINC |
| 0.8009 | 6PGD | CD14 | FRIL | CLIC1 | S10A6 | ILK | FINC | MMP9 |
| 0.8009 | APOE | CD14 | G3P | TBB3 | CLIC1 | GELS | RAN | HXK1 |
| 0.8009 | 1433Z | 6PGD | FRIL | G3P | HYOU1 | RAN | HXK1 | MMP9 |
| 0.8007 | GRP78 | MDHM | CD14 | FRIL | G3P | HYOU1 | GSLG1 | HXK1 |
| 0.8007 | 6PGD | APOE | G3P | GDIR2 | LRP1 | PRDX1 | TBB3 | RAN |
| 0.8007 | SODM | CERU | APOE | FRIL | ICAM3 | LRP1 | UGPA | GSLG1 |
| 0.8007 | ENOA | TETN | LUM | APOE | FRIL | G3P | RAN | HXK1 |
| 0.8007 | G3P | GDIR2 | ICAM3 | LRP1 | PRDX1 | PROF1 | FINC | HXK1 |
| 0.8005 | ALDOA | ENOA | FRIL | G3P | LRP1 | UGPA | ILK | FINC |
| 0.8005 | 6PGD | G3P | HYOU1 | PRDX1 | TBB3 | FINC | RAN | CEAM8 |
| 0.8003 | CD14 | FRIL | G3P | CLIC1 | FINC | GSLG1 | HXK1 | MMP9 |
| 0.8003 | LUM | 6PGD | APOE | FRIL | ICAM3 | TBB3 | GSLG1 | BST1 |
| 0.8003 | APOE | G3P | HYOU1 | ICAM3 | PRDX1 | UGPA | RAN | HXK1 |
| 0.8001 | 6PGD | CD14 | FRIL | G3P | PROF1 | FINC | HXK1 | MMP9 |
| 0.8001 | MDHM | VTNC | FRIL | G3P | CLIC1 | ILK | AMPN | HXK1 |
| 0.8001 | SODM | 1433Z | G3P | HYOU1 | LRP1 | PRDX1 | PROF1 | CEAM8 |
| 0.8001 | APOE | G3P | HYOU1 | LRP1 | PTGIS | TBB3 | PVR | RAN |
| 0.8001 | FRIL | G3P | ICAM3 | PROF1 | TBB3 | FINC | RAN | GSLG1 |

To calculate the combined AUC of each panel of 15 proteins, the highest intensity normalized transition was utilized. Logistic regression was used to calculate the AUC of the panel of 15 across all small samples. 5 panels of 15 proteins had combined AUC above 0.80.

Finally, the frequency of each of the 67 proteins on the 131 panels listed in Table 13 is presented in Table 12 both as raw counts (column 2) and percentage (column 3). It is an important observation that the panel size of 15 was pre-selected to prove that there are diagnostic proteins and panels. Furthermore, there are numerous such panels. Smaller panels selected from the list of 67 proteins can also be formed and can be generated using the same methods here.

Example 4

A Diagnostic Panel of 15 Proteins for Determining the Probability that a Blood Sample from a Patient with a PN of Size 2 cm or Less is Benign or Malignant In Table 14 a logistic regression classifier trained on all small samples is presented.

TABLE 14

| Protein | Transition | Transition column SEQ ID NO: | Normalized By | Normalized By column SEQ ID NO: | Logistic Regression Coefficient |
|---|---|---|---|---|---|
| ALDOA_HUMAN | ALQASALK_401.25_617.40 | 7 | YGFIEGHVVIPR_462.92_272.20 | 1 | −1.96079 |
| BGH3_HUMAN | LTLLAPLNSVFK_658.40_804.50 | 8 | YEVTVVSVR_526.29_759.50 | 2 | 2.21074 |
| CLIC1_HUMAN | LAALNPESNTAGLDIFAK_922.99_256.20 | 9 | ASSIIDELFQDR_465.24_565.30 | 3 | 0.88028 |
| CO6A3_HUMAN | VAVVQYSDR_518.77_767.40 | 10 | ASSIIDELFQDR_465.24_565.30 | 3 | −1.52046 |
| COIA1_HUMAN | AVGLAGTFR_446.26_721.40 | 11 | YGFIEGHVVIPR_462.92_272.20 | 1 | −0.76786 |
| FINC_HUMAN | VPGTSTSATLTGLTR_487.94_446.30 | 12 | FLNVLSPR_473.28_685.40 | 4 | 0.98842 |
| G3P_HUMAN | GALQNIIPASTGAAK_706.40_815.50 | 13 | TASDFITK_441.73_710.40 | 5 | 0.58843 |
| ISLR_HUMAN | ALPGTPVASSQPR_640.85_841.50 | 14 | FLNVLSPR_473.28_685.40 | 4 | 1.02005 |
| LRP1_HUMAN | TVLWPNGLSLDIPAGR_855.00_400.20 | 15 | YEVTVVSVR_526.29_759.50 | 2 | −2.14383 |
| PRDX1_HUMAN | QITVNDLPVGR_606.30_428.30 | 16 | YGFIEGHVVIPR_462.92_272.20 | 1 | −1.38044 |
| PROF1_HUMAN | STGGAPTFNVTVTK_690.40_503.80 | 17 | TASDFITK_441.73_710.40 | 5 | −1.78666 |
| PVR_HUMAN | SVDIWLR_444.75_702.40 | 18 | TASDFITK_441.73_710.40 | 5 | 2.26338 |
| TBB3_HUMAN | ISVYYNEASSHK_466.60_458.20 | 19 | FLNVLSPR_473.28_685.40 | 4 | −0.46786 |
| TETN_HUMAN | LDTLAQEVALLK_657.39_330.20 | 20 | TASDFITK_441.73_710.40 | 5 | −1.99972 |
| TPIS_HUMAN | VVFEQTK_425.74_652.30 | 21 | YGFIEGHVVIPR_462.92_272.20 | 1 | 2.65334 |
| Constant ($C_0$) | | | | | 21.9997 |

The classifier has the structure $$\text{Probability} = \frac{\exp(W)}{1+\exp(W)}$$

$$W = C_0 + \sum_{i=1}^{15} C_i * P_i$$

Where $C_0$ and $C_i$ are logistic regression coefficients, $P_i$ are logarithmically transformed normalized transition intensities. Samples are predicted as cancer if Probability ≥0.5 or as benign otherwise. In Table 14 the coefficients $C_i$ appear in the sixth column, $C_0$ in the last row, and the normalized transitions for each protein are defined by column 2 (protein transition) and column 4 (the normalizing factor).

The performance of this classifier, presented as a ROC plot, appears in FIG. 4. Overall AUC is 0.81. The performance can also be assessed by applying the classifier to each study site individually which yields the three ROC plots appearing in FIG. 5. The resulting AUCs are 0.79, 0.88 and 0.78 for Laval, NYU and UPenn, respectively.

Example 5

Figure 6:
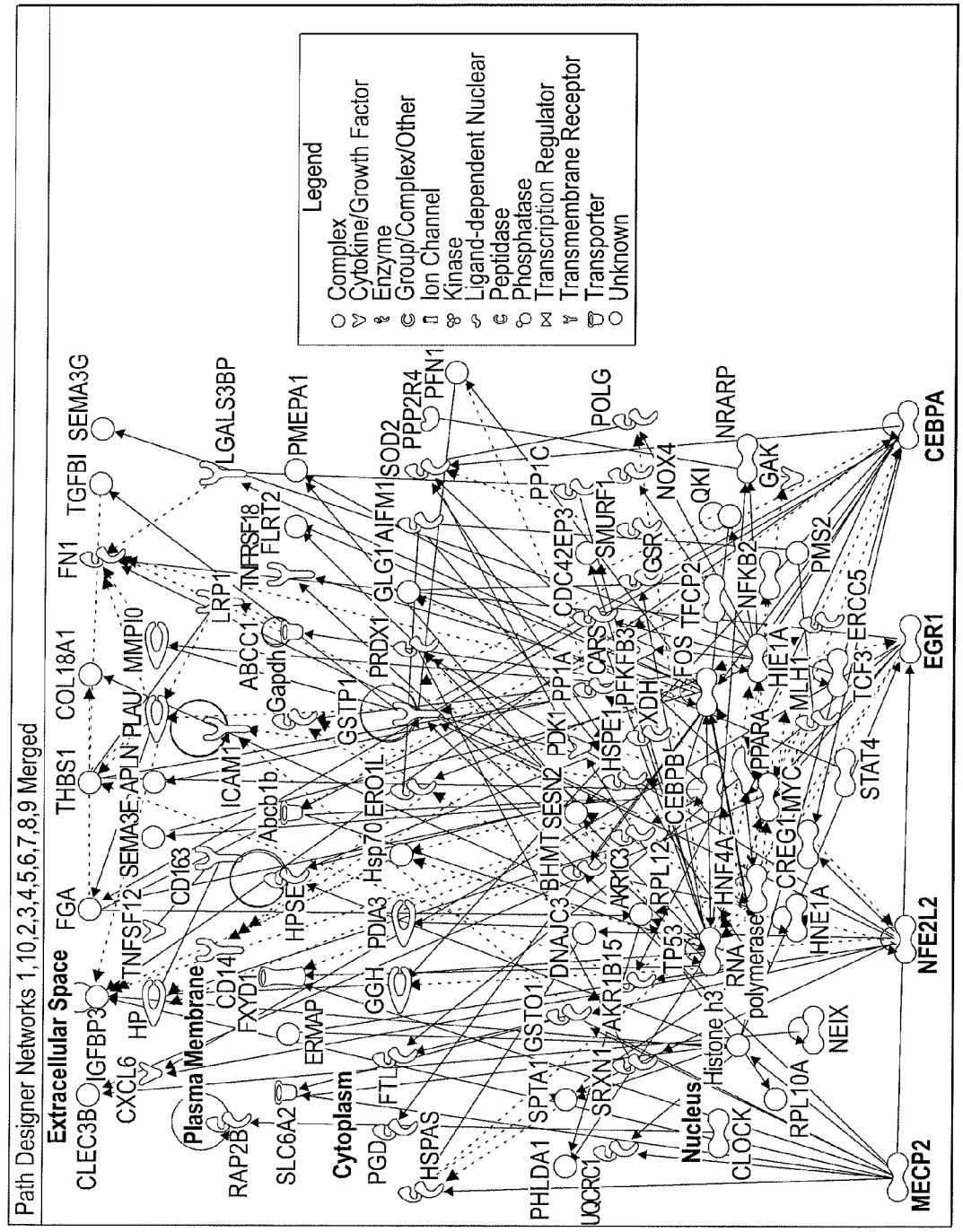
FIG. 6 shows the results of a query of blood proteins used to identify lung cancer using the "Ingenuity"® program.

The Program "Ingenuity"® was Used to Query the Blood Proteins that are Used to Identify Lung Cancer in Patients with Nodules that were Identified Using the Methods of the Present Invention Using a subset of 35 proteins (Table 15) from the 67 proteins identified as a diagnostic panel (Table 13), a backward systems analysis was performed. Two networks were queried that are identified as cancer networks with the identified 35 proteins. The results show that the networks that have the highest percentage of "hits" when the proteins are queried that are found in the blood of patients down to the level of the nucleus are initiated by transcription factors that are regulated by either cigarette smoke or lung cancer among others. See also Table 16 and FIG. 6.

These results are further evidence that the proteins that were identified using the methods of the invention as diagnostic for lung cancer are prognostic and relevant.

TABLE 15

| No. | Protein | Protein Name | Gene Symbol | Gene Name |
|---|---|---|---|---|
| 1 | 6PGD_HUMAN | 6-phosphogluconate dehydrogenase, decarboxylating | PGD | phosphogluconate dehydrogenase |
| 2 | AIFM1_HUMAN | Apoptosis-inducing factor 1, mitochondrial | AIFM1 | apoptosis-inducing factor, mitochondrion-associated, 1 |
| 3 | ALDOA_HUMAN | Fructose-bisphosphate aldolase A | ALDOA | aldolase A, fructose-bisphosphate |
| 4 | BGH3_HUMAN | Transforming growth factor-beta-induced protein ig-h3 | TGFBI | transforming growth factor, beta-induced, 68 kDa |
| 5 | C163A_HUMAN | Scavenger receptor cysteine-rich type 1 protein M130 | CD163 | CD163 molecule |
| 6 | CD14_HUMAN | Monocyte differentiation antigen CD14 | CD14 | CD14 molecule |
| 7 | COIA1_HUMAN | Collagen alpha-1(XVIII) chain | COL18A1 | collagen, type XVIII, alpha 1 |
| 8 | ERO1A_HUMAN | ERO1-like protein alpha | ERO1L | ERO1-like (*S. cerevisiae*) |
| 9 | FIBA_HUMAN | Fibrinogen alpha chain | FGA | fibrinogen alpha chain |
| 10 | FINC_HUMAN | Fibronectin | FN1 | fibronectin 1 |
| 11 | FOLH1_HUMAN | Glutamate carboxypeptidase 2 | FOLH1 | folate hydrolase (prostate-specific membrane antigen) 1 |
| 12 | FRIL_HUMAN | Ferritin light chain | FTL | ferritin, light polypeptide |
| 13 | GELS_HUMAN | Gelsolin | GSN | gelsolin (amyloidosis, Finnish type) |
| 14 | GGH_HUMAN | Gamma-glutamyl hydrolase | GGH | gamma-glutamyl hydrolase (conjugase, folylpolygammaglutamyl hydrolase) |
| 15 | GRP78_HUMAN | 78 kDa glucose-regulated protein | HSPA5 | heat shock 70 kDa protein 5 (glucose-regulated protein, 78 kDa) |
| 16 | GSLG1_HUMAN | Golgi apparatus protein 1 | GLG1 | golgi apparatus protein 1 |
| 17 | GSTP1_HUMAN | Glutathione S-transferase P | GSTP1 | glutathione S-transferase pi 1 |
| 18 | IBP3_HUMAN | Insulin-like growth factor-binding protein 3 | IGFBP3 | insulin-like growth factor binding protein 3 |
| 19 | ICAM1_HUMAN | Intercellular adhesion molecule 1 | ICAM1 | intercellular adhesion molecule 1 |
| 20 | ISLR_HUMAN | Immunoglobulin superfamily containing leucine-rich repeat protein | ISLR | immunoglobulin superfamily containing leucine-rich repeat |
| 21 | LG3BP_HUMAN | Galectin-3-binding protein | LGALS3BP | lectin, galactoside-binding, soluble, 3 binding protein |
| 22 | LRP1_HUMAN | Prolow-density lipoprotein receptor-related protein 1 | LRP1 | low density lipoprotein-related protein 1 (alpha-2-macroglobulin receptor) |

TABLE 15-continued

| No. | Protein | Protein Name | Gene Symbol | Gene Name |
|---|---|---|---|---|
| 23 | LUM_HUMAN | Lumican | LUM | lumican |
| 24 | MASP1_HUMAN | Mannan-binding lectin serine protease 1 | MASP1 | mannan-binding lectin serine peptidase 1 (C4/C2 activating component of Ra-reactive factor) |
| 25 | PDIA3_HUMAN | Protein disulfide-isomerase A3 | PDIA3 | protein disulfide isomerase family A, member 3 |
| 26 | PEDF_HUMAN | Pigment epithelium-derived factor | SERPINF1 | serpin peptidase inhibitor, clade F (alpha-2 antiplasmin, pigment epithelium derived factor), member 1 |
| 27 | PRDX1_HUMAN | Peroxiredoxin-1 | PRDX1 | peroxiredoxin 1 |
| 28 | PROF1_HUMAN | Profilin-1 | PFN1 | profilin 1 |
| 29 | PTPA_HUMAN | Serine/threonine-protein phosphatase 2A activator | PPP2R4 | protein phosphatase 2A activator, regulatory subunit 4 |
| 30 | PTPRJ_HUMAN | Receptor-type tyrosine-protein phosphatase eta | PTPRJ | protein tyrosine phosphatase, receptor type, J |
| 31 | RAP2B_HUMAN | Ras-related protein Rap-2b | RAP2B | RAP2B, member of RAS oncogene family |
| 32 | SEM3G_HUMAN | Semaphorin-3G | SEMA3G | sema domain, immunoglobulin domain (Ig), short basic domain, secreted, (semaphorin) 3G |
| 33 | SODM_HUMAN | Superoxide dismutase [Mn], mitochondrial | SOD2 | superoxide dismutase 2, mitochondrial |
| 34 | TETN_HUMAN | Tetranectin | CLEC3B | C-type lectin domain family 3, member B |
| 35 | TSP1_HUMAN | Thrombospondin-1 | THBS1 | thrombospondin 1 |

TABLE 16

| Gene Name | Protein | Lung Cancer PubMed Associations | Sample Publications |
|---|---|---|---|
| NFE2L2 (NRF2) | nuclear factor (erythroid-derived 2)-like 2 | 92 transcription factor protecting cell from oxidative stress | Cigarette Smoking Blocks the Protective Expression of Nrf2/ARE Pathway . . . Molecular mechanisms for the regulation of Nrf2-mediated cell proliferation in non-small-cell lung cancers . . . |
| EGR1 | early growth response | 38 transcription factor involved oxidative stress | Cigarette smoke-induced Egr-1 upregulates proinflammatory cytokines in pulmonary epithelial cells . . . EGR-1 regulates Ho-1 expression induced by cigarette smoke . . . Chronic hypoxia induces Egr-1 via activation of ERK1/2 and contributes to pulmonary vascular remodeling. Early growth response-1 induces and enhances vascular endothelial growth factor-A expression in lung cancer cells . . . |

Example 6

Cooperative Proteins for Diagnosing Pulmonary Nodules

To achieve unbiased discovery of cooperative proteins, selected reaction monitoring (SRM) mass spectrometry (Addona, Abbatiello et al. 2009) was utilized. SRM is a form of mass spectrometry that monitors predetermined and highly specific mass products of particularly informative (proteotypic) peptides of selected proteins. These peptides are recognized as specific transitions in mass spectra. SRM possesses the following required features that other technologies, notably antibody-based technologies, do not possess:

Highly multiplexed SRM assays can be rapidly and cost-effectively developed for tens or hundreds of proteins.

The assays developed are for proteins of one's choice and are not restricted to a catalogue of pre-existing assays. Furthermore, the assays can be developed for specific regions of a protein, such as the extracellular portion of a transmembrane protein on the cell surface of a tumor cell, or for a specific isoform.

SRM technology can be used from discovery to clinical testing. Peptide ionization, the foundation of mass spectrometry, is remarkably reproducible. Using a single technology platform avoids the common problem of translating an assay from one technology platform to another.

SRM has been used for clinical testing of small molecule analytes for many years, and recently in the development of biologically relevant assays [10].

Labeled and unlabeled SRM peptides are commercially available, together with an open-source library and data repository of mass spectra for design and conduct of SRM analyses. Exceptional public resources exist to accelerate assay development including the PeptideAtlas [11] and the Plasma Proteome Project [12, 13], the SRM Atlas and PASSEL, the PeptideAtlas SRM Experimental Library (www.systemsbiology.org/passel).

Two SRM strategies that enhance technical performance were introduced. First, large scale SRM assay development introduces the possibility of monitoring false signals. Using an extension of expression correlation techniques [14], the rate of false signal monitoring was reduced to below 3%. This is comparable and complementary to the approach used by mProphet (Reiter, Rinner et al. 2011).

Second, a panel of endogenous proteins was used for normalization. However, whereas these proteins are typically selected as "housekeeping" proteins (Lange, Picotti et al. 2008), proteins that were strong normalizers for the technology platform were identified. That is, proteins that monitored the effects of technical variation so that it could be controlled effectively. This resulted, for example, in the reduction of technical variation due to sample depletion of high abundance proteins from 23.8% to 9.0%. The benefits of endogenous signal normalization has been previously discussed (Price, Trent et al. 2007).

The final component of the strategy was to carefully design the discovery and validation studies using emerging best practices. Specifically, the cases (malignant nodules) and controls (benign nodules) were pairwise matched on age, nodule size, gender and participating clinical site. This ensures that the candidate markers discovered are not markers of age or variations in sample collection from site to site. The studies were well-powered, included multiple sites, a new site participated in the validation study, and importantly, were designed to address the intended use of the test. The careful selection and matching of samples resulted in an exceptionally valuable feature of the classifier. The classifier generates a score that is independent of nodule size and smoking status. As these are currently used risk factors for clinical management of IPNs, the classifier is a complementary molecular tool for use in the diagnosis of IPNs.

Selection of Biomarker Candidates for Assay Development

To identify lung cancer biomarkers in blood that originate from lung tumor cells, resected lung tumors and distal normal tissue of the same lobe were obtained. Plasma membranes were isolated from both endothelial and epithelial cells and analyzed by tandem mass spectrometry to identify cell surface proteins over expressed on tumor cells. Similarly, Golgi apparatus were isolated to identify over-secreted proteins from tumor cells. Proteins with evidence of being present in blood or secreted were prioritized resulting in a set of 217 proteins. See Example 7: Materials and Methods for details.

To ensure other viable lung cancer biomarkers were not overlooked, a literature search was performed and manually curated for lung cancer markers. As above, proteins with evidence of being present in blood or secreted were prioritized. This resulted in a set of 319 proteins. See Example 7: Materials and Methods for details.

The tissue (217) and literature (319) candidates overlapped by 148 proteins resulting in a final candidate list of 388 protein candidates. See Example 7: Materials and Methods.

Development of SRM Assays

SRM assays for the 388 proteins were developed using standard synthetic peptide techniques (See Example 7: Materials and Methods). Of the 388 candidates, SRM assays were successfully developed for 371 candidates. The 371 SRM assays were applied to benign and lung cancer plasma samples to evaluate detection rate in blood. 190 (51% success rate) of the SRM assays were detected. This success rate compares favorably to similar attempts to develop large scale SRM assays for detection of cancer markers in plasma. Recently 182 SRM assays for general cancer markers were developed from 1172 candidates (16% success rate) [15]. Despite focusing only on lung cancer markers, the 3-fold increase in efficiency is likely due to sourcing candidates from cancer tissues with prior evidence of presence in blood. Those proteins of the 371 that were previously detected by mass spectrometry in blood had a 64% success rate of detection in blood whereas those without had a 35% success rate. Of the 190 proteins detected in blood, 114 were derived from the tissue-sourced candidates and 167 derived from the literature-sourced candidates (91 protein overlap). See Example 7: Materials and Methods and Table 6.

Typically, SRM assays are manually curated to ensure assays are monitoring the intended peptide. However, this becomes unfeasible for large scale SRM assays such as this 371 protein assay. More recently, computational tools such as mProphet (Reiter, Rinner et al. 2011) enable automated qualification of SRM assays. A complementary strategy to mProphet was introduced that does not require customization for each dataset set. It utilizes correlation techniques (Kearney, Butler et al. 2008) to confirm the identity of protein transitions with high confidence. In FIG. 7 a histogram of the Pearson correlations between every pair of transitions in the assay is presented. The correlation between a pair of transitions is obtained from their expression profiles over all 143 samples in the discovery study detailed below. As expected, transitions from the same peptide are highly correlated. Similarly, transitions from different peptide fragments of the same protein are also highly correlated. In contrast, transitions from different proteins are not highly correlated and enables a statistical analysis of the quality of a protein's SRM assay. For example, if the correlation of transitions from two peptides from the same protein is above 0.5 then there is less than a 3% probability that the assay is false. See Example 7: Materials and Methods.

Classifier Discovery

A summary of the 143 samples used for classifier discovery appears in Table 17. Samples were obtained from three sites to avoid overfitting to a single site. Participating sites were Laval (Institut Universitaire de Cardiologie et de Pneumologie de Quebec), NYU (New York University) and UPenn (University of Pennsylvania). Samples were also selected to be representative of the intended use population in terms of nodule size (diameter), age and smoking status.

Benign and cancer samples were paired by matching on age, gender, site and nodule size (benign and cancer samples were required to have a nodule identified radiologically). The benign and cancer samples display a bias in smoking (pack years), however, the majority of benign and cancer samples were current or past smokers. In comparing malignant and benign samples, the intent was to find proteins that were markers of lung cancer; not markers of age, nodule size or differences in site sample collection. Note that cancer samples were pathologically confirmed and benign samples were either pathologically confirmed or radiologically confirmed (no tumor growth demonstrated over two years of CT scan surveillance).

TABLE 17

Clinical data summaries and demographic analysis for discovery and validation sets.

|  |  | Discovery | | | Validation | | |
| --- | --- | --- | --- | --- | --- | --- | --- |
|  |  | Cancer | Benign | P value | Cancer | Benign | P value |
| Sample (total) |  | 72 | 71 |  | 52 | 52 |  |
| Sample (Center) | Laval | 14 | 14 | 1.00† | 13 | 12 | 0.89† |
|  | NYU | 29 | 28 |  | 6 | 9 |  |
|  | UPenn | 29 | 29 |  | 14 | 13 |  |
|  | Vanderbilt | 0 | 0 |  | 19 | 18 |  |
| Sample (Gender) | Male | 29 | 28 | 1.00† | 25 | 27 | 0.85† |
|  | Female | 43 | 43 |  | 27 | 25 |  |
| Sample (Smoking History) | Never | 5 | 19 | 0.006† | 3 | 15 | 0.006† |
|  | Past | 60 | 44 |  | 38 | 29 |  |
|  | Current | 6 | 6 |  | 11 | 7 |  |
|  | No data | 1 | 2 |  | 0 | 1 |  |
| Age | Median (quartile range) | 65 (59-72) | 64 (52-71) | 0.46‡ | 63 (60-73) | 62 (56-67) | 0.03‡ |
| Nodule Size (mm) | Median (quartile range) | 13 (10-16) | 13 (10-18) | 0.69‡ | 16 (13-20) | 15 (12-22) | 0.68‡ |
| Pack-year§ | Median (quartile range) | 37 (20-52) | 20 (0-40) | 0.001‡ | 40 (19-50) | 27 (0-50) | 0.09‡ |

†Based on Fisher's exact test.
‡Based on Mann-Whitney test.
§No data (cancer, benign): Discovery (4, 6), Validation (2, 3)

The processing of samples was conducted in batches. Each batch contained a set of randomly selected cancer-benign pairs and three plasma standards, included for calibration and quality control purposes.

All plasma samples were immunodepleted, trypsin digested and analyzed by reverse phase HPLC-SRM-MS. Protein transitions were normalized using an endogenous protein panel. The normalization procedure was designed to reduce overall variability, but in particular, the variability introduced by the depletion step. Overall technical variability was reduced from 32.3% to 25.1% and technical variability due to depletion was reduced from 23.8% to 9.0%. Details of the sample analysis and normalization procedure are available in Example 7: Materials and Methods.

To assess panels of proteins, they were fit to a logistic regression model. Logistic regression was chosen to avoid the overfitting that can occur with non-linear models, especially when the number of variables measured (transitions) is similar or larger than the number of samples in the study. The performance of a panel was measured by partial area under the curve (AUC) with sensitivity fixed at 90% (McClish 1989). Partial AUC correlates to high NPV performance while maximizing ROR.

To derive the 13 protein classifier, four criteria were used:
The protein must have transitions that are reliably detected above noise across samples in the study.
The protein must be highly cooperative.
The protein must have transitions that are robust (high signal to noise, no interference, etc.)
The protein's coefficient within the logistic regression model must have low variability during cross validation, that is, it must be stable.

Details of how each of these criteria were applied appear in Example 7: Materials and Methods.

Finally, the 13 protein classifier was trained to a logistic regression model by Monte Carlo cross validation (MCCV) with a hold out rate of 20% and 20,000 iterations. The thirteen proteins for the rule-out classifier are listed in Table 18 along with their highest intensity transition and model coefficient.

TABLE 18

The 13 protein classifier.

| Protein | Transition | SEQ ID NO | Coefficient |
| --- | --- | --- | --- |
| Constant(α) |  |  | 36.16 |
| LRP1_HUMAN | TVLWPNGLSLDIPAGR_855.00_400.20 | 15 | −1.59 |
| BGH3_HUMAN | LTLLAPLNSVFK_658.40_804.50 | 8 | 1.73 |
| COIA1_HUMAN | AVGLAGTFR_446.26_721.40 | 11 | −1.56 |
| TETN_HUMAN | LDTLAQEVALLK_657.39_330.20 | 20 | −1.79 |
| TSP1_HUMAN | GFLLLASLR_495.31_559.40 | 22 | 0.53 |
| ALDOA_HUMAN | ALQASALK_401.25_617.40 | 7 | −0.80 |
| GRP78_HUMAN | TWNDPSVQQDIK_715.85_260.20 | 23 | 1.41 |
| ISLR_HUMAN | ALPGTPVASSQPR_640.85_841.50 | 14 | 1.40 |
| FRIL_HUMAN | LGGPEAGLGEYLFER_804.40_913.40 | 24 | 0.39 |
| LG3BP_HUMAN | VEIFYR_413.73_598.30 | 25 | −0.58 |
| PRDX1_HUMAN | QITVNDLPVGR_606.30_428.30 | 16 | −0.34 |

TABLE 18-continued

The 13 protein classifier.

| Protein | Transition | SEQ ID NO | Coefficient |
|---|---|---|---|
| FIBA_HUMAN | NSLFEYQK_514.76_714.30 | 26 | 0.31 |
| GSLG1_HUMAN | IIIQESALDYR_660.86_338.20 | 27 | −0.70 |

Validation of the Rule-Out Classifier 52 cancer and 52 benign samples (see Table 17) were used to validate the performance of the 13 protein classifier. All samples were independent of the discovery samples, in addition, over 36% of the validation samples were sourced from a new fourth site (Vanderbilt University). Samples were selected to be consistent with intended use and matched in terms of gender, clinical site and nodule size. We note a slight age bias, which is due to 5 benign samples from young patients. Anticipating a NPV of 90%, the 95% confidence interval is +/−5%.

At this point we refer to the 13 protein classifier trained on 143 samples the Discovery classifier. However, once validation is completed, to find the optimal coefficients for the classifier, it was retrained on all 247 samples (discovery and validation sets) as this is most predictive of future performance. We refer to this classifier as the Final classifier. The coefficients of the Final classifier appear in Table 21.

Figure 8:
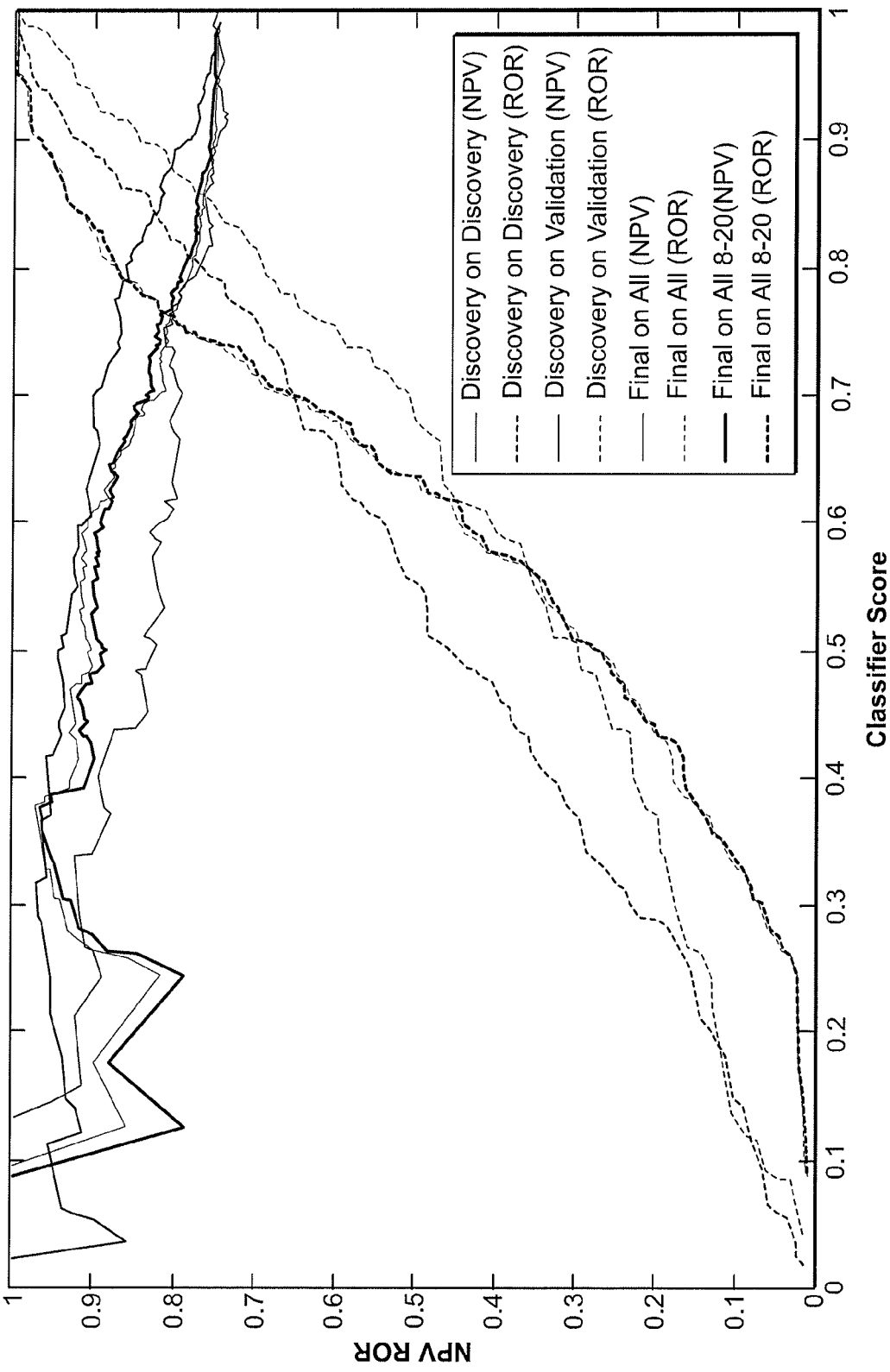
FIG. 8 is a graph showing performance of the classifier on the training samples, validation samples and all samples combined.

The performance of the Discovery and Final classifiers is summarized in FIG. 8. Reported are the NPV and ROR for the Discovery classifier when applied to the discovery set, the validation set. The NPV and ROR for the Final classifier are reported for all samples and also for all samples restricted to nodule size 8 mm to 20 mm (191 samples).

NPV and ROR are each reported as a fraction from 0 to 1. Similarly, the classifier produces a score between 0 and 1, which is the probability of cancer predicted by the classifier.

The discovery and validation curves for NPV and ROR are similar with the discovery curves superior as expected. This demonstrates the reproducibility of performance on an independent set of samples. A Discovery classifier rule out threshold of 0.40 achieves NPV of 96% and 90%, whereas ROR is 33% and 23%, for the discovery samples and the validation samples, respectively. Final classifier rule threshold of 0.60 achieves NPV of 91% and 90%, whereas ROR is 45% and 43%, for all samples and all samples restricted to be 8 mm-20 mm, respectively.

Applications of the Classifier

FIG. 9 presents the application of the final classifier to all 247 samples from the discovery and validation sets. The intent of FIG. 9 is to contrast the clinical risk factors of smoking (measured in pack years) and nodule size (proportional to the size of each circle) to the classifier score assigned to each sample.

First, note the density of cancer samples with high classifier scores. The classifier has been designed to detect a cancer signature in blood with high sensitivity. As a consequence, to the left of the rule out threshold (0.60) there are very few (<10%) cancer samples, assuming cancer prevalence of 25% [16, 17].

Third is the observation that nodule size does not appear to increase with the classifier score. Both large and small nodules are spread across the classifier score spectrum. Similarly, although there are a few very heavy smokers with very high classifier scores, increased smoking does not seem to increase with classifier score. To quantify this observation the correlation between the classifier score and nodule size, smoking and age were calculated and appear in Table 19. In all cases there is no significant relationship between the classifier score and the risk factors. The one exception is a weak correlation between benign classifier scores and benign ages. However, this correlation is so weak that the classifier score increases by only 0.04 every 10 years.

TABLE 19

Correlation between classifier scores and clinical risk factors.

|  | Age | Nodule Size | Smoking |
|---|---|---|---|
| Benign | 0.25 | −0.06 | 0.11 |
| Cancer | 0.01 | −0.01 | 0.06 |

This lack of correlation has clinical utility. It implies that the classifier provides molecular information about the disease status of an IPN that is incremental upon risk factors such as nodule size and smoking status. Consequently, it is a clinical tool for physicians to make more informed decisions around the clinical management of an IPN.

Figure 11:
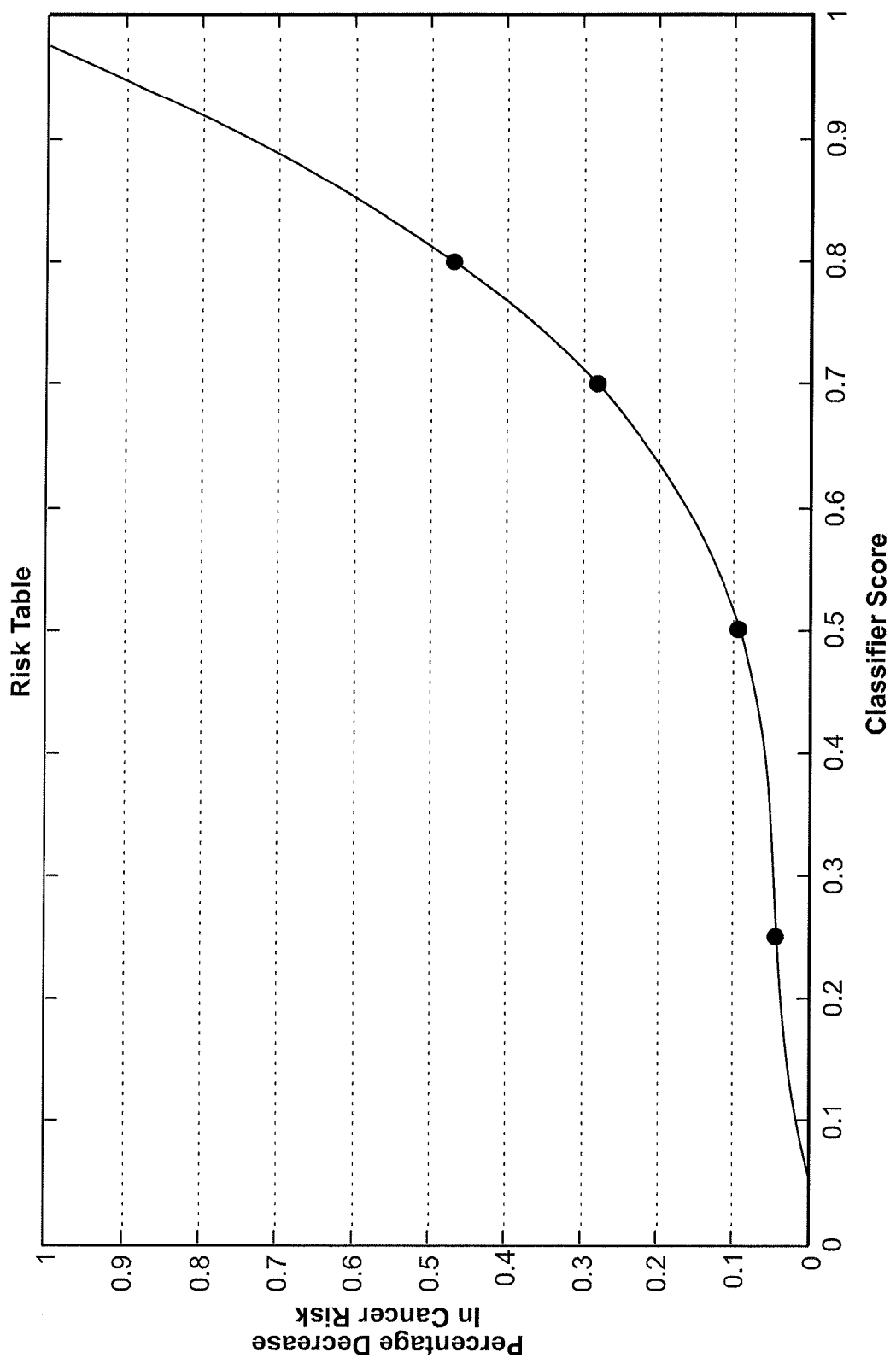
FIG. 11 is a graph depicting interpretation of classifier score in terms of risk.

To visual how this might be accomplished, we demonstrate how the cancer probability score generated by the classifier can be related to cancer risk (see FIG. 11)

At a given classifier score, some percentage of all cancer nodules will have a smaller score. This is the sensitivity of the classifier. For example, at classifier score 0.8, 47% of cancer patients have a lower score, at classifier score 0.7, 28% of cancer patients have a lower score, at classifier score 0.5, only 9% are lower and finally at score 0.25, only 4% are lower. This enables a physician to interpret a patient's classifier score in terms of relative risk.

The Molecular Foundations of the Classifier

The goal was to identify the molecular signature of a malignant pulmonary nodule by selecting proteins that were the cooperative, robustly detected by SRM and stable within the classifier. How well associated with lung cancer is the derived classifier? Is there a molecular foundation for the perturbation of these 13 proteins in blood? And finally, how unique is the classifier among other possible protein combinations?

To answer these questions the 13 proteins of the classifier were submitted for pathway analysis using IPA (Ingenuity Systems, www.ingenuity.com). The first step was to work from outside the cell inwards to identify the transcription factors most likely to cause a modulation of these 13 proteins. The five most significant were FOS, NRF2, AHR, HD and MYC. FOS is common to many forms of cancer. However, NRF2 and AHR are associated with lung cancer, response to oxidative stress and lung inflammation. MYC is associated with lung cancer and response to oxidative stress while HD is associated with lung inflammation and response to oxidative stress.

Figure 10:
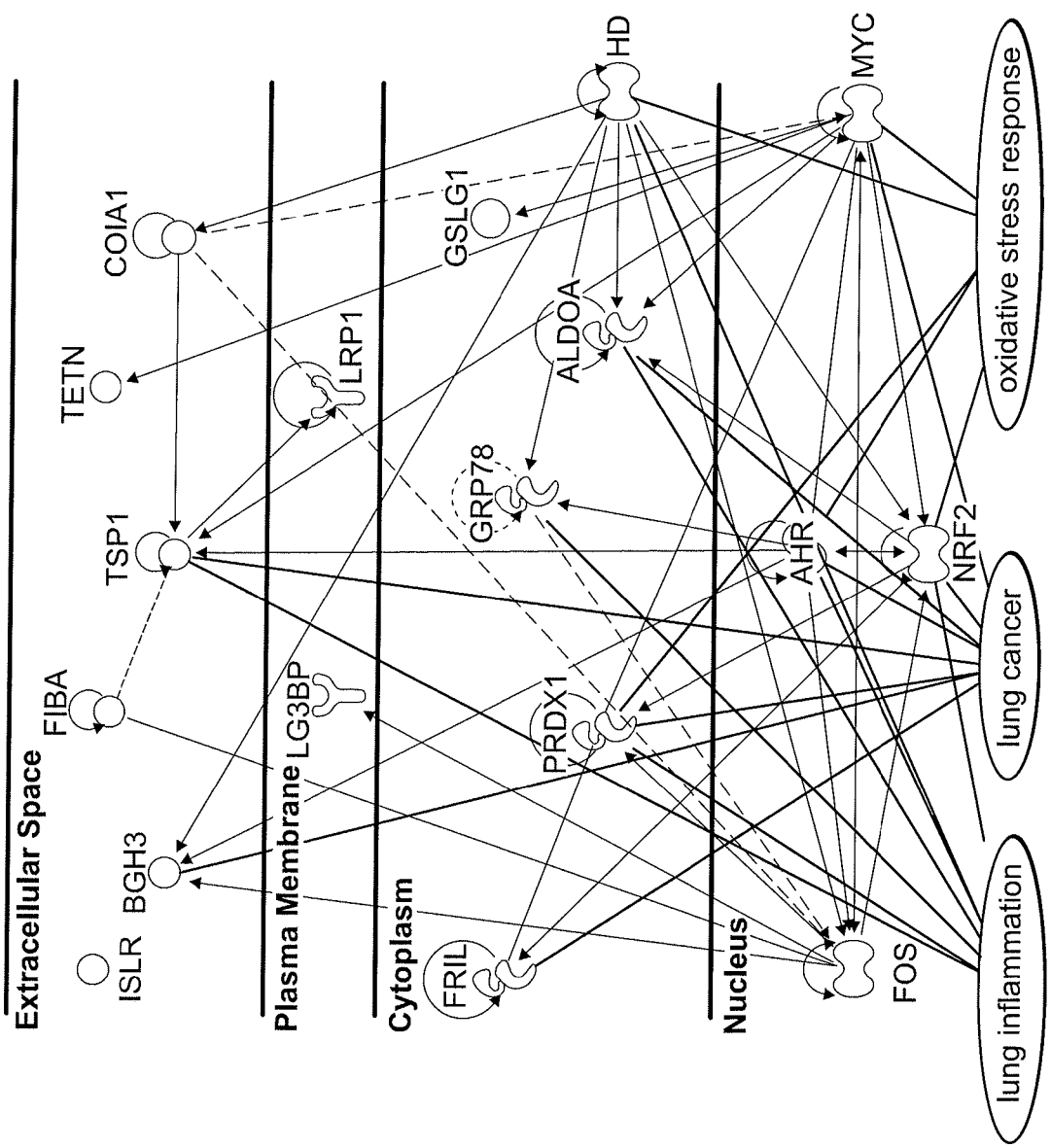
FIG. 10 is a schematic showing the molecular network containing the 13 classifier proteins (green), 5 transcription factors (blue) and the three networks (orange lines) of lung cancer, response to oxidative stress and lung inflammation.

The 13 classifier proteins are also highly specific to these three networks (lung cancer, response to oxidative stress and lung inflammation). This is summarized in FIG. 10 where the classifier proteins (green), transcription factors (blue) and the three merged networks (orange) are depicted. Only ISLR is not connected through these three lung specific networks to the other proteins, although it is connected through cancer networks not specific to cancer. In summary, the modulation of the 13 classifier proteins can be tracked back to a few transcription factors specific to lung cancer, lung inflammation and oxidative stress networks.

To address the question of classifier uniqueness, every classifier from the 21 robust and cooperative proteins was formed (Table 20). Due to the computational overhead, these classifiers could not be fully trained by Monte Carlo cross validation, consequently, only estimates of their performance could be obtained. Five high preforming alternative classifiers were identified and then fully trained. The classifier and the five high performing alternatives appear in Table 20. The frequency of each protein appears in the tally column, in particular, the first 11 proteins appear in 4 out of the 6 classifiers. These 11 proteins have significantly higher cooperative scores than the remaining proteins. By this analysis it appears that there is a core group of proteins that form the blood signature of a malignant nodule.

affinity protocols. Golgi apparatus were isolated from each pair of samples from 33 patients (18 adenocarcinoma, 14 squamous, 1 adenosquamous) using isopycnic centrifugation followed by ammonium carbonate extraction. Plasma membrane isolations and Golgi isolations were then analyzed by tandem mass spectrometry to identify proteins overexpressed in lung cancer tissue over normal tissue, for both plasma membranes and Golgi.

Assay Development Candidates Sourced from Literature

Candidate lung cancer biomarkers were identified from two public and one commercial database: Entrez, NBK3836, UniProt and NextBio. Terminologies were predefined for the database queries which were automated using PERL scripts. The mining was carried out on May 6, 2010 (UniProt), May 17, 2010 (Entrez) and Jul. 8, 2010 (NextBio), respectively. Biomarkers were then assembled and mapped to UniProt identifiers.

Evidence of Presence in Blood

The tissue-sourced and literature-source biomarker candidates were required to have evidence of presence in blood. For

TABLE 20

The classifier and the high performing alternatives; coefficients for proteins the respective panels are shown.

| Protein | Classifier | Panel 110424 | Panel 130972 | Panel 126748 | Panel 109919 | Panel 60767 | Protein Tally | Cooperative Score |
|---|---|---|---|---|---|---|---|---|
| Constant | 36.16 | 27.72 | 27.69 | 23.47 | 21.32 | 23.17 | — | — |
| ALDOA | −0.8 | −0.67 | −0.87 | −0.83 | −0.64 | −0.68 | 6 | 1.3 |
| COIA1 | −1.56 | −1.04 | −1.68 | −1.37 | −0.94 | −1.2 | 6 | 3.7 |
| TSP1 | 0.53 | 0.53 | 0.39 | 0.42 | 0.47 | 0.41 | 6 | 1.8 |
| FRIL | 0.39 | 0.45 | 0.39 | 0.41 | 0.41 | 0.41 | 6 | 2.8 |
| LRP1 | −1.59 | −0.84 | −1.32 | 1.15 | −0.84 | −0.87 | 6 | 4.0 |
| GRP78 | 1.41 | 1.14 | 1.31 | −0.34 | 0.78 | 0.6 | 6 | 1.4 |
| ISLR | 1.4 | 1.03 | 1.08 | 0.75 | 0.74 | | 5 | 1.4 |
| IBP3 | | −0.23 | −0.21 | −0.38 | −0.33 | −0.54 | 5 | 3.4 |
| TETN | −1.79 | −1.23 | −1.99 | −1.26 | | | 4 | 2.5 |
| PRDX1 | −0.34 | −0.38 | | | −0.36 | −0.4 | 4 | 1.5 |
| LG3BP | −0.58 | | −0.61 | | −0.38 | −0.48 | 4 | 4.3 |
| CD14 | | | 0.99 | 1.08 | | 1.4 | 3 | 4.0 |
| BGH3 | 1.73 | | 1.67 | −0.83 | | | 3 | 1.8 |
| KIT | | | | | −0.31 | −0.56 | 3 | 1.4 |
| GGH | | | | | 0.44 | 0.52 | 3 | 1.3 |
| AIFM1 | | | −0.51 | | | | 1 | 1.4 |
| FIBA | 0.31 | | | | | | 1 | 1.1 |
| GSLG1 | −0.7 | | | | | | 1 | 1.2 |
| ENPL | | | | | | | 0 | 1.1 |
| EF1A1 | | | | | | | 0 | 1.2 |
| TENX | | | | | | | 0 | 1.1 |

This result suggests that there is a core group of proteins that define a high performance classifier, but alternative panels exist. However, changes in panel membership affect the tradeoff between NPV and ROR.

Example 7

Materials and Methods

Assay Development Candidates Sourced from Tissue

Patient samples obtained from fresh lung tumor resections were collected from Centre Hospitalier de l'Université de Montreal and McGill University Health Centre under IRB approval and with informed patient consent. Samples were obtained from the tumor as well as from distal normal tissue in the same lung lobe. Plasma membranes of each pair of samples were then isolated from the epithelial cells of 30 patients (19 adenocarcinoma, 6 squamous, 5 large cell carcinoma) and endothelial cells of 38 patients (13 adenocarcinoma, 18 squamous, 7 large cell carcinoma) using immuneevidence by mass spectrometry detection, three datasets were used. HUPO9504 contains 9504 human proteins identified by tandem mass spectrometry [13]. HUPO889, a higher confidence subset of HUPO9504, contains 889 human proteins [18]. The PeptideAtlas (November 2009 build) was also used. A biomarker candidate was marked as previously detected if it contained at least one HUPO889, or at least two HUPO9504 peptides, or at least two PeptideAtlas peptides.

In addition to direct evidence of detection in blood by mass spectrometry, annotation as secreted proteins or as single-pass membrane proteins [19] were also accepted as evidence of presence in blood. Furthermore, proteins in UniProt or designation as plasma proteins three programs for predicting whether or not a protein is secreted into the blood were used. These programs were TMHMM [20], SignalP [21] and SecretomeP [22]. A protein was predicted as secreted if TMHMM predicted the protein had one transmembrane domain and SignalP predicted the transmembrane domain was cleaved; or TMHMM predicted the protein had no transmembrane domain and either SignalP or SecretomeP predicted the protein was secreted.

SRM Assay Development

SRM assays for 388 targeted proteins were developed based on synthetic peptides, using a protocol similar to those described in the literature [15, 23, 24]. Up to five SRM suitable peptides per protein were identified from public sources such as the PeptideAtlas, Human Plasma Proteome Database or by proteotypic prediction tools [25] and synthesized. SRM triggered MS/MS spectra were collected on an ABSciex 5500 QTrap for both doubly and triply charged precursor ions. The obtained MS/MS spectra were assigned to individual peptides using MASCOT (cutoff score ≥15) [26]. Up to four transitions per precursor ion were selected for optimization. The resulting corresponding optimal retention time, declustering potential and collision energy were assembled for all transitions. Optimal transitions were measured on a mixture of all synthetic peptides, a pooled sample of benign patients and a pooled sample of cancer patients. Transitions were analyzed in batches, each containing up to 1750 transitions. Both biological samples were immuno-depleted and digested by trypsin and were analyzed on an ABSciex 5500 QTrap coupled with a reversed-phase (RP) high-performance liquid chromatography (HPLC) system. The obtained SRM data were manually reviewed to select the two best peptides per protein and the two best transitions per peptide. Transitions having interference with other transitions were not selected. Ratios between intensities of the two best transitions of peptides in the synthetic peptide mixture were also used to assess the specificity of the transitions in the biological samples. The intensity ratio was considered as an important metric defining the SRM assays.

Processing of Plasma Samples

Plasma samples were sequentially depleted of high- and medium-abundance proteins using immuno-depletion columns packed with the IgY14-Supermix resin from Sigma. The depleted plasma samples were then denatured, digested by trypsin and desalted. Peptide samples were separated using a capillary reversed-phase LC column (Thermo BioBasic 18 KAPPA; column dimensions: 320 μm×150 mm; particle size: 5 μm; pore size: 300 Å) and a nano-HPLC system (nanoACQUITY, Waters Inc.). The mobile phases were (A) 0.2% formic acid in water and (B) 0.2% formic acid in acetonitrile. The samples were injected (8 μl) and separated using a linear gradient (98% A to 70% A over 19 minutes, 5 μl/minute). Peptides were eluted directly into the electrospray source of the mass spectrometer (5500 QTrap LC/MS/MS, AB Sciex) operating in scheduled SRM positive-ion mode (Q1 resolution: unit; Q3 resolution: unit; detection window: 180 seconds; cycle time: 1.5 seconds). Transition intensities were then integrated by software MultiQuant (AB Sciex). An intensity threshold of 10,000 was used to filter out noisy data and undetected transitions.

Plasma Samples Used for Discovery and Validation Studies

Aliquots of plasma samples were provided by the Institut Universitaire de Cardiologie et de Pneumologie de Quebec (IUCPQ, Hospital Laval), New York University, the University of Pennsylvania, and Vanderbilt University (see Table 17). Subjects were enrolled in clinical studies previously approved by their Ethics Review Board (ERB) or Institutional Review Boards (IRB), respectively. In addition, plasma samples were provided by study investigators after review and approval of the sponsor's study protocol by the respective institution's IRB as required. Sample eligibility for the proteomic analysis was based on the satisfaction of the study inclusion and exclusion criteria, including the subject's demographic information, the subject's corresponding lung nodule radiographic characterization by chest computed tomography (CT), and the histopathology of the lung nodule obtained at the time of diagnostic surgical resection. Cancer samples had a histopathologic diagnosis of either non-small cell lung cancer (NSCLC), including adenocarcinoma, squamous cell, large cell, or bronchoalveolar cell carcinoma and a radiographic nodule of 30 mm or smaller. Benign samples, including granulomas, hamartomas and scar tissue, were also required to have a radiographic nodule of 30 mm or smaller and either histopathologic confirmation of being non-malignant or radiological confirmation in alignment with clinical guidelines. To ensure the accuracy of the clinical data, independent monitoring and verification of the clinical data associated with both the subject and lung nodule were performed in accordance with the guidance established by the Health Insurance Portability and Accountability Act (HIPAA) of 1996 to ensure subject privacy.

Study Design

The objective of the study design was to eliminate clinical and technical bias. Clinically, cancer and benign samples were paired so that they were from the same site, same gender, nodule sizes within 10 mm, age within 10 years, and smoking history within 20 pack years. Up to 15 pairs of matched cancer and benign samples per batch were assigned iteratively to processing batches until no statistical bias was demonstrable based on age, gender or nodule size.

Paired samples within each processing batch were further randomly and repeatedly assigned to positions within the processing batch, until the absolute values of the corresponding Pearson correlation coefficients between position and gender, nodule size, and age were less than 0.1. Afterwards, each pair of cancer and benign samples was randomized to their relative positions. To provide a control for sample batching, three 200 μl aliquots of a pooled human plasma standard (HPS) (Bioreclamation, Hicksville, N.Y.) were positioned at the beginning, middle and end of each processing batch, respectively. Samples within a batch were analyzed together.

Logistic Regression Model

The logistic regression classification method [27] was used to combine a panel of transitions into a classifier and to calculate a classification probability score between 0 and 1 for each sample. The probability score ($P_s$) of a sample was determined as $P_s=1/[1+\exp(-\alpha-\Theta_{i=1}^{N}\beta_i * I_{i,s})]$, where $I_{i,s}$ was the logarithmically transformed (base 2), normalized intensity of transition i in sample s, $\beta_i$ was the corresponding logistic regression coefficient, α was a classifier-specific constant, and N was the total number of transitions in the classifier. A sample was classified as benign if $P_s$ was less than a decision threshold. The decision threshold can be increased or decreased depending on the desired NPV. To define the classifier, the panel of transitions (i.e. proteins), their coefficients, the normalization transitions, classifier coefficient α and the decision threshold must be learned (i.e. trained) from the discovery study and then confirmed using the validation study.

Discovery of the Rule-Out Classifier

A summary of the 143 samples used for classifier discovery appears in Table 17 and processed as described above.

Protein transitions were normalized as described above. Transitions that were not detected in at least 50% of the cancer samples or 50% of the benign samples were eliminated leaving 117 transitions for further consideration. Missing values for these transitions were replaced by half the minimum detected value over all samples for that transition.

The next step was finding the set of most cooperative proteins. The cooperative score of a protein is the number of high performing panels it participates in divided by the number of such panels it could appear on by chance alone. Hence, a cooperative score above 1 is good, and a score below 1 is not. The cooperative score for each protein is estimated by the following procedure:

One million random panels of 10 proteins each, selected from the 117 candidates, were generated. Each panel of 10 proteins was trained using the Monte Carlo cross validation (MCCV) method with a 20% hold-off rate and one hundred sample permutations per panel) to fit a logistic regression model and its performance assessed by partial AUC [28].

By generating such a large number of panels, we sample the space of classifiers sufficiently well to find some high performers by chance. The one hundred best random panels (see Table 2) out of the million generated were kept and for each of the 117 proteins we determined how frequently each occurred on these top panels. Of the 117 proteins, 36 had frequency more than expected by chance, after endogenous normalizers were removed. (Table 22) The expected number of panels on which a protein would appear by chance is 100*10/117=8.33. The cooperative score for a protein is the number of panels it appears on divided by 8.33.

TABLE 21

| Category | Protein (UniProt) | Official Gene Name | Cooperative Score | Partial AUC | Coefficient CV | Transition | SEQ ID NO | Coefficient (Discovery) alpha = 36.16 | Coefficient (Final) alpha = 26.25 | Tissue Candidate | Predicted Concentration (ng/ml) |
|---|---|---|---|---|---|---|---|---|---|---|---|
| Classifier | TSP1_HUMAN | THBS1 | 1.8 | 0.25 | 0.24 | GFLLLASLR_495.31_559.40 | 22 | 0.53 | 0.44 | | 510 |
| Classifier | COIA1_HUMAN | COL18A1 | 3.7 | 0.16 | 0.25 | AVGLAG-TFR_446.26_721.40 | 11 | -1.56 | -0.91 | | 35 |
| Classifier | ISLR_HUMAN | ISLR | 1.4 | 0.32 | 0.25 | ALPGTPVASS-QPR_640.85_841.50 | 14 | 1.40 | 0.83 | | — |
| Classifier | TETN_HUMAN | CLEC3B | 2.5 | 0.26 | 0.26 | LDTLAQE-VALLK_657.39_330.20 | 20 | -1.79 | -1.02 | | 58000 |
| Classifier | FRIL_HUMAN | FTL | 2.8 | 0.31 | 0.26 | LGG-PEAGLGEYLFER_804.40_913.40 | 24 | 0.39 | 0.17 | Secreted, Epi, Endo | 12 |
| Classifier | GRP78_HUMAN | HSPA5 | 1.4 | 0.27 | 0.27 | TWNDPSVQQDIK_715.85_260.20 | 23 | 1.41 | 0.55 | Secreted, Epi, Endo | 100 |
| Classifier | ALDOA_HUMAN | ALDOA | 1.3 | 0.26 | 0.28 | ALQASALK_401.25_617.40 | 7 | -0.80 | -0.26 | Secreted, Epi | 250 |
| Classifier | BGH3_HUMAN | TGFBI | 1.8 | 0.21 | 0.28 | LTLLAPLNSVFK_658.40_804.50 | 8 | 1.73 | 0.54 | Epi | 140 |
| Classifier | LG3BP_HUMAN | LGALS3BP | 4.3 | 0.29 | 0.29 | VE-IFYR_413.73_598.30 | 25 | -0.58 | -0.21 | Secreted | 440 |
| Classifier | LRP1_HUMAN | LRP1 | 4.0 | 0.13 | 0.32 | TVIWPNGLSLDIPAGR_855.00_400.20 | 15 | -1.59 | -0.83 | Epi | 20 |
| Classifier | FI-BA_HUMAN | FGA | 1.1 | 0.31 | 0.35 | NSLFEYQK_514.76_714.30 | 26 | 0.31 | 0.13 | | 130000 |
| Classifier | PRDX1_HUMAN | PRDX1 | 1.5 | 0.32 | 0.37 | QITVNDLPVGR_606.30_428.30 | 16 | -0.34 | -0.26 | Epi | 60 |
| Classifier | GSLG1_HUMAN | GLG1 | 1.2 | 0.34 | 0.45 | IIQESALDYR_660.86_338.20 | 27 | -0.70 | -0.44 | Epi, Endo | — |
| Classifier | KIT_HUMAN | KIT | 1.4 | 0.33 | 0.46 | | | | | | 8.2 |
| Robust | CD14_HUMAN | CD14 | 4.0 | 0.33 | 0.48 | | | | | Epi | 420 |
| Robust | EF1A1_HUMAN | EEF1A1 | 1.2 | 0.32 | 0.56 | | | | | Secreted, Epi | 61 |
| Robust | TENX_HUMAN | TNXB | 1.1 | 0.30 | 0.56 | | | | | Endo | 70 |
| Robust | AIFM1_HUMAN | AIFM1 | 1.4 | 0.32 | 0.70 | | | | | Epi, Endo | 1.4 |
| Robust | GGH_HUMAN | GGH | 1.3 | 0.32 | 0.81 | | | | | | 250 |
| Robust | IBP3_HUMAN | IGFBP3 | 3.4 | 0.32 | 1.82 | | | | | Secreted, Epi, Endo | 5700 |
| Robust | ENPL_HUMAN | HSP90B1 | 1.1 | 0.29 | 5.90 | | | | | Secreted, Epi, Endo | 88 |
| Robust | ERO1A_HUMAN | ERO1L | 6.2 | | | | | | | | — |
| Non-Robust | 6PGD_HUMAN | PGD | 4.3 | | | | | | | Epi, Endo | 29 |
| Non-Robust | ICAM1_HUMAN | ICAM1 | 3.9 | | | | | | | | 71 |
| Non-Robust | PTPA_HUMAN | PPP2R4 | 2.1 | | | | | | | Endo | 3.3 |
| Non-Robust | NCF4_HUMAN | NCF4 | 2.0 | | | | | | | Endo | — |
| Non-Robust | SEM3G_HUMAN | SEMA3G | 1.9 | | | | | | | | — |
| Non-Robust | 1433T_HUMAN | YWHAQ | 1.5 | | | | | | | Epi | 180 |
| Non-Robust | RAP2B_HUMAN | RAP2B | 1.5 | | | | | | | Epi | — |
| Non-Robust | MMP9_HUMAN | MMP9 | 1.4 | | | | | | | | 28 |

TABLE 21-continued

| Category | Protein (UniProt) | Official Gene Name | Cooperative Score | Partial AUC | Co-efficient CV | Transition | SEQ ID NO | Coefficient (Discovery) alpha = 36.16 | Coefficient (Final) alpha = 26.25 | Tissue Candidate | Predicted Concentration (ng/ml) |
|---|---|---|---|---|---|---|---|---|---|---|---|
| Non-Robust | FOLH1_HUMAN | FOLH1 | 1.3 | | | | | | | | — |
| Non-Robust | GSTP1_HUMAN | GSTP1 | 1.3 | | | | | | | Endo | 32 |
| Non-Robust | EF2_HUMAN | EEF2 | 1.3 | | | | | | | Secreted, Epi | 30 |
| Non-Robust | RAN_HUMAN | RAN | 1.2 | | | | | | | Secreted, Epi | 4.6 |
| Non-Robust | SODM_HUMAN | SOD2 | 1.2 | | | | | | | Secreted | 7.1 |
| Non-Robust | DSG2_HUMAN | DSG2 | 1.1 | | | | | | | Endo | 2.7 |

The 36 most cooperative proteins are listed in Table 22.

TABLE 22

| Category | Protein (UniProt) | Official Gene Name | Cooperative Score | Partial AUC | Co-efficient CV | Transition | SEQ ID NO | Coefficient (Discovery) alpha = 36.16 | Coefficient (Final) alpha = 26.25 | Tissue Candidate | Predicted Concentration (ng/ml) |
|---|---|---|---|---|---|---|---|---|---|---|---|
| Classifier | TSP1_HUMAN | THBS1 | 1.8 | 0.25 | 0.24 | GFLLLASLR_495.31_559.40 | 22 | 0.53 | 0.44 | | 510 |
| Classifier | COIA1_HUMAN | COL18A1 | 3.7 | 0.16 | 0.25 | AVGLAGTFR_446.26_721.40 | 11 | -1.56 | -0.91 | | 35 |
| Classifier | ISLR_HUMAN | ISLR | 1.4 | 0.32 | 0.25 | ALPGTPVASS-QPR_640.85_841.50 | 14 | 1.40 | 0.83 | | — |
| Classifier | TETN_HUMAN | CLEC3B | 2.5 | 0.26 | 0.26 | LDITLAQE-VALLK_657.39_330.20 | 20 | -1.79 | -1.02 | | 58000 |
| Classifier | FRIL_HUMAN | FTL | 2.8 | 0.31 | 0.26 | LGG-PEAGLGEYLFER_804.40_913.40 | 24 | 0.39 | 0.17 | Secreted, | 12 |
| Classifier | GRP78_HUMAN | HSPA5 | 1.4 | 0.27 | 0.27 | TWNDPSVQQDIK_715.85_260.20 | 23 | 1.41 | 0.55 | Secreted, Epi, Endo | 100 |
| Classifier | ALDOA_HUMAN | ALDOA | 1.3 | 0.26 | 0.28 | ALQASALK_401.25_617.40 | 7 | -0.80 | -0.26 | Secreted, Epi | 250 |
| Classifier | BGH3_HUMAN | TGFBI | 1.8 | 0.21 | 0.28 | LTLLAPLNSVFK_658.40_804.50 | 8 | 1.73 | 0.54 | Epi | 140 |
| Classifier | LG3BP_HUMAN | LGALS3BP | 4.3 | 0.29 | 0.29 | VEIFYR_413.73_598.30 | 25 | -0.58 | -0.21 | Secreted | 440 |
| Classifier | LRP1_HUMAN | LRP1 | 4.0 | 0.13 | 0.32 | TVLWPNGLSLDIPAGR_855.00_400.20 | 15 | -1.59 | -0.83 | Epi | 20 |
| Classifier | FIBA_HUMAN | FGA | 1.1 | 0.31 | 0.35 | | | | | | 130000 |
| Classifier | PRDX1_HUMAN | PRDX1 | 1.5 | 0.32 | 0.37 | NSLFEYQK_514.76_714.30 | 26 | 0.31 | 0.13 | Epi | 60 |
| Classifier | GSLG1_HUMAN | GLG1 | 1.2 | 0.34 | 0.45 | QITVNDLPVGR_606.30_428.30 | 16 | -0.34 | -0.26 | Epi, Endo | — |
| Robust | KIT_HUMAN | KIT | 1.4 | 0.33 | 0.46 | IIIQESALDYR_660.86_338.20 | 27 | -0.70 | -0.44 | Epi | 8.2 |
| Robust | CD14_HUMAN | CD14 | 4.0 | 0.33 | 0.48 | | | | | Secreted, | 420 |
| Robust | EF1A1_HUMAN | EEF1A1 | 1.2 | 0.32 | 0.56 | | | | | Epi | 61 |
| Robust | TENX_HUMAN | TNXB | 1.1 | 0.30 | 0.56 | | | | | Endo | 70 |
| Robust | AIFM1_HUMAN | AIFM1 | 1.4 | 0.32 | 0.70 | | | | | Epi, Endo | 1.4 |
| Robust | GGH_HUMAN | GGH | 1.3 | 0.32 | 0.81 | | | | | | 250 |
| Robust | IBP3_HUMAN | IGFBP3 | 3.4 | 0.32 | 1.82 | | | | | | 5700 |
| Robust | ENPL_HUMAN | HSP90B1 | 1.1 | 0.29 | 5.90 | | | | | | 88 |
| Non-Robust | ERO1A_HUMAN | ERO1L | 6.2 | | | | | | | Secreted, Epi, Endo | — |
| Non-Robust | 6PGD_HUMAN | PGD | 4.3 | | | | | | | Secreted, Epi, Endo | 29 |
| Non-Robust | ICAM1_HUMAN | ICAM1 | 3.9 | | | | | | | Epi, Endo | 71 |
| Non-Robust | PTPA_HUMAN | PPP2R4 | 2.1 | | | | | | | Endo | 3.3 |
| Non-Robust | NCF4_HUMAN | NCF4 | 2.0 | | | | | | | Endo | — |
| Non-Robust | SEM3G_HUMAN | SEMA3G | 1.9 | | | | | | | | — |
| Non-Robust | 1433T_HUMAN | YWHAQ | 1.5 | | | | | | | Epi | 180 |
| Non-Robust | RAP2B_HUMAN | RAP2B | 1.5 | | | | | | | Epi | — |
| Non-Robust | MMP9_HUMAN | MMP9 | 1.4 | | | | | | | | 28 |
| Non-Robust | FOLH1_HUMAN | FOLH1 | 1.3 | | | | | | | Endo | — |
| Non-Robust | GSTP1_HUMAN | GSTP1 | 1.3 | | | | | | | Secreted, | 32 |
| Non-Robust | EF2_HUMAN | EEF2 | 1.3 | | | | | | | Epi | 30 |
| Non-Robust | RAN_HUMAN | RAN | 1.2 | | | | | | | Secreted, Epi | 4.6 |
| Non-Robust | SODM_HUMAN | SOD2 | 1.2 | | | | | | | Secreted | 7.1 |
| Non-Robust | DSG2_HUMAN | DSG2 | 1.1 | | | | | | | Endo | 2.7 |

The set of 36 cooperative proteins was further reduced to a set of 21 proteins by manually reviewing raw SRM data and eliminating proteins that did not have robust SRM transitions due to low signal to noise or interference.

Proteins were iteratively eliminated from the set of 21 proteins until a classifier with the optimal partial AUC was obtained. The criteria for elimination was coefficient stability. In a logistic regression model each protein has a coefficient. In the process of training the model the coefficient for each protein is determined. When this is performed using cross validation (MCCV), hundreds of coefficient estimates for each protein are derived. The variability of these coefficients is an estimate of the stability of the protein. At each step the proteins were trained using MCCV (hold out rate 20%, ten thousand sample permutations per panel) to a logistic regression model and their stability measured. The least stable protein was eliminated. This process continued until a 13 protein classifier with optimal partial AUC was reached.

Finally, the 13 protein classifier was trained to a logistic regression model by MCCV (hold out rate 20%, twenty thousand sample permutations). The thirteen proteins for the rule-out classifier are listed in Table 18 along with their highest intensity transition and model coefficient.

Selection of a Decision Threshold

Assuming the cancer prevalence of lung nodules is prev, the performance of a classifier (NPV and ROR) on the patient population with lung nodules was calculated from sensitivity (sens) and specificity (spec) as follows:

$$NPV = \frac{(1 - prev) * spec}{prev * (1 - sens) + (1 - prev) * spec}, \quad (1)$$

$$PPV = \frac{prev * sens}{prev * sens + (1 - prev) * (1 - spec)}, \quad (2)$$

$$ROR = prev * (1 - sens) + (1 - prev) * spec. \quad (3)$$

The threshold separating calls for cancer or benign samples was then selected as the probability score with NPV≥90% and ROR≥20%. As we expect the classifier's performance measured on the discovery set to be an overestimate, the threshold is selected to be a range, as performance will usually degrade on an independent validation set.

Validation of the Rule-Out Classifier 52 cancer and 52 benign samples (see Table 17) were used to validate the performance of the 13 protein classifier. Half of the samples were placed in pre-determined processing batches analyzed immediately after the discovery samples and the other half of samples were analyzed at a later date. This introduced variability one would expect in practice. More specifically, the three HPS samples run in each processing batch were utilized as external calibrators. Details on HPS calibration are described below.

Calibration by HPS Samples

For label-free MS approach, variation on signal intensity between different experiments is expected. To reduce this variation, we utilized HPS samples as an external standard and calibrated the intensity between the discovery and validation studies. Assume that $\check{I}_{i,s}$ is the logarithmically transformed (base 2), normalized intensity of transition i in sample s, $\check{I}_{i,dis}$ and $\check{I}_{i,val}$ are the corresponding median values of HPS samples in the discovery and the validation studies, respectively. Then the HPS corrected intensity is $$\check{I}_{i,s} = \check{I}_{i,s} - \check{I}_{i,val} + \check{I}_{i,dis}$$

Consequently, assume that the probability for cancer of a clinical sample in the validation study is predicted as prob by the classifier. Then the HPS corrected probability of cancer of the clinical sample is calculated as follows:

$$probability_{corrected} = \frac{1}{1 + e^{-S_{corrected}}}$$

where $$S_{corrected} = S - S_{HPS,val} + S_{HPS,dis}$$

and $$S = \ln\frac{prob}{1 - prob}.$$

Here $S_{HPS,dis}$ and $S_{HPS,val}$ were the median value of S of all HPS samples in the discovery and validation studies, respectively.

Statistical Analysis

All statistical analyses were performed with Stata, R and/or MatLab.

Depletion Column Drift

We observed an increase of signal intensity as more and more samples were depleted by the same column. We used transition intensity in HPS samples to quantify this technical variability. Assuming $I_{i,s}$ was the intensity of transition i in a HPS sample s, the drift of the sample was defined as $$drift_s = median\left(\frac{I_{i,s} - \hat{I}_s}{\hat{I}_s}\right),$$

where $\hat{I}_i$ was the mean value of $I_{i,s}$ among all HPS samples that were depleted by the same column and the median was taken over all detected transitions in the sample. Then the drift of the column was defined as $$drift_{col} = median(drift_s > 0) - median(drift_s < 0).$$

Here the median was taken over all HPS samples depleted by the column. If no sample drift was greater or less than zero, the corresponding median was taken as 0. The median column drift was the median of drifts of all depletion columns used in the study.

Identification of Endogenous Normalizing Proteins

The following criteria were used to identify a transition as a normalizer:

Possessed the highest median intensity of all transitions from the same protein.

Detected in all samples.

Ranked high in reducing median technical CV (median CV of transition intensities that were measured on HPS samples) as a normalizer.

Ranked high in reducing median column drift that was observed in sample depletion.

Possessed low median technical CV and low median biological CV (median CV of transition intensities that were measured on clinical samples).

Six transitions were selected and appear in Table 23.

TABLE 23

Panel of endogenous normalizers.

| Normalizer | Transition | SEQ ID NO | Median Technical CV (%) | Median Column Drift (%) |
|---|---|---|---|---|
| PEDF_HUMAN | LQSLFDSPDFSK_692.34_593.30 | 28 | 25.8 | 6.8 |
| MASP1_HUMAN | TGVITSPDFPNPYPK_816.92_258.10 | 6 | 26.5 | 18.3 |
| GELS_HUMAN | TASDFITK_441.73_710.40 | 5 | 27.1 | 16.8 |
| LUM_HUMAN | SLEDLQLTHNK_433.23_499.30 | 29 | 27.1 | 16.1 |
| C163A_HUMAN | INPASLDK_429.24_630.30 | 30 | 26.6 | 14.6 |
| PTPRJ_HUMAN | VITEPIPVSDLR_669.89_896.50 | 31 | 27.2 | 18.2 |
| | Normalization by Panel of Transitions | | 25.1 | 9.0 |
| | Without Normalization | | 32.3 | 23.8 |

Data Normalization

A panel of six normalization transitions (see Table 23) were used to normalize raw SRM data for two purposes: (A) to reduce sample-to-sample intensity variations within same study and (B) to reduce intensity variations between different studies. For the first purpose, a scaling factor was calculated for each sample so that the intensities of the six normalization transitions of the sample were aligned with the corresponding median intensities of all HGS samples. Assuming that $N_{i,s}$ is the intensity of a normalization transition i in sample s and $\hat{N}_i$ the corresponding median intensity of all HGS samples, then the scaling factor for sample s is given by $\hat{S}/S_s$, where $$S_s = \text{median}\left(\frac{N_{1,s}}{\hat{N}_1}, \frac{N_{2,s}}{\hat{N}_2}, \ldots, \frac{N_{6,s}}{\hat{N}_6}\right)$$

is the median of the intensity ratios and $\hat{S}$ is the median of $S_s$ over all samples in the study. For the second purpose, a scaling factor was calculated between the discovery and the validation studies so that the median intensities of the six normalization transitions of all HGS samples in the validation study were comparable with the corresponding values in the discovery study. Assuming that the median intensities of all HGS samples in the two studies are $\hat{N}_{i,dis}$ and $\hat{N}_{i,val}$, respectively, the scaling factor for the validation study is given by $$R = \text{median}\left(\frac{\hat{N}_{1,dis}}{\hat{N}_{1,val}}, \frac{\hat{N}_{2,dis}}{\hat{N}_{2,val}}, \ldots, \frac{\hat{N}_{6,dis}}{\hat{N}_{6,val}}\right)$$

Finally, for each transition of each sample, its normalized intensity was calculated as $$\tilde{I}_{i,s} = I_{i,s} * R * \hat{S}/S_s$$

where $I_{i,s}$ was the raw intensity.

Isolation of Membrane Proteins from Tissues

Endothelial plasma membrane proteins were isolated from normal and tumor lung tissue samples that were obtained from fresh lung resections. Briefly, tissues were washed in buffer and homogenates were prepared by disrupting the tissues with a Polytron. Homogenates were filtered through a 180-μm mesh and filtrates were centrifuged at 900×g for 10 min, at 4° C. Supernatants were centrifuged on top of a 50% (w:v) sucrose cushion at 218,000×g for 60 min at 4° C. to pellet the membranes. Pellets were resuspended and treated with micrococcal nuclease. Membranes from endothelial cells were incubated with a combination of anti-thrombo-modulin, anti-ACE, anti-CD34 and anti-CD144 antibodies, and then centrifuged on top of a 50% (w:v) sucrose cushion at 280,000×g for 60 min at 4° C. After pellets were resuspended, endothelial cell plasma membranes were isolated using MACS microbeads, treated with potassium iodide to remove cytoplasmic peripheral proteins.

Epithelial plasma membrane proteins from normal and tumor lung tissue samples were isolated from fresh lung resections. Tissues were washed and homogenates as described above for endothelial plasma membrane proteins preparation. Membranes from epithelial cells were labeled with a combination of anti-ESA, anti-CEA, anti-CD66c and anti-EMA antibodies, and then centrifuged on top of a 50% (w:v) sucrose cushion at 218,000×g for 60 min at 4° C. Epithelial cell plasma membranes were isolated using MACS microbeads and the eluate was centrifuged at 337,000×g for 30 minutes at 4° C. over a 33% (w:v) sucrose cushion. After removing the supernatant and sucrose cushion, the pellet was resuspended in Laemmli/Urea/DTT.

Isolation of Secreted Proteins from Tissues

Secreted proteins were isolated from normal and tumor lung tissue samples that were isolated from fresh lung resections. Tissues were washed and homogenized using a Polytron homogenization. The density of the homogenates was adjusted to 1.4 M with concentrated sucrose prior to isolating the secretory vesicles by isopycnic centrifugation at 100,000×g for 2 hr at 4° C. on a 0.8 and 1.2 M discontinuous sucrose gradient. Vesicles concentrating at the 0.8/1.2 M interface were collected and further incubated for 25 minutes with 0.5 M KCl (final concentration) to remove loosely bound peripheral proteins. Vesicles were recuperated by ultracentrifugation at 150,000×g for one hour at 4° C. and then opened with 100 mM ammonium carbonate pH 11.0 for 30 minutes at 4° C. Secreted proteins were recovered in the supernatant following a 1-hour ultracentrifugation at 150,000×g at 4° C.

Preparation of IgY14-SuperMix Immunoaffinity Columns

Immunoaffinity columns were prepared in-house using a slurry containing a 2:1 ratio of IgY14 and SuperMix immunoaffinity resins, respectively (Sigma Aldrich). Briefly, a slurry (10 ml, 50%) of mixed immunoaffinity resins was added to a glass chromatography column (Tricorn, GE Healthcare) and the resin was allowed to settle under gravity flow, resulting in a 5 ml resin volume in the column. The column was capped and placed on an Agilent 1100 series HPLC system for further packing (20 minutes, 0.15M ammonium bicarbonate, 2 ml/min). The performance of each column used in the study was then assessed by replicate injections of aliquots of HPS sample. Column performance was assessed prior to beginning immunoaffinity separation of each batch of clinical samples.

IgY14-Sumermix Immunoaffinity Chromatography

Plasma samples (60 µl) were diluted (0.15M ammonium bicarbonate, 1:2 v/v, respectively) and filtered (0.2 µm Acro-Prep 96-well filter plate, Pall Life Sciences) prior to immunoaffinity separation. Dilute plasma (90 µl) was separated on the IgY14-SuperMix column connected to an Agilent 1100 series HPLC system using a three buffers (loading/washing: 0.15M ammonium bicarbonate; stripping/elution: 0.1M glycine, pH 2.5; neutralization: 0.01M Tris-HCl, 0.15M NaCl, pH 7.4) with a load-wash-elute-neutralization-re-equilibration cycle (36 minutes total time). The unbound and bound fractions were monitored using a UV absorbance (280 nm) and were baseline resolved after separation. Only the unbound fraction containing the low abundance proteins was collected for downstream processing and analysis. Unbound fractions were lyophilized prior to enzymatic digestion.

Enzymatic Digestion of Low Abundance Proteins

Low abundance proteins were reconstituted under mild denaturing conditions (200 µl of 1:1 0.1M ammonium bicarbonate/trifluoroethanol v/v) and allowed to incubate (30 minutes, room temperature, orbital shaker). Samples were then diluted (800 µl of 0.1M ammonium bicarbonate) and digested with trypsin (Princeton Separations; 0.4 µg trypsin per sample, 37° C., 16 hours). Digested samples were lyophilized prior to solid-phase extraction.

Solid-Phase Extraction

Solid phase extraction was used to reduce salt and buffer contents in the samples prior to mass spectrometry. The lyophilized samples containing tryptic peptides were reconstituted (350 µl 0.01M ammonium bicarbonate) and allowed to incubate (15 minutes, room temperature, orbital shaker). A reducing agent was then added to the samples (30 µl 0.05M TCEP) and the samples were incubated (60 minutes, room temperature). Dilute acid and a low percentage of organic solvent (375 µl 90% water/10% acetonitrile/0.2% trifluoroacetic acid) were added to optimize the solid phase extraction of peptides. The extraction plate (Empore C18, 3M Bioanalytical Technologies) was conditioned according to manufacturer protocol. Samples were loaded onto the solid phase extraction plate, washed (500 µl 95% water/5% acetonitrile/0.1% trifluoroacetic acid) and eluted (200 µl 52% water/48% acetonitrile/0.1% trifluoroacetic acid) into a collection plate. The eluate was split into two equal aliquots and each aliquot was taken to dryness in a vacuum concentrator. One aliquot was used immediately for mass spectrometry, while the other was stored (−80° C.) and used as needed. Samples were reconstituted (12 µl 90% water/10% acetonitrile/0.2% formic acid) just prior to LC-SRM MS analysis.

Inclusion and Exclusion Criteria

Plasma samples were eligible for the studies if they were (A) obtained in EDTA tubes, (B) obtained from subjects previously enrolled in IRB-approved studies at the participating institutions, and (C) archived, e.g. labeled, aliquotted and frozen, as stipulated by the study protocols. The samples must also satisfy the following inclusion and exclusion criteria:

1) Inclusion Criteria:
2) Sample eligibility was based on clinical parameters, including the following subject, nodule and clinical staging parameters:
   a) Subject
      i) age ≥40
      ii) any smoking status, e.g. current, former, or never
      iii) co-morbid conditions, e.g. COPD
      iv) prior malignancy with a minimum of 5 years in clinical remission
      v) prior history of skin carcinomas—squamous or basal cell
   b) Nodule
      i) Radiology
         (1) size ≥4 mm and ≤70 mm (up to Stage 2B eligible)
         (2) any spiculation or ground glass opacity
      ii) pathology
         (1) malignant—adenocarcinoma, squamous, or large cell
         (2) benign—inflammatory (e.g. granulomatous, infectious) or non-inflammatory (e.g. hamartoma)
   c) Clinical stage
      i) Primary tumor: ≤T2 (e.g. 1A, 1B, 2A and 2B)
      ii) Regional lymph nodes: N0 or N1 only
      iii) Distant metastasis: M0 only
3) Exclusion Criteria
   a) Subject: prior malignancy within 5 years of IPN diagnosis
   b) Nodule:
      i) size data unavailable
      ii) for cancer or benign SPNs, no pathology data available
      iii) pathology—small cell lung cancer
   c) Clinical stage
      i) Primary tumor: ≥T3
      ii) Regional lymph nodes: ≥N2
      iii) Distant metastasis: ≥M1

Power Analysis for the Discovery Study

The power analysis for the discovery study was based on the following assumptions: 1) The overall false positive rate (α) was set to 0.05. 2) Šidák correction for multiple testing was used to calculate the effective $\alpha_{eff}$ for testing 200 proteins, i.e., $$\text{i.e., } \alpha_{eff} = 1 - \sqrt[200]{1-\alpha}.$$

3) The effective sample size was reduced by a factor of 0.864 to account for the larger sample requirement for the Mann-Whitney test than for the t-test. 4) The overall coefficient of variation was set to 0.43 based on a previous experience. 5) The power (1−β) of the study was calculated based on the formula for the two-sample, two-sided t-test, using effective $\alpha_{eff}$ and effective sample size. The power for the discovery study was tabulated in Table 24 by the sample size per cohort and the detectable fold difference between control and disease samples.

TABLE 24

Cohort size required to detect protein fold changes with a given probability.

| Cohort Size | Detectable Protein Fold Difference | | | |
| --- | --- | --- | --- | --- |
| | 1.25 | 1.5 | 1.75 | 2 |
| 20 | 0.011 | 0.112 | 0.368 | 0.653 |
| 30 | 0.025 | 0.277 | 0.698 | 0.925 |
| 40 | 0.051 | 0.495 | 0.905 | 0.992 |
| 50 | 0.088 | 0.687 | 0.977 | 0.999 |
| 60 | 0.129 | 0.812 | 0.994 | 1 |
| 70 | 0.183 | 0.902 | 0.999 | 1 |
| 80 | 0.244 | 0.953 | 1 | 1 |
| 90 | 0.302 | 0.977 | 1 | 1 |
| 100 | 0.369 | 0.99 | 1 | 1 |

Power Analysis for the Validation Study

Sufficient cancer and benign samples are needed in the validation study to confirm the performance of the rule-out classifier obtained from the discovery study. We are interested in obtaining the 95% confidence intervals (CIs) on NPV and ROR for the rule-out classifier. Using the Equations in the Selection of a Decision Threshold section herein, one can derive sensitivity (sens) and specificity (spec) as functions of NPV and ROR, i.e., sens=1−ROR*(1−NPV)/prev, spec=ROR*NPV/(1−prev), where prev is the cancer prevalence in the intended use population. Assume that the validation study contains $N_C$ cancer samples and $N_B$ benign samples. Based on binomial distribution, variances of sensitivity and specificity are given by var(sens)=sens*(1−sens)/$N_C$ var(spec)=spec*(1−spec)/$N_B$ Using the Equations in the Selection of a Decision Threshold section herein, the corresponding variances of NPV and ROR can be derived under the large-sample, normal-distribution approximation as $$\mathrm{var}(NPV) = NPV^2(1 - NPV)^2\left[\frac{\mathrm{var}(sens)}{(1 - sens)^2} + \frac{\mathrm{var}(spec)}{spec^2}\right],$$

$$\mathrm{var}(ROR) = prev^2 * \mathrm{var}(sens) + (1 - prev)^2 * \mathrm{var}(spec).$$

The two-sided 95% CIs of NPV and ROR are then given by $\pm z_{\alpha/2}\sqrt{\mathrm{var}(NPV)}$ and $\pm z_{\alpha/2}\sqrt{\mathrm{var}(ROR)}$, respectively, where $z_{\alpha/2}=1.959964$ is the 97.5% quantile of the normal distribution. The anticipated 95% CIs for the validation study were tabulated in Table 25 by the sample size ($N_C=N_B=N$) per cohort.

TABLE 25

The 95% confidence interval (CI) of NPV as a function of cohort size. The corresponding 95% CI of ROR is also listed. The prevalence was set at 28.5%. The expected NPV and ROR were set to values in the discovery study, i.e., 90% and 52%, respectively.

| Cohort Size | 95% CI of NPV (± %) | 95% CI of ROR (± %) |
|---|---|---|
| 10 | 12.5 | 22.1 |
| 20 | 8.8 | 15.7 |
| 30 | 7.2 | 12.8 |
| 40 | 6.2 | 11.1 |
| 50 | 5.6 | 9.9 |
| 60 | 5.1 | 9.0 |
| 70 | 4.7 | 8.4 |
| 80 | 4.4 | 7.8 |
| 90 | 4.2 | 7.4 |
| 100 | 3.9 | 7.0 |
| 150 | 3.2 | 5.7 |
| 200 | 2.8 | 5.0 |

Calculation of Q-Values of Peptide and Protein Assays

To determine the false positive assay rate the q-values of peptide SRM assays were calculated as follows. Using the distribution of Pearson correlations between transitions from different proteins as the null distribution (FIG. 7), an empirical p-value was assigned to a pair of transitions from the same peptide, detected in at least five common samples otherwise a value of 'NA' is assigned. The empirical p-value was converted to a q-value using the "qvalue" package in Bioconductor. Peptide q-values were below 0.05 for all SRM assays presented in Table 6.

The q-values of protein SRM assays were calculated in the same way except Pearson correlations of individual proteins were calculated as those between two transitions from different peptides of the protein. For proteins not having two peptides detected in five or more common samples, their q-values could not be properly evaluated and were assigned 'NA'.

Impact of Categorical Confounding Factors

TABLE 26

Impact of categorical confounding factors on classifier score.

| | | Cancer | p-value | Benign | p-value |
|---|---|---|---|---|---|
| Gender | # Female | 70 | 0.786* | 68 | 0.387* |
| | Median score | 0.701 | | 0.570 | |
| | (quartile range) | (0.642-0.788) | | (0.390-0.70) | |
| | # Male | 54 | | 55 | |
| | Median | 0.736 | | 0.621 | |
| | (quartile range) | (0.628-0.802) | | (0.459-0.723) | |
| Smoking Status | # Never | 8 | 0.435** | 34 | 0.365** |
| | Median score | 0.664 | | 0.554 | |
| | (quartile range) | (0.648-0.707) | | (0.452-0.687) | |
| | # Past | 98 | | 73 | |
| | Median | 0.703 | | 0.586 | |
| | (quartile range) | (0.618-0.802) | | (0.428-0.716) | |
| | # Current | 17 | | 13 | |
| | Median score | 0.749 | | 0.638 | |
| | (quartile range) | (0.657-0.789) | | (0.619-0.728) | |

*p-value by Mann-Whitney test
**p-value by Kruskal-Wallis test

Impact of Continuous Confounding Factors

TABLE 27

Impact of continuous confounding factors on classifier score.

| | | Correlation | Coefficient of linear fit (95% CI) | p-value |
|---|---|---|---|---|
| Age | All | 0.198 | 0.003 (0.001-0.005) | 0.002 |
| | Cancer | 0.012 | 0.000 (−0.003-0.003) | 0.893 |
| | Benign | 0.248 | 0.004 (0.001-0.007) | 0.006 |
| Nodule size | All | −0.057 | −0.002 (−0.005-0.002) | 0.372 |
| | Cancer | −0.013 | 0.000 (−0.005-0.004) | 0.889 |
| | Benign | −0.055 | −0.001 (−0.006-0.003) | 0.542 |
| Pack-year | All | 0.154 | 0.001 (0.00-0.002) | 0.019 |
| | Cancer | 0.060 | 0.000 (−0.001-0.001) | 0.520 |
| | Benign | 0.108 | 0.001 (0.00-0.002) | 0.254 |

Example 8

A Systems Biology-Derived, Blood-Based Proteomic Classifier for the Molecular Characterization of Pulmonary Nodules Summary Each year millions of pulmonary nodules are discovered by computed tomography but remain undiagnosed as malignant or benign. As the majority of these nodules are benign, many patients undergo unnecessary and costly invasive procedures. This invention presents a 13-protein blood-based classifier for the identification of benign nodules. Using a systems biology strategy, 371 protein candidates were identified and selected reaction monitoring (SRM) assays developed for each. The SRM assays were applied in a multisite discovery study (n=143) with benign and cancer plasma samples matched on nodule size, age, gender and clinical site. Rather than identify the best individual performing proteins, the 13-protein classifier was formed from proteins performing best on panels. The classifier was validated on an independent set of plasma samples (n=104) demonstrating high negative predictive value (92%) and specificity (27%) sufficiently high to obviate one-in-four patients with benign nodules from invasive procedures. Importantly, validation performance on a non-discovery clinical site showed NPV of 100% and specificity of 28%, arguing for the general effectiveness of the classifier. A pathway analysis demonstrated that the classifier proteins are likely modulated by a few transcription regulators (NF2L2, AHR, MYC, FOS) highly associated with lung cancer, lung inflammation and oxidative stress networks. Remarkably, the classifier score was independent of patient nodule size, smoking history and age. As these are the currently used risk factors for clinical management of pulmonary nodules, the application of this molecular test would provide a powerful complementary tool for physicians to use in lung cancer diagnosis.

Rationale

Computed tomography (CT) identifies millions of pulmonary nodules annually with many being undiagnosed as malignant or benign. The vast majority of these nodules are benign, but due to the threat of cancer, a significant number of patients with benign nodules undergo unnecessary invasive medical procedures costing the healthcare system billions of dollars annually. Consequently, there is a high unmet need for a non-invasive clinical test that can identify benign nodules with high probability.

Presented is a 13-protein plasma test, or classifier, for identifying benign nodules. To develop the classifier, a systems biology approach based on the supposition that biological networks in tumors become disease-perturbed and alter the expression of their cognate proteins was adopted. This systems approach employs a variety of strategies to identify blood proteins that directly reflect lung cancer-perturbed networks.

First, candidate biomarkers prioritized for inclusion on the classifier were those proteins secreted by or shed from the cell surface of lung cancer cells in contrast to normal lung cells. These are proteins both associated with lung cancer and also most likely to be emitted by a malignant pulmonary nodule into blood. The literature was also surveyed to identify blood proteins associated with lung cancer. In total, an initial list of 388 protein candidates for inclusion on the classifier were derived from these three sources.

Another system-driven approach was to prioritize the 388 protein candidates for inclusion on the classifier by how frequently they appear on high performing protein panels, as opposed to their individual diagnostic performance. This strategy is motivated by the intent to capture the integrated behavior of proteins within lung cancer-perturbed networks. Proteins that appear frequently on high performing panels are called cooperative proteins. This is a defining step in the discovery of the classifier as the most cooperative proteins are often not the proteins with best individual performance.

Third, the classifier is deconstructed in terms of its relationship to lung cancer networks. Ideally, the classifier consists of multiple proteins from multiple lung cancer-perturbed networks. We conjecture that measuring multiple proteins from the same lung cancer associated pathway increases the signal-to-noise ratio thus enhancing performance of the classifier.

Selected reaction monitoring (SRM) mass spectrometry (MS) was utilized to measure the concentrations of the candidate proteins in plasma. SRM is a form of MS that monitors predetermined and highly specific mass products, called transitions, of particularly informative (proteotypic or protein-specific) peptides of targeted proteins. Briefly, SRM assays for proteins are based on the high reproducibility of peptide ionization, the foundation of MS. During a SRM analysis, the mass spectrometer is programmed to monitor for transitions of the specific protein(s) being assayed. The resulting chromatograms are integrated to provide quantitative or semi-quantitative protein abundance information. The benefits of SRM assays include high protein specificity, large multiplexing capacity, and both rapid and reliable assay development and deployment. SRM has been used for clinical testing of small molecule analytes for many years, and recently in the development of biologically relevant assays. Exceptional public resources exist to accelerate SRM assay development including the PeptideAtlas, the Plasma Proteome Project, the SRM Atlas and the PeptideAtlas SRM Experimental Library.

In accordance with evolving guidelines for clinical test development, the classifier was discovered (n=143) and validated (n=104) using independent plasma sets from multiple clinical sites consistent with an intended use population of patients with lung nodules, defined as round opacities up to 30 mm in size. In contrast to other biomarker studies, utilizing biospecimens associated with the broad clinical spectrum of lung cancer (Stages I to IV), the cancer plasma samples analyzed were limited to Stage IA, which corresponds to the intended use population of lung nodules of size 30 mm or less. The classifier yielded a performance amendable to further clinical stratification of the intended use by parameters such as age, smoking history or nodule size, as guided by a clinician's diagnostic needs.

Validated performance of the 13-protein classifier demonstrated a negative predictive value (NPV) of 92% and a specificity of 27%. For clinical utility, the classifier must reliably and frequently provide information that can participate in a physician's decision to avoid an invasive procedure. High NPV is required to ensure that the classifier reliably identifies benign nodules. Equivalently, malignant nodules are rarely (8% or less) reported as benign by the classifier. A specificity of 27% implies that one-in-four patients with a benign nodule can avoid invasive procedures, and so, frequently provides information of clinical utility. All validation samples were independent of discovery samples, and 37 came from a new clinical site. Performance on the samples from the new site demonstrated a NPV of 100% and a specificity of 28% suggesting that the classifier performance extends to new clinical settings. Remarkably, the classifier score is demonstrated to be independent of the patient's age, smoking history and nodule size, thereby complementing current clinical risk factors with an informative molecular dimension for evaluating the disease status of a pulmonary nodule.

Results

Table 28 presents the steps taken in the refinement of the initial 388 protein candidates down to the set of 13 classifier proteins used for validation and performance assessment. The results are presented in the same sequence.

TABLE 28

Steps in refining the 388 candidates down to the 13-protein classifier

| Number of Proteins | Refinement |
|---|---|
| 388 | Lung cancer associated protein candidates sourced from tissue and literature. |
| 371 | Number of the 388 protein candidates successfully developed into a SRM assay. |
| 190 | Number of the 371 SRM protein assays detected in plasma. |
| 125 | Number of the 190 SRM protein assays detected in at least 50% of cancer or 50% of benign discovery samples. |
| 36 | Number of the 125 detected proteins that were cooperative. |
| 21 | Number of the 36 cooperative proteins with robust SRM assays (i.e. no interfering signals, good signal-to-noise, etc.) |

TABLE 28-continued

Steps in refining the 388 candidates down to the 13-protein classifier

| Number of Proteins | Refinement |
|---|---|
| 13 | Number of the 21 robust and cooperative proteins with stable logistic regression coefficients. |

Selection of Biomarker Candidates for Assay Development.

To identify lung cancer biomarkers in blood that are shed or secreted from lung tumor cells, proteins overexpressed on the cell surface or over-secreted from lung cancer tumor cells relative to normal lung cells were identified from freshly resected lung tumors using organelle isolation techniques combined with mass spectrometry. In addition, an extensive literature search for lung cancer biomarkers was performed using public and private resources. Both the tissue-sourced biomarkers and literature-sourced biomarkers were required to have evidence of previous detection in blood. The tissue (217) and literature (319) candidates overlapped by 148 proteins, resulting in a list of 388 protein candidates.

Development of SRM Assays.

Standard synthetic peptide techniques were used to develop a 371-protein multiplexed SRM assay from the 388 protein candidates. For 17 of the candidates, appropriate synthetic peptides could not be developed or confidently identified. The 371 SRM assays were applied to plasma samples from patients with pathologically confirmed benign nodules and pathologically confirmed malignant lung nodules to determine how many of the 371 proteins could be detected in plasma. A total of 190 SRM assays were able to detect their target proteins in plasma (51% success rate). This success rate (51%) compares very favorably to similar efforts (16%) to develop large scale SRM assays for the detection of diverse cancer markers in blood. Of the 190 proteins detected in blood, 114 were derived from the tissue-sourced candidates and 167 derived from the literature-sourced candidates (91 protein overlap). It is conjectured that the 49% of candidate proteins not detected in blood were present, but below the level of detection of the technology.

Classifier Discovery.

A summary of the features of the 143 samples used for classifier discovery appears in Table 29. Samples were obtained from three clinical sites to avoid overfitting to a single clinical site. Participating clinical sites were Institut Universitaire de Cardiologie et de Pneumologie de Quebec (IUCPQ), New York University (NYU) and University of Pennsylvania (UPenn). All samples were selected to be consistent with intended use, specifically, having nodule size 30 mm or less. Cancer and benign samples were pathologically confirmed.

TABLE 29

Clinical characteristics of subjects and nodules in the discovery and validation studies

| Characteristics | Cancer n | Benign n | p value | Cancer n | Benign n | p value |
|---|---|---|---|---|---|---|
| | Discovery Study | | | Validation Study | | |
| Subjects | 72 | 71 | | 52 | 52 | |
| Age (year)* | 65 | 64 | 0.46† | 63 | 62 | 0.03† |
| | (59-72) | (52-71) | | (60-73) | (56-67) | |
| Gender | | | 1.00‡ | | | 0.85‡ |
| Male | 29 | 28 | | 25 | 27 | |
| Female | 43 | 43 | | 27 | 25 | |

TABLE 29-continued

Clinical characteristics of subjects and nodules in the discovery and validation studies

| Characteristics | Cancer n | Benign n | p value | Cancer n | Benign n | p value |
|---|---|---|---|---|---|---|
| | Discovery Study | | | Validation Study | | |
| Smoking History | | | | | | |
| Status | | | 0.006[‡] | | | 0.006[‡] |
| Never[§] | 5 | 19 | | 3 | 15 | |
| Former | 60 | 44 | | 38 | 29 | |
| Current | 6 | 6 | | 11 | 7 | |
| No Data | 1 | 2 | | 0 | 1 | |
| Pack-Year*[¶] | 37 | 20 | 0.001[†] | 40 | 27 | 0.09[†] |
| | (20-52) | (0-40) | | (19-50) | (0-50) | |
| Nodules | | | | | | |
| Size (mm)* | 13 | 13 | 0.69[†] | 16 | 15 | 0.68[†] |
| | (10-16) | (10-18) | | (13-20) | (12-22) | |
| Source | | | 1.00[‡] | | | 0.89[‡] |
| IUCPQ[‖] | 14 | 14 | | 13 | 12 | |
| New York | 29 | 28 | | 6 | 9 | |
| Pennsylvania | 29 | 29 | | 14 | 13 | |
| Vanderbilt | 0 | 0 | | 19 | 18 | |
| Histopathology | | | | | | |
| Benign Diagnosis | | | | | | |
| Granuloma | — | 48 | | — | 26 | |
| Hamartoma | — | 9 | | — | 6 | |
| Scar | — | 2 | | — | 2 | |
| Other** | — | 12 | | — | 18 | |
| Cancer Diagnosis | | | | | | |
| Adenocarcinoma | 41 | — | | 25 | — | |
| Squamous Cell | 3 | — | | 15 | — | |
| Large Cell | 0 | — | | 2 | — | |
| Bronchioloalveolar (BAC) | 3 | — | | 0 | — | |
| Adenocarcinoma/BAC | 21 | — | | 5 | — | |
| Other[††] | 4 | — | | 5 | — | |

*Data shown are median values with quartile ranges indicated in parentheses.
[†]Mann-Whitney test.
[‡]Fisher's exact test.
[§]A never smoker is defined as an individual who has a lifetime history of smoking less than 100 cigarettes.
[¶]A pack-year is defined as the product of the total number of years of smoking and the average number of packs of cigarettes smoked daily. Pack-year data were not available for 4 cancer and 6 benign subjects in the discovery set and 2 cancer and 3 benign subjects in the validation set.
[‖]IUCPQ is the Institute Universitaire de Cardiologie et de Pneumologie de Quebec.
**For the discovery study, the Benign Diagnosis "Other" category included: amyloidosis, n = 2; fibroelastic nodule, n = 1; fibrosis, n = 1; hemorrhagic infarct, n = 1; lymphoid aggregate, n = 1; organizing pneumonia, n = 3; pulmonary infarct, n = 1; sclerosing hemangioma, n = 1; and subpleural fibrosis with benign lymphoid hyperplasia, n = 1. For the validation study, the Benign Diagnosis "Other" category included: amyloidosis, n = 1; bronchial epithelial cells, n = 4; bronchiolitis interstitial fibrosis, n = 1; emphysematous lung, n = 1; fibrotic inflammatory lesion, n = 1; inflammation, n = 1; parenchymal intussusception, n = 1; lymphangioma, n = 1; mixed lymphocytes and histiocytes, n = 1; normal parenchyma, n = 1; organizing pneumonia, n = 1; pulmonary infarct, n = 2; respiratory bronchiolitis, n = 1; and squamous metaplasia, n = 1.
[††]For the discovery study, the non-small cell lung cancer (NSCLC) Diagnosis "Other" category included: adenocarcinoma squamous cell mixed, n = 1; large cell squamous cell mixed, n = 1; pleomorphic carcinoma, n = 1, and not specified, n = 1. For the validation study, the NSCLC Diagnosis "Other" category included: carcinoid, n = 2; large cell squamous cell mixed, n = 1; and not specified, n = 2.

Benign and cancer samples were paired by matching on age, gender, nodule size and clinical site to avoid bias during SRM analysis and also to ensure that the biomarkers discovered were not markers of age, gender, nodule size or clinical site.

The 371-protein SRM assay was applied to the 143 discovery samples and the resulting transition data were analyzed to derive a 13-protein classifier using a logistic regression model (Table 30). The key step in this refinement (Table 28) was the identification of 36 cooperative proteins of which 21 had robust SRM signal. A protein was deemed cooperative if found more frequently on the best performing panels than expected by chance alone, with the significance determined using the following statistical estimation procedure. Briefly, a million random 10-protein panels were generated and the frequency of each protein among the best performing panels (p value ≤ $10^{-4}$) was calculated. These proteins were sampled from the list of 125 proteins reproducibly detected in either benign samples or in cancer samples (see Table 28). Full details of the estimation procedure and the full discovery process are described in Materials and Methods in Example 9. Importantly, the 13-protein classifier was fully defined before validation was performed.

TABLE 30

The 13-protein logistic regression classifier

| Protein (Human) | Transition | SEQ ID NO | Co-efficient |
|---|---|---|---|
| LRP1 | TVLWPNGLSLDIPAGR_855.00_400.20 | 15 | −1.59 |
| BGH3 | LTLLAPLNSVFK_658.40_804.50 | 8 | 1.73 |
| COIA1 | AVGLAGTFR_446.26_721.40 | 11 | −1.56 |
| TETN | LDTLAQEVALLK_657.39_330.20 | 20 | −1.79 |
| TSP1 | GFLLLASLR_495.31_559.40 | 22 | 0.53 |

TABLE 30-continued

The 13-protein logistic regression classifier

| Protein (Human) | Transition | SEQ ID NO | Co-efficient |
|---|---|---|---|
| ALDOA | ALQASALK_401.25_617.40 | 7 | −0.80 |
| GRP78 | TWNDPSVQQDIK_715.85_260.20 | 23 | 1.41 |
| ISLR | ALPGTPVASSQPR_640.85_841.50 | 14 | 1.40 |
| FRIL | LGGPEAGLGEYLFER_804.40_913.40 | 24 | 0.39 |
| LG3BP | VEIFYR_413.73_598.30 | 25 | −0.58 |
| PRDX1 | QITVNDLPVGR_606.30_428.30 | 16 | −0.34 |
| FIBA | NSLFEYQK_514.76_714.30 | 26 | 0.31 |
| GSLG1 | IIIQESALDYR_660.86_338.20 | 27 | −0.70 |

Constant ($\alpha$) equals to 36.16.

Classifier Validation.

A total of 52 cancer and 52 benign samples (Table 29) were used to validate the performance of the 13-protein classifier. All validation samples were from different patients than the discovery samples. In addition, 36% of the validation samples were sourced from a new fourth clinical site, Vanderbilt University (Vanderbilt). A new clinical site participating in the validation study provides greater confidence that the classifier's performance generalizes beyond the discovery study. The remaining validation samples were selected randomly from the discovery sites. Samples were selected to be consistent with intended use and matched as in the discovery study.

Figure 12:
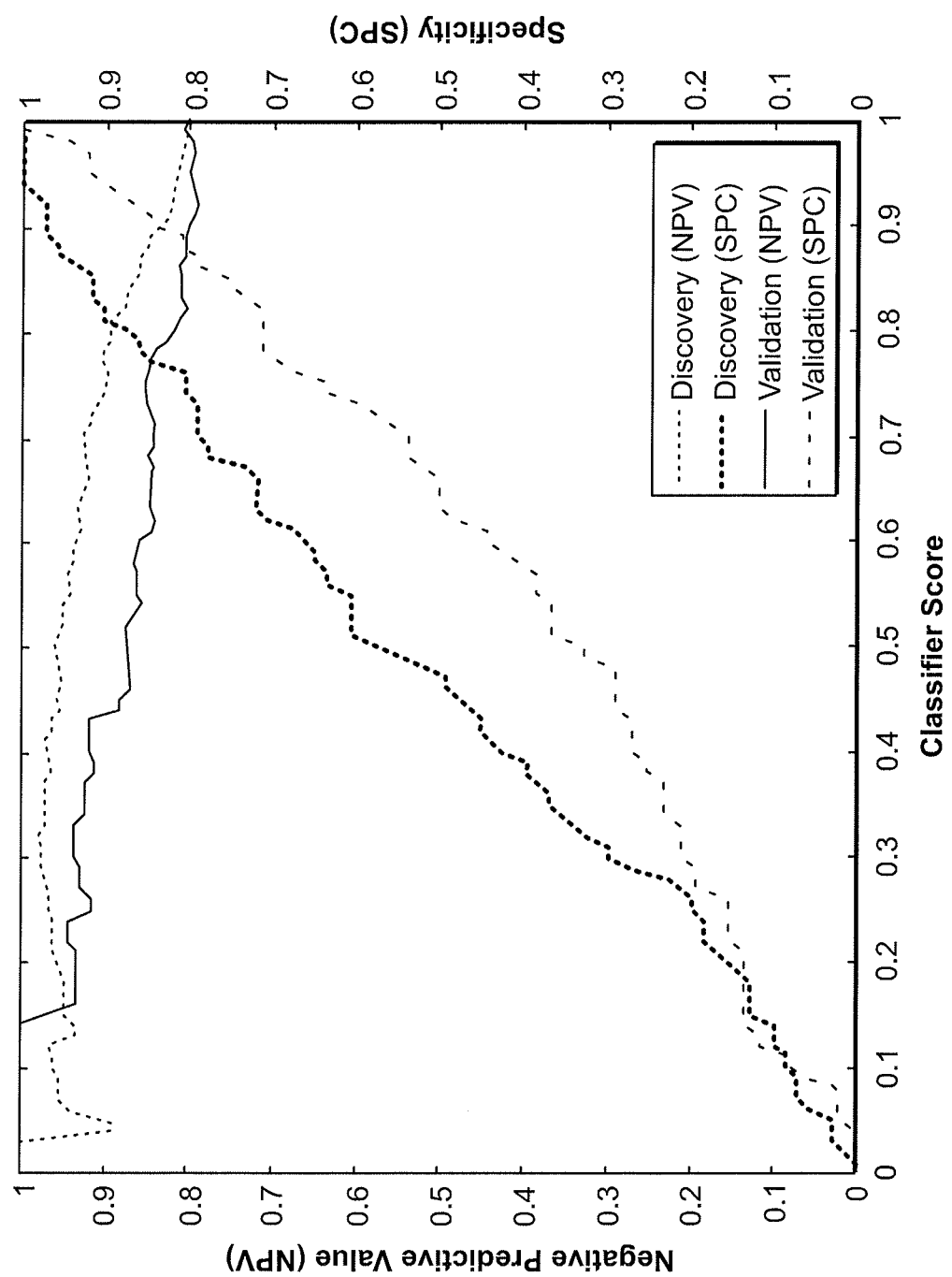
FIG. 12 is a graph showing performance of the classifier on the discovery samples (n=143) and validation samples (n=104). Negative predictive value (NPV) and specificity (SPC) are presented in terms of classifier score. A cancer prevalence of 20% was assumed.

The classifier was applied to the validation samples and analyzed (Materials and Methods in Example 9). The performance of the classifier is presented in FIG. 12 in terms of negative predictive value (NPV) and specificity (SPC), as these are the two most clinically relevant measures. NPV is the population-based probability that a nodule predicted to be benign by the classifier is truly benign. As the NPV is representative of the classifier's performance on the intended use population, it can be calculated from the classifier's sensitivity, specificity and the estimated cancer prevalence (20%) in the intended use population. Specificity is the percentage of benign nodules that are predicted to be benign by the classifier. The classifier generates a cancer probability score, ranging from 0 to 1. Any reference value in this range can be defined so that a sample is predicted to be benign if the sample's classifier score is below the reference value, or predicted to be malignant if the sample's classifier score is above the reference value. The reference value used in practice depends primarily on the physician and his/her minimum required NPV. For the purposes of illustration we assume that the NPV requirement is 90%.

At reference value 0.43, the classifier has NPV of 96%+/−4% and specificity of 45%+/−13% on the discovery samples, where 95% confidence intervals are reported. At the same reference value of 0.43, the classifier has NPV of 92%+/−7% and specificity of 27%+/−12% on the validation samples. Table 31 reports the classifier's performance for discovery and validation sample sets and for multiple lung cancer prevalences. For each lung cancer prevalence, the reference value was selected to ensure NPV is 90% or more.

TABLE 31

Performance of the classifier in discovery and validation at three cancer prevalences

| Dataset | Prevalence (%) | Reference Value | Sensitivity (%) | Specificity (%) | NPV (%) | PPV (%) |
|---|---|---|---|---|---|---|
| Discovery | 20 | 0.43 | 93 | 45 | 96 | 30 |
| (n = 143) | 25 | 0.37 | 96 | 38 | 96 | 34 |
|  | 30 | 0.33 | 96 | 34 | 95 | 38 |
| Validation | 20 | 0.43 | 90 | 27 | 92 | 24 |
| (n = 104) | 25 | 0.37 | 92 | 23 | 90 | 29 |
|  | 30 | 0.33 | 94 | 21 | 90 | 34 |
| Vander | 20 | 0.43 | 100 | 28 | 100 | 26 |
| bilt | 25 | 0.37 | 100 | 22 | 100 | 30 |
| (n = 37) | 30 | 0.33 | 100 | 17 | 100 | 34 |

NPV is negative predictive value.

PPV is positive predictive value.

The performance of the 13-protein classifier on validation samples from the new clinical site (Vanderbilt) is a great indicator of the classifier's performance on future samples, and a strong sign that the classifier is not overfit to the three discovery sites. The NPV and specificity on the Vanderbilt samples are 100% and 28%, respectively, at the same reference value 0.43.

Figure 13:
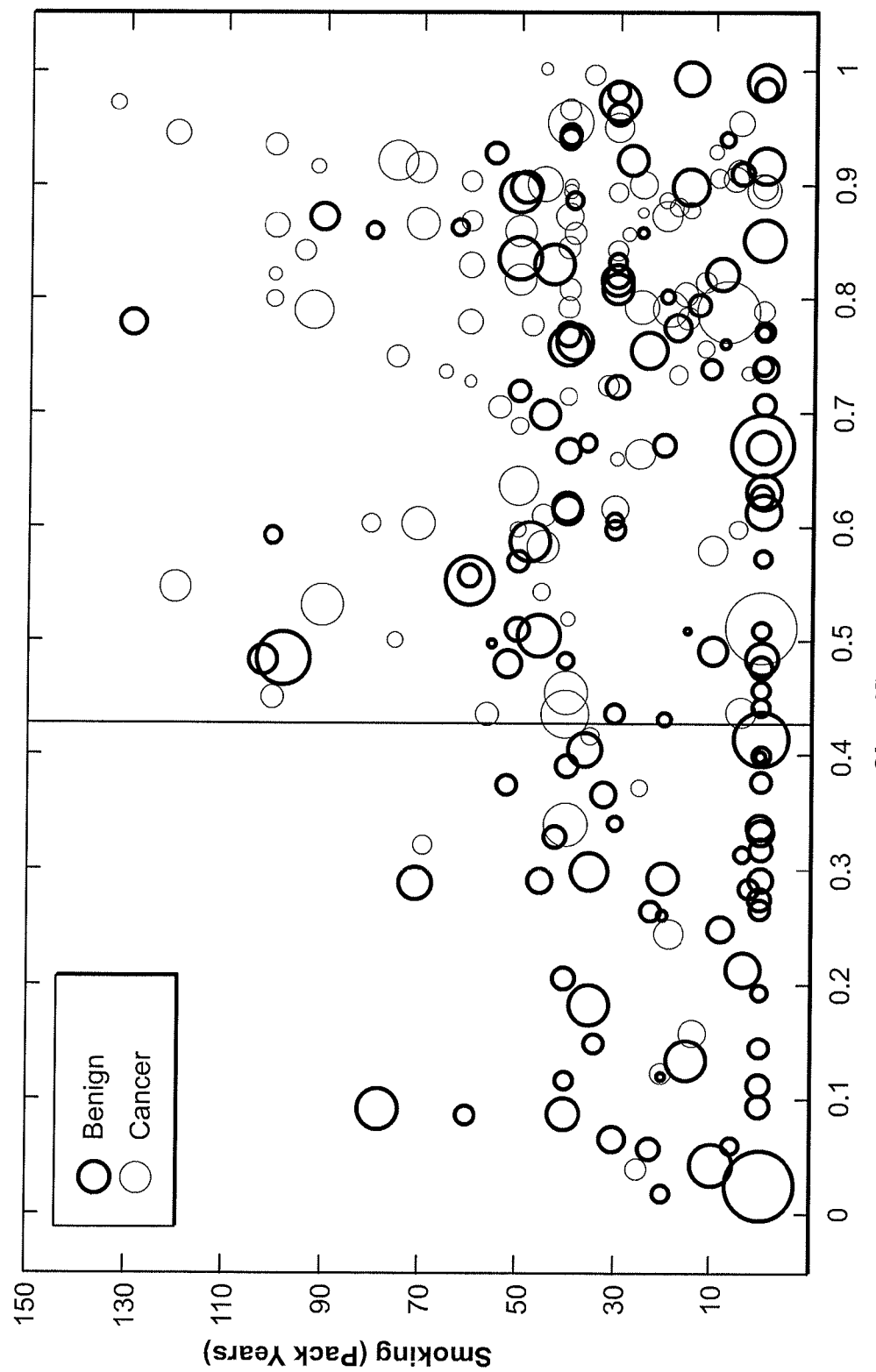
FIG. 13 is a graph showing multivariate analysis of clinical (smoking, nodule size) and molecular (classifier score) factors as they relate to cancer and benign samples (n=247) in the discovery and validation studies. Smoking is measured by pack-years on the vertical. Nodule size is represented by circle diameter. A reference value of 0.43 is presented to illustrate the discrimination between low numbers of cancer samples less than the reference value as compared to the high number of cancer samples above the reference value.
Figure 15:
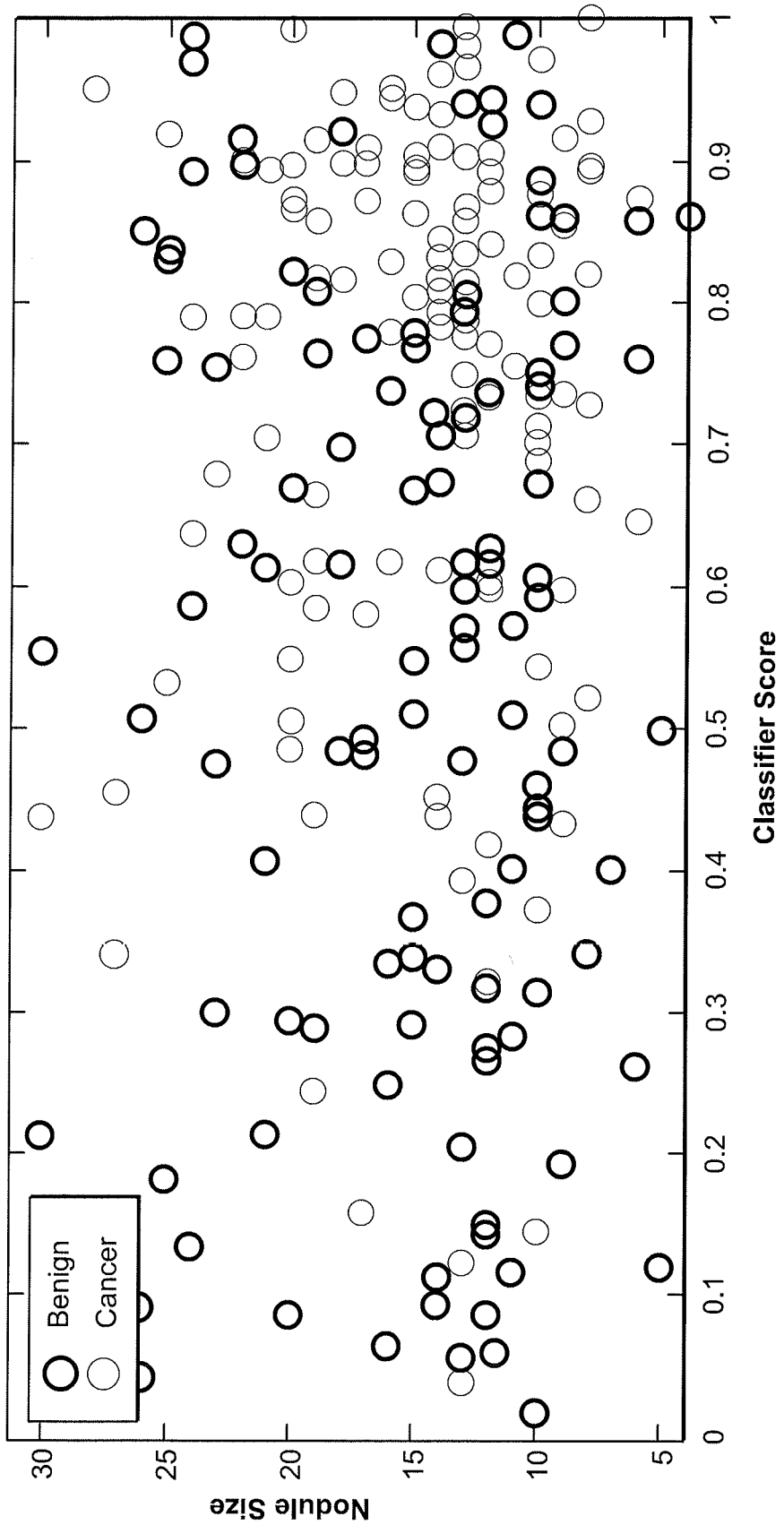
FIG. 15 is a graph showing scattering plot of nodule size vs. classifier score of all 247 patients, demonstrating the lack of correlation between the two variables.

FIG. 13 presents the application of the classifier to all 247 discovery and validation samples. FIG. 13 compares the clinical risk factors of smoking (measured in pack years) and nodule size (proportional to the diameter of each circle) to the classifier score assigned to each sample. Nodule size does not appear to increase with the classifier score. Indeed, both large and small nodules are spread across the classifier score spectrum. To quantify this observation, the Pearson correlation between the classifier score and nodule size, smoking history pack-year and age were calculated and found to be insignificant (Table 32). The implication of this observation is remarkable. The classifier provides information on the disease status of a pulmonary nodules that is independent of the three currently used risk factors for malignancy (age, smoking history and nodule size), and thus provides incremental molecular information of great added clinical value. For a similar plot of nodule size vs. classifier score, see FIG. 15.

TABLE 32

Impact of clinical characteristics on classifier score

Continuous Clinical Characteristics

| Characteristics | Sample Group | Pearson Correlation | Coefficient of Linear Fit | 95% CI* of Coefficient | p-value on Coefficient |
|---|---|---|---|---|---|
| Subject | | | | | |
| Age | All | 0.190 | 0.005 | (0.002, −0.008) | 0.003 |
|  | Cancer | 0.015 | 0.000 | (−0.004, −0.004) | 0.871 |
|  | Benign | 0.227 | 0.005 | (0.001, −0.010) | 0.012 |

TABLE 32-continued

Impact of clinical characteristics on classifier score

| | | | | | |
|---|---|---|---|---|---|
| Smoking History Pack-Years | All | 0.185 | 0.002 | (0.000, −0.003) | 0.005 |
| | Cancer | 0.089 | 0.001 | (−0.001, −0.002) | 0.339 |
| | Benign | 0.139 | 0.001 | (0.000, −0.003) | 0.140 |

Nodule

| | | | | | |
|---|---|---|---|---|---|
| Size | All | −0.071 | −0.003 | (−0.008, −0.002) | 0.267 |
| | Cancer | −0.081 | −0.003 | (−0.009, −0.003) | 0.368 |
| | Benign | −0.035 | −0.001 | (−0.008, −0.005) | 0.700 |

Categorical Clinical Characteristics

| Characteristics | Classifier Score | Cancer | p-value on Cancer | Benign | p-value on Benign |
|---|---|---|---|---|---|
| Gender | | | 0.477† | | 0.110† |
| Female | Median (quartile range) | 0.786 (0.602-0.894) | | 0.479 (0.282-0.721) | |
| Male | Median (quartile range) | 0.815 (0.705-0.885) | | 0.570 (0.329-0.801) | |
| Smoking History Status | | | 0.652† | | 0.539† |
| Never | Median (quartile range) | 0.707 (0.558-0.841) | | 0.468 (0.317-0.706) | |
| Past | Median (quartile range) | 0.804 (0.616-0.892) | | 0.510 (0.289-0.774) | |
| Current | Median (quartile range) | 0.790 (0.597-0.876) | | 0.672 (0.437-0.759) | |

The Molecular Foundations of the Classifier.

To address the biological relevance of the 13 classifier proteins, they were submitted for pathway analysis using IPA (Ingenuity Systems, www.ingenuity.com). It is identified that the transcription regulators most likely to cause a modulation of these 13 proteins. Using standard IPA analysis parameters, the four most significant (see Materials and Methods in Example 9) nuclear transcription regulators were FOS (proto-oncogene c-Fos), NF2L2 (nuclear factor erythroid 2-related factor 2), AHR (aryl hydrocarbon receptor) and MYC (myc proto-oncogene protein). These proteins regulate 12 of the 13 classifier proteins, with ISLR being the exception (see below).

Figure 14:
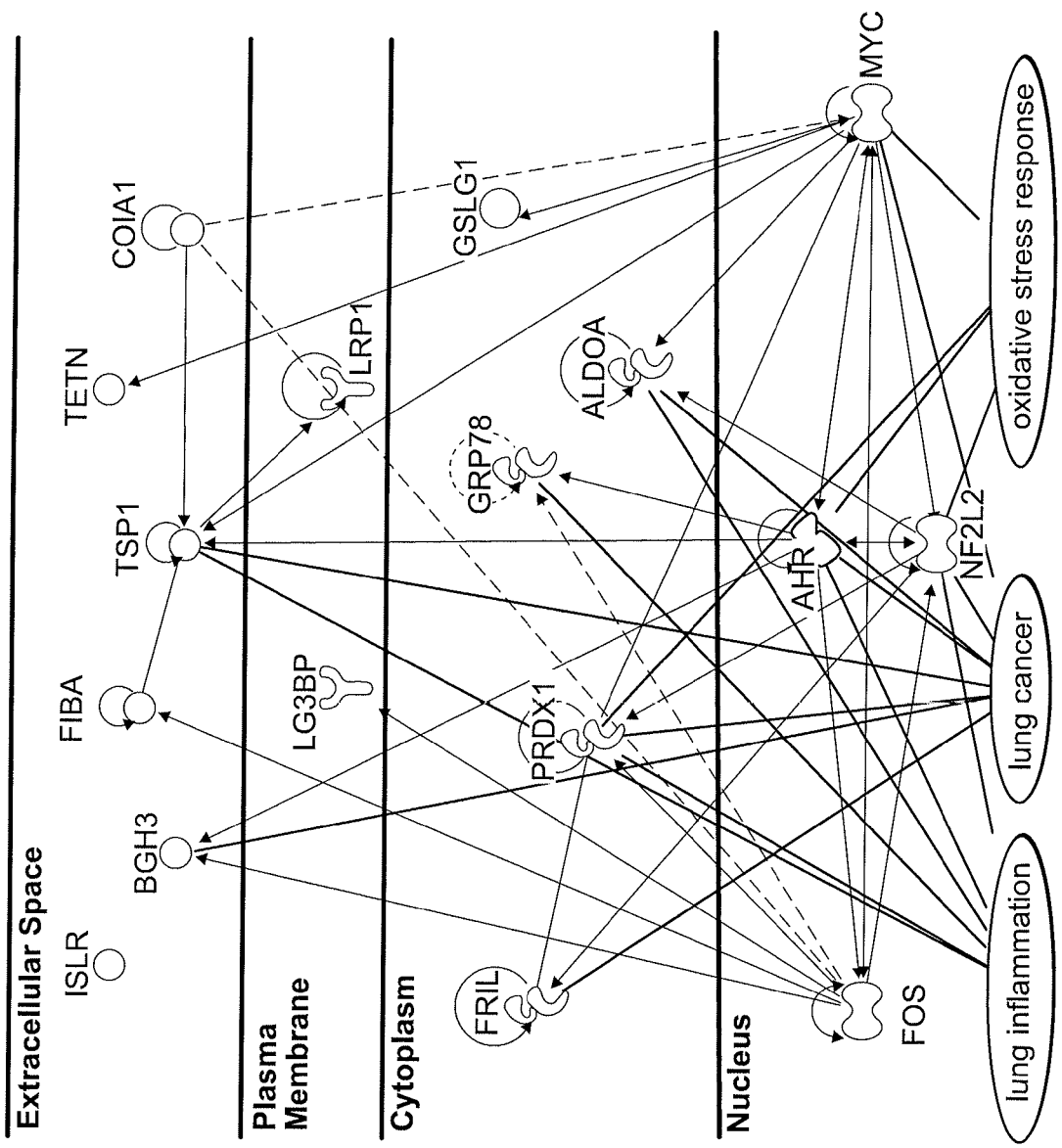
FIG. 14 is a graph showing the 13 classifier proteins (green), 4 transcription regulators (blue) and the three networks (orange lines) of lung cancer, oxidative stress response and lung inflammation. All references are human UniProt identifiers.

FOS is common to many forms of cancer. NF2L2 and AHR are associated with lung cancer, oxidative stress response and lung inflammation. MYC is associated with lung cancer and oxidative stress response. These four transcription regulators and the 13 classifier proteins, collectively, are also highly associated (p-value 1.0e−07) with the same three biological networks, namely, lung cancer, lung inflammation and oxidative stress response. This is summarized in FIG. 14 where the classifier proteins (green), transcription regulators (blue) and the three merged networks (orange) are depicted. Only ISLR (Immunoglobulin superfamily containing leucine-rich repeat protein) is not connected through these three networks to other classifier proteins, although it is connected through cancer networks not specific to lung. In summary, the modulation of the 13 classifier proteins can be linked back to a few transcription regulators highly associated with lung cancer, lung inflammation and oxidative stress response networks; three biological processes reflecting aspects of lung cancer.

The present invention distinguishes itself in multiple ways. First, the performance of the 13-protein classifier achieves intended use performance requirements with NPV (and sensitivity) of at least 90% or higher in validation, across multiple prevalence estimates (see Table 31). Second, intended use population samples (nodule size 30 mm or less and/or Stage IA) were used in discovery and validation, in contrast to prior studies where non-intended use samples ranging from Stage I to Stage IV were used. In some cases, nodule size information was not disclosed in prior work. Third, the 13-protein classifier was demonstrated to provide a score that is independent of the currently used cancer risk parameters of nodule size, smoking history and age.

The utilization of SRM technology enables global interrogation of proteins associated with lung cancer processes in contrast to technologies such as those that multiplex antibodies where it is often not feasible to multiplex hundreds of candidate markers for a specific disease.

Clinical Study Designs.

The design and conduct of biomarker studies is necessarily impacted by the eventual intended use population and performance requirements for the clinical test. Emerging guidelines help in the design of studies that have greater chance of translating into clinical impact. In the design of the discovery and validation studies presented here, four requirements were especially important. First, conducting a multiple clinical site discovery study enabled us to determine those proteins robust to variations introduced by differences in site-to-site sample processing and management, as well as from any biological differences in the populations being served by the different site hospitals. Such a design is critical as site-to-site sources of variations can often exceed biological signal. Second, utilizing intended use samples, as defined by age, smoking history and nodule size, in discovery and validation phases enabled us to obtain a realistic estimate of the performance envelop of the classifier. Third, careful matching of cancer and benign cohorts on age, gender, nodule size and clinical site was critical in not only avoiding bias, but in the discovery and validation of a classifier that provides a score independent of these clinical factors as well as smoking history. Fourth, validation samples were from different patients than the discovery samples. Furthermore, 36% of the validation samples were from an entirely new clinical site, a critical validation step to show that results are not overfit to the sites used in the discovery phase. Performance on samples from the new clinical site was exceptionally high (NPV of 100%, specificity of 28%), yielding a high level of confidence in the performance of the test in clinical practice.

Systems Biology and Blood Signatures.

The integration of a systems biology approach to biomarker discovery with SRM technology enabled the simultaneous exploration of a large number of lung cancer relevant proteins, resulting in a highly sensitive classifier. The systems approach employed several strategies.

First, proteins secreted or shed from the cell surface of lung cancer cells were identified (i.e. tissue-sourced) as these are likely lung cancer perturbed proteins to be detected in blood. Of the classifier's 13 proteins, seven were tissue-sourced, demonstrating that tissue-sourcing is an effective method for prioritizing proteins for SRM assay development.

A second systems driven approach was the identification of the most cooperative protein biomarkers. Cooperative proteins are those that may not be the best individual performers but appear frequently on high performance panels. Motivating this approach is the desire to derive a classifier with multiple proteins from multiple lung cancer associated networks. By monitoring multiple proteins and networks, it was expected that the classifier would be highly sensitive to the circulating signature of a malignant nodule, as demonstrated in validation.

There are two confirmations of the effectiveness of the cooperative protein approach. A pathway analysis demonstrated that the classifier proteins are likely modulated by a small number of transcription regulators (AHR, NF2L2, MYC, FOS) highly associated with lung cancer, lung inflammation and oxidative stress response networks/processes. Chronic lung inflammation and oxidative stress response are both linked to NSCLC development. A strength of the classifier is that it monitors multiple proteins from these multiple lung cancer associated processes. This multiple protein, multiple process survey accounts for the high sensitivity of the classifier for detecting the circulating signature emitted by malignant nodules, and so, high NPV when the classifier calls a nodule benign.

The second validation of the cooperative approach is a direct comparison to traditional biomarker strategies. Typically, proteins are shortlisted in the discovery process by filtering on individual diagnostic performance. To contrast the difference between filtering proteins based on strong individual performance as opposed to frequency on high performance panels, we calculated a p-value for each protein using the Mann-Whitney non-parametric test. Only 2 of the 36 cooperative proteins had a p-value below 0.05, a commonly used significance threshold for measuring individual performance. More importantly, we derived a "p-classifier" using the same steps for the 13-protein classifier derivation (see Table 28 and Materials and Methods in Example 9) except that the Mann Whitney p-value was used in place of cooperative score. The p-classifier achieved NPV 96% and specificity 18% in discovery and NPV 91% and specificity 19% in validation as compared to the 13-protein classifier performance of NPV 96% and specificity 45% in discovery and NPV 92% and specificity 27% in validation. Note that the reference value thresholds were selected to ensure NPV of at least 90%. Hence, we expect similar high NPV performance between the 13-protein cooperative classifier and the p-classifier. Specificity is the performance measure where a comparison can be made. This is where a significant drop in performance from the 13-protein cooperative classifier to the p-classifier is observed. This confirms that the best individual protein performers are not necessarily the best proteins for classifiers Most Informative Proteins.

Which proteins in the classifier are most informative? To answer this question all possible classifiers were constructed from the set of robust cooperative proteins and their performance measured. The frequency of each protein among the 100 best performing panels was determined. Four proteins (LRP1, COIA1, ALDOA, LG3BP) were highly enriched with 95% of the 100 best classifiers having at least three of these four proteins (p-value <1.0e−100). Seven of eight proteins (LRP1, COIA1, ALDOA, LG3BP, BGH3. PRDX1, TETN, ISLR) appeared together on over half of all the best classifiers (p-value <1.0e−100). Note that the 13-protein classifier contains additional proteins as they further increase performance, likely by measuring proteins in the same three lung cancer networks (lung cancer, lung inflammation and oxidative stress). The conclusion is that high performance panels of cooperative proteins for pulmonary nodule characterization are similar in composition to one another with a preference for a set of particularly informative (cooperative) proteins.

In summary, by integrating systems biology strategies for biomarker discovery (tissue-sourced candidates with cancer relevance, cooperative proteins, multiple proteins from multiple lung cancer associated networks), enabling technologies (SRM for global proteomic interrogation) and clinical focus (designing studies for intended use), this invention identifies a 13-protein proteomic classifier that provides molecular insight into the disease status of pulmonary nodules.

Example 9

Materials and Methods

Identification of Candidate Plasma Proteins.

Two approaches were employed to identify candidate proteins for a lung cancer classifier, including analysis of the proteome of lung tissues with a histopathologic diagnosis of NSCLC and a search of literature databases for lung cancer-associated proteins. All candidate proteins were also assessed for evidence of blood circulation and satisfied one or more requirement(s) for the evidence.

Analysis of Plasma Samples Using SRM-MS.

Briefly, the protocol for SRM-MS analysis of plasma aliquots included immunodepletion on IgY14-Supermix resin columns (Sigma) of medium- and high-abundance proteins, denaturation, trypsin digestion, and desalting, followed by reversed-phase liquid chromatography and SRM-MS analysis of the obtained peptide samples.

Development of SRM Assays.

SRM assays for candidate proteins were developed based on synthetic peptides, as previously described. After identification and synthesis of up to five suitable peptides per protein, SRM triggered MS/MS spectra were collected on a 5500 QTrap® mass spectrometer for both doubly and triply charged precursor ions. The obtained MS/MS spectra were assigned to individual peptides using MASCOT and with a minimum cutoff score of 15. Up to four transitions per precursor ion were then selected for optimization. The resulting corresponding optimal retention time, declustering potential and collision energy were assembled for all transitions. Optimal transitions were measured on a mixture of all synthetic peptides and on two pooled plasma samples, each obtained from ten subjects with either benign or malignant, i.e. NSCLC, lung nodules at the Institut Universitaire de Cardiologie et de Pneumologie de Quebec (IUCPQ, Quebec, Canada). All subjects provided informed consent and contributed biospecimens in studies approved by the institution's Ethics Review Board (ERB). Plasma samples were processed as described above. Batches of 1750 transitions were analyzed by SRM-MS, with SRM-MS data manually reviewed to select the two best peptides per protein and the two best transitions per peptide. The intensity ratio, defined as the ratio between the intensities of the two best transitions of a peptide in the synthetic peptide mixture, was used to assess the specificity of the transitions in a biological sample. Transitions demonstrating interference with other transitions were not selected. A method to ensure the observed transitions corresponded to the peptides and proteins they were intended to measure was developed. In particular, 93% of peptide transitions developed had an error rate below 5%.

Discovery Study Design.

A retrospective, multi-center, case-control study was performed using archival K2-EDTA plasma aliquots previously obtained from subjects who provided informed consent and contributed biospecimens in studies approved by the Ethics Review Board (ERB) or the Institutional Review Boards (IRB) at the IUCPQ or New York University (New York, N.Y.) and the University of Pennsylvania (Philadelphia, Pa.), respectively. In addition, plasma samples were provided by study investigators after review and approval of the sponsor's study protocol by the respective institution's ERB or IRB, as required. Sample eligibility for the proteomic analysis was based on the satisfaction of the study inclusion and exclusion criteria, including the subject's demographic information; the subject's corresponding lung nodule radiographic characterization by chest CT scan and a maximal linear dimension of 30 mm; and the histopathology of the lung nodule obtained at the time of diagnostic surgical resection, i.e. either NSCLC or a benign, i.e. non-malignant, process. Each cancer-benign sample pair was matched, as much as possible among eligible samples, by gender, nodule size (±10 mm), age (±10 years), smoking history pack-years (±20 pack-years), and by center. Independent monitoring and verification of the clinical data associated with both the subject and lung nodule were performed in accordance with the guidance established by the Health Insurance Portability and Accountability Act (HIPAA) of 1996 to ensure subject privacy. The study was powered with a probability of 92% to detect 1.5 fold differences in protein abundance between malignant and benign lung nodules.

Logistic Regression Model.

The logistic regression classification method was used to combine a panel of transitions into a classifier and to calculate a classification probability score between 0 and 1 for each sample. The probability score ($P_s$) of a sample was determined as $$P_s = 1/[1+\exp(-\alpha - \Sigma_{i=1}^{N} \beta_i * \check{I}_{i,s})], \quad (1)$$

where $\check{I}_{i,s}$ was the logarithmically transformed (base 2), normalized intensity of transition i in sample s, $\beta_i$ was the corresponding logistic regression coefficient, $\alpha$ was a classifier-specific constant, and N was the total number of transitions in the classifier. A sample was classified as benign if $P_s$ was less than a reference value or cancer otherwise. The reference value can be increased or decreased depending on the desired NPV. To define the classifier, the panel of transitions (i.e. proteins), their coefficients, the normalization transitions, classifier coefficient $\alpha$ and the reference value must be learned (i.e. trained) from the discovery study and then confirmed using the validation study.

Lung Nodule Classifier Development. The goal of the discovery study was to derive a multivariate classifier with a target performance sufficient for clinical utility in the intended use population, i.e. a classifier having an NPV of 90% or higher. This goal was incorporated in the data analysis strategies. The classifier development included the following: normalization and filtering of raw SRM-MS data; identification of candidate proteins that occurred with a high frequency in top-performing panels; evaluation of candidate proteins based on SRM-MS signal quality; selection of candidate proteins for the final classifier based on their stability in performance; and training to a logistic regression model to derive the final classifier. Table 28 provides a summary overview of the primary steps.

Normalization of raw SRM-MS data was performed to reduce sample-to-sample intensity variations using a panel of six endogenous proteins. After data normalization, SRM-MS data were filtered down to transitions having the highest intensities of the corresponding proteins and satisfying the criterion for detection in a minimum of 50% of the cancer or 50% of the benign samples. A total of 125 proteins satisfied these criteria of reproducible detection. Missing values were replaced by half the minimum detected values of the corresponding transitions in all samples.

Remaining transitions were then used to identify proteins, defined as cooperative proteins, that occurred with high frequency on top-performing protein panels. The cooperative proteins were derived using the following estimation procedure as it is not computational feasible to evaluate the performance of all possible protein panels.

Monte Carlo cross validation (MCCV) (36) was performed on $1 \times 10^6$ panels, each panel comprised of 10 randomly selected proteins and fitted to a logistic regression model, as described above, using a 20% holdout rate and $10^2$ sample permutations. The receiver operating characteristic (ROC) curve of each panel was generated and the corresponding partial area under the ROC curve (AUC) but above the boundary of sensitivity being 90%, defined as the partial AUC (37, 38), was used to assess the performance of the panel. By focusing on the performance of individual panels at high sensitivity region, the partial AUC allows for the identification of panels with high and reliable performance on NPV. The candidate proteins that occurred in the top 100 performing panels with a frequency greater than that expected by chance were identified as cooperative proteins. For each protein the cooperative score is defined as its frequency on the 100 high performance panels divided by the expected frequency. Highly cooperative proteins had a score of 1.75 or higher (the corresponding one-sided p value <0.05) while non-cooperative proteins had a score of 1 or less. Note that one million panels were sampled to ensure that the 100 top performing panels were exceptional (empirical p value $\leq 10^{-4}$). In addition, panels of size 10 were used in this procedure based on empirical evidence that larger panels did not change the resulting list of cooperative proteins. We also wanted to avoid overfitting the logistic regression model. In total, 36 cooperative proteins were identified, including 15 highly cooperative proteins.

Raw chromatograms of all transitions of cooperative proteins were then manually reviewed. Proteins with low signal-to-noise ratios and/or showing evidence of any interference were removed from further consideration for the final classifier. In total, 21 cooperative and robust proteins were identified.

Remaining candidate proteins were then evaluated in an iterative, stepwise procedure to derive the final classifier. In each step, MCCV was performed using a holdout rate of 20% and 104 sample permutations to train the remaining candidate proteins to a logistic regression model and to assess the variability, i.e. stability, of the coefficient derived for each protein by the model. The protein having the least stable coefficient was identified and removed. Proteins for the final classifier were identified when the corresponding partial AUC was optimal. Seven of the 13 proteins in the final classifier were highly cooperative.

Proteins in the final classifier were further trained to a logistic regression model by MCCV with a holdout rate of 20% and $2 \times 10^4$ sample permutations.

Lung Nodule Classifier Validation.

The design of the validation study was identical to that of the discovery study, but involved K2-EDTA plasma samples associated with independent subjects and independent lung nodules not evaluated in the discovery study. Additional specimens were obtained from Vanderbilt University (Nashville, Tenn.) with similar requirements for patient consent, IRB approval, and satisfaction of HIPAA requirements. Of the 104 total cancer and benign samples in the validation study, half were analyzed immediately after the discovery study, while the other half was analyzed later. The study was powered to observe the expected 95% confidence interval (CI) of NPV being 90±8%.

The raw SRM-MS dataset in the validation study was normalized in the same way as the discovery dataset. Variability between the discovery and the validation studies was mitigated by utilizing human plasma standard (HPS) samples in both studies as external calibrator. Missing data in the validation study were then replaced by half the minimum detected values of the corresponding transitions in the discovery study. Transition intensities were applied to the logistic regression model of the final classifier learned previously in the training phase, from which classifier scores were assigned to individual samples. The performance of the lung nodule classifier on the validation samples was then assessed based on the classifier scores.

IPA Pathway Analysis.

Standard parameters were used. Specifically, in the search for nuclear transcription regulators, requirements were p-value <0.01 with a minimum of 3 proteins modulated. Significance was determined using a right-tailed Fisher's exact test using the IPA Knowledge Database as background.

Candidate Biomarker Identification.

Candidate Biomarkers Identified by Tissue Proteomics.

Specimens of resected NSCLC (adenocarcinoma, squamous cell and large cell) lung tumors and non-adjacent normal tissue in the same lobe were obtained from patients who provided informed consent in studies approved by the Ethics Review Boards at the Centre Hospitalier de l'Université de Montréal and the McGill University Health Centre.

The proteomic analyses of lung tumor tissues targeted membrane-associated proteins on endothelial cells (adenocarcinoma, n=13; squamous cell, n=18; and large cell, n=7) and epithelial cells (adenocarcinoma, n=19; squamous cell, n=6; and large cell, n=5), and those associated with the Golgi apparatus (adenocarcinoma, n=13; squamous cell, n=15; and large cell, n=5).

Membrane proteins from endothelial cells or epithelial cells and secreted proteins were isolated from normal or tumor tissues from fresh lung resections after washing in buffer and disruption with a Polytron to prepare homogenates. The cell membrane protocol included filtration using 180 μm mesh and centrifugation at 900×g for 10 min at 4° C., supernatants prior to layering on 50% (w:v) sucrose and centrifugation at 218,000×g for 1 h at 4° C. to pellet the membranes. Membrane pellets were resuspended and treated with micrococcal nuclease, and incubated with the following antibodies specified by plasma membrane type: endothelial membranes (anti-thrombomodulin, anti-ACE, anti-CD34 and anti-CD144 antibodies); epithelial membranes (anti-ESA, anti-CEA, anti-CD66c and anti-EMA antibodies), prior to centrifugation on top of a 50% (w:v) sucrose cushion at 280,000×g (endothelial) or 218,000×g (epithelial) for 1 h at 4° C. After pellet resuspension, plasma membranes were isolated using MACS microbeads. Endothelial plasma membranes were treated with KI to remove cytoplasmic peripheral proteins. The eluate of epithelial plasma membranes was centrifuged at 337,000×g for 30 min at 4° C. over a 33% (w:v) sucrose cushion, with resuspension of the pellet in Laemmli/Urea/DTT after removal of the supernatant and sucrose cushion.

To isolate secreted tissue proteins, the density of the tissue homogenates (prepared as described above) was adjusted to 1.4 M sucrose prior to isolating the secretory vesicles by isopycnic centrifugation at 100,000×g for 2 h at 4° C. on a 0.8 and 1.2 M discontinuous sucrose gradient. Vesicles concentrating at the 0.8/1.2 M interface were collected and further incubated for 25 min with 0.5 M KCl to remove loosely bound peripheral proteins. Vesicles were recuperated by ultracentrifugation at 150,000×g for 1 h at 4° C. and then opened with 100 mM $(NH_4)HCO_3$ (pH 11.0) for 30 min at 4° C. Secreted proteins were recovered in the supernatant following ultracentrifugation at 150,000×g for 1 h at 4° C.

Membrane or secreted proteins were then analyzed by CellCarta® (Caprion, Montreal, Québec) proteomics platform, including digestion by trypsin, separation by strong cation exchange chromatography, and analysis by reversed-phase liquid chromatography coupled with electrospray tandem mass spectrometry (MS/MS). Peptides in the samples were identified by database searching of MS/MS spectra using MASCOT and quantified by a label-free approach based on their signal intensity in the samples, similar to those described in the literature. Proteins whose tumor-to-normal abundance ratio was either ≥1.5 or ≤⅔ were then identified as candidate biomarkers.

Candidate Biomarkers Identified by Literature Searches.

Automated literature searches using predefined terms and automated PERL scripts were performed on the following databases: UniProt on May 6, 2010, Entrez, NBK3836 on May 17, 2010, and NextBio on Jul. 8, 2010. Biomarker candidates were compiled and mapped to UniProt identifiers using the UniProt Knowledge Base.

Presence of Candidate Biomarkers in the Blood.

The tissue- and literature-identified biomarker candidates were required to demonstrate documented evidence in the literature or a database as a soluble or solubilized circulating protein. The first criterion was evidence by mass spectrometry detection, with a candidate designated as previously detected by the following database-specific criteria: a minimum of 2 peptides in HUPO9504, which contains 9,504 human proteins identified by MS/MS; a minimum of 1 peptide in HUPO889, which is a higher confidence subset of HUPO9504 containing 889 human proteins; or at least 2 peptides in Peptide Atlas (November 2009 build). The second criterion was annotation as either a secreted or single-pass membrane protein in UniProt. The third criterion was designation as a plasma protein in the literature. The fourth criterion was prediction as a secreted protein based on the use of various programs: prediction by TMHMM as a protein with one transmembrane domain, which however is cleaved based on prediction by SignalP; or prediction by TMHMM as having no transmembrane domain and prediction by either SignalP or SecretomeP as a secreted protein. All candidate proteins satisfied one or more of the criteria.

Study Designs and Power Analyses.

Sample, Subject and Lung Nodule Inclusion and Exclusion Criteria.

The inclusion criteria for plasma samples were collection in EDTA-containing blood tubes; obtained from subjects previously enrolled in the Ethics Review Board (ERB) or the Institutional Review Boards (IRB) approved studies at the participating institutions; and archived, e.g. labeled, aliquoted and frozen, as stipulated by the study protocols.

The inclusion criteria for subjects were the following: age ≥40; any smoking status, e.g. current, former, or never; any co-morbid conditions, e.g. chronic obstructive pulmonary disease (COPD); any prior malignancy with a minimum of 5 years in clinical remission; any prior history of skin carcinomas, e.g. squamous or basal cell. The only exclusion criterion was prior malignancy within 5 years of lung nodule diagnosis.

The inclusion criteria for the lung nodules included radiologic, histopathologic and staging parameters. The radiologic criteria included size ≥4 mm and ≤30 mm, and any spiculation or ground glass opacity. The histopathologic criteria included either diagnosis of malignancy, e.g. non-small cell lung cancer (NSCLC), including adenocarcinoma (and bronchioloalveolar carcinoma (BAC), squamous, or large cell, or a benign process, including inflammatory (e.g. granulomatous, infectious) or non-inflammatory (e.g. hamartoma) processes. The clinical staging parameters included: primary tumor: ≤T1 (e.g. 1A and 1B); regional lymph nodes: N0 or N1 only; distant metastasis: M0 only. The exclusion criteria for lung nodules included the following: nodule size data unavailable; no pathology data available, histopathologic diagnosis of small cell lung cancer; and the following clinical staging parameters: primary tumor: ≥T2, regional lymph nodes: ≥N2, and distant metastasis: ≥M1.

Sample Layout.

Up to 15 paired samples per batch were assigned randomly and iteratively to experimental processing batches until no statistical bias was demonstrable on age, gender or nodule size. Paired samples within each processing batch were further randomly and repeatedly assigned to positions within the processing batch until the absolute values of the corresponding Pearson correlation coefficients between position and age, gender and nodule size were less than 0.1. Each pair of cancer and benign samples was then randomized to their relative positions in the batch. To provide a positive control for quality assessment, three 200 µl aliquots of a pooled human plasma standard (HPS) (Bioreclamation, Hicksville, N.Y.) were positioned at the beginning, middle and end of each processing batch, respectively. Samples within a batch were analyzed together: sequentially during immunodepletion and SRM-MS analysis but in parallel during denaturing, digestion, and desalting.

Power Analysis for the Classifier Discovery Study.

The power analysis for the discovery study was based on the following assumptions: (A) The overall false positive rate ($\alpha$) was set to 0.05. (B) Šidák correction for multiple testing was used to calculate the effective $\alpha_{eff}$ for testing 200 proteins, i.e.

i.e. $\alpha_{eff} = 1 - \sqrt[200]{1-\alpha}$.

(C) The effective sample size was reduced by a factor of 0.864 to account for the larger sample requirement for the Mann-Whitney test than for the t-test (13). (D) The overall coefficient of variation was set to 0.43 based on a previous experience. (E) The power (1−β) of the study was calculated based on the formula for the two-sample, two-sided t-test, using effective $\alpha_{eff}$ and effective sample size.

Power Analysis for the Classifier Validation Study.

Sufficient cancer and benign samples are needed in the validation study to confirm the performance of the lung nodule classifier obtained from the discovery study. We are interested in obtaining the 95% confidence intervals (CIs) on NPV and specificity for the classifier. Assuming the cancer prevalence of lung nodules is prev, the negative predictive value (NPV) and the positive predictive value (PPV) of a classifier on the patient population with lung nodules were calculated from sensitivity (sens) and specificity (spec) as follows:

$$NPV = \frac{(1-prev)*spec}{prev*(1-sens)+(1-prev)*spec} \quad (S1)$$

$$PPV = \frac{prev*sens}{prev*sens+(1-prev)*(1-spec)} \quad (S2)$$

Using Eq. (S1) above, one can derive sensitivity as a function of NPV and specificity, i.e.

$$sens = 1 - \frac{1-NPV}{NPV}\frac{1-prev}{prev}spec \quad (S3)$$

Assume that the validation study contains $N_C$ cancer samples and $N_B$ benign samples. Based on binomial distribution, variances of sensitivity and specificity are given by $$var(sens) = sens*(1-sens)/N_C \quad (S4)$$

$$var(spec) = spec*(1-spec)/N_B \quad (S5)$$

Using Eqs. (S1, S2) above, the corresponding variances of NPV and PPV can be derived under the large-sample, normal-distribution approximation as $$var(NPV) = NPV^2(1-NPV)^2\left[\frac{var(sens)}{(1-sens)^2}+\frac{var(spec)}{spec^2}\right], \quad (S6)$$

$$var(PPV) = PPV^2(1-PPV)^2\left[\frac{var(sens)}{sens^2}+\frac{var(spec)}{(1-spec)^2}\right]. \quad (S7)$$

The two-sided 95% CIs of sensitivity, specificity, NPV and PPV are then given by $\pm z_{\alpha/2}\sqrt{var(sens)}$, $\pm z_{\alpha/2}\sqrt{var(spec)}$, $\pm z_{\alpha/2}\sqrt{var(NPV)}$ and $\pm z_{\alpha/2}\sqrt{var(PPV)}$, respectively, where $z_{\alpha/2}=1.959964$ is the 97.5% quantile of the normal distribution.

Experimental Procedures.

Immunoaffinity Chromatography.

An immunoaffinity column was prepared by adding 10 ml of a 50% slurry containing a 2:1 ratio of IgY14 and SuperMix resins (Sigma Aldrich), respectively, to a glass chromatography column (Tricorn, GE Healthcare) and allowed to settle by gravity, yielding a 5 ml volume of resin in the column. The column was capped and placed on an HPLC system (Agilent 1100 series) for further packing with 0.15 M $(NH_4)HCO_3$ at 2 ml/min for 20 min, with performance assessed by replicate injections of HPS aliquots. Column performance was assessed prior to immunoaffinity separation of each sample batch.

To isolate low abundance proteins, 60 µl of plasma were diluted in 0.15M (NH$_4$)HCO$_3$ (1:2 v/v) to a 180 µl final volume and filtered using a 0.2 µm AcroPrep 96-well filter plate (Pall Life Sciences). Immunoaffinity separation was conducted on a IgY14-SuperMix column connected to an HPLC system (Agilent 1100 series) using 3 buffers (loading/washing: 0.15 M (NH$_4$)HCO$_3$; stripping/elution: 0.1 M glycine, pH 2.5; and neutralization: 0.01 M Tris-HCl and 0.15 M NaCl, pH 7.4) with a cycle comprised of load, wash, elute, neutralization and re-equilibration lasting 36 min. The unbound and bound fractions were monitored at 280 nm and were baseline resolved after separation. Unbound fractions (containing the low abundance proteins) were collected for downstream processing and analysis, and lyophilized prior to enzymatic digestion.

Enzymatic Digestion and Solid-Phase Extraction.

Lyophilized fractions containing low abundance proteins were digested with trypsin after being reconstituted under mild denaturing conditions in 200 µl of 1:1 0.1 M (NH$_4$)HCO$_3$/trifluoroethanol (TFE) (v/v) and then allowed to incubate on an orbital shaker for 30 min at RT. Samples were diluted in 800 µl of 0.1 M (NH$_4$)HCO$_3$ and digested with 0.4 µg trypsin (Princeton Separations) per sample for 16 h at 37° C. and lyophilized. Lyophilized tryptic peptides were reconstituted in 350 µl of 0.01 M (NH$_4$)HCO$_3$ and incubated on an orbital shaker for 15 min at RT, followed by reduction using 30 µl of 0.05 M TCEP and incubation for 1 h at RT and dilution in 375 µl of 90% water/10% acetonitrile/0.2% trifluoroacetic acid. The extraction plate (Empore C18, 3M Bioanalytical Technologies) was conditioned according to the manufacturer's protocol, and after sample loading were washed in 500 µl of 95% water/5% acetonitrile/0.1% trifluoroacetic acid and eluted by 200 µl of 52% water/48% acetonitrile/0.1% trifluoroacetic acid into a collection plate. The eluate was split into 2 equal aliquots and was taken to dryness in a vacuum concentrator. One aliquot was used immediately for mass spectrometry, while the other was stored at −80° C. Samples were reconstituted in 12 µl of 90% water/10% acetonitrile/0.2% formic acid just prior to LC-SRM MS analysis.

SRM-MS Analysis.

Peptide samples were separated using a capillary reversed-phase LC column (Thermo BioBasic 18 KAPPA; column dimensions: 320 µm×150 mm; particle size: 5 µm; pore size: 300 Å) and a nano-HPLC system (nanoACQUITY, Waters Inc.). The mobile phases were (A) 0.2% formic acid in water and (B) 0.2% formic acid in acetonitrile. The samples were injected (8 µl) and separated using a linear gradient (98% A to 70% A) at 5 µl/minute for 19 min. Peptides were eluted directly into the electrospray source of the mass spectrometer (5500 QTrap LC/MS/MS, AB Sciex) operating in scheduled SRM positive-ion mode (Q1 resolution: unit; Q3 resolution: unit; detection window: 180 seconds; cycle time: 1.5 seconds). Transition intensities were then integrated by software MultiQuant (AB Sciex). An intensity threshold of 10,000 was used to filter out non-specific data and undetected transitions.

Normalization and Calibration of Raw SRM-MS Data.

Definition of Depletion Column Drift.

Due to changes in observed signal intensity after repetitive use of each immunoaffinity column, the column's performance was assessed by quantifying the transition intensity in the control HPS samples. Assuming $I_{i,s}$ was the intensity of transition i in an HPS sample s, the drift of the sample was defined as $$\text{drift}_s = \text{median}\left(\frac{I_{i,s} - \hat{I}_s}{\hat{I}_s}\right), \quad (S8)$$

where $\hat{I}_i$ was the mean value of $I_{i,s}$ among all HPS samples that were depleted by the same column, and the median was taken over all detected transitions in the sample. The column variability, or drift, was defined as $$\text{drift}_{col} = \text{median}(\text{drift}_s > 0) - \text{median}(\text{drift}_s < 0). \quad (S9)$$

Here the median was taken over all HPS samples depleted by the column. If no sample drift were greater or less than zero, the corresponding median was taken as 0. The median column drift was the median of drifts of all depletion columns used in the study.

Identification of Endogenous Normalizing Proteins.

The following criteria were used to identify a transition of a normalization protein: (A) possession of the highest median intensity of all transitions from the same protein; (B) detected in all samples; (C) ranking high in reducing median technical coefficient of variation (CV), i.e. median CV of transition intensities that were measured on HPS samples, as a normalizer; (D) ranking high in reducing median column drift that was observed in sample depletion; and (E) possession of low median technical CV and low median biological CV, i.e. median CV of transition intensities that were measured on clinical samples. Six endogenous normalizing proteins were identified and are listed in Table 33.

TABLE 33

List of endogenous normalizing proteins

| Normalizing Protein | Transition | SEQ ID NO | Median Technical CV (%) | Median Column Drift (%) |
|---|---|---|---|---|
| PEDF_HUMAN | LQSLFDSPDFSK_692.34_593.30 | 28 | 25.8 | 6.8 |
| MASP1_HUMAN | TGVITSPDFPNPYPK_816.92_258.10 | 6 | 26.5 | 18.3 |
| GELS_HUMAN | TASDFITK_441.73_710.40 | 5 | 27.1 | 16.8 |
| LUM_HUMAN | SLEDLQLTHNK_433.23_499.30 | 29 | 27.1 | 16.1 |
| C163A_HUMAN | INPASLDK_429.24_630.30 | 30 | 26.6 | 14.6 |
| PTPRJ_HUMAN | VITEPIPVSDLR_669.89_896.50 | 31 | 27.2 | 18.2 |
| | Normalization by Panel of Transitions | | 25.1 | 9.0 |
| | Without Normalization | | 32.3 | 23.8 |

Normalization of Raw SRM-MS Data.

Six normalization transitions were used to normalize raw SRM-MS data to reduce sample-to-sample intensity variations within same study. A scaling factor was calculated for each sample so that the intensities of the six normalization transitions of the sample were aligned with the corresponding median intensities of all HPS samples. Assuming that $N_{i,s}$ is the intensity of a normalization transition i in sample s and $\hat{N}_i$ the corresponding median intensity of all HPS samples, then the scaling factor for sample s is given by $\hat{S}/S_s$, where $$S_s = \text{median}\left(\frac{N_{1,s}}{\hat{N}_1}, \frac{N_{2,s}}{\hat{N}_2}, \ldots, \frac{N_{6,s}}{\hat{N}_6}\right) \quad (S10)$$

is the median of the intensity ratios and $\hat{S}$ is the median of $S_s$ over all samples in the study. Finally, for each transition of each sample, its normalized intensity was calculated as $$\tilde{I}_{i,s} = I_{i,s} * \hat{S}/S_s \quad (S11)$$

where $I_{i,s}$ was the raw intensity.

Calibration by Human Plasma Standard (HPS) Samples.

For a label-free MS approach, variation on signal intensity between different experiments is expected. To reduce this variation, we utilized HPS samples as an external standard and calibrated the intensity between the discovery and validation studies. Assume that $\breve{I}_{i,s}$ is the logarithmically transformed (base 2), normalized intensity of transition i in sample s, $\breve{I}_{i,dis}$ and $\breve{I}_{i,val}$ are the corresponding median values of HPS samples in the discovery and the validation studies, respectively. Then the HPS corrected intensity is $$\breve{I}_{i,s} = \breve{I}_{i,s} - \breve{I}_{i,val} + \breve{I}_{i,dis} \quad (S12)$$

Figure 16:
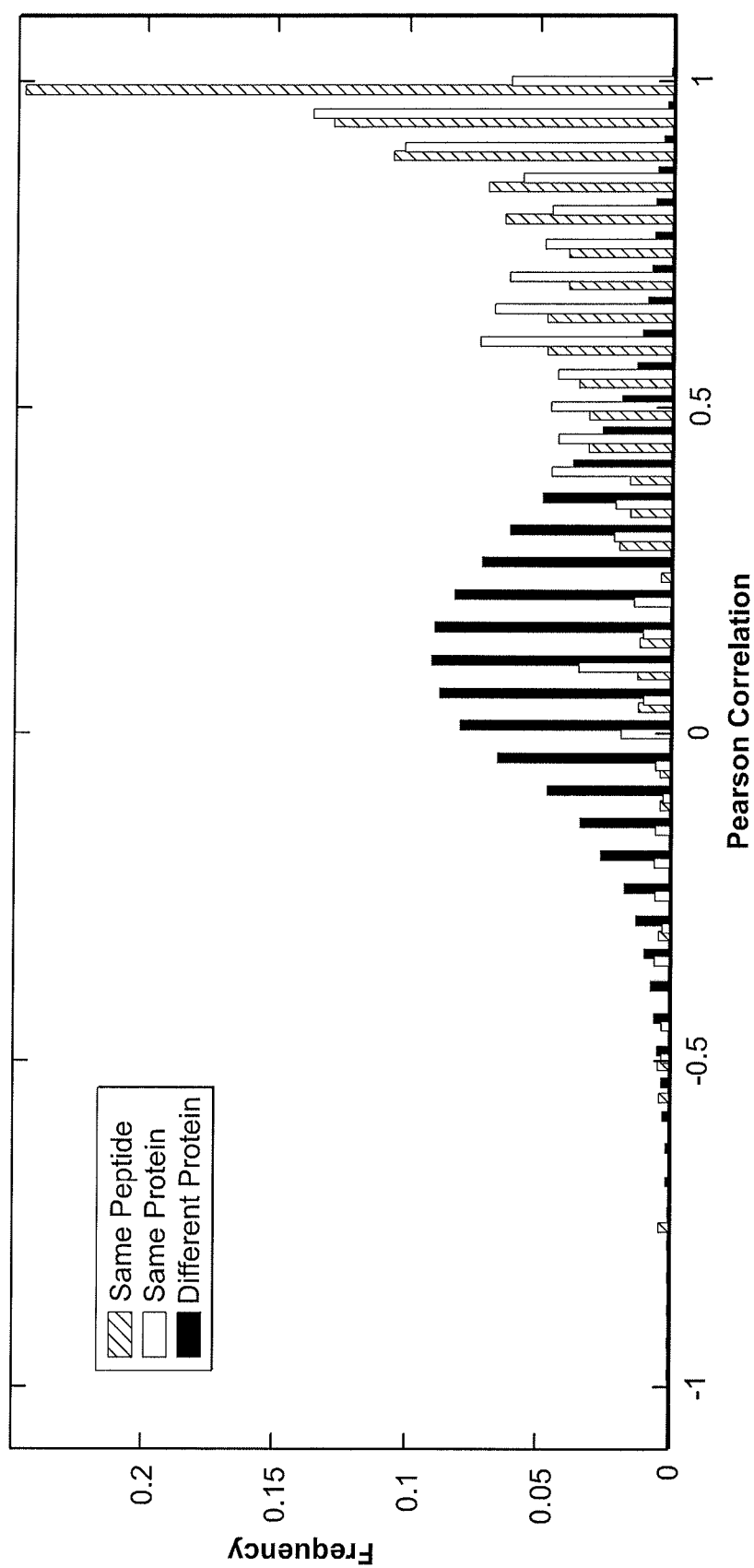
FIG. 16 is a diagram showing the Pearson correlations for peptides from the same peptide (blue), from the same protein (green) and from different proteins (red).

Calculation of q-Values of Peptide and Protein Assays. In the development of SRM assays, it is important to ensure that the transitions detected correspond to the peptides and proteins they were intended to measure. Computational tools such as mProphet (15) enable automated qualification of SRM assays. We introduced a complementary strategy to mProphet that does not require customization for each dataset. It utilizes expression correlation techniques (16) to confirm the identity of transitions from the same peptide and protein with high confidence. In FIG. 16, a histogram of the Pearson correlations between every pair of transitions in the assay is presented. The correlation between a pair of transitions is obtained from their expression profiles over all samples in the discovery study. As expected, transitions from the same peptide are highly correlated. Similarly, transitions from different peptide fragments of the same protein are also highly correlated. In contrast, transitions from different proteins are not highly correlated, which enables a statistical analysis of the quality of a protein's SRM assay.

To determine the false positive assay rate we calculated the q-values (17) of peptide SRM assays. Using the distribution of Pearson correlations between transitions from different proteins as the null distribution (FIG. 16), an empirical p-value was assigned to a pair of transitions from the same peptide, detected in at least five common samples. A value of 'NA' is assigned if the pair of transitions was detected in less than five common samples. The empirical p-value was converted to a q-value using the "qvalue" package in Bioconductor (www.bioconductor.org/packages/release/bioc/html/qvalue.html). We calculated the q-values of protein SRM assays in the same way except Pearson correlations of individual proteins were calculated as those between two transitions from different peptides of the protein. For proteins not having two peptides detected in five or more common samples, their q-values could not be properly evaluated and were assigned 'NA'. If the correlation of transitions from two peptides from the same protein is above 0.5 then there was less than a 3% probability that the assay is false.

Most 36 cooperative proteins are shown in table below.

TABLE 34

Cooperative classifiers

| Category | Protein (UniProt) | Official Gene Name | Cooperative Score | Partial AUC | Coefficient CV | Frequency | Transition for Quantitation |
|---|---|---|---|---|---|---|---|
| Classifier | TSP1_HUMAN | THBS1 | 1.8 | 0.25 | 0.24 | 59 | GFLLLASLR_495.31_559.40 |
| Classifier | COIA1_HUMAN | COL18A1 | 3.7 | 0.16 | 0.25 | 91 | AVGLAGTFR_446.26_721.40 |
| Classifier | ISLR_HUMAN | ISLR | 1.4 | 0.32 | 0.25 | 64 | ALPGTPVASSQPR_640.85_841.50 |
| Classifier | TETN_HUMAN | CLEC3B | 2.5 | 0.26 | 0.26 | 67 | LDTLAQEVALLK_657.39_330.20 |
| Classifier | FRIL_HUMAN | FTL | 2.8 | 0.31 | 0.26 | 53 | LGGPEAGLGEYLFER_804.40_913.40 |
| Classifier | GRP78_HUMAN | HSPA5 | 1.4 | 0.27 | 0.27 | 40 | TWNDPSVQQDIK_715.85_260.20 |
| Classifier | ALDOA_HUMAN | ALDOA | 1.3 | 0.26 | 0.28 | 88 | ALQASALK_401.25_617.40 |
| Classifier | BGH3_HUMAN | TGFBI | 1.8 | 0.21 | 0.28 | 69 | LTLLAPLNSVFK_658.40_804.50 |
| Classifier | LG3BP_HUMAN | LGALS3BP | 4.3 | 0.29 | 0.29 | 76 | VEIFYR_413.73_598.30 |
| Classifier | LRP1_HUMAN | LRP1 | 4.0 | 0.13 | 0.32 | 93 | TVLWPNGLSLDIPAGR_855.00_400.20 |
| Classifier | FIBA_HUMAN | FGA | 1.1 | 0.31 | 0.35 | 11 | NSLFEYQK_514.76_714.30 |
| Classifier | PRDX1_HUMAN | PRDX1 | 1.5 | 0.32 | 0.37 | 68 | QITVNDLPVGR_606.30_428.30 |
| Classifier | GSLG1_HUMAN | GLG1 | 1.2 | 0.34 | 0.45 | 23 | IIIQESALDYR_660.86_338.20 |
| Robust | KIT_HUMAN | KIT | 1.4 | 0.33 | 0.46 | 28 | YVSELHLTR_373.21_263.10 |
| Robust | CD14_HUMAN | CD14 | 4.0 | 0.33 | 0.48 | 73 | ATVNPSAPR_456.80_527.30 |
| Robust | EF1A1_HUMAN | EEF1A1 | 1.2 | 0.32 | 0.56 | 52 | IGGIGTVPVGR_513.30_428.30 |
| Robust | TENX_HUMAN | TNXB | 1.1 | 0.30 | 0.56 | 22 | YEVTVVSVR_526.29_759.50 |
| Robust | AIFM1_HUMAN | AIFM1 | 1.4 | 0.32 | 0.70 | 6 | ELWFSDDPNVTK_725.85_558.30 |
| Robust | GGH_HUMAN | GGH | 1.3 | 0.32 | 0.81 | 43 | YYIAASYVK_539.28_638.40 |
| Robust | IBP3_HUMAN | IGFBP3 | 3.4 | 0.32 | 1.82 | 58 | FLNVLSPR_473.28_685.40 |
| Robust | ENPL_HUMAN | HSP90B1 | 1.1 | 0.29 | 5.90 | 22 | SGYLLPDTK_497.27_460.20 |
| Non-Robust | ERO1A_HUMAN | ERO1L | 6.2 | | | | VLPFFERPDFQLFTGNK_685.70_318.20 |
| Non-Robust | 6PGD_HUMAN | PGD | 4.3 | | | | LVPLLDTGDIIIDGGNSEYR_1080.60_897.40 |
| Non-Robust | ICAM1_HUMAN | ICAM1 | 3.9 | | | | VELAPLPSWQPVGK_760.93_342.20 |
| Non-Robust | PTPA_HUMAN | PPP2R4 | 2.1 | | | | FGSLLPIHPVTSG_662.87_807.40 |
| Non-Robust | NCF4_HUMAN | NCF4 | 2.0 | | | | GATGIFPLSFVK_618.85_837.50 |

TABLE 34-continued

| | | Cooperative classifiers | | | |
|---|---|---|---|---|---|
| Non-Robust | SEM3G_HUMAN | SEMA3G | 1.9 | | LFLGGLDALYSLR_719.41_837.40 |
| Non-Robust | 1433T_HUMAN | YWHAQ | 1.5 | | TAFDEAIAELDTLNEDSYK_1073.00_748.40 |
| Non-Robust | RAP2B_HUMAN | RAP2B | 1.5 | | VDLEGER_409.21_603.30 |
| Non-Robust | MMP9_HUMAN | MMP9 | 1.4 | | AFALWSAVTPLTFTR_840.96_290.20 |
| Non-Robust | FOLH1_HUMAN | FOLH1 | 1.3 | | LGSGNDFEVFFQR_758.37_825.40 |
| Non-Robust | GSTP1_HUMAN | GSTP1 | 1.3 | | ALPGQLKPFETLLSQNQGGK_709.39_831.40 |
| Non-Robust | EF2_HUMAN | EEF2 | 1.3 | | FSVSPVVR_445.76_470.30 |
| Non-Robust | RAN_HUMAN | RAN | 1.2 | | LVLVGDGGTGK_508.29_591.30 |
| Non-Robust | SODM_HUMAN | SOD2 | 1.2 | | NVRPDYLK_335.52_260.20 |
| Non-Robust | DSG2_HUMAN | DSG2 | 1.1 | | GQIIGNFQAFDEDTGLPAHAR_753.04_299.20 |

| Category | SEQ ID NO | P Value (Mann-Whitney test) | Transition for Qualification | Peptide Q Value | Tissue Candidate | Predicted Concentration (ng/ml) |
|---|---|---|---|---|---|---|
| Classifier | 22 | 0.23 | GFLLLASLR_495.31_318.20 | 1.90E-05 | | 510 |
| Classifier | 11 | 0.16 | AVGLAGTFR_446.26_551.30 | 6.70E-04 | | 35 |
| Classifier | 14 | 0.74 | ALPGTPVASSQPR_640.85_440.30 | 4.40E-03 | | — |
| Classifier | 20 | 0.14 | LDTLAQEVALLK_657.39_871.50 | 3.70E-05 | | 58000 |
| Classifier | 24 | 0.19 | LGGPEAGLGEYLFER_804.40_525.30 | 4.30E-05 | Secreted, Epi, Endo | 12 |
| Classifier | 23 | 0.44 | TWNDPSVQQDIK_715.85_288.10 | 1.80E-03 | Secreted, Epi, Endo | 100 |
| Classifier | 7 | 0.57 | ALQASALK_401.25_489.30 | 3.70E-05 | Secreted, Epi | 250 |
| Classifier | 8 | 0.57 | LTLLAPLNSVFK_658.40_875.50 | 1.40E-04 | | 140 |
| Classifier | 25 | 0.45 | VEIFYR_413.73_485.30 | 2.80E-05 | Secreted | 440 |
| Classifier | 15 | 0.26 | TVLWPNGLSLDIPAGR_855.00_605.30 | 1.40E-04 | Epi | 20 |
| Classifier | 26 | 0.57 | NSLFEYQK_514.76_315.20 | 1.90E-05 | | 130000 |
| Classifier | 16 | 0.24 | QITVNDLPVGR_606.30_770.40 | 1.90E-05 | Epi | 60 |
| Classifier | 27 | 0.27 | IIIQESALDYR_660.86_724.40 | 6.70E-03 | Epi, Endo | — |
| Robust | 32 | 0.27 | YVSELHLTR_373.21_526.30 | 2.40E-03 | | 8.2 |
| Robust | 33 | 0.72 | ATVNPSAPR_456.80_386.20 | 4.30E-04 | Epi | 420 |
| Robust | 34 | 0.53 | IGGIGTVPVGR_513.30_628.40 | 4.50E-04 | Secreted, Epi | 61 |
| Robust | 2 | 0.54 | YEVTVVSVR_526.29_660.40 | 1.10E-03 | Endo | 70 |
| Robust | 35 | 0.20 | ELWFSDDPNVTK_725.85_875.40 | 3.70E-02 | Epi, Endo | 1.4 |
| Robust | 36 | 0.24 | YYIAASYVK_539.28_567.30 | 1.70E-03 | | 250 |
| Robust | 4 | 0.04 | FLNVLSPR_473.28_359.20 | 2.80E-05 | | 5700 |
| Robust | 37 | 0.57 | SGYLLPDTK_497.27_573.30 | 1.10E-03 | Secreted, Epi, Endo | 88 |
| Non-Robust | 38 | 0.06 | VLPFFERPDFQLFTGNK_685.70_419.20 | 1.20E-02 | Secreted, Epi, Endo | — |
| Non-Robust | 39 | 0.03 | LVPLLDTGDIIIDGGNSEYR_1080.60_974.50 | 5.50E-03 | Epi, Endo | 29 |
| Non-Robust | 40 | 0.31 | VELAPLPSWQPVGK_760.93_413.20 | 2.80E-02 | | 71 |
| Non-Robust | 41 | 0.26 | FGSLLPIHPVTSG_662.87_292.10 | 1.90E-03 | Endo | 3.3 |
| Non-Robust | 42 | 0.11 | GATGIFPLSFVK_618.85_690.40 | 7.90E-04 | Endo | — |
| Non-Robust | 43 | 0.20 | LFLGGLDALYSLR_719.41_538.30 | 1.10E-03 | | — |
| Non-Robust | 44 | 0.69 | TAFDEAIAELDTLNEDSYK_1073.00_969.50 | 1.10E-02 | Epi | 180 |
| Non-Robust | 45 | 0.34 | VDLEGER_409.21_361.20 | 1.20E-03 | Epi | — |
| Non-Robust | 46 | 0.36 | AFALWSAVTPLTFTR_840.96_589.30 | 4.00E-03 | | 28 |
| Non-Robust | 47 | 0.06 | LGSGNDFEVFFQR_758.37_597.30 | 5.80E-03 | | — |

TABLE 34-continued

| | | | Cooperative classifiers | | | |
|---|---|---|---|---|---|---|
| Non-Robust | 48 | 0.46 | ALPGQLKPFETLLSQNQGGK_709.39_261.20 | 1.70E−04 | Endo | 32 |
| Non-Robust | 49 | 0.79 | FSVSPVVR_445.76_557.30 | 1.10E−02 | Secreted, Epi | 30 |
| Non-Robust | 50 | 0.27 | LVLVGDGGTGK_508.29_326.20 | 2.80E−03 | Secreted, Epi | 4.6 |
| Non-Robust | 51 | 0.86 | NVRPDYLK_335.52_423.30 | 2.40E−02 | Secreted | 7.1 |
| Non-Robust | 52 | 0.08 | GQIIGNFQAFDEDTGLPAHAR_753.04_551.30 | 5.70E−03 | Endo | 2.7 |

A P-classifier using the same steps for the 13-protein classifier derivation (see Table 28 and Materials and Methods in Example 9) except that the Mann Whitney p-value was used in place of cooperative score was also derived.

TABLE 35

| | | | | | | | | |
|---|---|---|---|---|---|---|---|---|
| | | | | P-Classifiers | | | | |
| Category | Protein (UniProt) | Official Gene Name | Transition for Quantitation | SEQ ID NO | P Value (Mann-Whitney test) | Coefficient ($\alpha = 27.24$) | Coefficient CV | Cooperative Protein |
| P-Classifier | FRIL_HUMAN | FTL | LGGPEAGLGEYLFER_804.40_913.40 | 24 | 0.19 | 0.39 | 0.21 | Yes |
| P-Classifier | TSP1_HUMAN | THBS1 | GFLLLASLR_495.31_559.40 | 22 | 0.23 | 0.48 | 0.21 | Yes |
| P-Classifier | LRP1_HUMAN | LRP1 | TVLWPNGLSLDIPAGR_855.00_400.20 | 15 | 0.26 | −0.81 | 0.22 | Yes |
| P-Classifier | PRDX1_HUMAN | PRDX1 | QITVNDLPVGR_606.30_428.30 | 16 | 0.24 | −0.51 | 0.24 | Yes |
| P-Classifier | TETN_HUMAN | CLEC3B | LDTLAQEVALLK_657.39_330.20 | 20 | 0.14 | −1.08 | 0.27 | Yes |
| P-Classifier | TBB3_HUMAN | TUBB3 | ISVYYNEASSHK_466.60_458.20 | 19 | 0.08 | −0.21 | 0.29 | No |
| P-Classifier | COIA1_HUMAN | COL18A1 | AVGLAGTFR_446.26_721.40 | 11 | 0.16 | −0.72 | 0.29 | Yes |
| P-Classifier | GGH_HUMAN | GGH | YYIAASYVK_539.28_638.40 | 36 | 0.24 | 0.74 | 0.33 | Yes |
| P-Classifier | A1AG1_HUMAN | ORM1 | YVGGQEHFAHLLILR_584.99_263.10 | 53 | 0.27 | 0.30 | 0.36 | No |
| Robust | AIFM1_HUMAN | AIFM1 | ELWFSDDPNVTK_725.85_558.30 | 35 | 0.20 | | | Yes |
| Robust | AMPN_HUMAN | ANPEP | DHSAIPVINR_374.54_402.20 | 54 | 0.16 | | | No |
| Robust | CRP_HUMAN | CRP | ESDTSYVSLK_564.77_347.20 | 55 | 0.17 | | | No |
| Robust | GSLG1_HUMAN | GLG1 | IIIQESALDYR_660.86_338.20 | 27 | 0.27 | | | Yes |
| Robust | IBP3_HUMAN | IGFBP3 | FLNVLSPR_473.28_685.40 | 4 | 0.04 | | | Yes |
| Robust | KIT_HUMAN | KIT | YVSELHLTR_373.21_263.10 | 32 | 0.27 | | | Yes |
| Robust | NRP1_HUMAN | NRP1 | SFEGNNNYDTPELR_828.37_514.30 | 56 | 0.22 | | | No |
| Non-Robust | 6PGD_HUMAN | PGD | LVPLLDTGDIIIDGGNSEYR_1080.60_897.4 | 39 | 0.03 | | | Yes |
| Non-Robust | CH10_HUMAN | HSPE1 | VLLPEYGGTK_538.80_751.40 | 57 | 0.07 | | | No |
| Non-Robust | CLIC1_HUMAN | CLIC1 | FSAYIK_364.70_581.30 | 9 | 0.14 | | | No |
| Non-Robust | COF1_HUMAN | CFL1 | YALYDATYETK_669.32_827.40 | 58 | 0.08 | | | No |
| Non-Robust | CSF1_HUMAN | CSF1 | ISSLRPQGLSNPSTLSAQPQLSR_813.11_600.30 | 59 | 0.23 | | | No |
| Non-Robust | CYTB_HUMAN | CSTB | SQVVAGTNYFIK_663.86_315.20 | 60 | 0.16 | | | No |
| Non-Robust | DMKN_HUMAN | DMKN | VSEALGQGTR_509.27_631.40 | 61 | 0.17 | | | No |
| Non-Robust | DSG2_HUMAN | DSG2 | GQIIGNFQAFDEDTGLPAHAR_753.04_299.20 | 52 | 0.08 | | | Yes |
| Non-Robust | EREG_HUMAN | EREG | VAQVSITK_423.26_448.30 | 62 | 0.16 | | | No |
| Non-Robust | ERO1A_HUMAN | ERO1L | VLPFFERPDFQLFTGNK_685.70_318.20 | 38 | 0.06 | | | Yes |
| Non-Robust | FOLH1_HUMAN | FOLH1 | LGSGNDFEVFFQR_758.37_825.40 | 47 | 0.06 | | | Yes |
| Non-Robust | ILEU_HUMAN | SERPINB1 | TYNFLPEFLVSTQK_843.94_379.20 | 63 | 0.09 | | | No |
| Non-Robust | K1C19_HUMAN | KRT19 | FGAQLAHIQALISGIEAQLGDVR_803.11_274.20 | 64 | 0.17 | | | No |

TABLE 35-continued

P-Classifiers

| Category | Protein (UniProt) | Official Gene Name | Transition for Quantitation | SEQ ID NO | P Value (Mann-Whitney test) | Coefficient ($\alpha = 27.24$) | Coefficient CV | Cooperative Protein |
|---|---|---|---|---|---|---|---|---|
| Non-Robust | LYOX_HUMAN | LOX | TPILLIR_413.28_514.40 | 65 | 0.22 | | | No |
| Non-Robust | MMP7_HUMAN | MMP7 | LSQDDIK_409.72_705.30 | 66 | 0.23 | | | No |
| Non-Robust | NCF4_HUMAN | NCF4 | GATGIFPLSFVK_618.85_837.50 | 42 | 0.11 | | | Yes |
| Non-Robust | PDIA3_HUMAN | PDIA3 | ELSDFISYLQR_685.85_779.40 | 67 | 0.04 | | | No |
| Non-Robust | PTGIS_HUMAN | PTGIS | LLLFPFLSPQR_665.90_340.30 | 68 | 0.06 | | | No |
| Non-Robust | PTPA_HUMAN | PPP2R4 | FGSLLPIHPVTSG_662.87_807.40 | 41 | 0.26 | | | Yes |
| Non-Robust | RAN_HUMAN | RAN | LVLVGDGGTGK_508.29_591.30 | 50 | 0.27 | | | Yes |
| Non-Robust | SCF_HUMAN | KITLG | LFTPEEFFR_593.30_261.20 | 69 | 0.16 | | | No |
| Non-Robust | SEM3G_HUMAN | SEMA3G | LFLGGLDALYSLR_719.41_837.40 | 43 | 0.20 | | | Yes |
| Non-Robust | TBA1B_HUMAN | TUBA1B | AVFVDLEPTVIDEVR_851.50_928.50 | 70 | 0.15 | | | No |
| Non-Robust | TCPA_HUMAN | TCP1 | IHPTSVISGYR_615.34_251.20 | 71 | 0.17 | | | No |
| Non-Robust | TERA_HUMAN | VCP | GILLYGPPGTGK_586.80_284.20 | 72 | 0.29 | | | No |
| Non-Robust | TIMP1_HUMAN | TIMP1 | GFQALGDAADIR_617.32_717.40 | 73 | 0.26 | | | No |
| Non-Robust | TNF12_HUMAN | TNFSF12 | AAPFLTYFGLFQVH_805.92_700.40 | 74 | 0.29 | | | No |
| Non-Robust | UGPA_HUMAN | UGP2 | LVEIAQVPK_498.80_784.50 | 75 | 0.08 | | | No |

REFERENCES

1. Albert & Russell Am Fam Physician 80:827-831 (2009)
2. Gould et al. Chest 132:108S-130S (2007)
3. Kitteringham et al. J Chromatrog B Analyt Technol Biomed Life Sci 877:1229-1239 (2009)
4. Lange et al. Mol Syst Biol 4:222 (2008)
5. Lehtio & De Petris J Proteomics 73:1851-1863 (2010)
6. MacMahon et al. Radiology 237:395-400 (2005)
7. Makawita Clin Chem 56:212-222 (2010)
8. Ocak et al. Proc Am Thorac Soc 6:159-170 (2009)
9. Ost, D. E. and M. K. Gould, *Decision making in patients with pulmonary nodules*. Am J Respir Crit Care Med, 2012. 185(4): p. 363-72.
10. Cima, I., et al., *Cancer genetics-guided discovery of serum biomarker signatures for diagnosis and prognosis of prostate cancer*. Proc Natl Acad Sci USA, 2011. 108(8): p. 3342-7.
11. Desiere, F., et al., *The PeptideAtlas project*. Nucleic Acids Res, 2006. 34 (Database issue): p. D655-8.
12. Farrah, T., et al., *A high-confidence human plasma proteome reference set with estimated concentrations in PeptideAtlas*. Mol Cell Proteomics, 2011. 10(9): p. M110 006353.
13. Omenn, G. S., et al., *Overview of the HUPO Plasma Proteome Project: results from the pilot phase with 35 collaborating laboratories and multiple analytical groups, generating a core dataset of 3020 proteins and a publicly-available database*. Proteomics, 2005. 5(13): p. 3226-45.
14. Kearney, P., et al., *Protein identification and Peptide expression resolver: harmonizing protein identification with protein expression data*. J Proteome Res, 2008. 7(1): p. 234-44.
15. Huttenhain, R., et al., *Reproducible quantification of cancer-associated proteins in body fluids using targeted proteomics*. Sci Transl Med, 2012. 4(142): p. 142ra94.
16. Henschke, C. I., et al., *CT screening for lung cancer: suspiciousness of nodules according to size on baseline scans*. Radiology, 2004. 231(1): p. 164-8.
17. Henschke, C. I., et al., *Early Lung Cancer Action Project: overall design and findings from baseline screening*. Lancet, 1999. 354(9173): p. 99-105.
18. States, D. J., et al., *Challenges in deriving high-confidence protein identifications from data gathered by a HUPO plasma proteome collaborative study*. Nat Biotechnol, 2006. 24(3): p. 333-8.
19. Polanski, M. and N. L. Anderson, *A list of candidate cancer biomarkers for targeted proteomics*. Biomark Insights, 2007. 1: p. 1-48.
20. Krogh, A., et al., *Predicting transmembrane protein topology with a hidden Markov model: application to complete genomes*. J Mol Biol, 2001. 305(3): p. 567-80.
21. Bendtsen, J. D., et al., *Improved prediction of signal peptides: SignalP 3.0*. J Mol Biol, 2004. 340(4): p. 783-95.
22. Bendtsen, J. D., et al., *Feature-based prediction of non-classical and leaderless protein secretion*. Protein Eng Des Sel, 2004. 17(4): p. 349-56.
23. Lange, V., et al., *Selected reaction monitoring for quantitative proteomics: a tutorial*. Mol Syst Biol, 2008. 4: p. 222.
24. Picotti, P., et al., *High-throughput generation of selected reaction-monitoring assays for proteins and proteomes*. Nat Methods, 2010. 7(1): p. 43-6.
25. Mallick, P., et al., *Computational prediction of proteotypic peptides for quantitative proteomics*. Nat Biotechnol, 2007. 25(1): p. 125-31.

26. Perkins, D. N., et al., *Probability-based protein identification by searching sequence databases using mass spectrometry data.* Electrophoresis, 1999. 20(18): p. 3551-67.
27. Hastie, T., R. Tibshirani, and J. H. Friedman, *The elements of statistical learning: data mining, inference, and prediction: with 200 full-color illustrations.* Springer series in statistics. 2001, New York: Springer. xvi, 533 p.

28. McClish, D. K., *Analyzing a portion of the ROC curve.* Med Decis Making, 1989. 9(3): p. 190-5.

What is claimed is:

1. A method of determining the likelihood that a pulmonary nodule in a subject is not lung cancer, comprising:
   (a) measuring an abundance of a plurality of transitions in a blood sample obtained from the subject, wherein each transition consists of a precursor ion m/z and a fragment ion m/z thereof, wherein said plurality of transitions comprise at least 3 transitions comprising a transition of ALQASALK (SEQ ID NO: 7) comprising m/z 401.25 and m/z 617.40, a transition of LGGPEAGLGEYLFER (SEQ ID NO: 24) comprising m/z 804.40 and m/z 913.40, and a transition of VEIFYR (SEQ ID NO: 25) comprising m/z 413.73 and m/z 598.30, and wherein said measuring is performed by selected reaction monitoring mass spectrometry;
   (b) calculating a probability of lung cancer score based on the abundance of a plurality transitions of step (a); and
   (c) ruling out lung cancer for the subject if the score in step (b) is lower than a pre-determined score.

2. The method of claim 1, wherein said plurality of transitions further comprises at least one transition selected from the group consisting of a transition of AVGLAGTFR (SEQ ID NO: 11) comprising m/z 446.26 and m/z 721.40, a transition of GFLLLASLR (SEQ ID NO: 22) comprising m/z 495.31 and m/z 559.40, a transition of LTLLAPLNSVFK (SEQ ID NO: 8) comprising m/z 658.40 and m/z 804.50, a transition of NSLFEYQK (SEQ ID NO: 26) comprising m/z 514.76 and m/z 714.30, a transition of IIIQESALDYR (SEQ ID NO: 27) comprising m/z 660.86 and m/z 338.20, a transition of TWNDPSVQQDIK (SEQ ID NO: 23) comprising m/z 715.85 and m/z 260.20, a transition of LDTLAQEVALLK (SEQ ID NO: 20) comprising m/z 657.39 and m/z 330.20, a transition of QITVNDLPVGR (SEQ ID NO: 16) comprising m/z 606.30 and m/z 428.30, and a transition of ATVNPSAPR (SEQ ID NO: 33) comprising m/z 456.80 and m/z 527.30.

3. The method of claim 1, wherein when lung cancer is ruled out the subject does not receive a treatment protocol.

4. The method of claim 3, wherein said treatment protocol is a pulmonary function test (PFT), pulmonary imaging, a biopsy, a surgery, a chemotherapy, a radiotherapy, or any combination thereof.

5. The method of claim 4, where said pulmonary imaging is an x-ray, a chest computed tomography (CT) scan, or a positron emission tomography (PET) scan.

6. The method of claim 1, wherein said pulmonary nodule has a diameter of less than or equal to 3 cm.

7. The method of claim 1, wherein said pulmonary nodule has a diameter of about 0.8 cm to 3.0 cm.

8. The method of claim 1, wherein said score is calculated from a logistic regression model applied to the transition measurements.

9. The method of claim 1, wherein said score is determined as $P_s = 1/[1+\exp(-\alpha - \Sigma_{i=1}^{N} \beta_i * \check{I}_{i,s})]$, where $\check{I}_{i,s}$ is logarithmically transformed and normalized intensity of transition i in said sample (s), $\beta_i$ is the corresponding logistic regression coefficient, $\alpha$ was a panel-specific constant, and N was the total number of transitions in said panel.

10. The method of claim 8, further comprising normalizing the transition measurements.

11. The method of claim 10, wherein the transition measurements are normalized by one or more transitions selected from the group consisting of a transition of LQSLFDSPDFSK (SEQ ID NO:28) comprising m/z 692.34 and m/z 593.30, a transition of TGVITSPDFPNPYPK (SEQ ID NO:6) comprising m/z 816.92 and m/z 258.10, a transition of TASDFITK (SEQ ID NO:5) comprising m/z 441.73 and m/z 710.40, a transition of SLEDLQLTHNK (SEQ ID NO:29) comprising m/z 433.23 and m/z 499.30, a transition of INPASLDK (SEQ ID NO:30) comprising m/z 429.24 and m/z 630.30, and a transition of VITEPIPVSDLR (SEQ ID NO:31) comprising m/z 669.89 and m/z 896.50.

12. The method of claim 1, wherein said blood sample is selected from the group consisting of plasma, serum, and whole blood.

13. The method of claim 1, wherein the determining the likelihood that a pulmonary nodule in a subject is not lung cancer is determined by the sensitivity, specificity, negative predictive value or positive predictive value associated with the score.

14. The method of claim 1, wherein said score determined in step (c) has a negative predictive value (NPV) that is at least about 80%.

15. A method of determining the likelihood that a pulmonary nodule in a subject is not lung cancer, comprising:
(a) measuring an abundance of a plurality of transitions in a blood sample obtained from the subject, wherein each transition consists of a precursor ion m/z and a fragment ion m/z thereof, wherein said plurality of transitions comprise a transition of ALQASALK (SEQ ID NO: 7) comprising m/z 401.25 and m/z 617.40, a transition of LGGPEAGLGEYLFER (SEQ ID NO: 24) comprising m/z 804.40 and m/z 913.40, a transition of VEIFYR (SEQ ID NO: 25) comprising m/z 413.73 and m/z 598.30, a transition of GFLLLASLR (SEQ ID NO: 22) comprising m/z 495.31 and m/z 559.40, and a transition of AVGLAGTFR (SEQ ID NO: 11) comprising m/z 446.26 and m/z 721.40, and wherein said measuring is performed by selected reaction monitoring mass spectrometry;
(b) calculating a probability of lung cancer score based on the abundance of a plurality of transitions of step (a); and
(c) ruling out lung cancer for the subject if the score in step (b) is lower than a pre-determined score.

16. The method of claim 15, wherein said plurality of transitions further comprises at least one transition selected from the group consisting of a transition of LTLLAPLNSVFK (SEQ ID NO: 8) comprising m/z 658.40 and m/z 804.50, a transition of NSLFEYQK (SEQ ID NO: 26) comprising m/z 514.76 and m/z 714.30, a transition of IIIQESALDYR (SEQ ID NO: 27) comprising m/z 660.86 and m/z 338.20, a transition of TWNDPSVQQDIK (SEQ ID NO: 23) comprising m/z 715.85 and m/z 260.20, a transition of LDTLAQEVALLK (SEQ ID NO: 20) comprising m/z 657.39 and m/z 330.20, a transition of QITVNDLPVGR (SEQ ID NO: 16) comprising m/z 606.30 and m/z 428.30, and a transition of ATVNPSAPR (SEQ ID NO: 33) comprising m/z 456.80 and m/z 527.30.

* * * * *

UNITED STATES PATENT AND TRADEMARK OFFICE
CERTIFICATE OF CORRECTION

PATENT NO. : 9,304,137 B2  
APPLICATION NO. : 13/775494  
DATED : April 5, 2016  
INVENTOR(S) : Kearney Page 1 of 1

It is certified that error appears in the above-identified patent and that said Letters Patent is hereby corrected as shown below:

In the claims

Claim 9, Column 223, line 18:

Replace $P_s = 1/[1+\exp(-\alpha - \sum_{i=1}^{N} \beta_i * \bar{I}_{i,s})]$ with $P_s = 1/[1+\exp(-\alpha - \sum_{i=1}^{N} \beta_i * \bar{I}_{i,s})]$ Signed and Sealed this  
Twenty-eighth Day of June, 2016

Michelle K. Lee  
*Director of the United States Patent and Trademark Office*